(12) United States Patent
Storch

(10) Patent No.: US 11,286,529 B2
(45) Date of Patent: Mar. 29, 2022

(54) DIAGNOSTIC METHODS FOR INFECTIOUS DISEASE USING ENDOGENOUS GENE EXPRESSION

(71) Applicant: Washington University, St. Louis, MO (US)

(72) Inventor: Gregory Storch, Saint Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/797,733

(22) Filed: Feb. 21, 2020

(65) Prior Publication Data

US 2020/0216904 A1 Jul. 9, 2020

Related U.S. Application Data

(63) Continuation of application No. 15/080,236, filed on Mar. 24, 2016, now abandoned, which is a continuation of application No. PCT/US2014/057164, filed on Sep. 24, 2014.

(60) Provisional application No. 61/881,508, filed on Sep. 24, 2013.

(51) Int. Cl.
| | |
|---|---|
| *C12Q 1/6883* | (2018.01) |
| *C12Q 1/689* | (2018.01) |
| *C12Q 1/70* | (2006.01) |
| *G01N 33/569* | (2006.01) |
| *C12Q 1/04* | (2006.01) |
| *A61K 31/00* | (2006.01) |
| *A61K 45/00* | (2006.01) |

(52) U.S. Cl.
CPC ............ *C12Q 1/6883* (2013.01); *A61K 31/00* (2013.01); *A61K 45/00* (2013.01); *C12Q 1/04* (2013.01); *C12Q 1/689* (2013.01); *C12Q 1/70* (2013.01); *G01N 33/56911* (2013.01); *G01N 33/56983* (2013.01); *C12Q 2600/112* (2013.01); *C12Q 2600/158* (2013.01); *G01N 2469/10* (2013.01); *G01N 2469/20* (2013.01)

(58) Field of Classification Search
None
See application file for complete search history.

(56) References Cited

U.S. PATENT DOCUMENTS

| | | |
|---|---|---|
| 2003/0225528 A1 | 12/2003 | Baker et al. |
| 2008/0020379 A1 | 1/2008 | Agan et al. |
| 2014/0323391 A1 | 10/2014 | Tsalik et al. |
| 2016/0208331 A1 | 7/2016 | Storch |

FOREIGN PATENT DOCUMENTS

| | | |
|---|---|---|
| JP | 0193524 A | 4/1989 |
| RU | 2144832 C1 | 1/2000 |
| UA | 51728 U | 7/2010 |
| WO | 1996001050 A1 | 1/1996 |
| WO | 2008024642 A2 | 2/2008 |
| WO | 2011066008 A2 | 6/2011 |
| WO | 2011066008 A3 | 6/2011 |
| WO | 2013085152 A1 | 6/2013 |
| WO | 2015048098 A1 | 4/2015 |

OTHER PUBLICATIONS

Hu (PNAS vol. 110 No. 31 pp. 12792-12797 Jul. 30, 2013).*
Ramilo (Blood Mar. 1, 2007 vol. 109 No. 5).*
Oosterheert (Clinical Infectious Diseases vol. 41 pp. 1438-1444 (Nov. 2005).*
Aaroe, J. et al., "Gene expression profiling of perihperal blood cells for early detection of breast cancer," Breast Cancer Res., 2010, pp. 1-11, vol. 12, No. R7.
Alizadeh, A. et al., "Distinct types of diffuse large B-cell lymphoma identified by gene expression profiling," Nature, Feb. 3, 2000, pp. 503-511, vol. 403.
Allantaz, F. et al., "Blood leukocyte microarrays to diagnose systemic onset juvenile idiopathic arthritis and follow the response to IL-1 blockade," J. Exp. Med., Sep. 3, 2007, pp. 2131-2144, vol. 204, No. 9.
Ardura, M. et al., "Enhanced Monocyte Response and Decreased Central Memory T Cells in Children with Invasive *Staphylococcus aureus* Infections," PLoS One, May 2009, pp. 1-17. vol. 4, No. 5, e5446.
Chan, G&P Magazine, 2006, pp. 20-26, vol. 6, No. 3.
Chaussabel, D. et al., "Analysis of Significance Patterns Identifies Ubiquitous and Disease-Specific Gene-Expression Signatures in Patient Peripheral Blood Leukocytes," Annals NY Acad. Sci., Dec. 2005, pp. 146-154, vol. 1062, No. 1.
Chaussabel, D. et al., "Blood Transcriptional Fingerprints to Assess the Immune Status of Human Subjects," Immunologic Signatures of Rejection, F. Marincola and E. Wang (eds.), 2011, pp. 105-125.

(Continued)

*Primary Examiner* — Amanda Haney
(74) *Attorney, Agent, or Firm* — Polsinelli PC

(57) ABSTRACT

Disclosed are methods of diagnosis of a pathogen-associated disease. These methods comprise: providing a biological sample from a human subject; determining presence, absence and/or quantity of a bacterial pathogen, a viral pathogen, or a combination thereof, by a pathogen culture, a serum antibody detection test, a pathogen antigen detection test, a pathogen DNA and/or RNA detection test, or a combination thereof; determining in the sample, expression levels of at least one endogenous gene in which aberrant expression levels are associated with infection with a pathogen, by a microarray hybridization assay, RNA-seq assay, polymerase chain reaction assay, a LAMP assay, a ligase chain reaction assay, a Southern, Northern, or Western blot assay, an ELISA or a combination thereof. The subject can be diagnosed with the disease if the subject comprises the pathogen and an aberrant level of expression of an endogenous gene.

10 Claims, 97 Drawing Sheets

(56) References Cited

OTHER PUBLICATIONS

Colvin, J. et al., "Detection of Viruses in Young Children With Fever Without an Apparent Source," Pediatrics, Dec. 2012, pp. e1455-e1462, vol. 130, No. 6.
Hu, X. et al., "Gene expression profiles in febrile children with defined viral and bacterial infection," PNAS, Jul. 30, 2013, pp. 12792-12797, vol. 110, No. 31.
International Search Report and Written Opinion dated Dec. 18, 2014 from related Patent Application No. PCT//US2014/057164; 8 pgs.
Oosterheert, J. et al., "Impact of Rapid Detection of Viral and Atypical Bacterial Pathogens by Real-Time Polymerase Chain Reaction for Patients with Lower Respiratory Tract Infection," Clin. Infect. Dis., Nov. 15, 2005, pp. 1438-1444, vol. 41.
Pankla, R. et al., "Genomic transcriptional profiling identifies a candidate blood biomarker signature for the diagnosis of septicemic melioidosis," Genome Biol., 2009, pp. 1-22, vol. 10, No. 11, Article R127.
Ramilo, O. et al., "Gene expression patterns in blood leukocytes discriminate patients with acute infections," Blood, Mar. 1, 2007, pp. 2066-2077, vol. 109, No. 5.
Schena, M. et al., "Parallel human genome analysis: Microarray-based expression monitoring of 1000 genes," PNAS, Oct. 1996, pp. 10614-10619, vol. 93.
Tibshirani, R. et al., "Diagnosis of multiple cancer types by shrunken centroids of gene expression," PNAS, May 14, 2002, pp. 6567-6572, vol. 99, No. 10.
Wang, Z. et al., "Gene expression profile in human skeletal muscle cells infected with human adenovirus type 36," J. Med. Virol., Aug. 2012, pp. 1254-1266, vol. 84, No. 8.
Whitehead, A. et al., "Variation in tissue-specific gene expression among natural populations," Genome Biol., 2005, pp. 1-14, vol. 6, No. 2, Article R13.
Wylie, K. et al., "Sequence analysis of the human virome in febrile and afebrile children," PLoS One, Jun. 2012, pp. 1-10, vol. 7, No. 6, e27735.
Zaas, A. et al., "Gene Expression Signatures Diagnose Influenza and Other Symptomatic Respiratory Viral Infections in Humans," Cell Host Microbe, Sep. 17, 2009, pp. 207-217, vol. 6.
Baraff, L. et al., "Practice Guideline for the Management of Infants and Children 0 to 36 Months of Age With Fever Without Source," Ann. Emerg. Med., Jul. 1993, pp. 1198-1210, vol. 22, No. 7.
Berry, M. et al., "An interferon-inducible neutrophil-driven blood transcriptional signature in human tuberculosis," Nature, Aug. 19, 2010, pp. 973-977, vol. 466, with Methods, 2 pgs.
Bleeker, S. et al., "Predicting serious bacterial infection in young children with fever without apparent source," Acta Paediatr. Nov. 2001, pp. 1226-1232, vol. 90, No. 11.
GEO Accession No. GSE40396, "Whole blood transcriptional signature distinguishes viral infection from bacterial infection in febrile young children," Oct. 15, 2002; 2 pgs.
Herz, A. et al., "Changing Epidemiology of Outpatient Bacteremia in 3- to 36-Month-Old Children After the Introduction of the Heptavalent-Conjugated Pneumococcal Vaccine," Pediatr. Infect. Dis. J., 2006, pp. 293-300, vol. 25.
Loughman, J. et al., "Virulence Gene Expression in Human Community-Acquired *Staphylococcus aureus* Infection," J. Infect. Dis., Feb. 1, 2009, pp. 294-301, vol. 199.
Office Action dated Aug. 22, 2019 from related U.S. Appl. No. 15/080,236; 10 pgs.
Office Action dated Feb. 12, 2019 from related U.S. Appl. No. 15/080,236; 27 pgs.
Office Action dated Jul. 23, 2018 from related U.S. Appl. No. 15/080,236; 42 pgs.
Office Action dated Nov. 14, 2018 from related U.S. Appl. No. 15/080,236; 27 pgs.
Paschos, K. et al., "Epigenetic reprogramming of host genes in viral and microbial pathogenesis," Trends Microbiol., Oct. 2010, pp. 439-447, vol. 18, No. 10.
Popper, S. et al., "Gene Transcript Abundance Pro! les Distinguish Kawasaki Disease from Adenovirus Infection," J. Infect. Dis., Aug. 15, 2009, pp. 657-666, vol. 200.
Ramilo, O. et al., "Shifting the Paradigm: Host Gene Signatures for Diagnosis of Infectious Diseases," Cell Host Microbe, Sep. 17, 2009, pp. 199-200, vol. 6.
Rudinsky, S. et al., "Serious Bacterial Infections in Febrile Infants in the Post-Pneumococcal Conjugate Vaccine Era," Acad. Emerg. Med., 2009, pp. 585-590, vol. 16.
Stojanov, S. et al., "Periodic fever, aphthous stomatitis, pharyngitis, and adenitis (PFAPA) is a disorder of innate immunity and Th1 activation responsive to IL-1 blockade," PNAS, Apr. 26, 2011, pp. 7148-7153, vol. 108, No. 17.
Takeuchi, O. et al., "Pattern Recognition Receptors and Inflammation," Cell, Mar. 19, 2010, pp. 805-820, vol. 140.
Thompson, M. et al., "Pattern Recognition Receptors and the Innate Immune Response to Viral Infection," Viruses, 2011, pp. 920-940, vol. 3.

\* cited by examiner

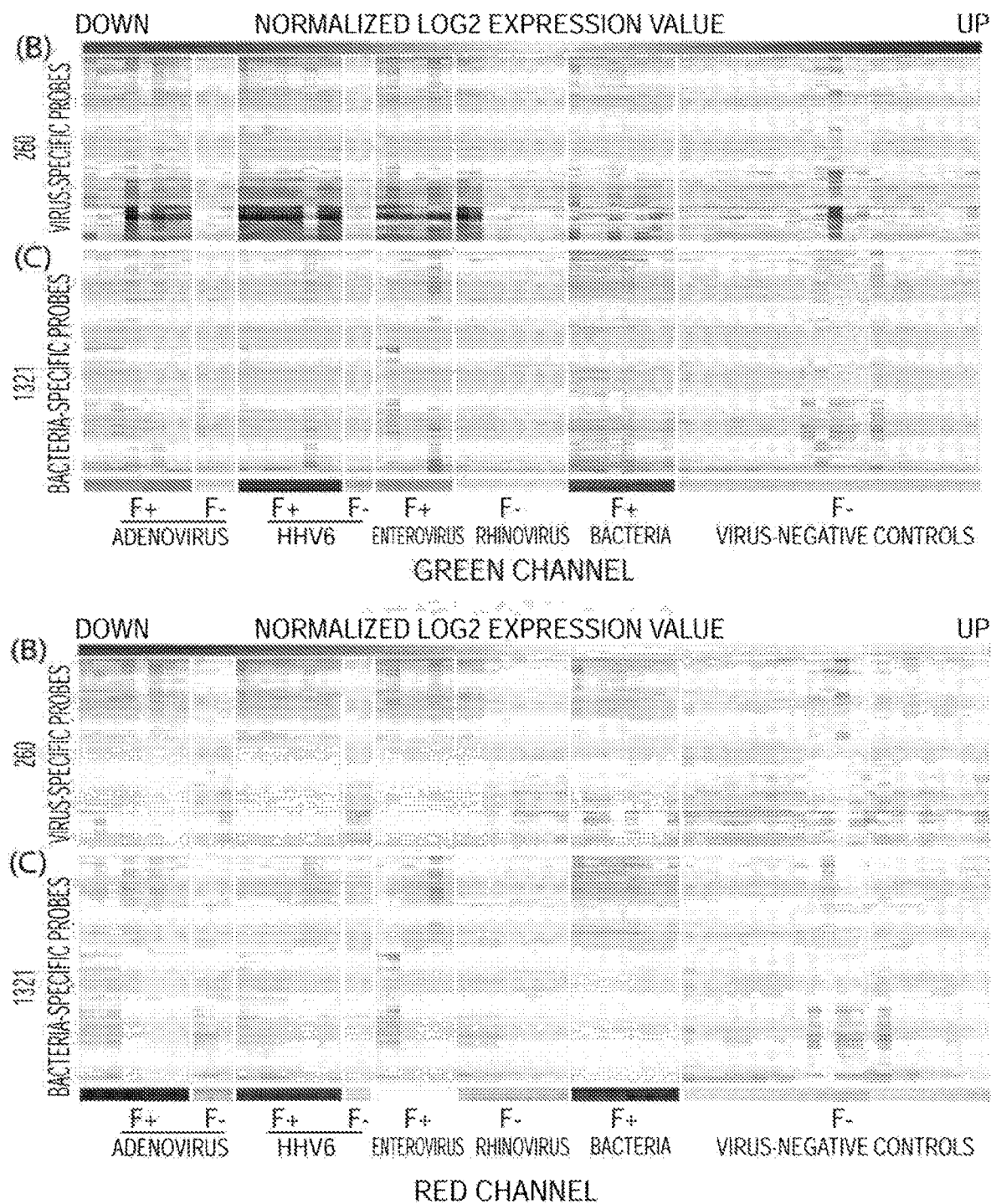
FIG. 1 Con.

FIG. 1 Con.
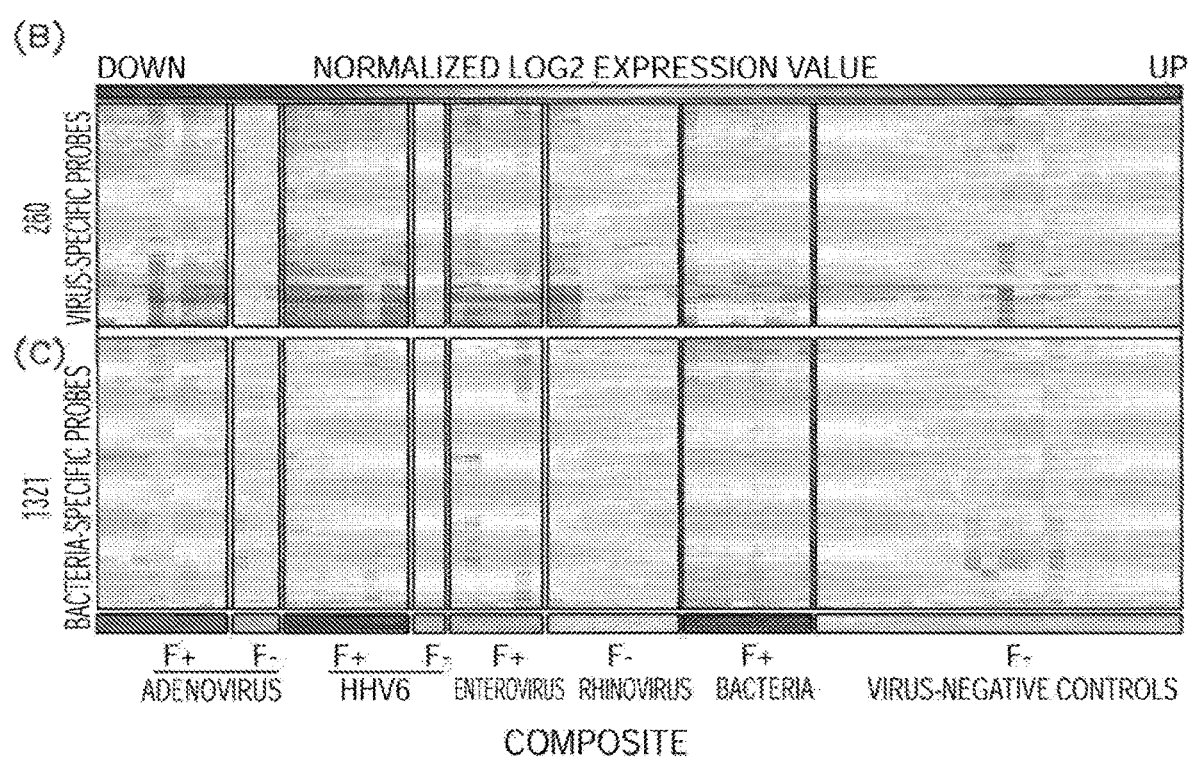

FIG. 2A Con.
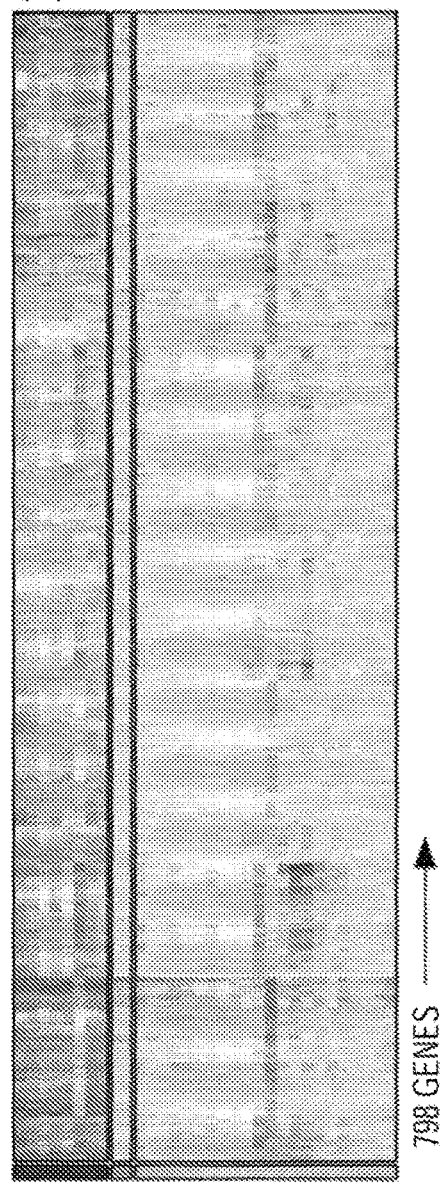

FIG. 2C Con.
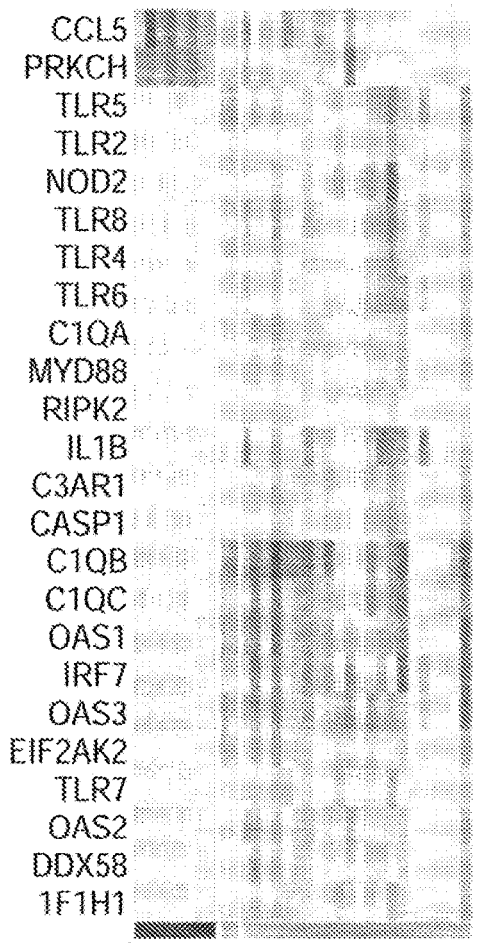
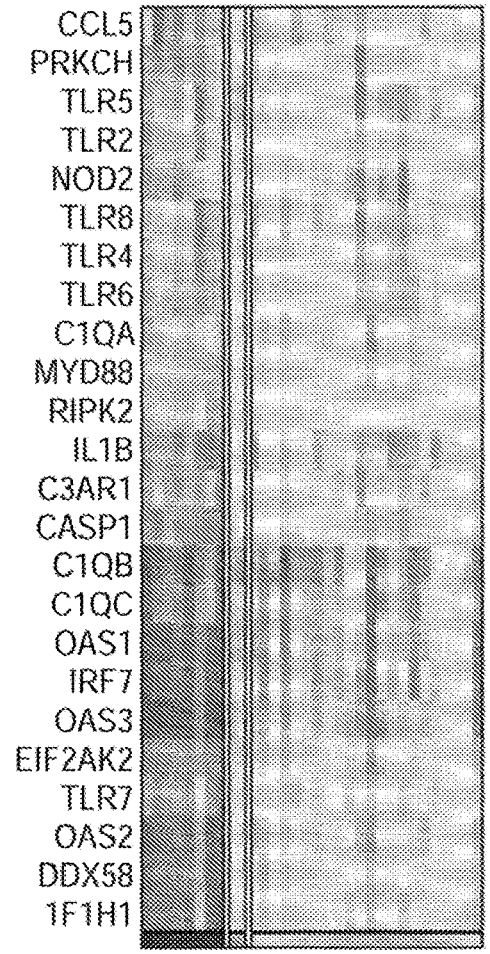

FIG. 2D Con.
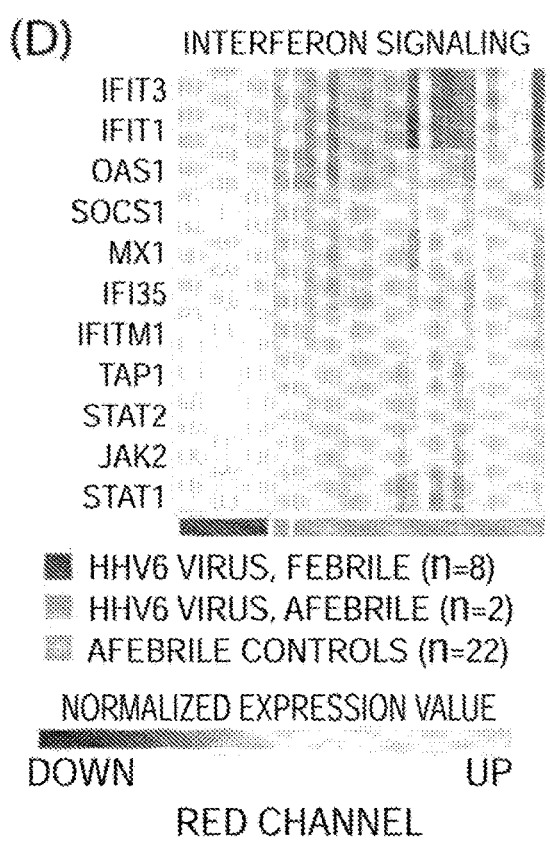
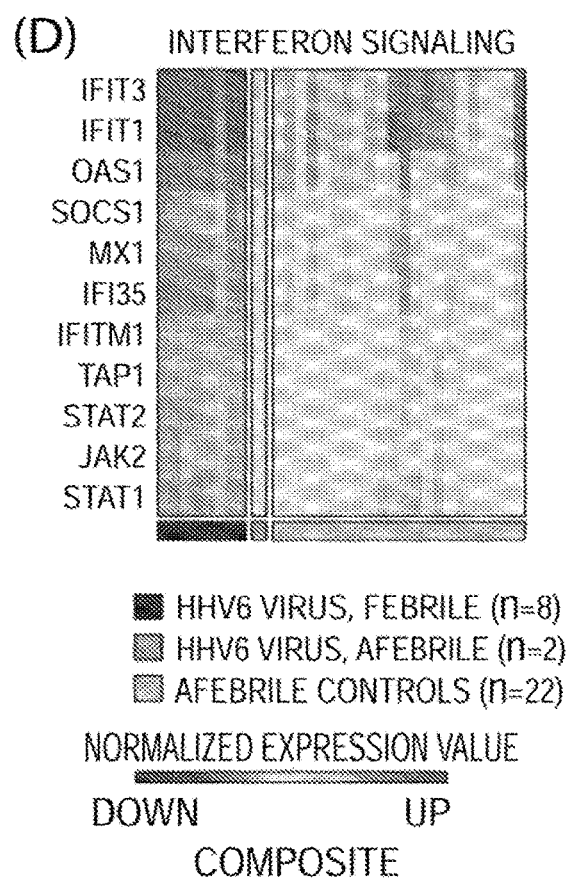

FIG. 2E Con.
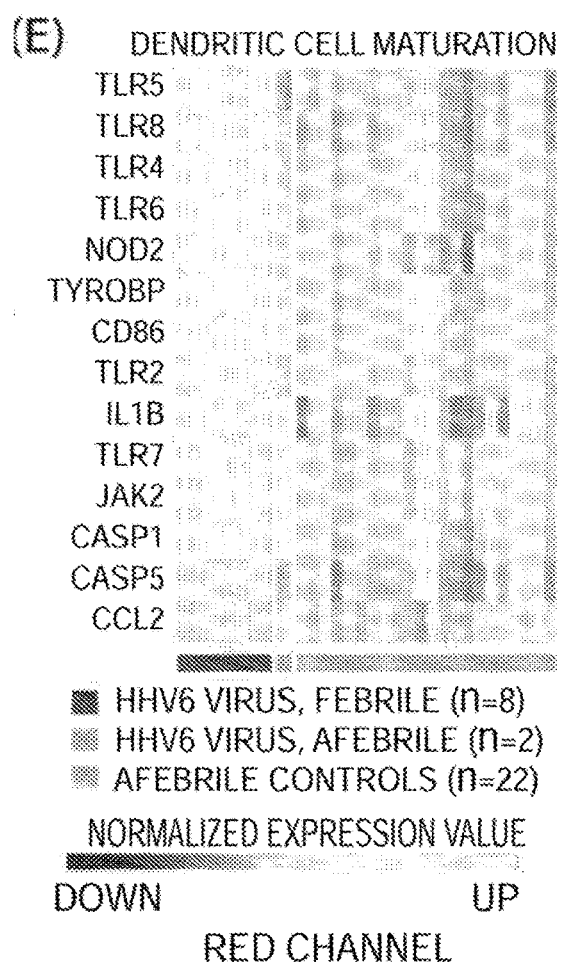
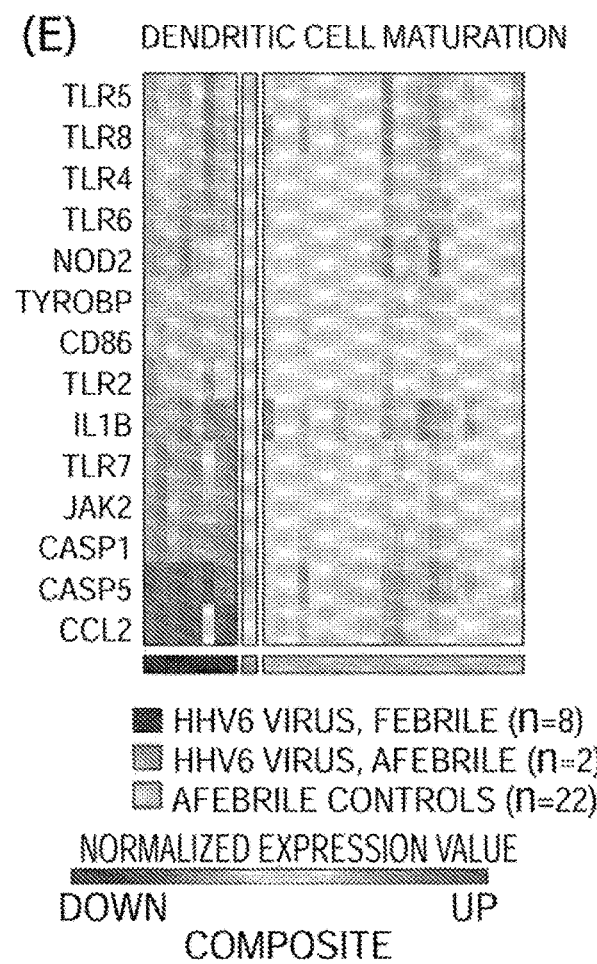

FIG. 2F Con.
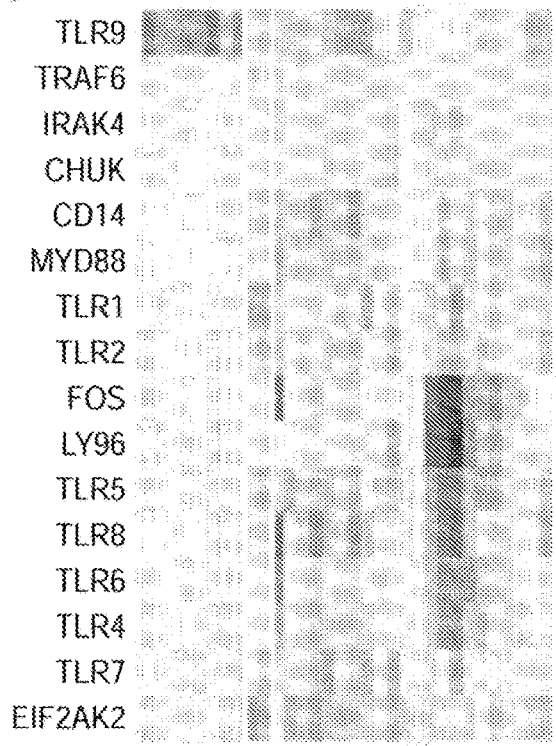
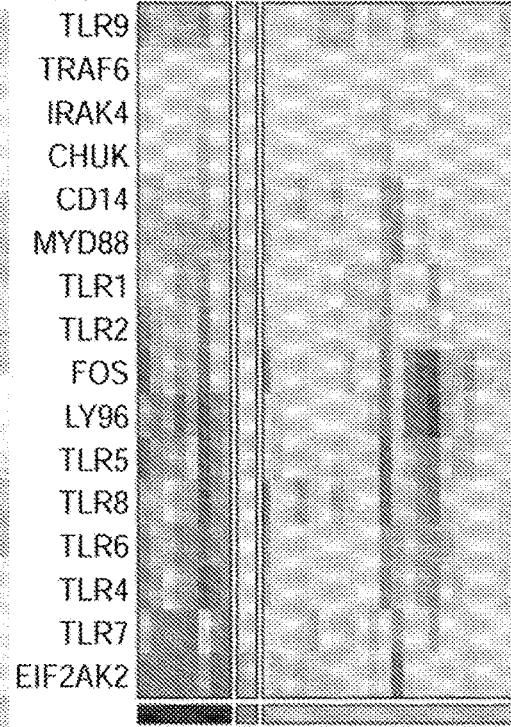

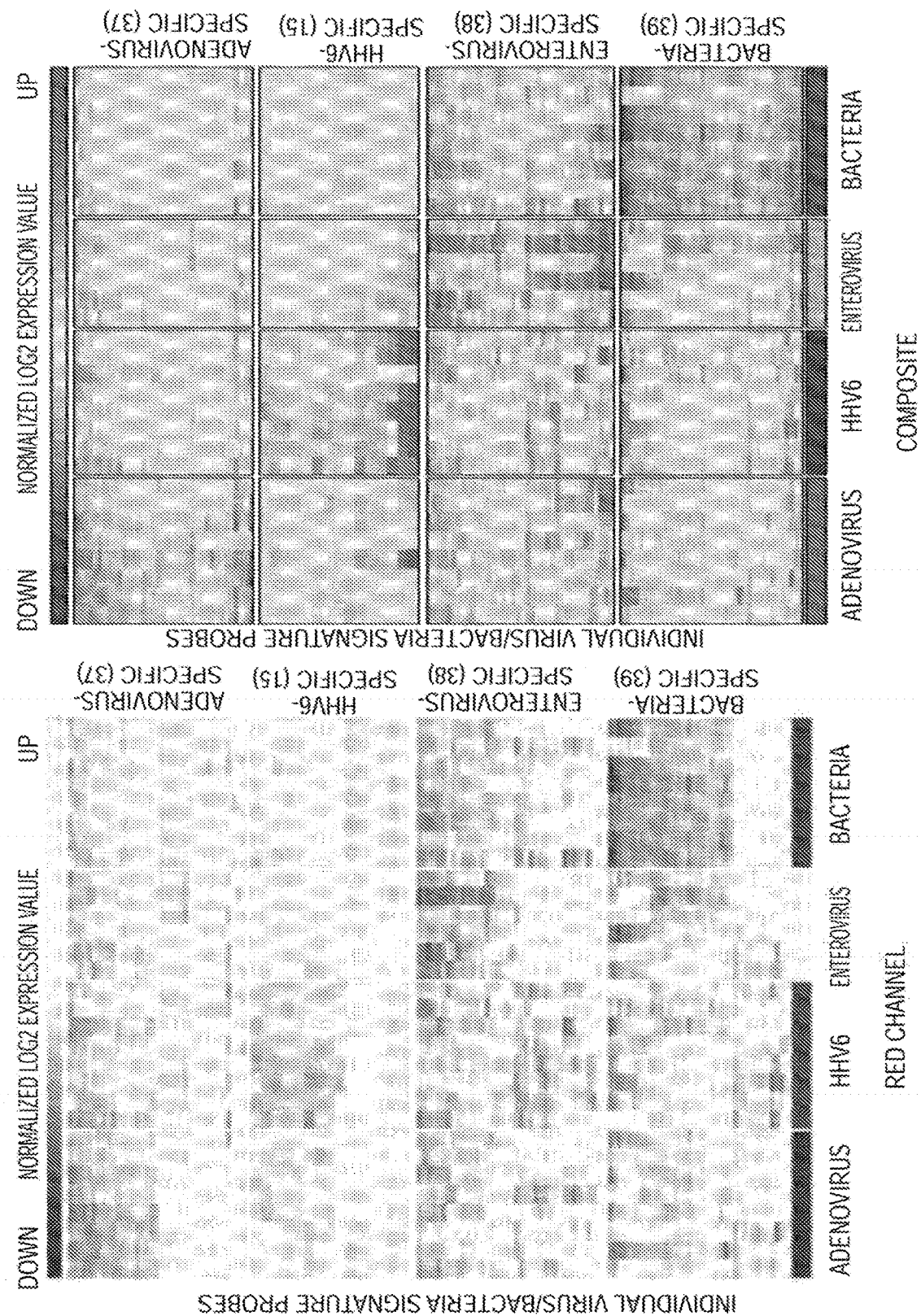
FIG. 3 Con.

FIG. 4A Con.
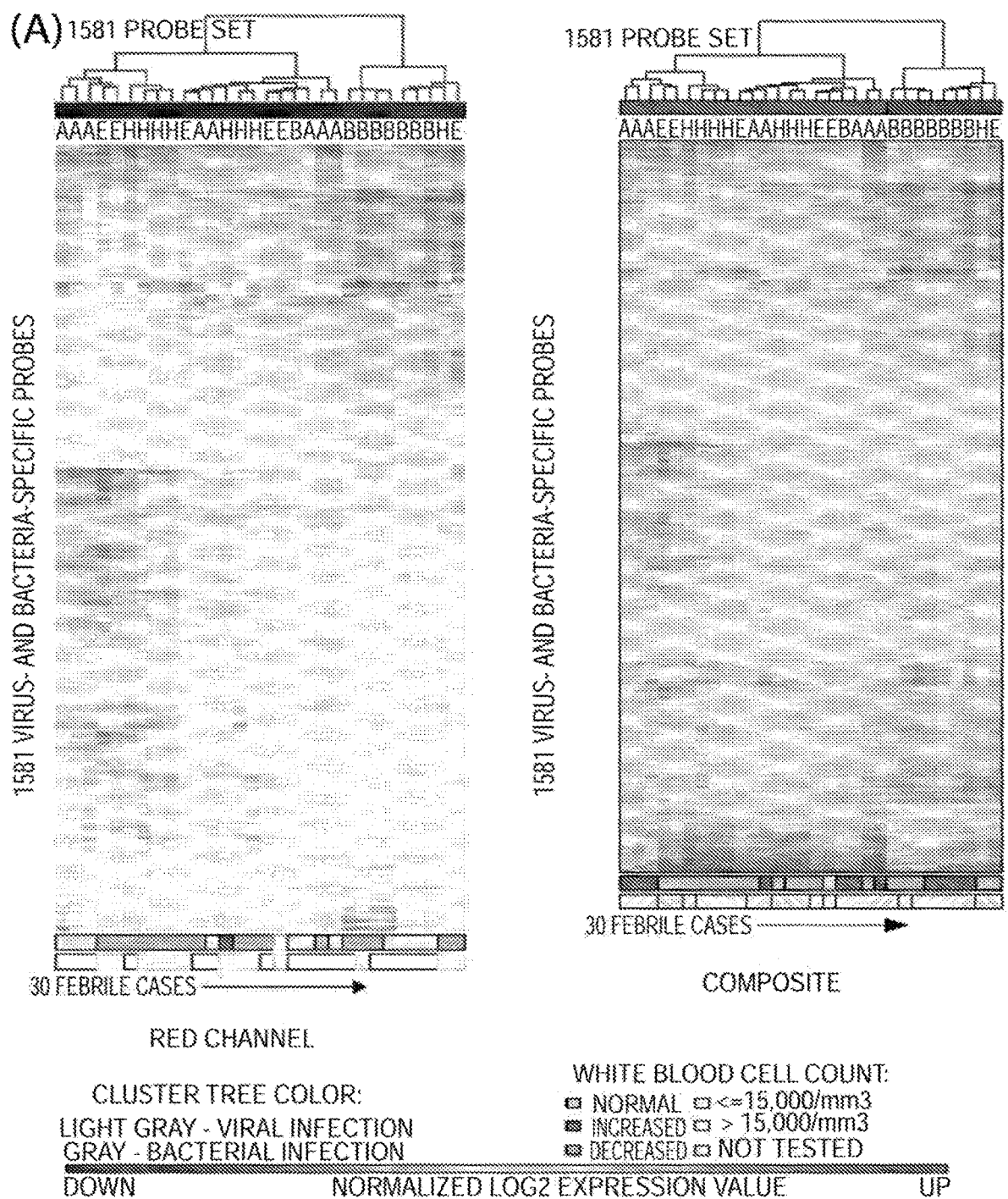

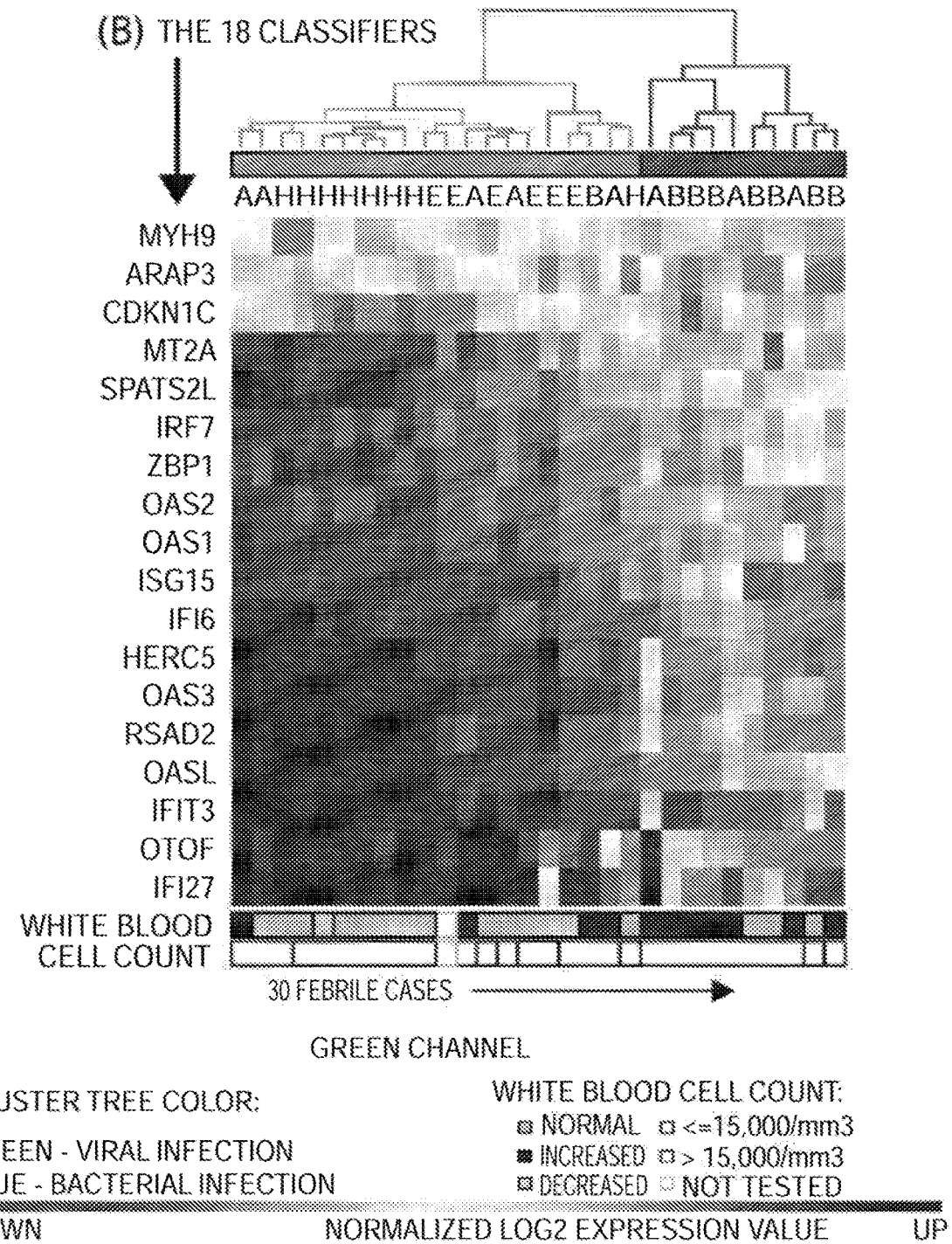
FIG. 4B Con.

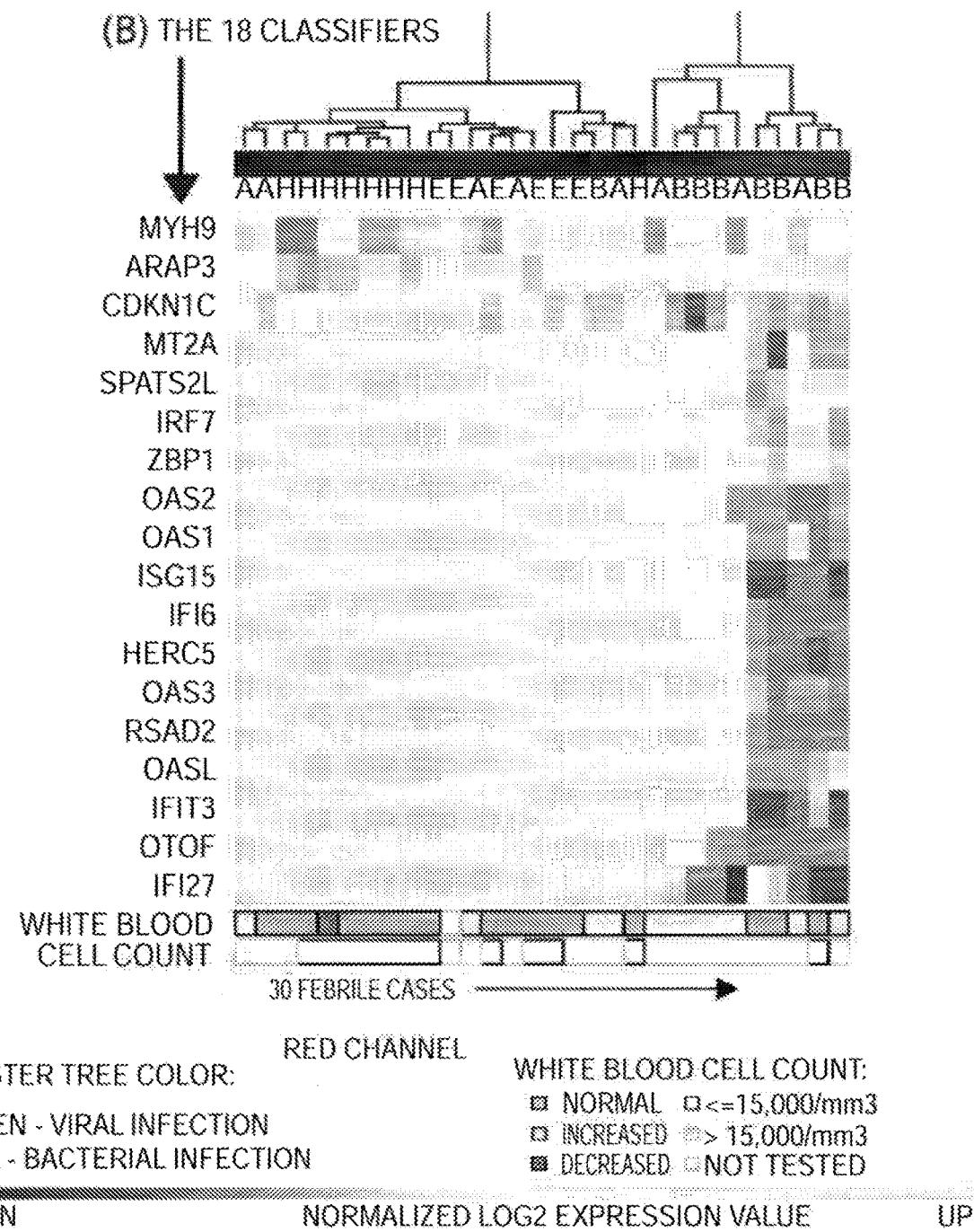
FIG. 4B Con.

FIG. 4B Con.
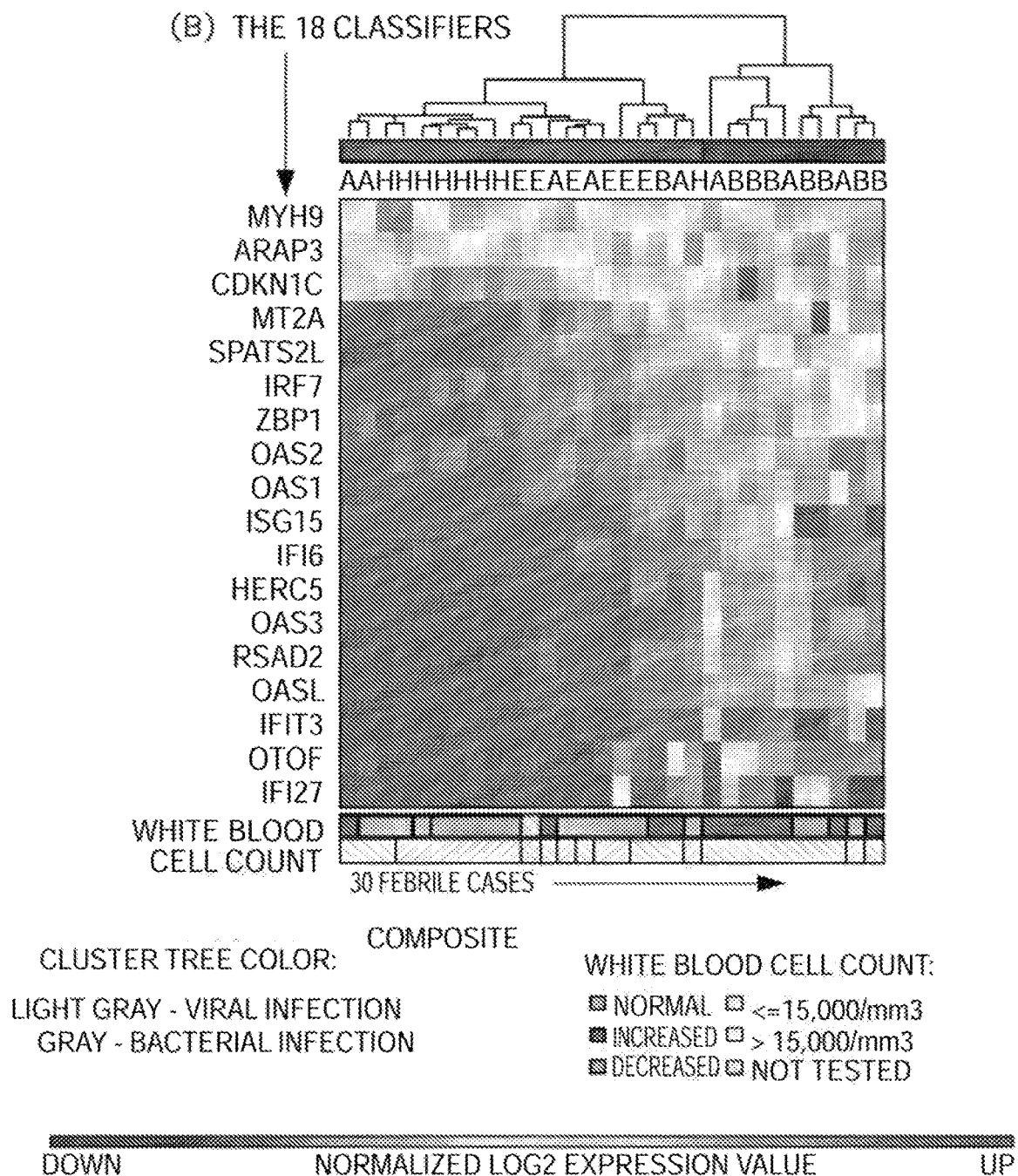

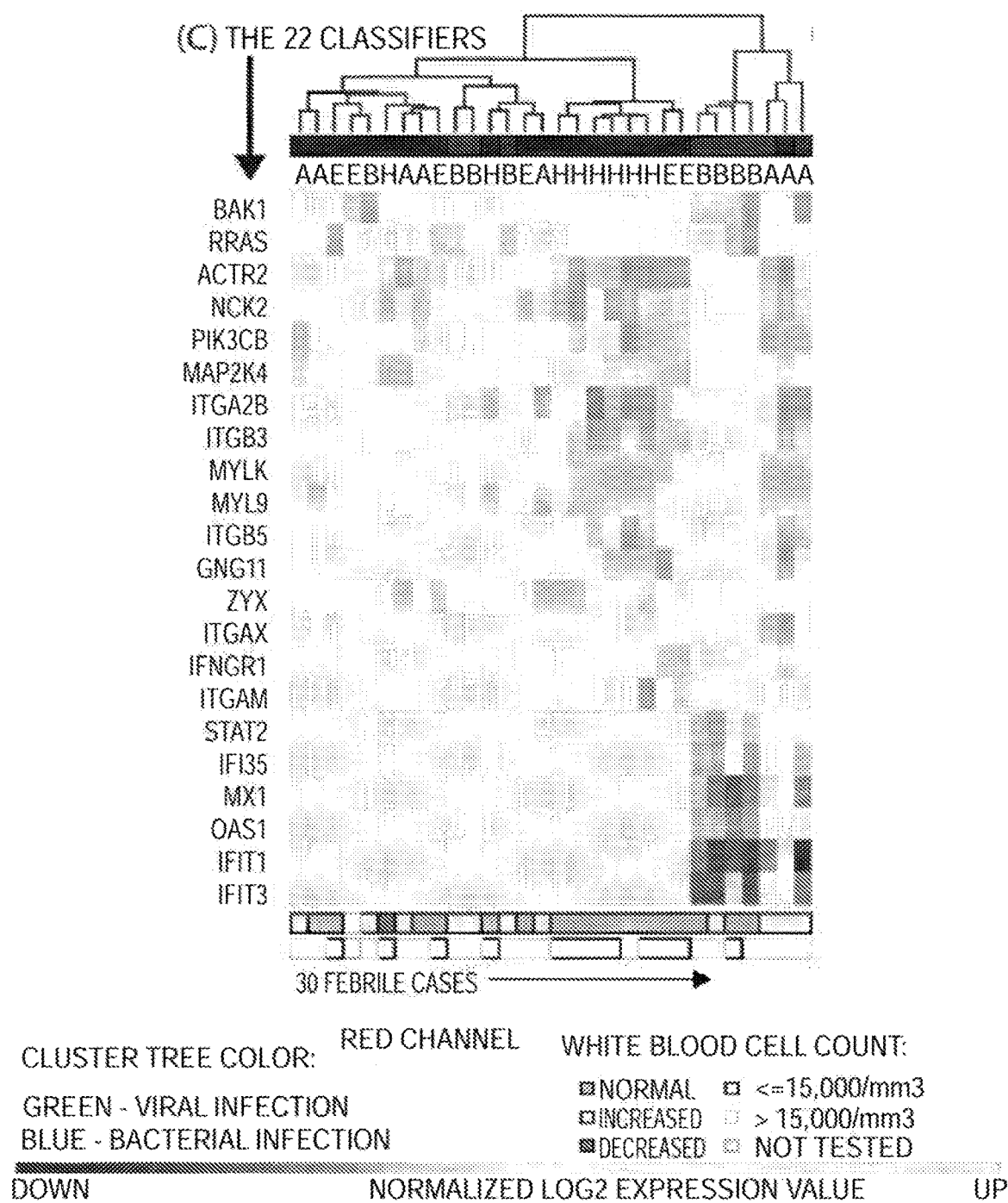
FIG. 4C Con.

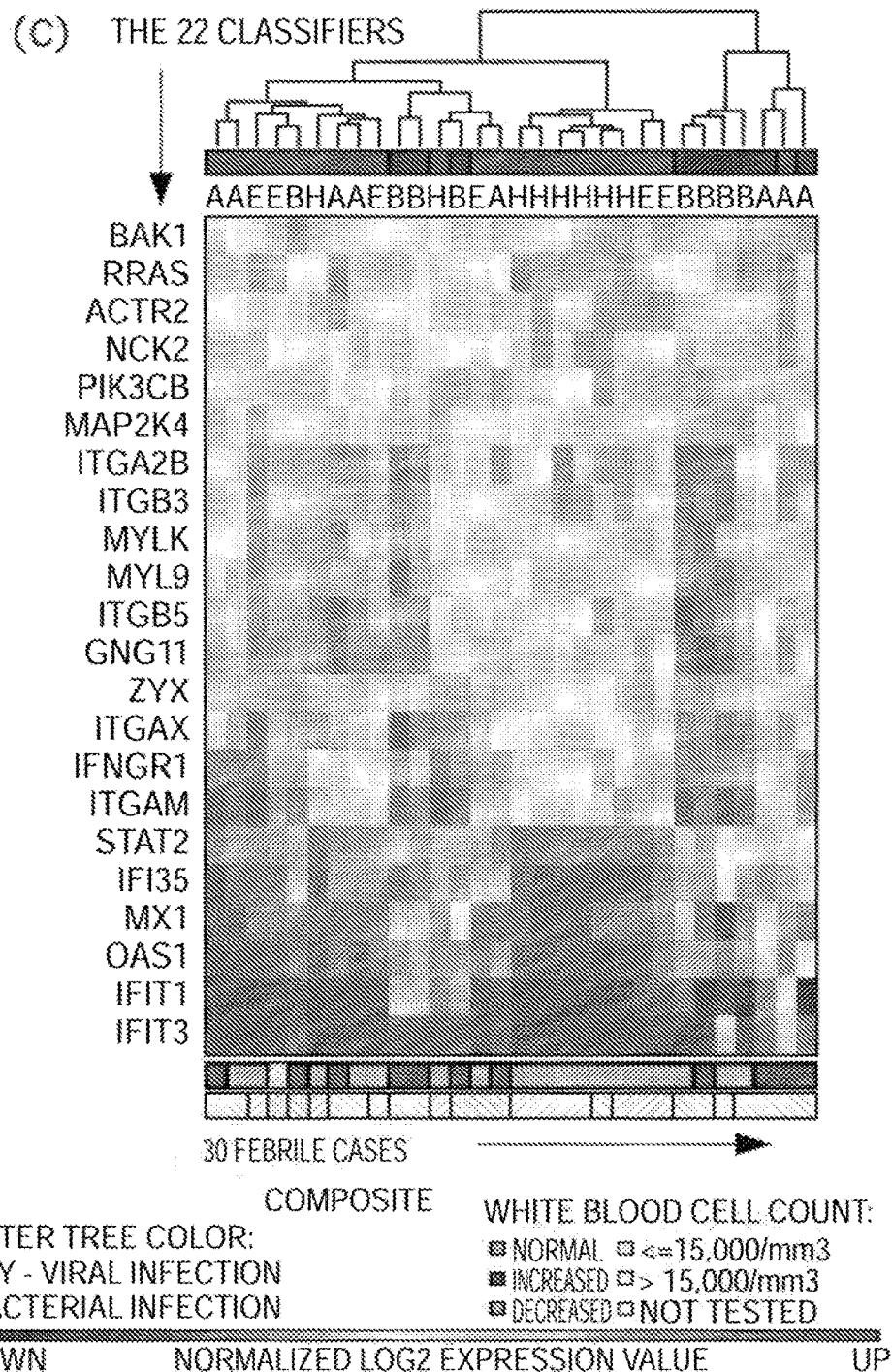
FIG. 4C Con.

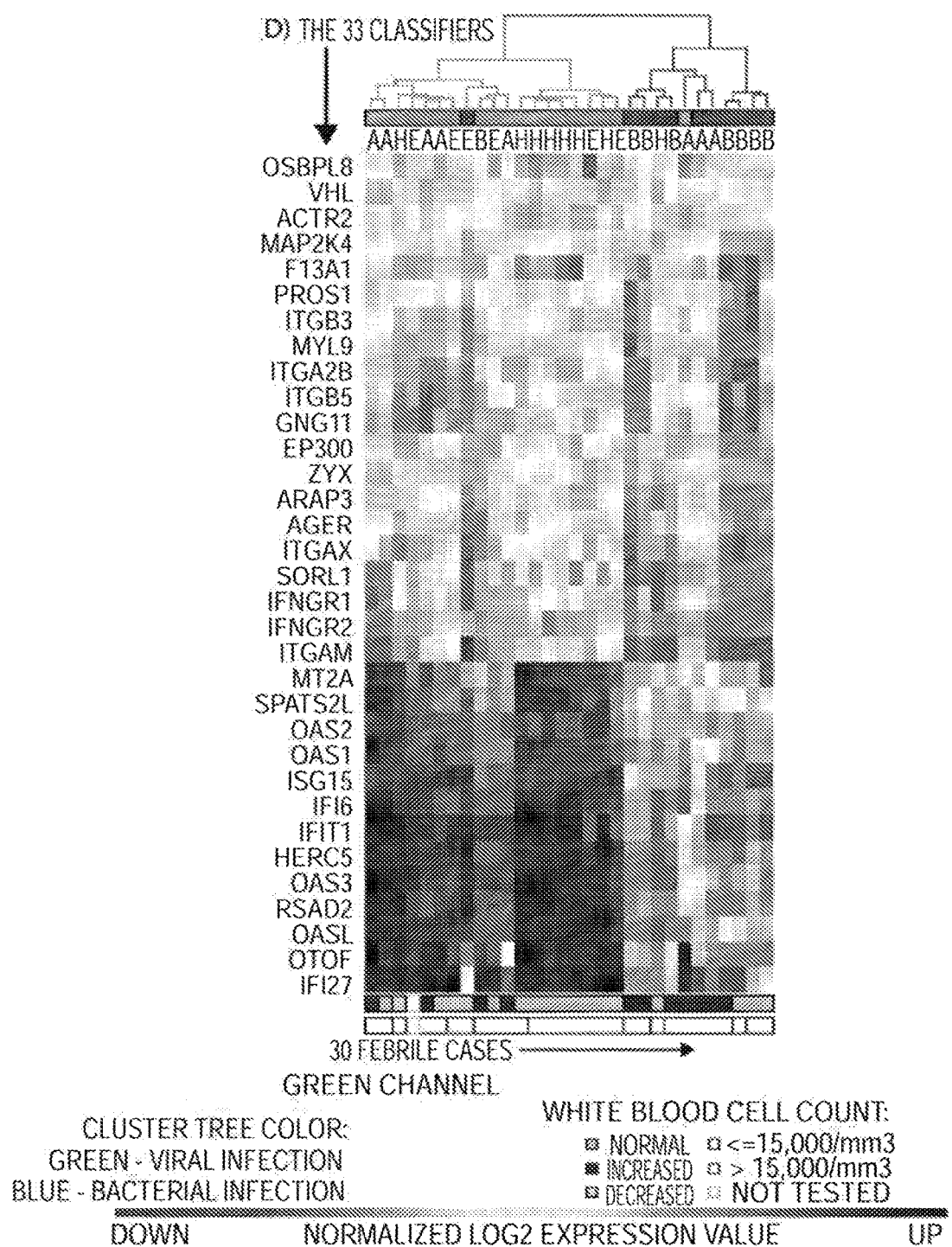

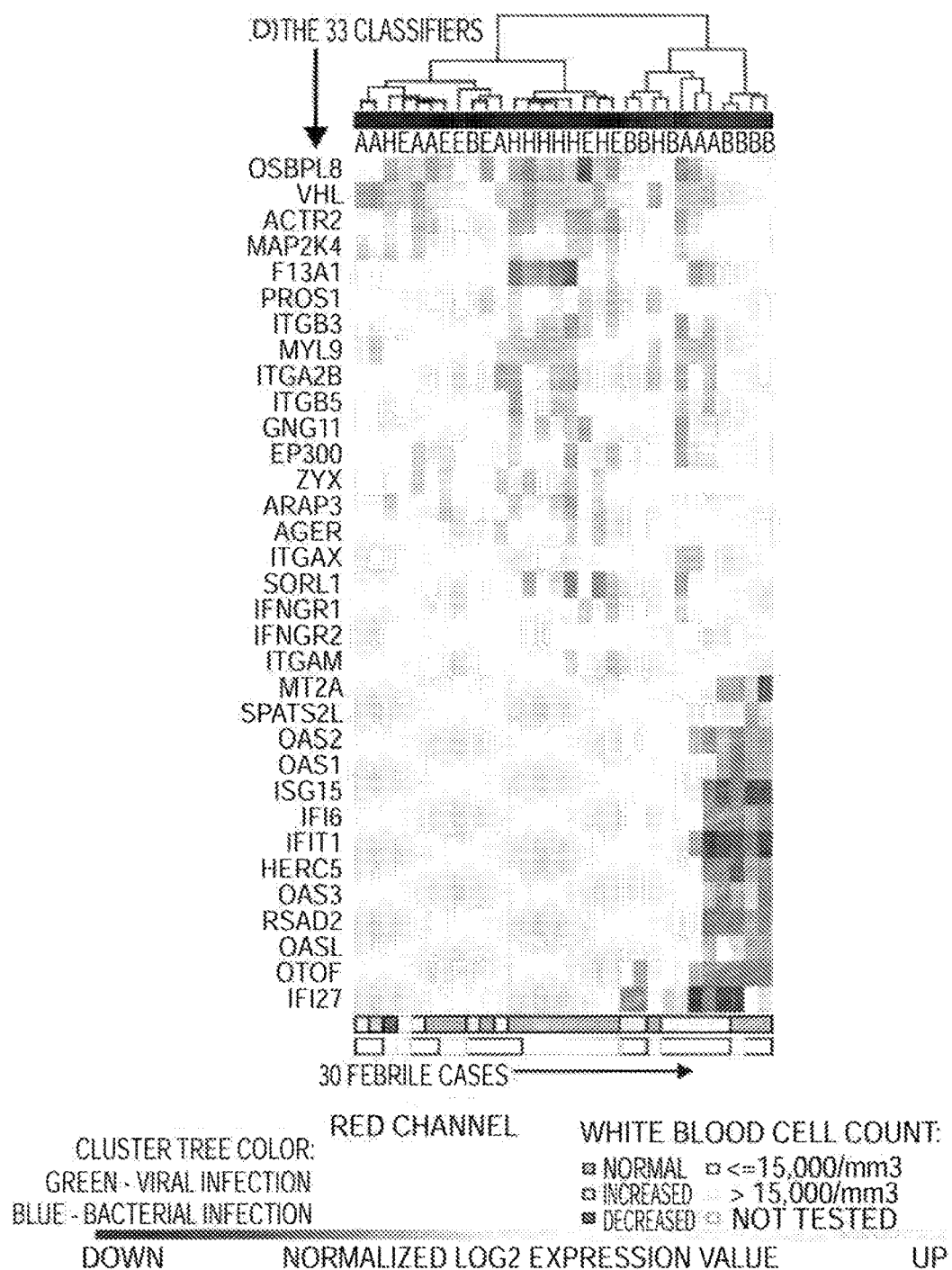
FIG. 4D Con.

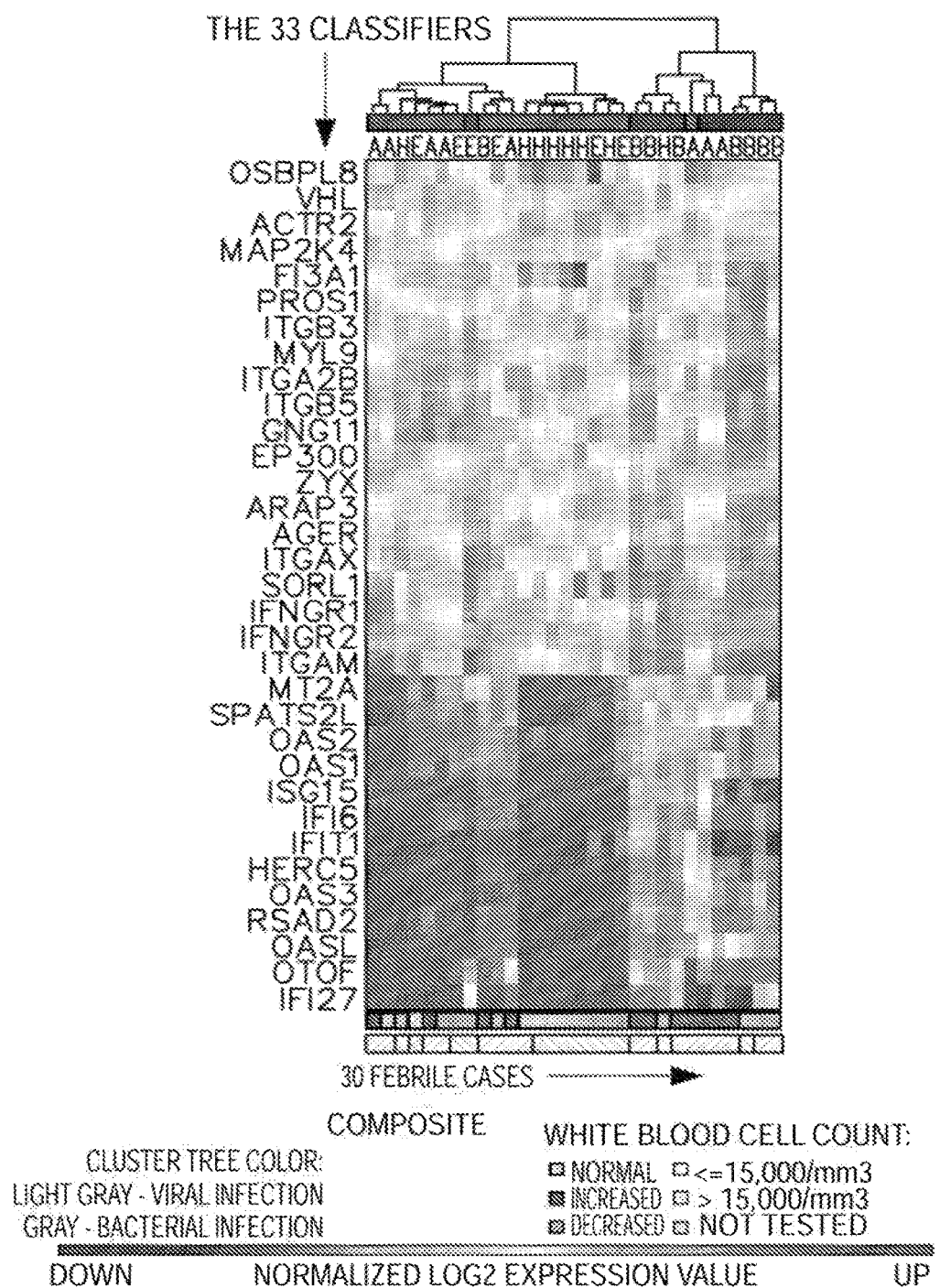

FIG. 5A Con.
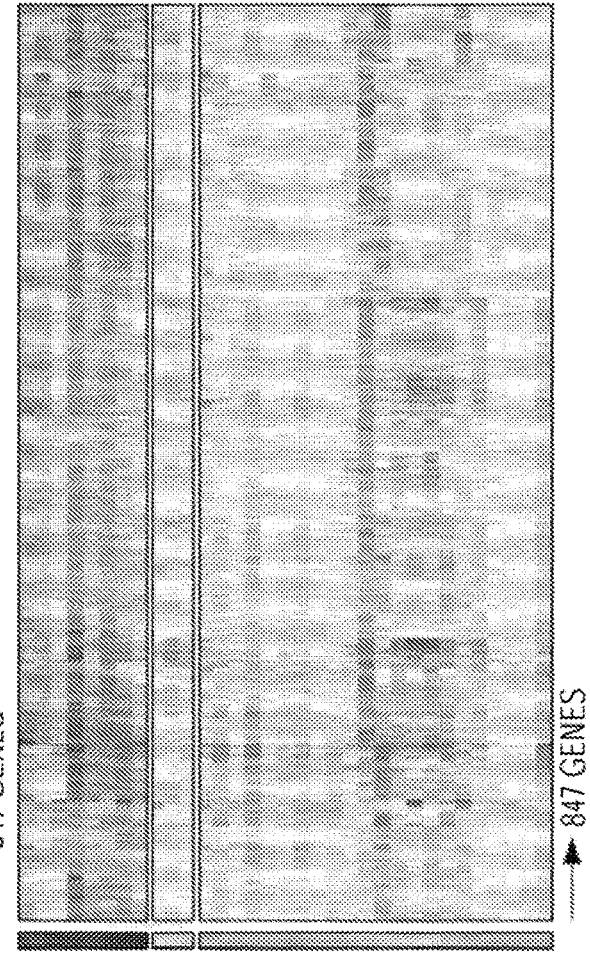

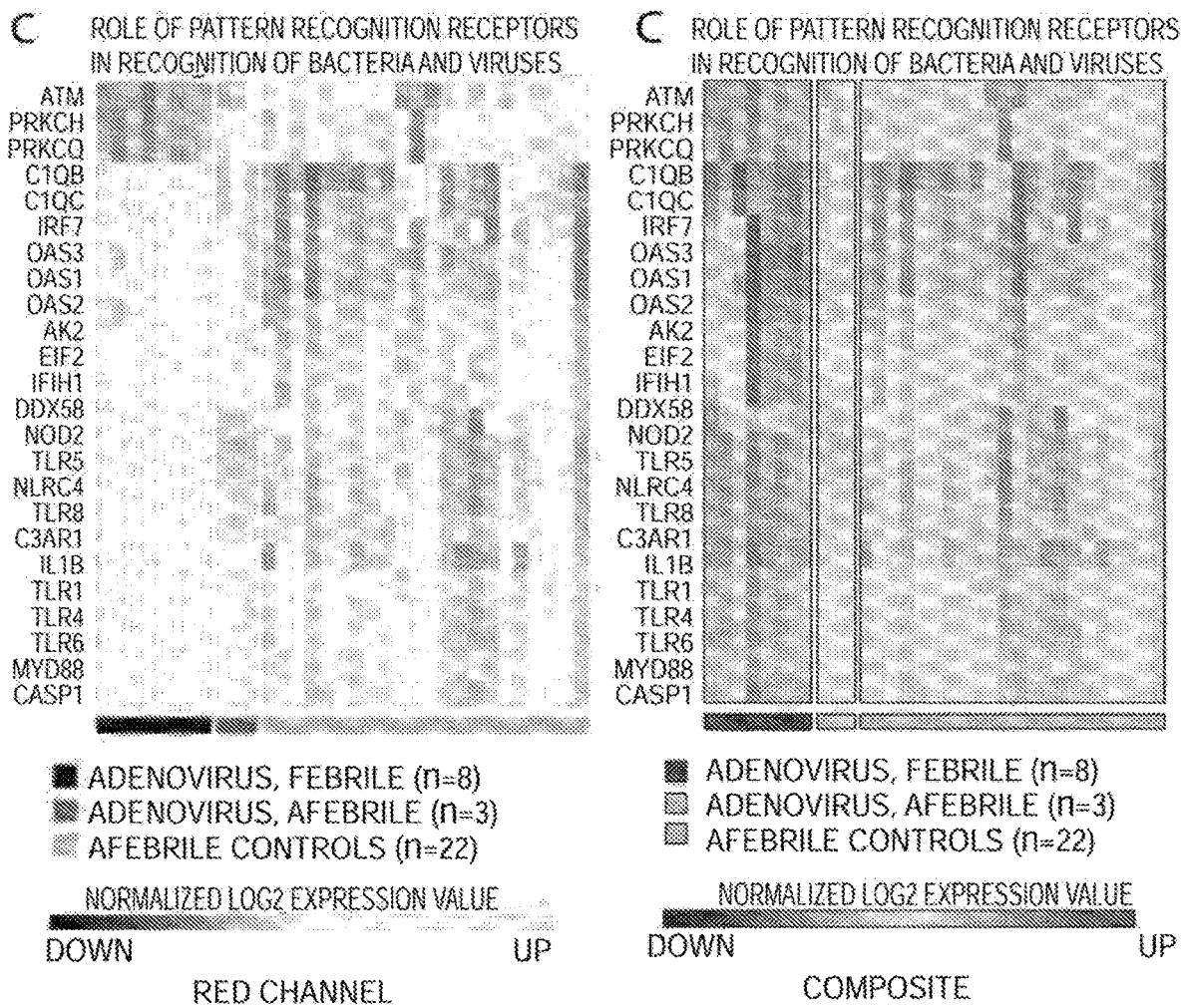
FIG. 5C Con.

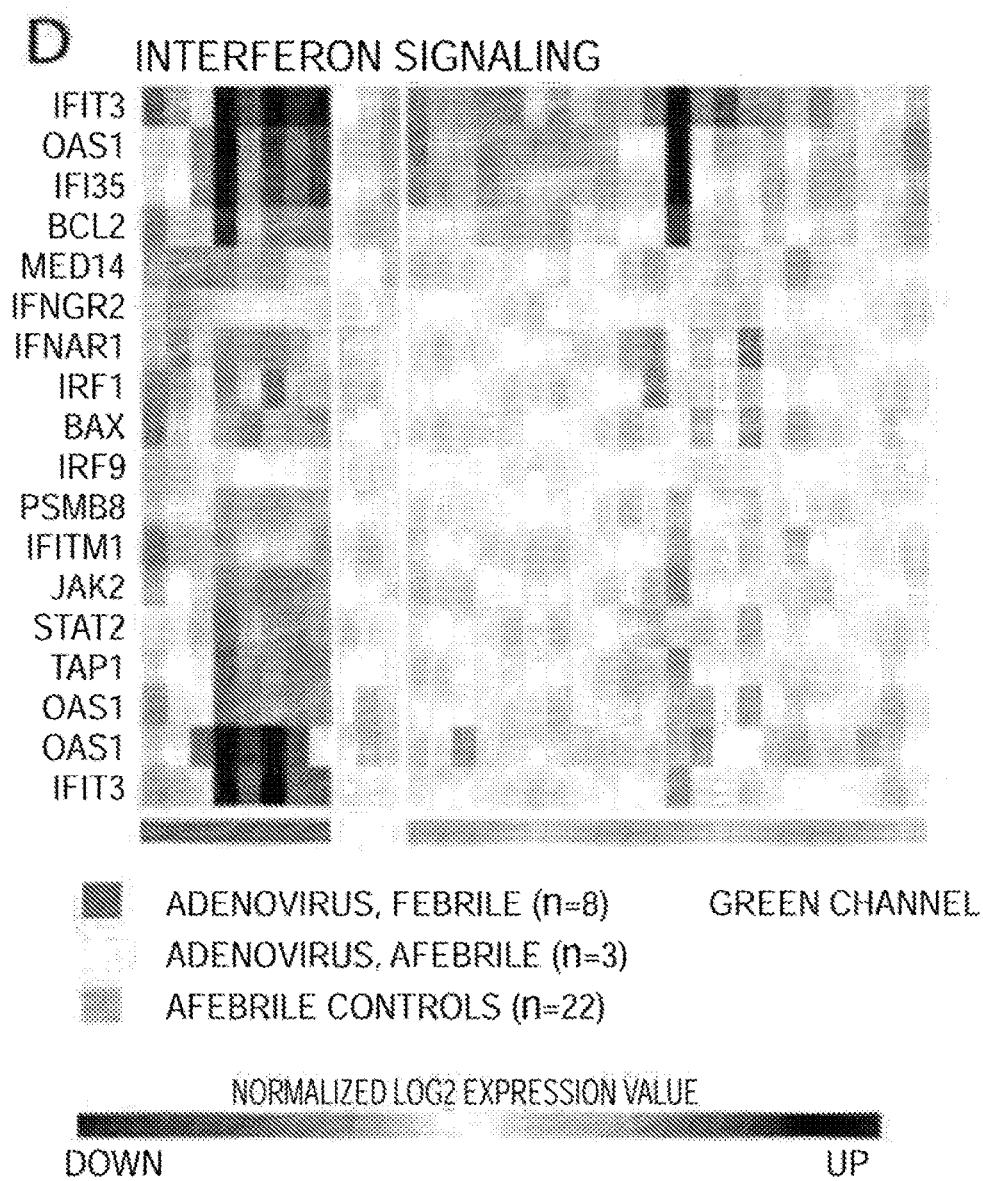
FIG. 5D Con.

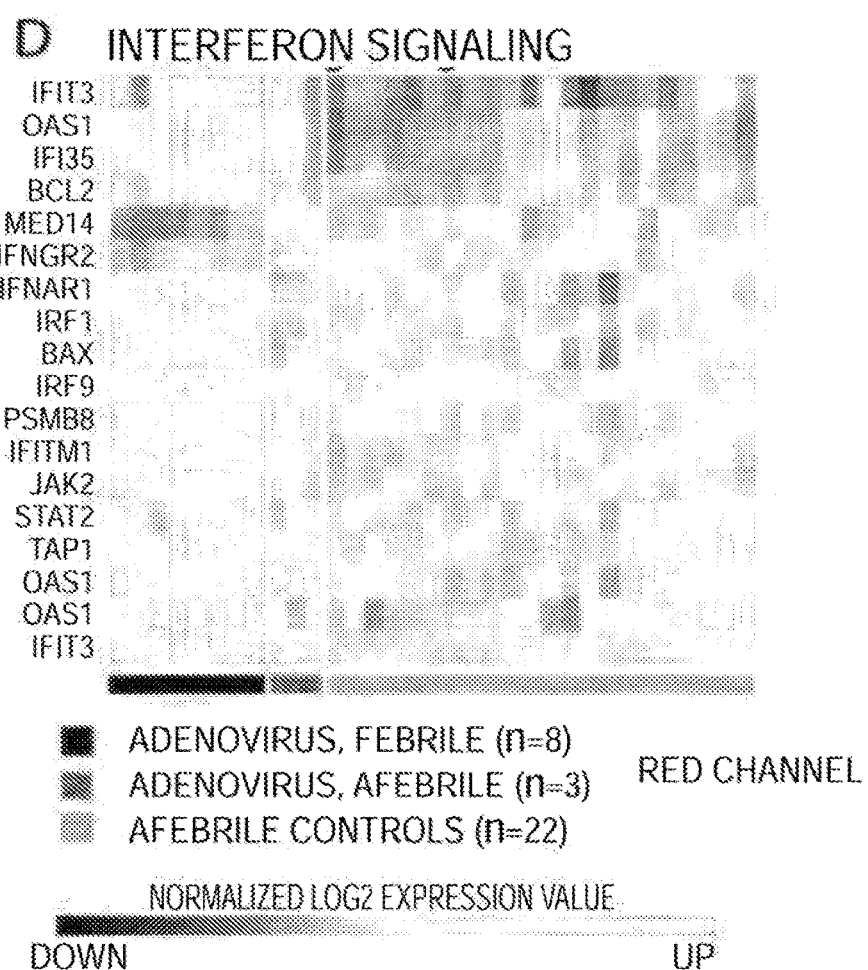
FIG. 5D Con.

FIG. 5D Con.
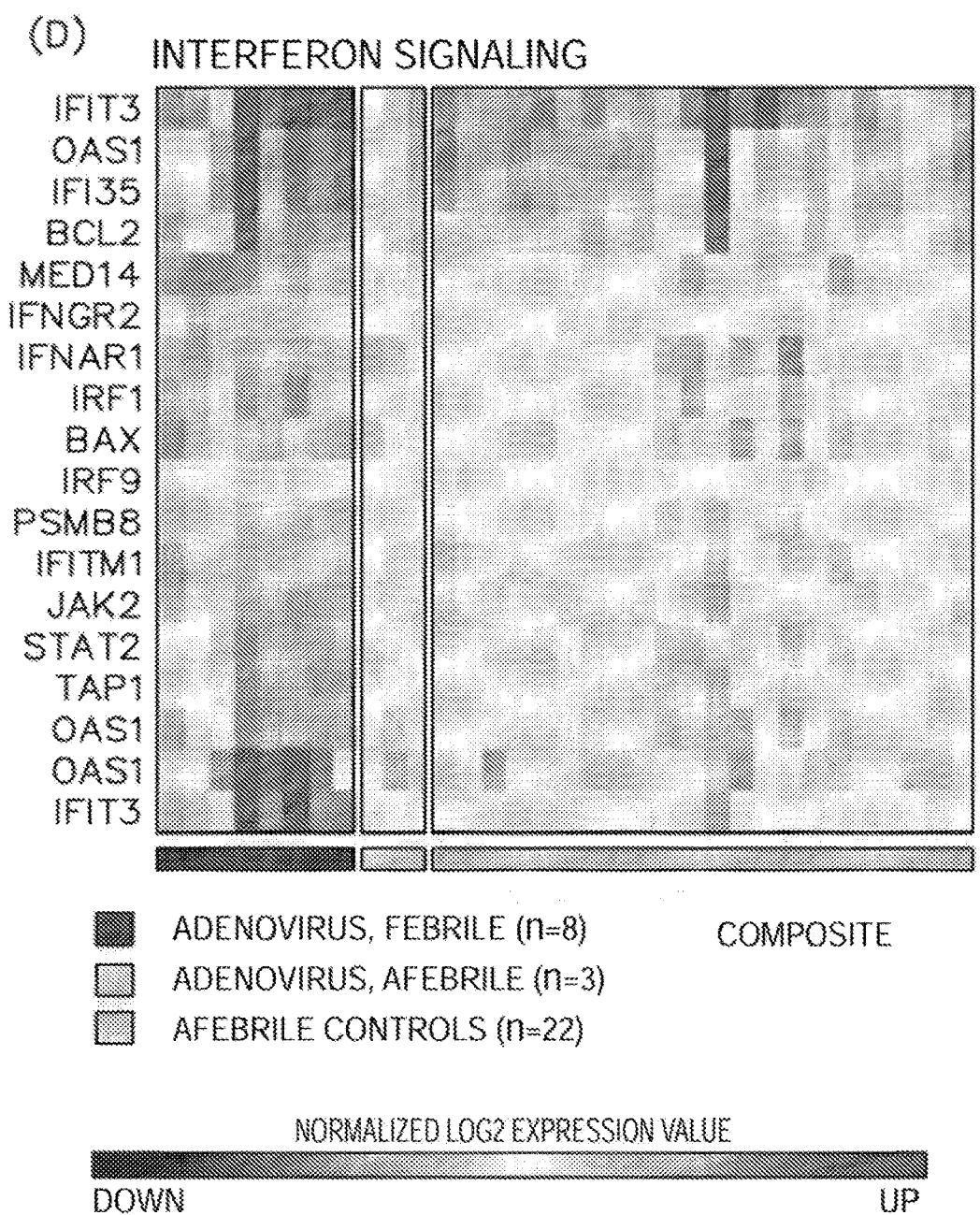

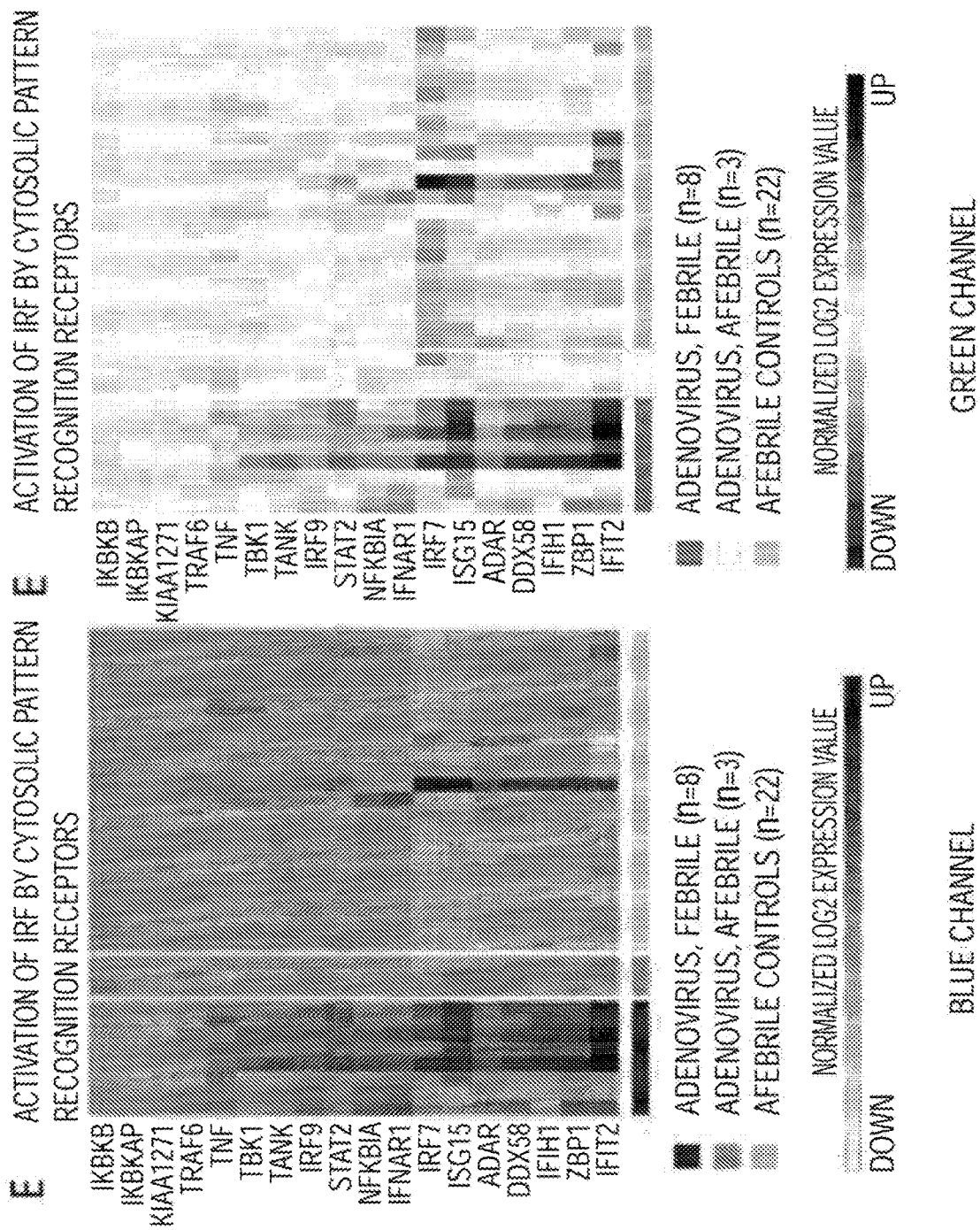

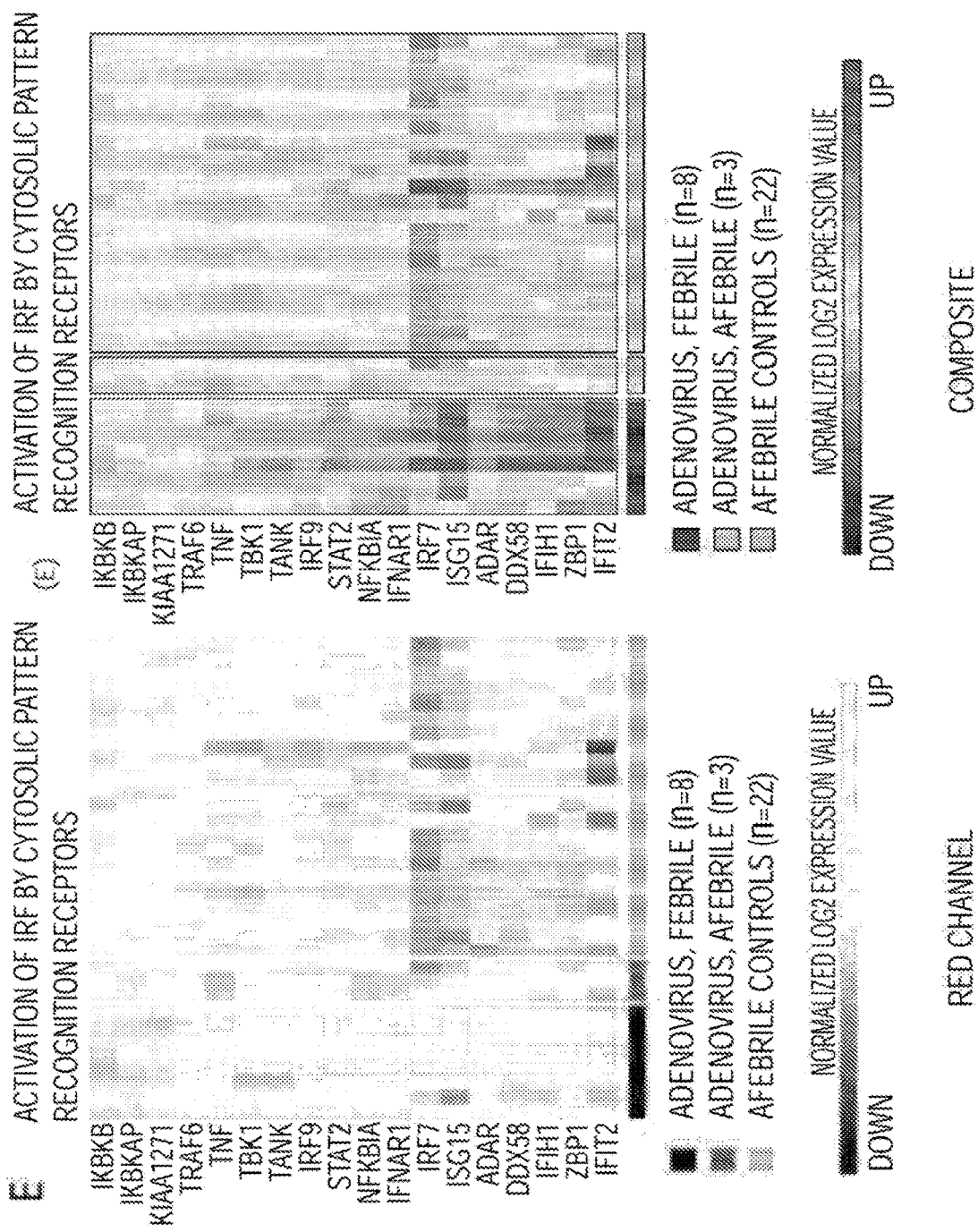
FIG. 5E Con.

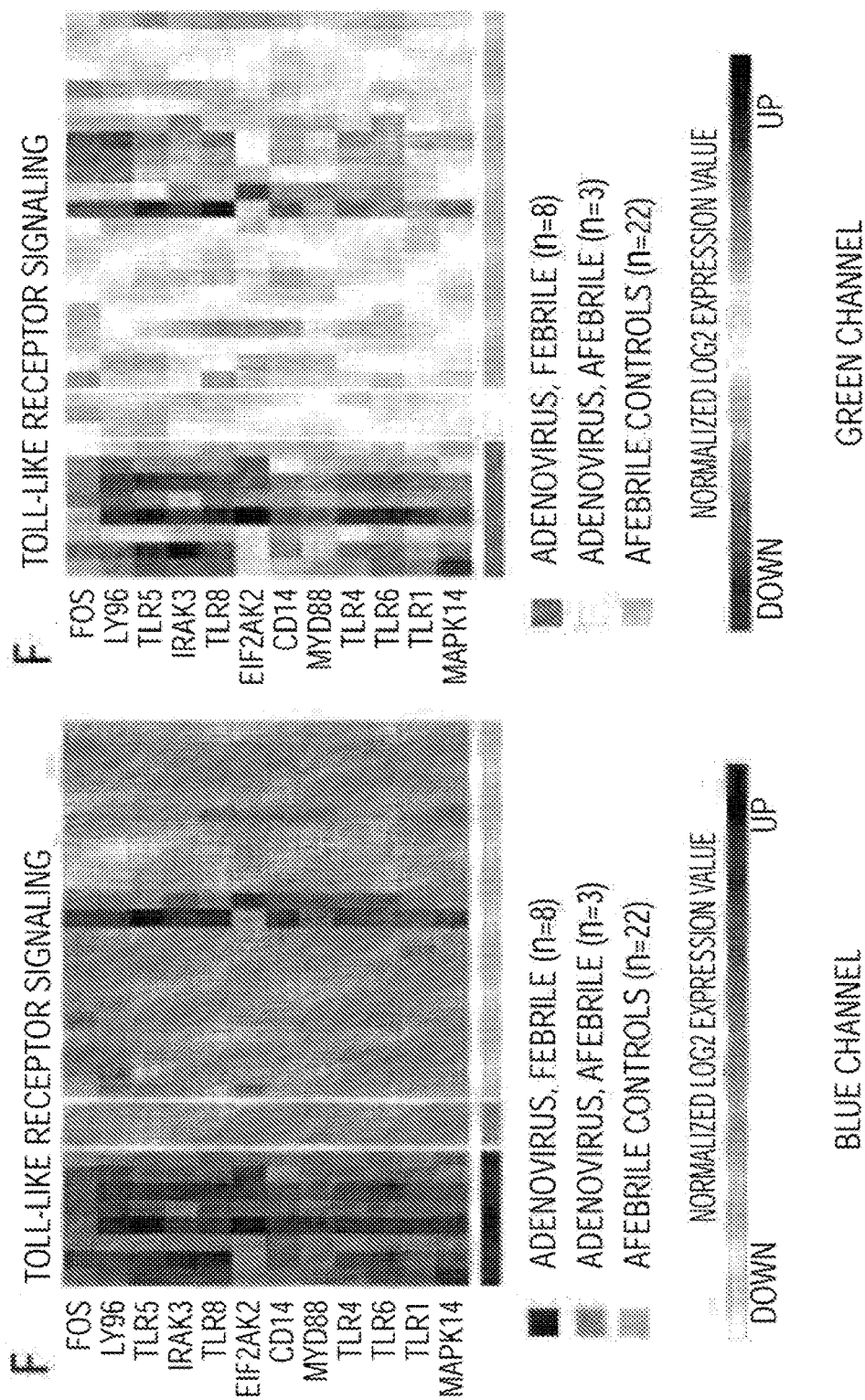

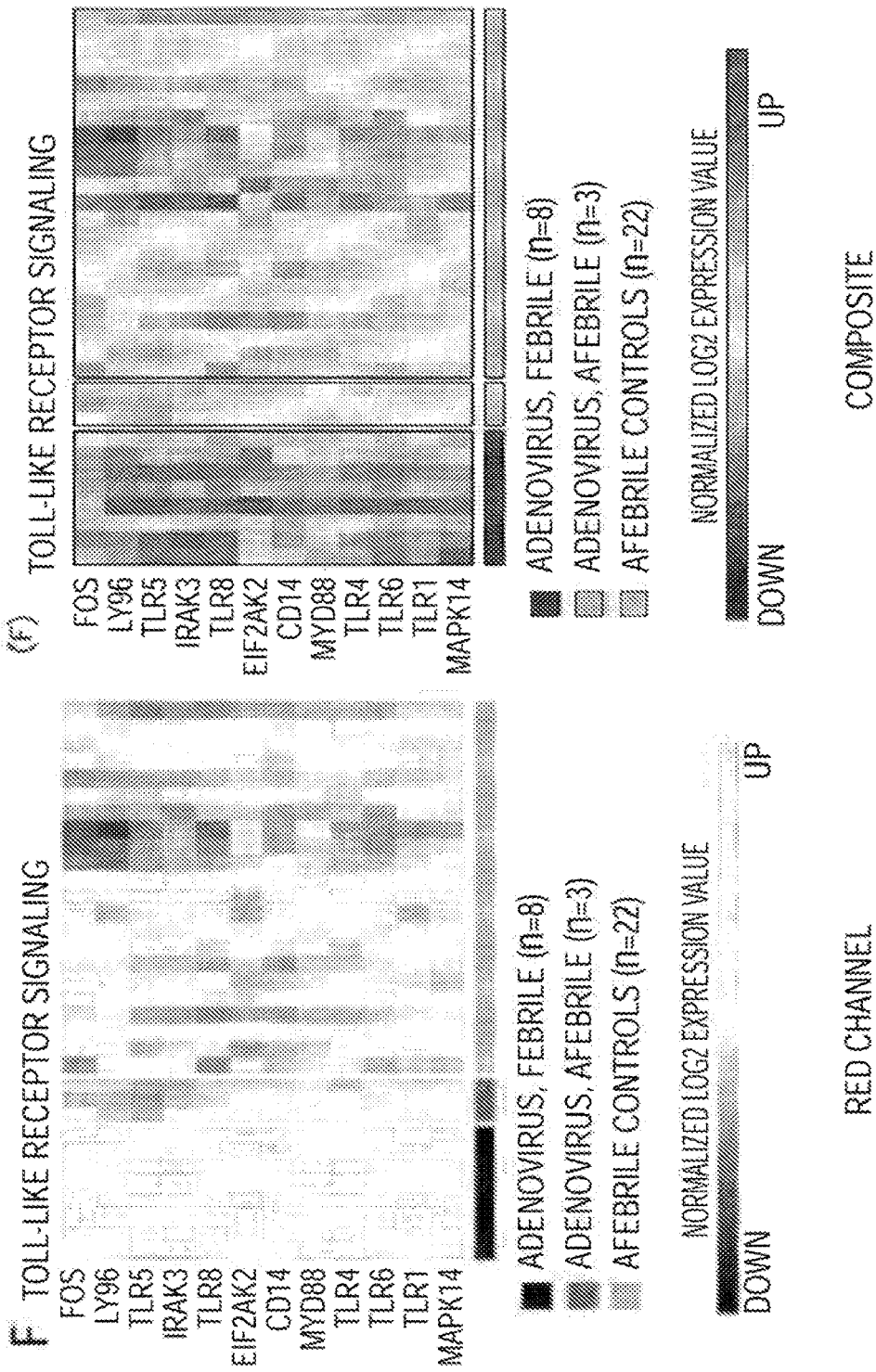
FIG. 5F Con.

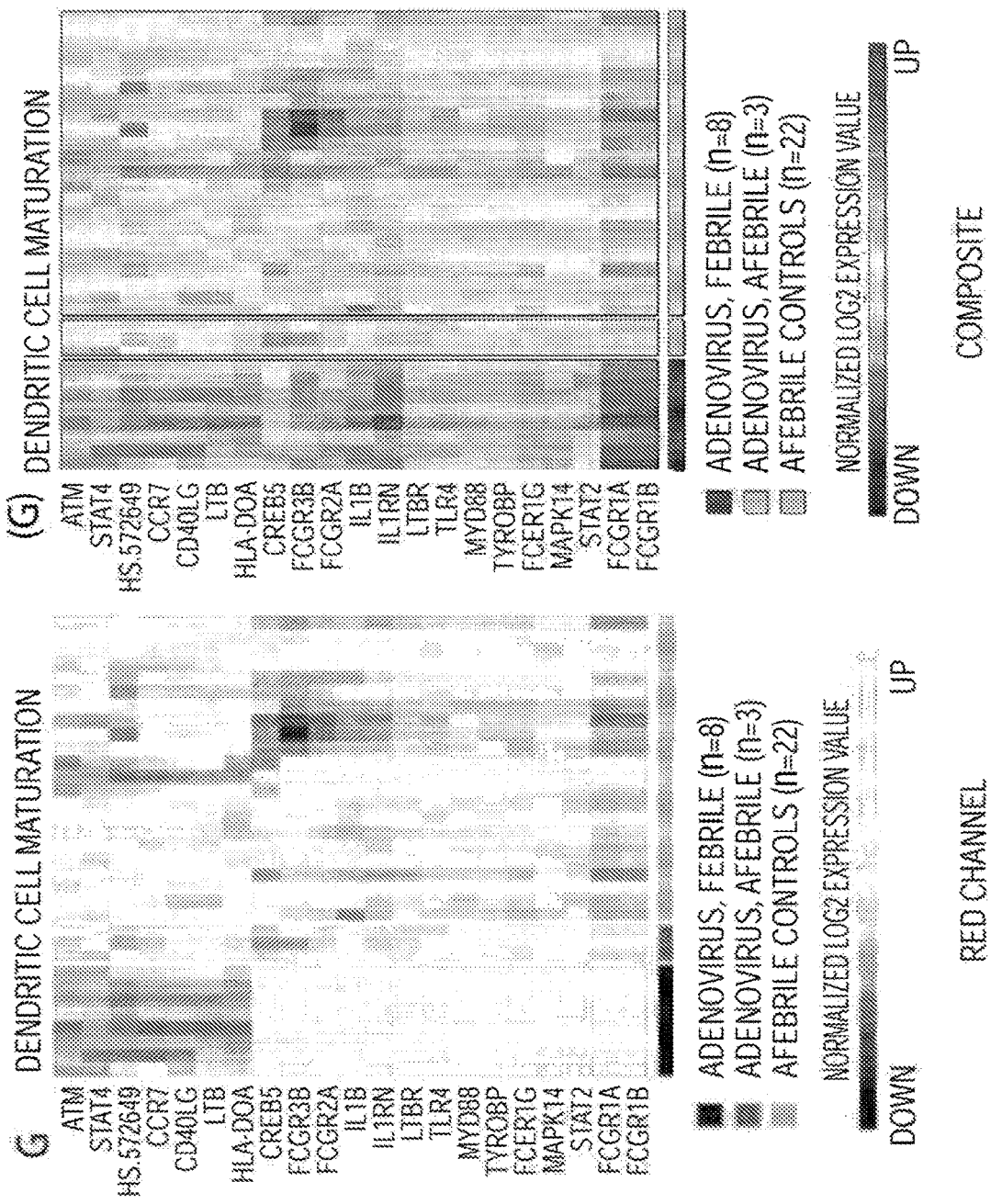
FIG. 5G Con.

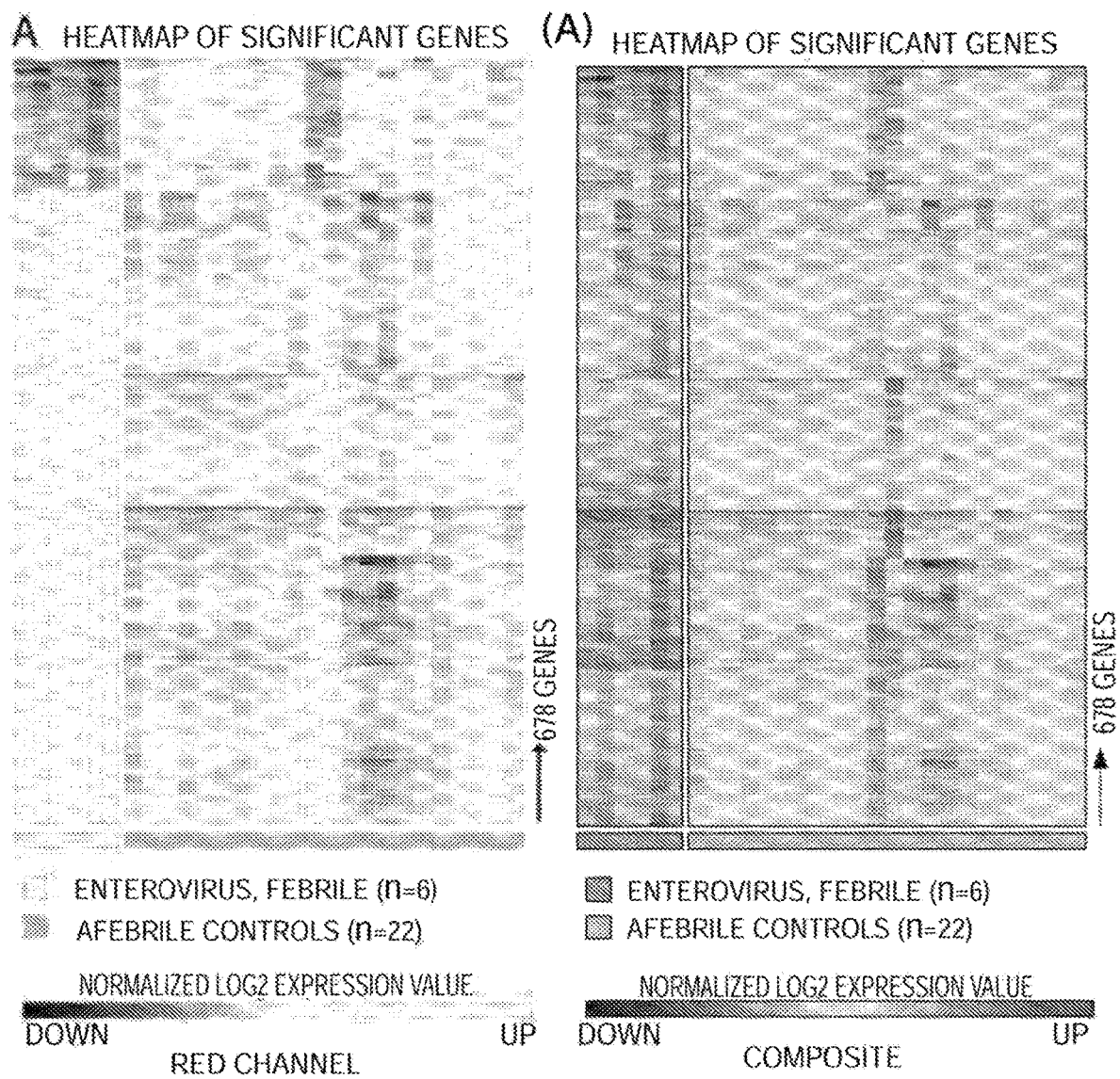
FIG. 6A Con

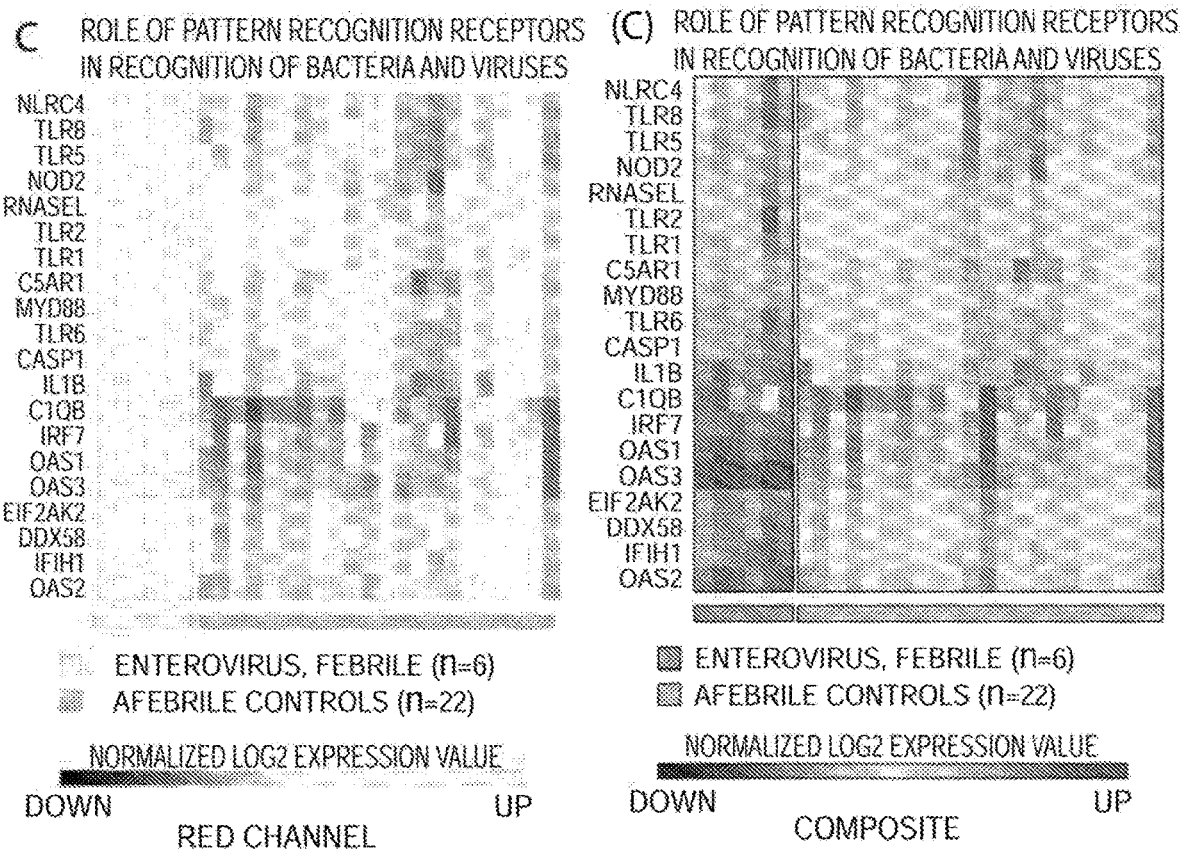
FIG. 6C Con.

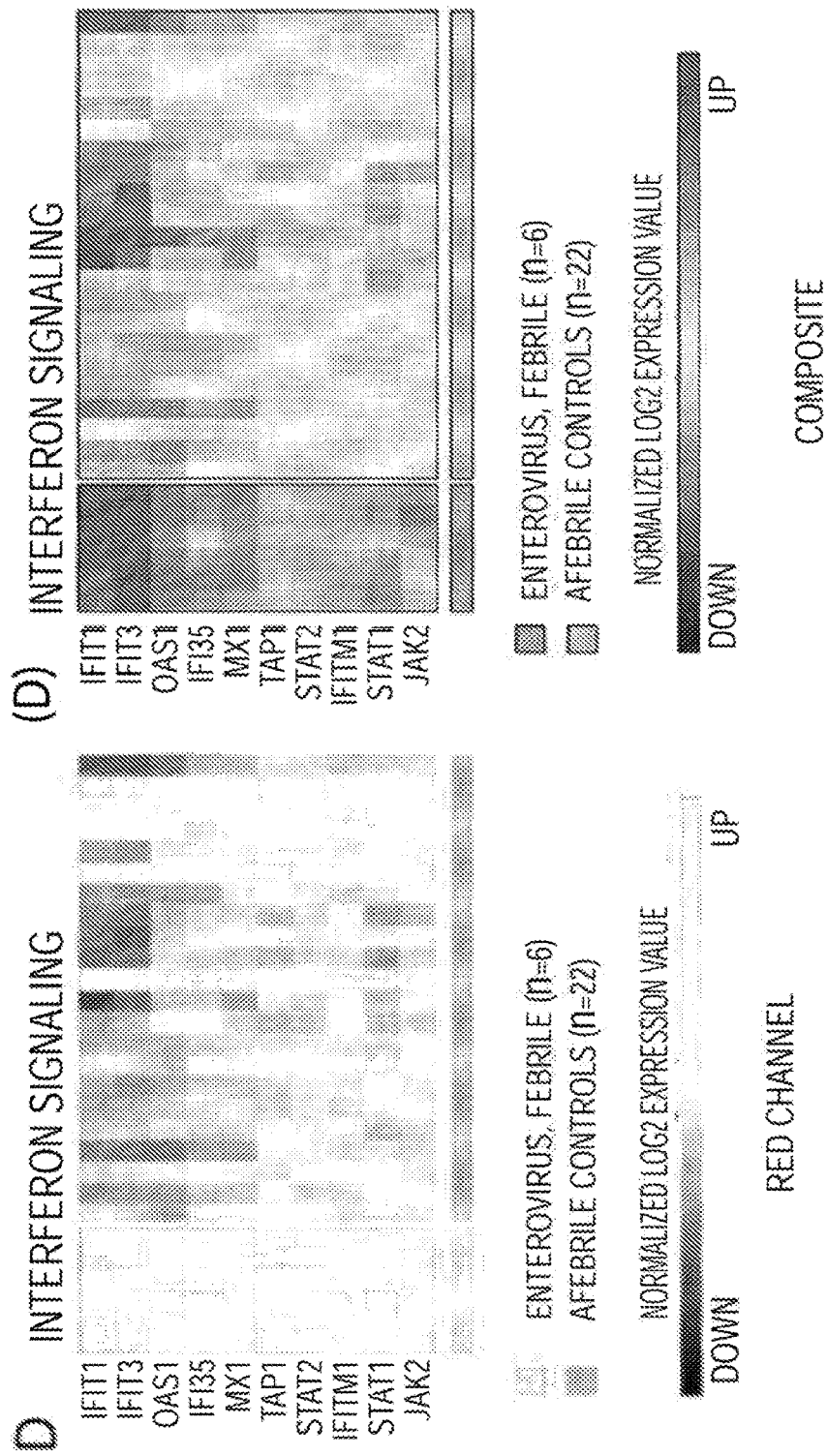
FIG. 6D Con.

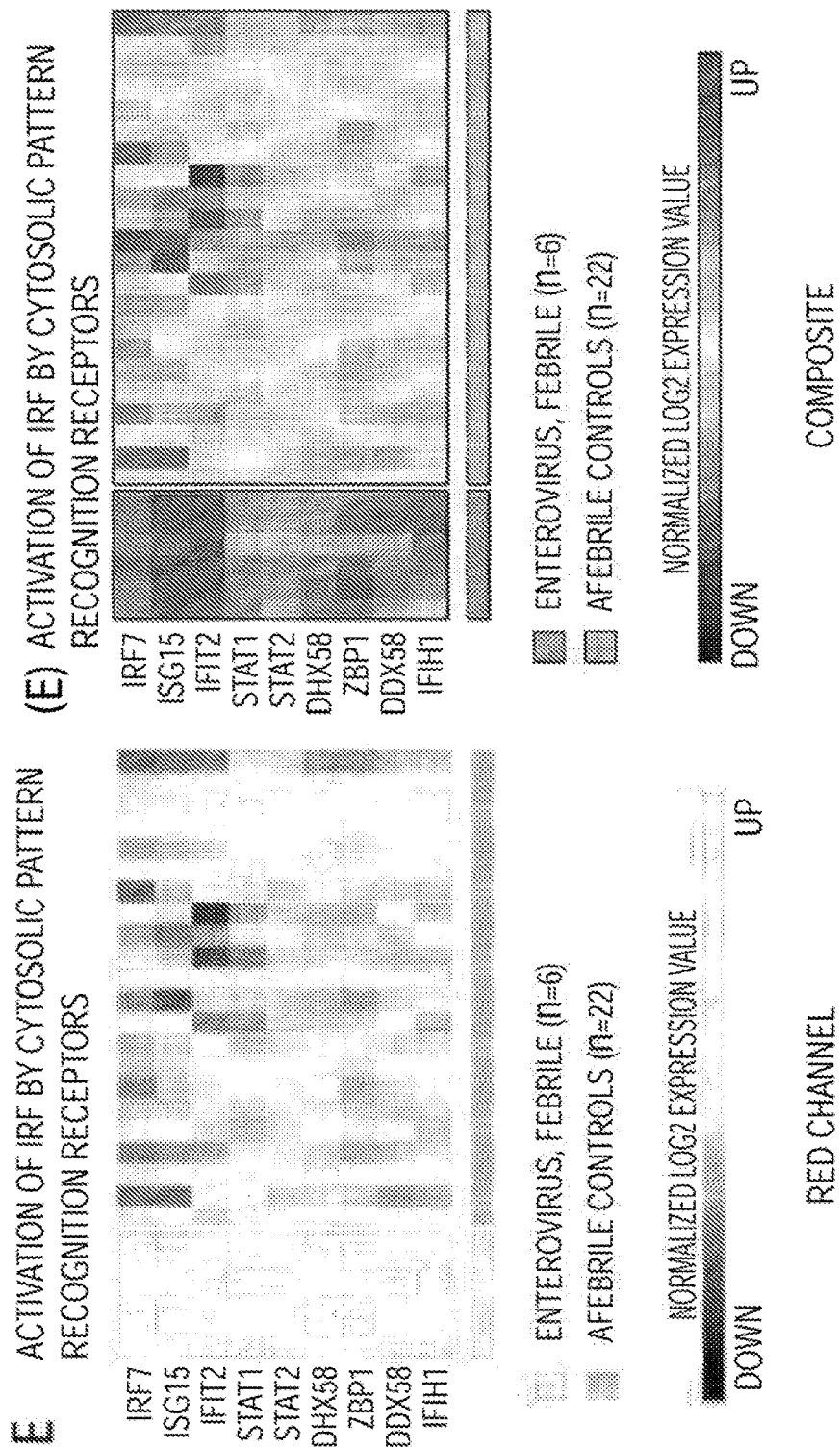
FIG. 6E Con.

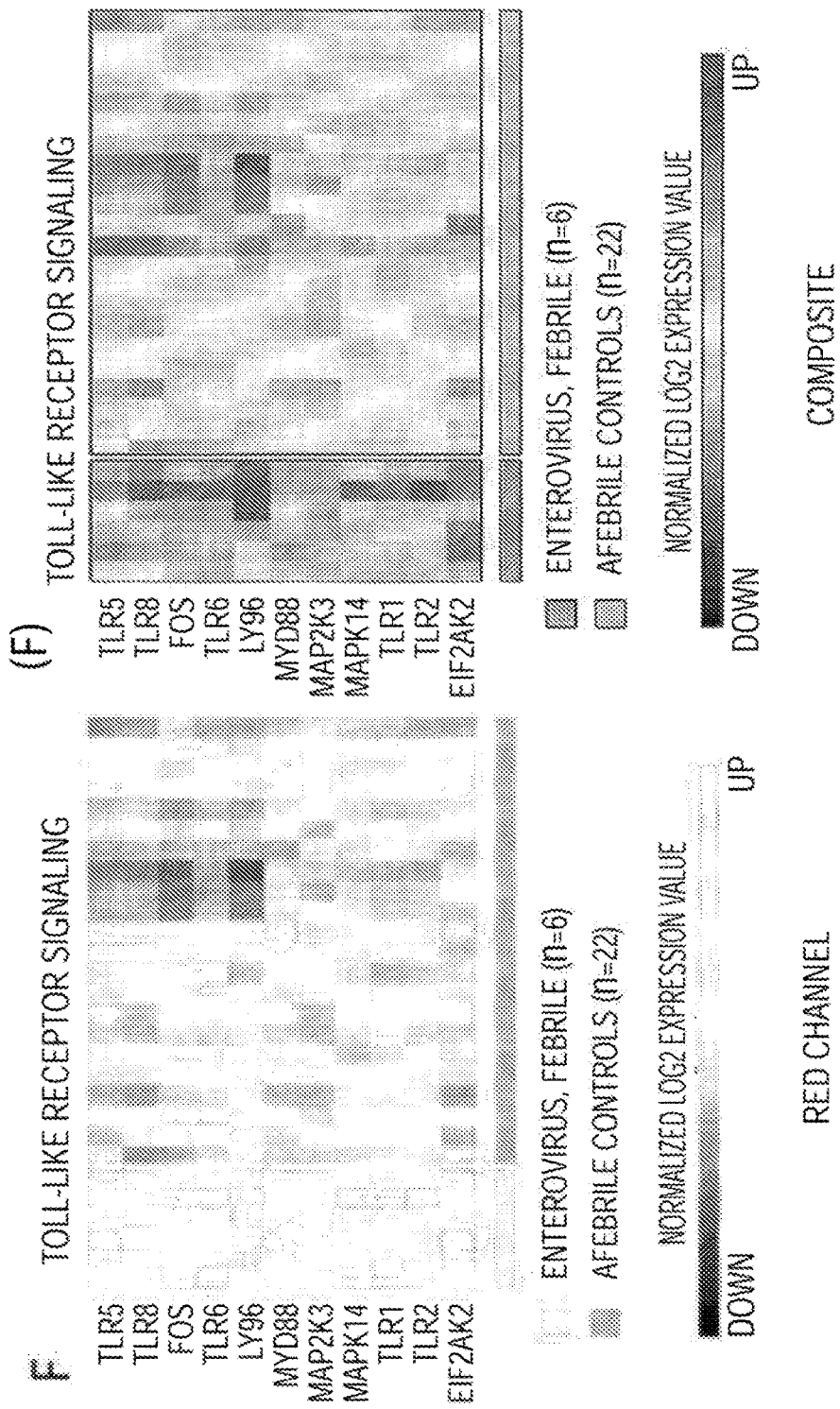
FIG. 6F Con.

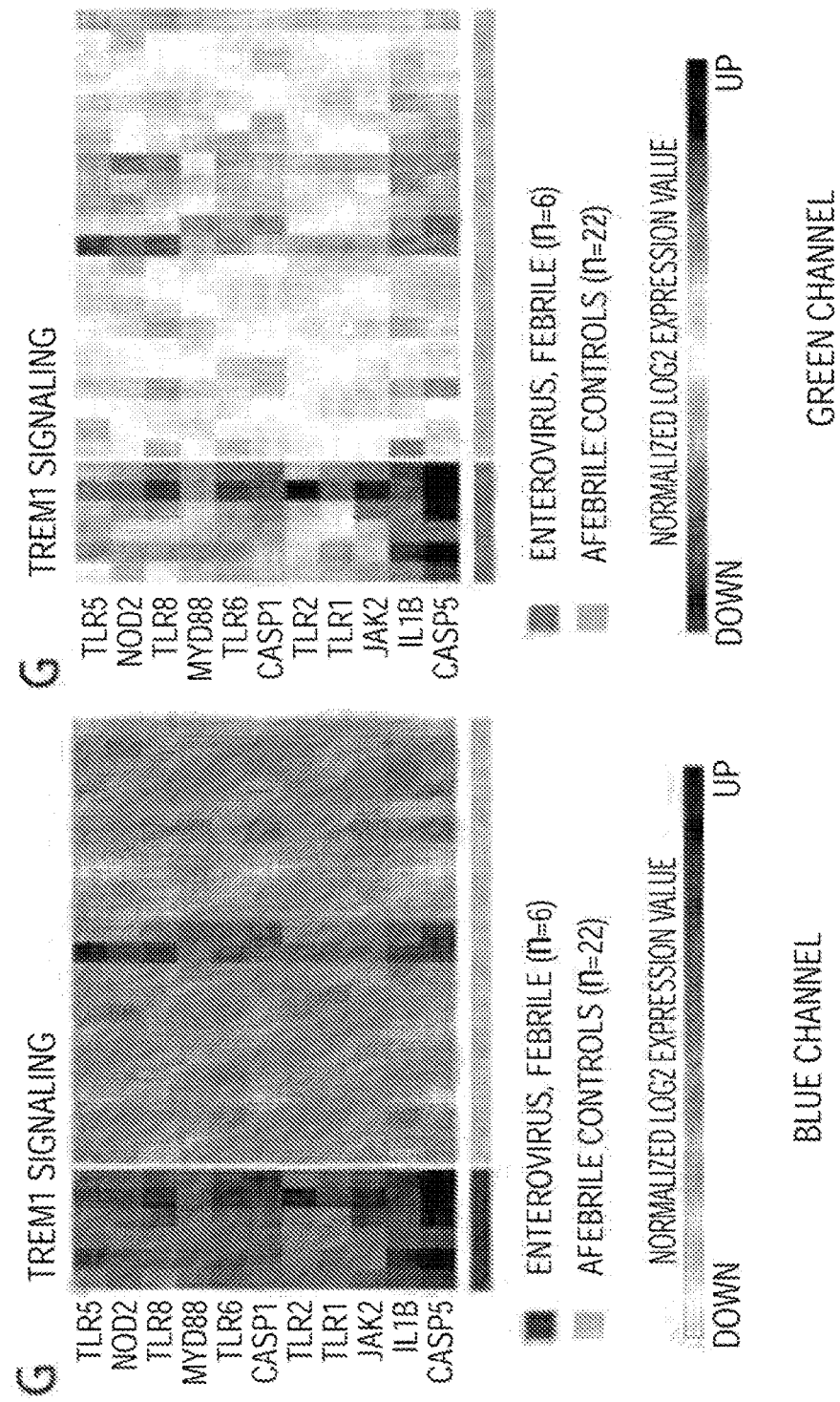

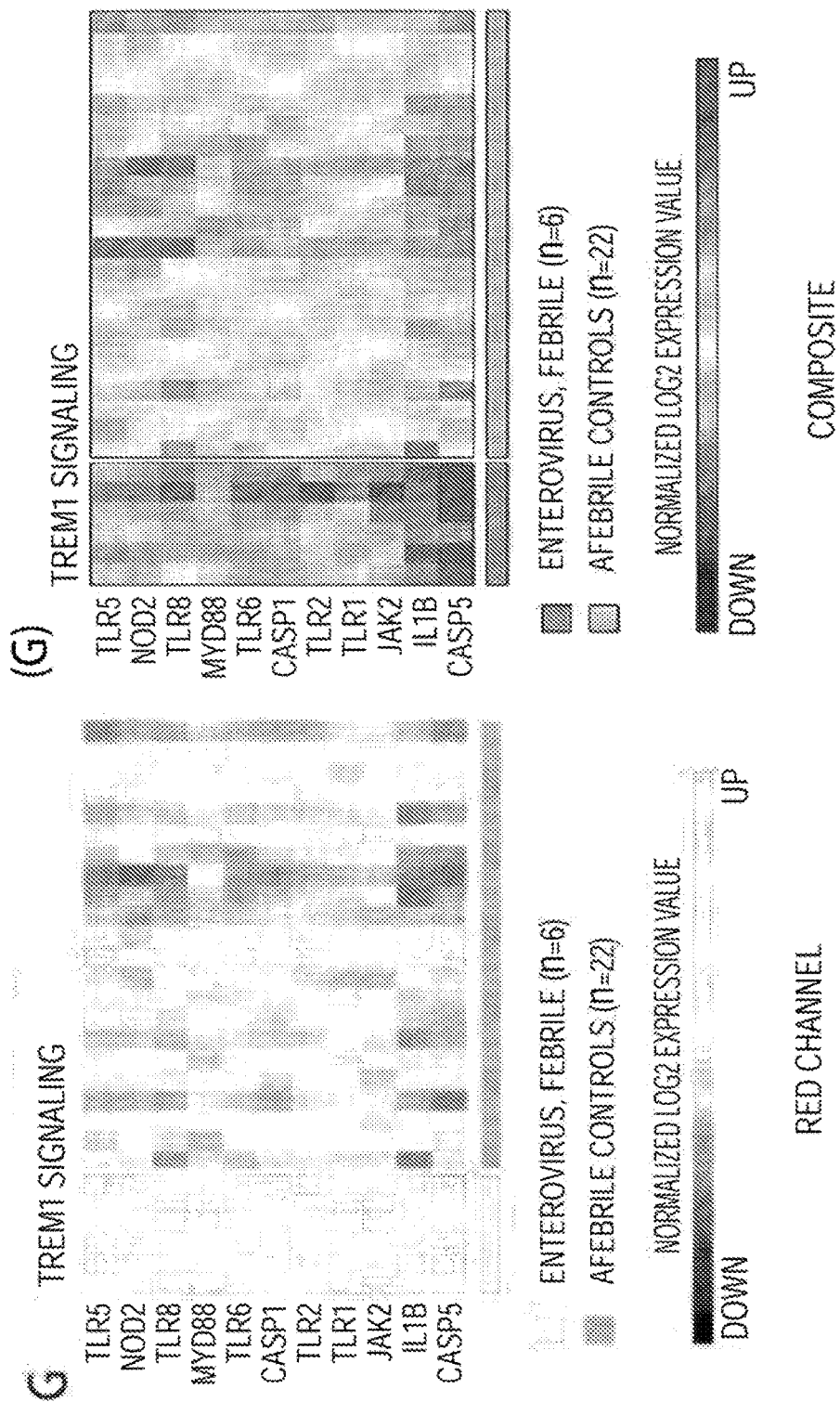
FIG. 6G Con.

FIG. 7A Con.
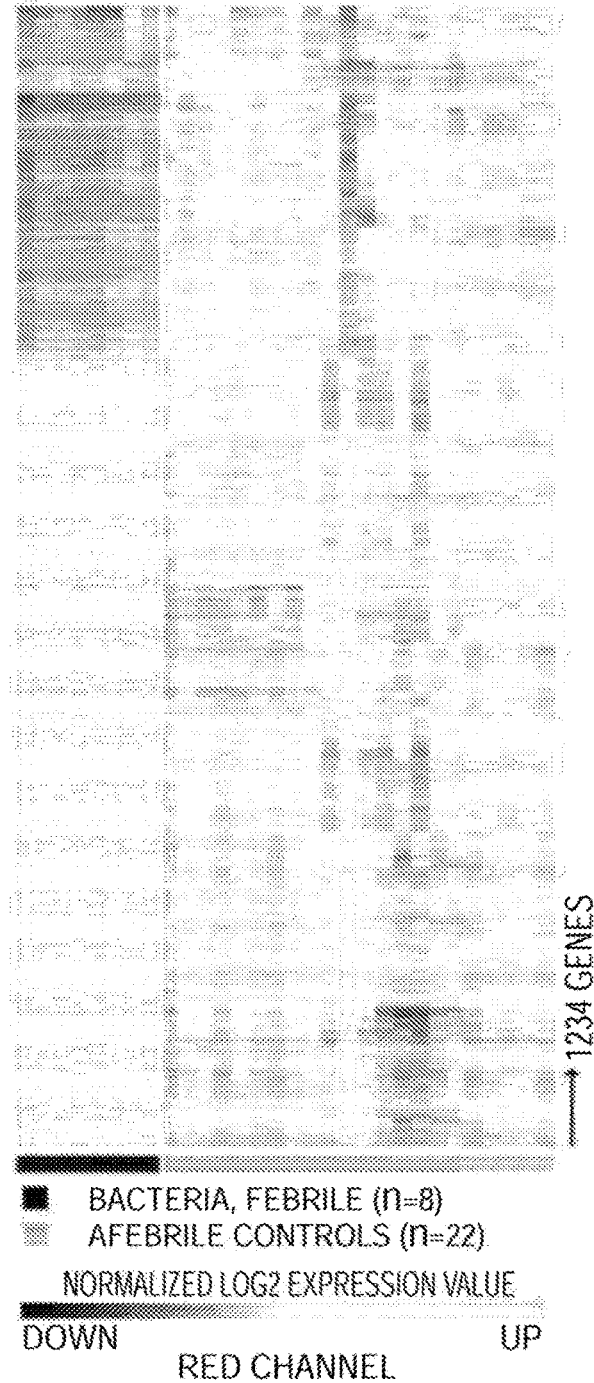
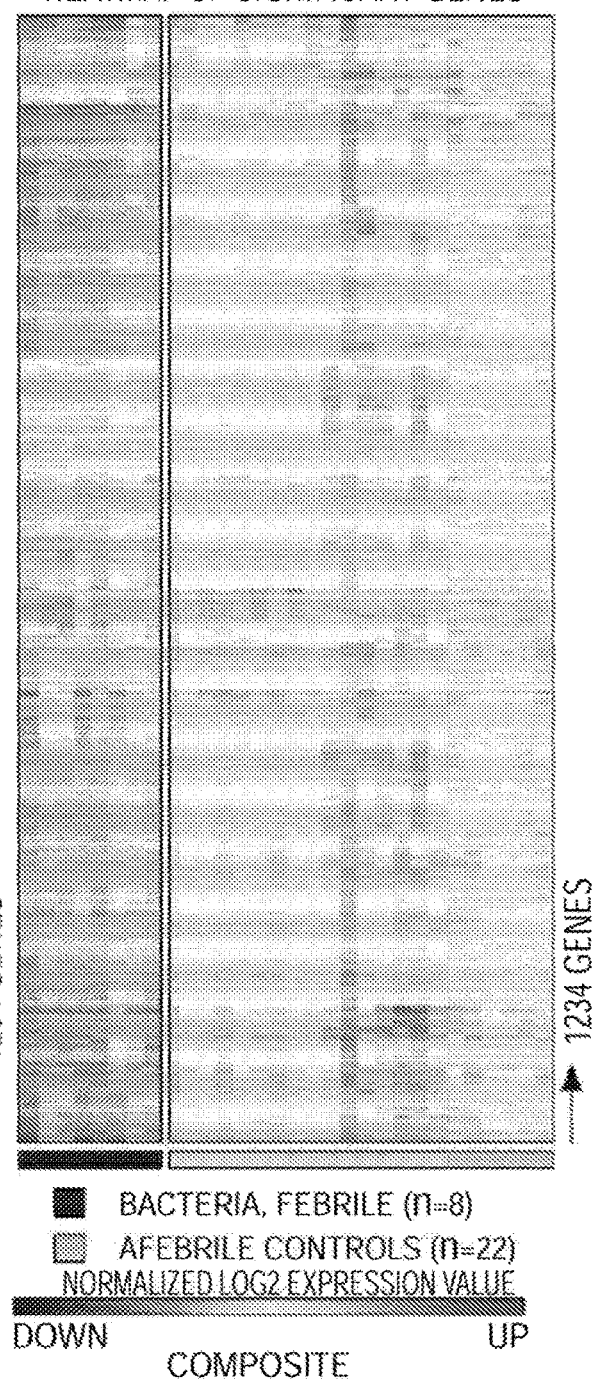

FIG. 7C Con.
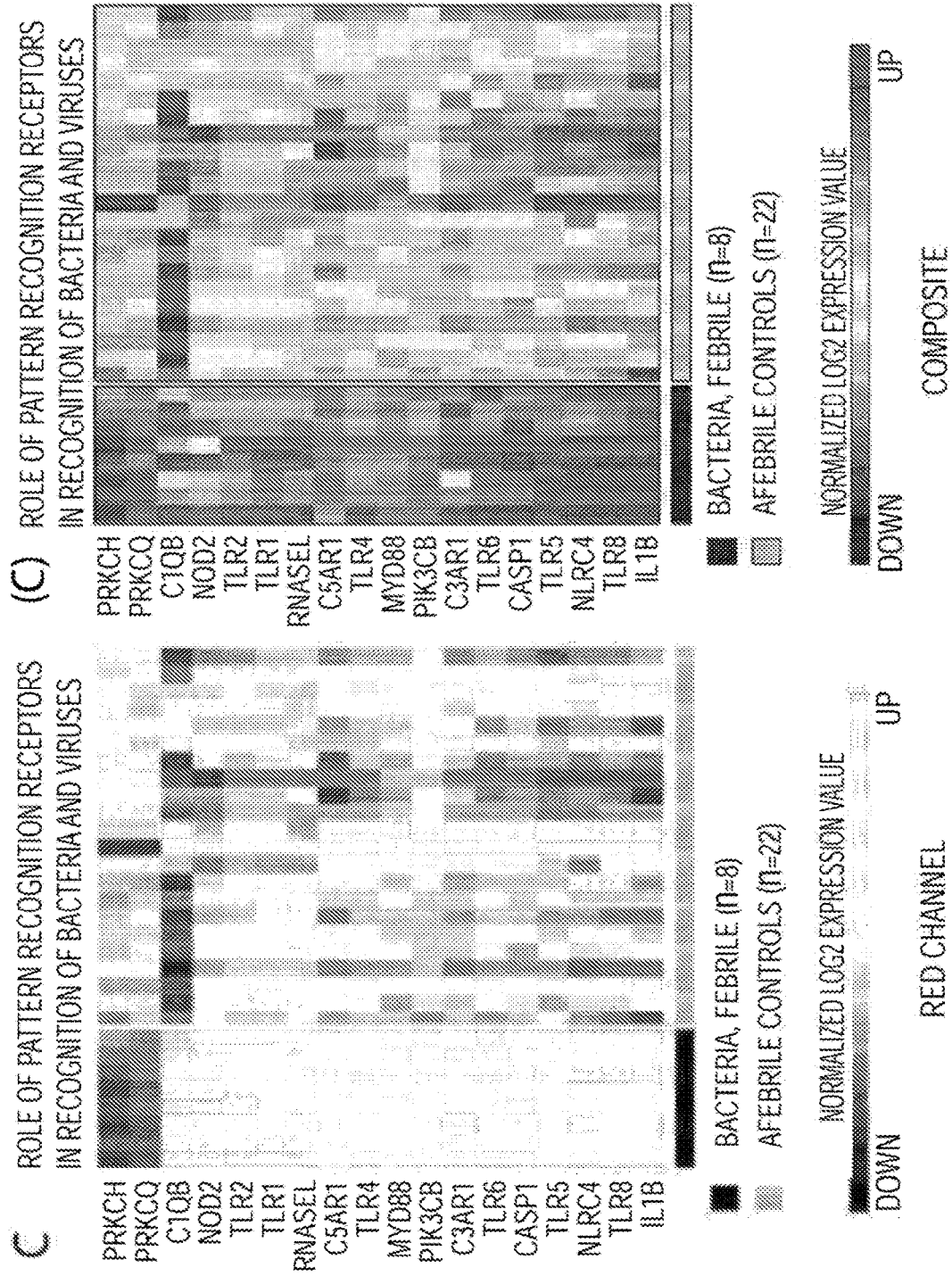

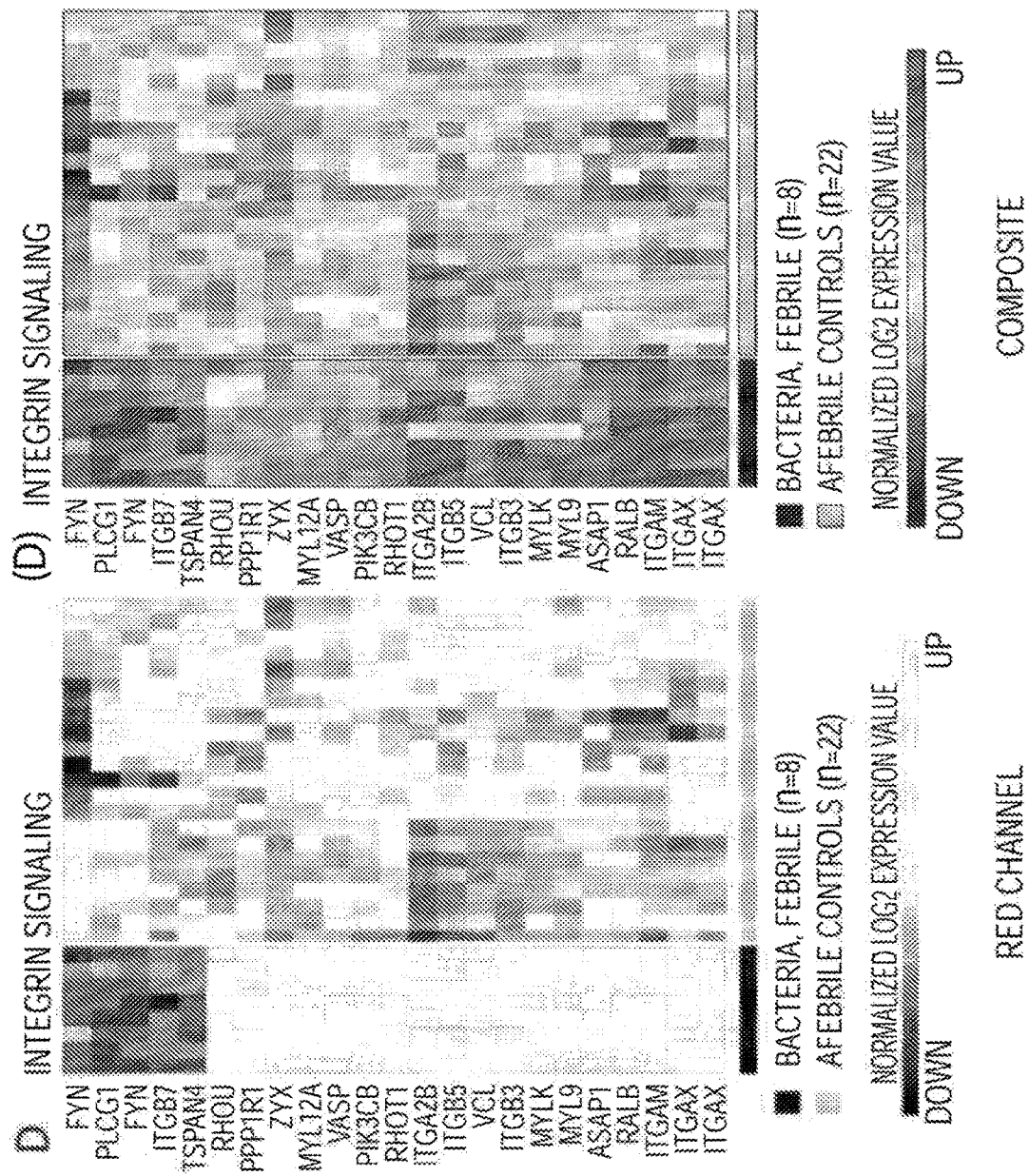
FIG. 7D Con.

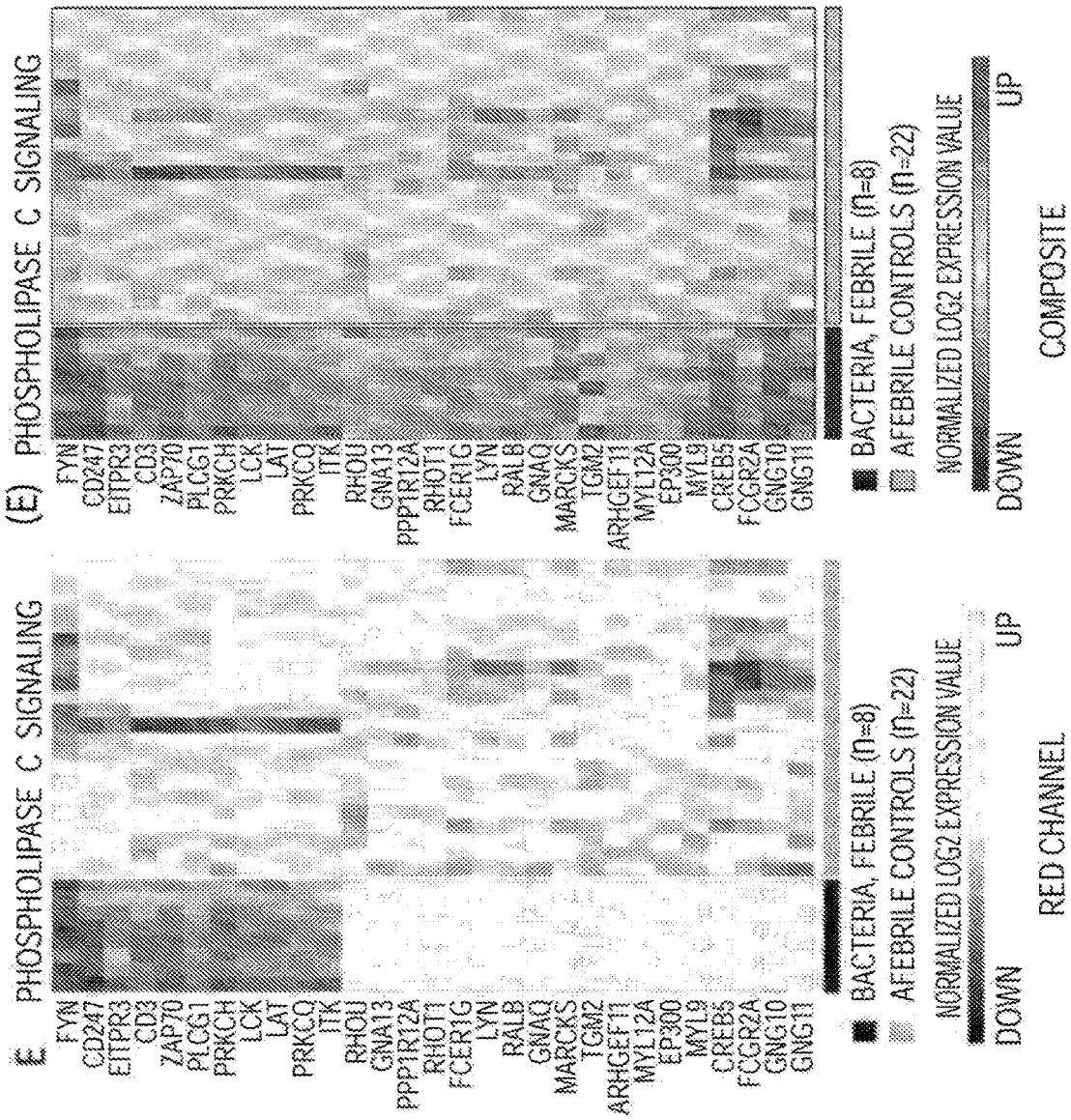
FIG. 7E Con.

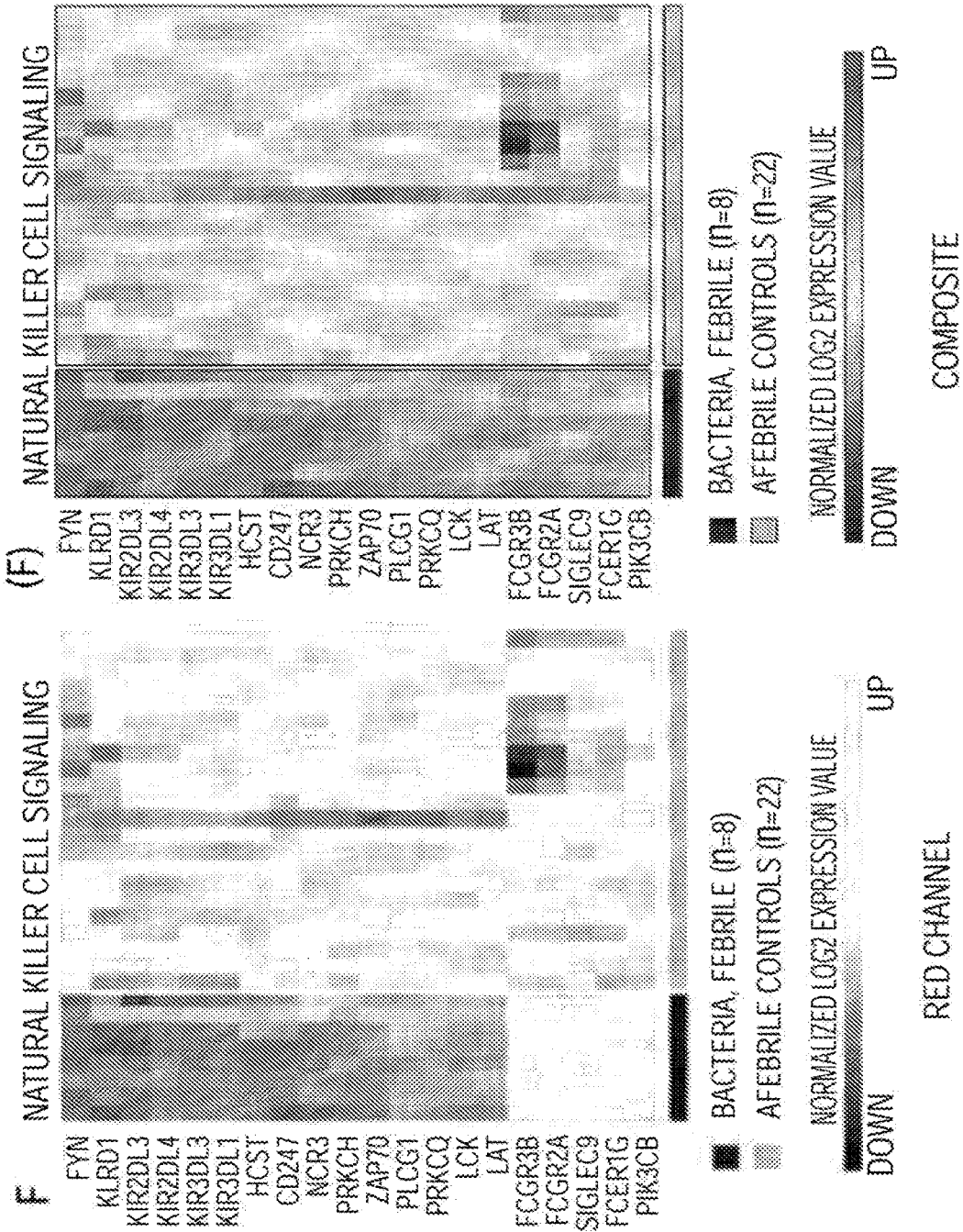
FIG. 7F Con.

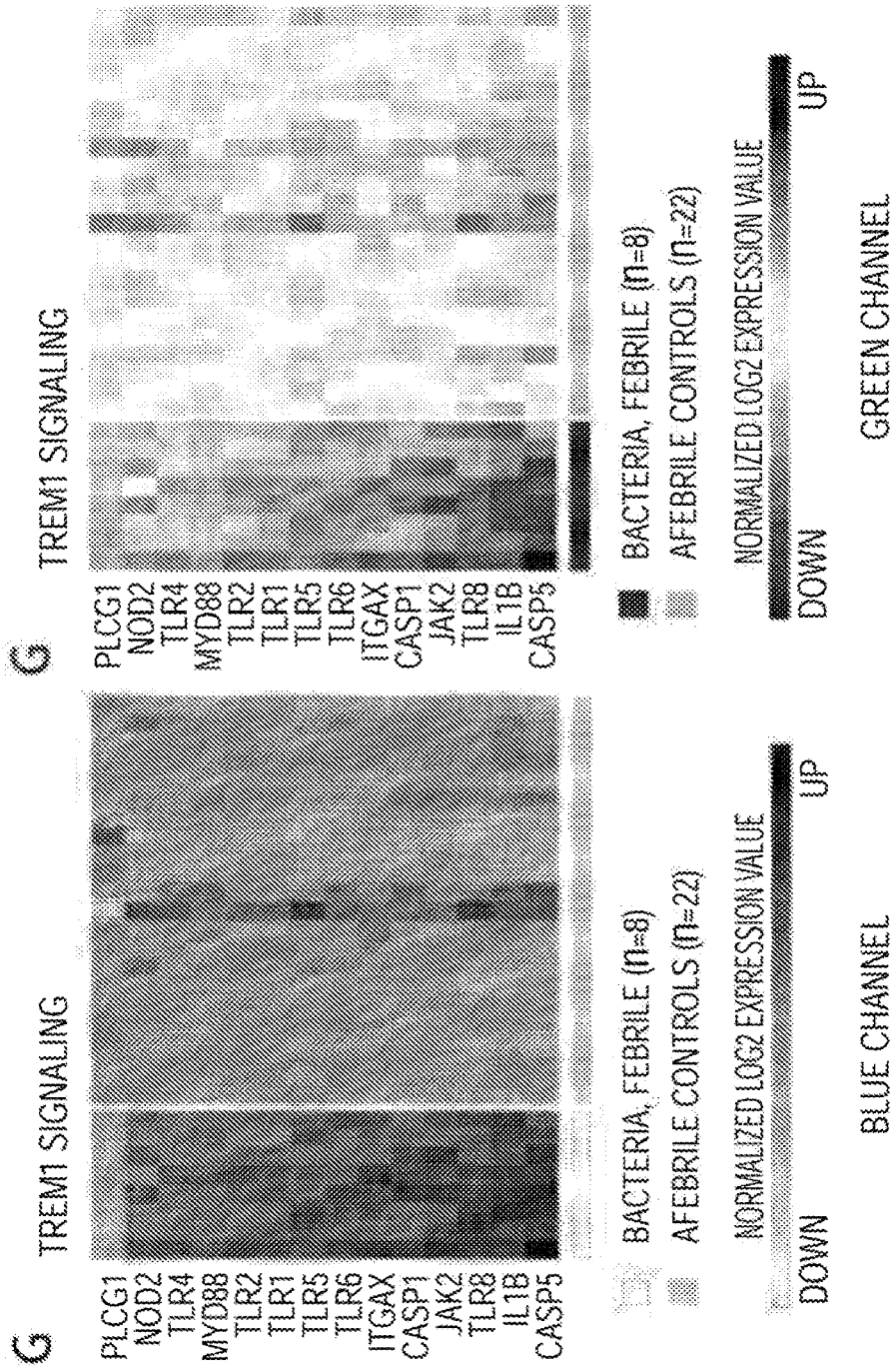

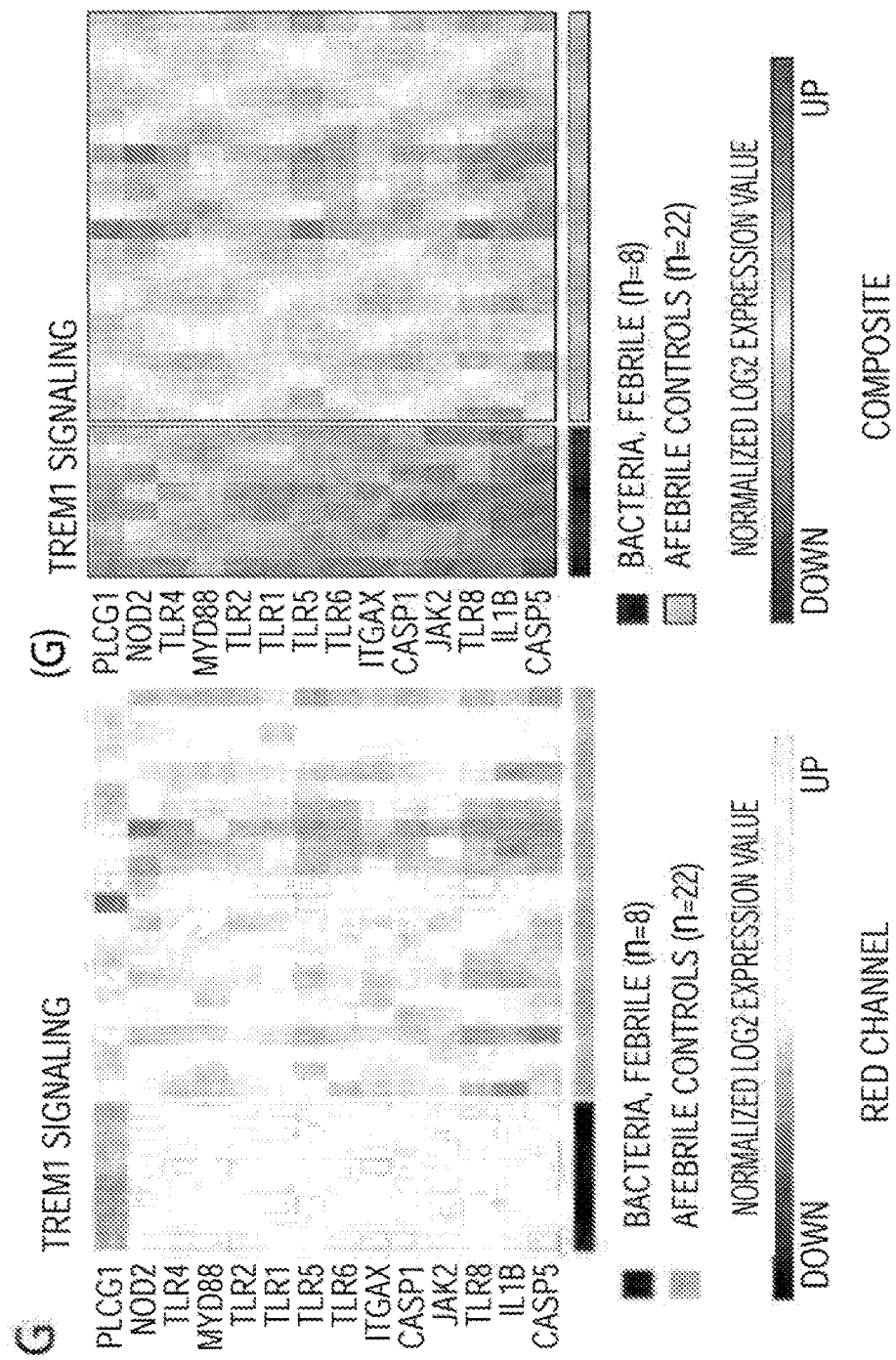
FIG. 7G Con.

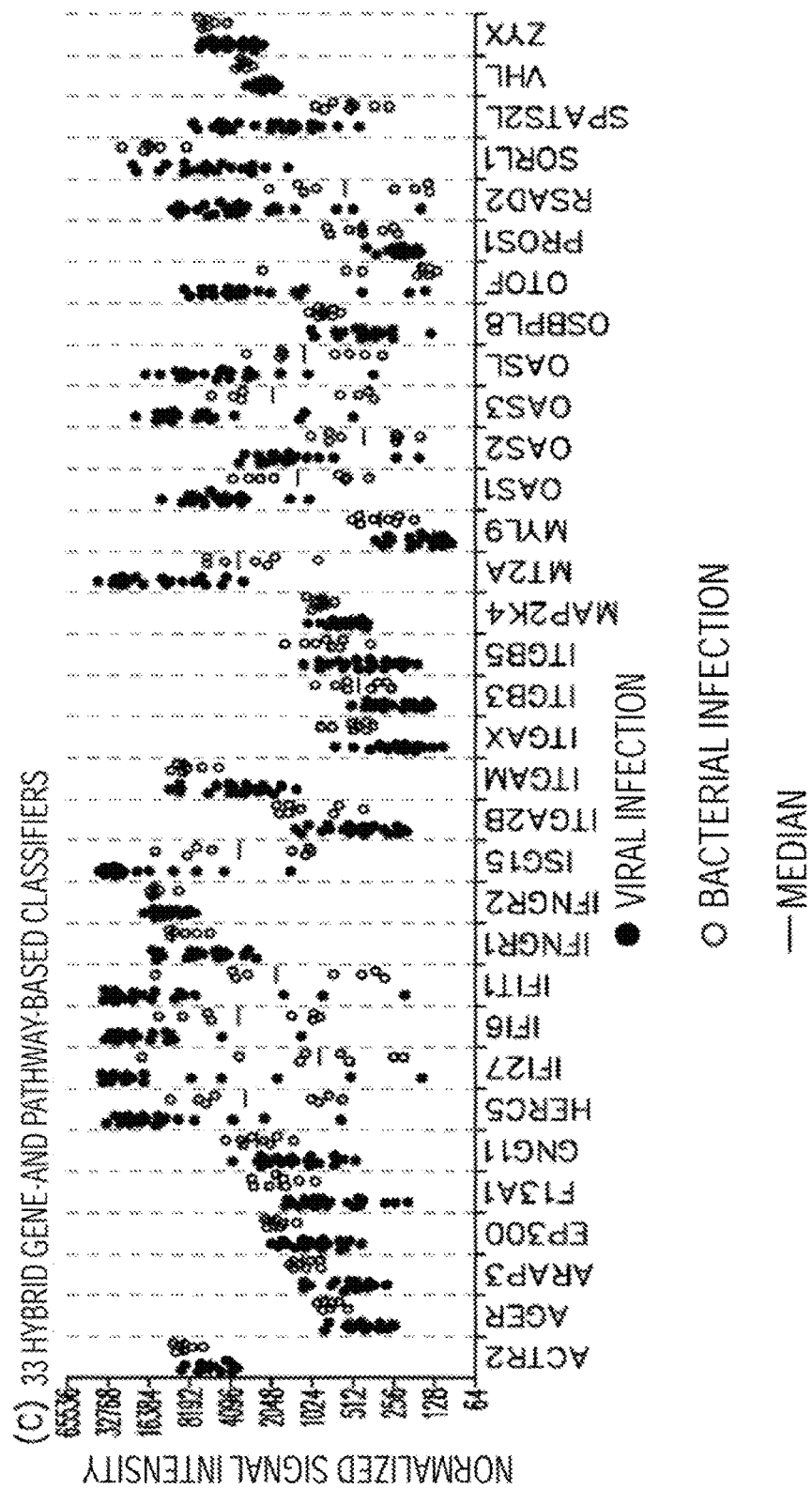

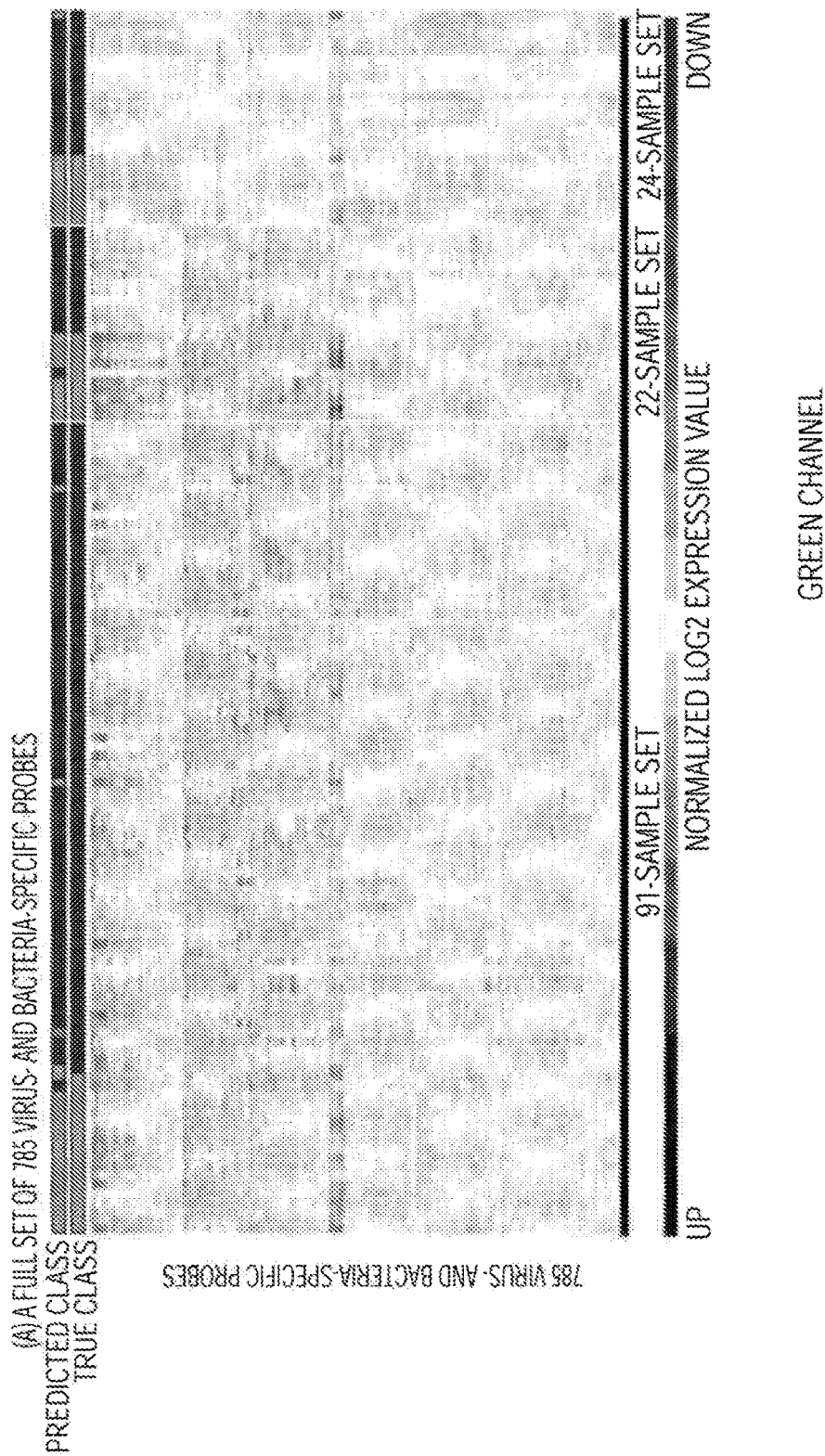
FIG. 10A Con.

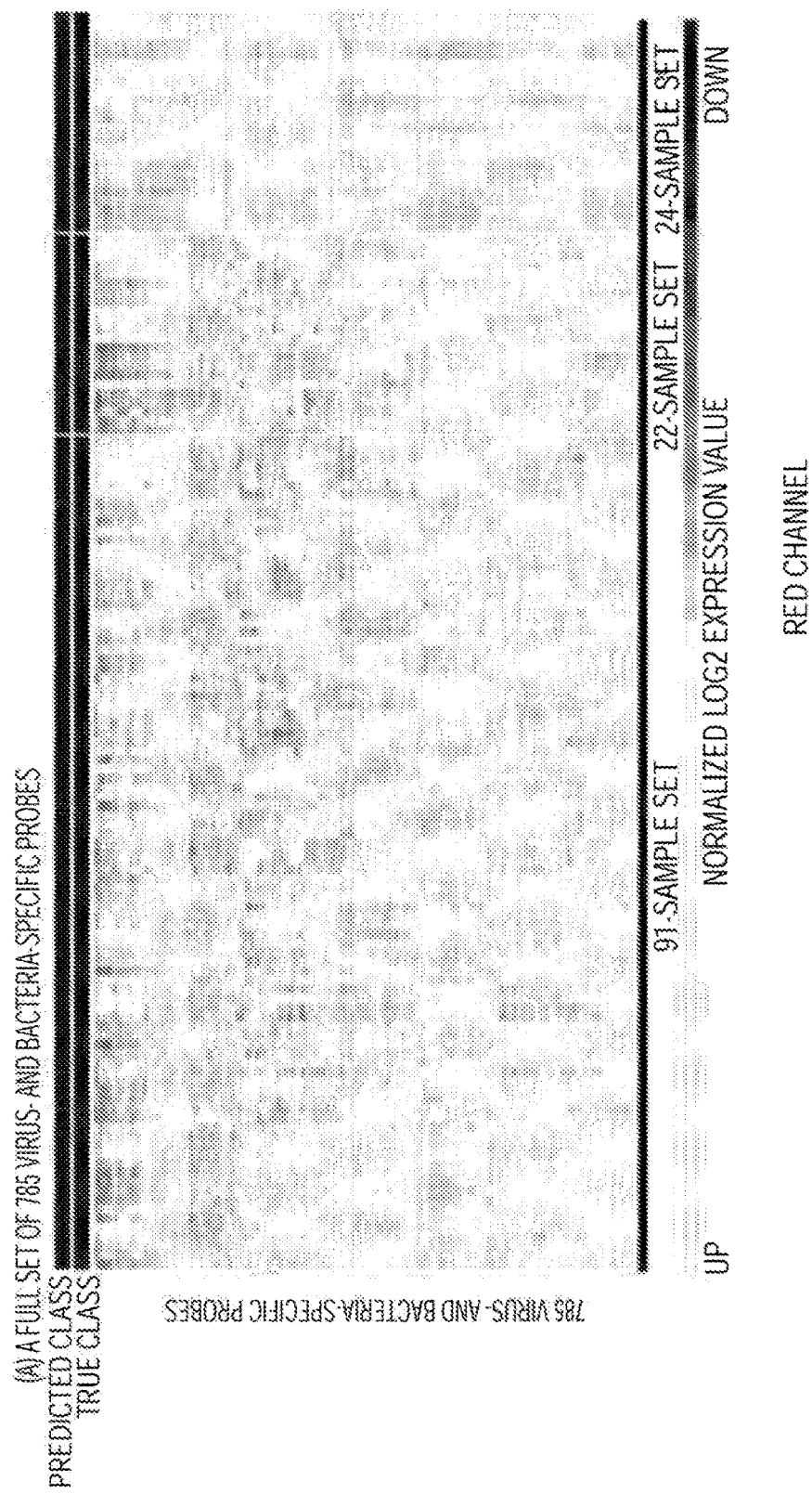
FIG. 10A Con.

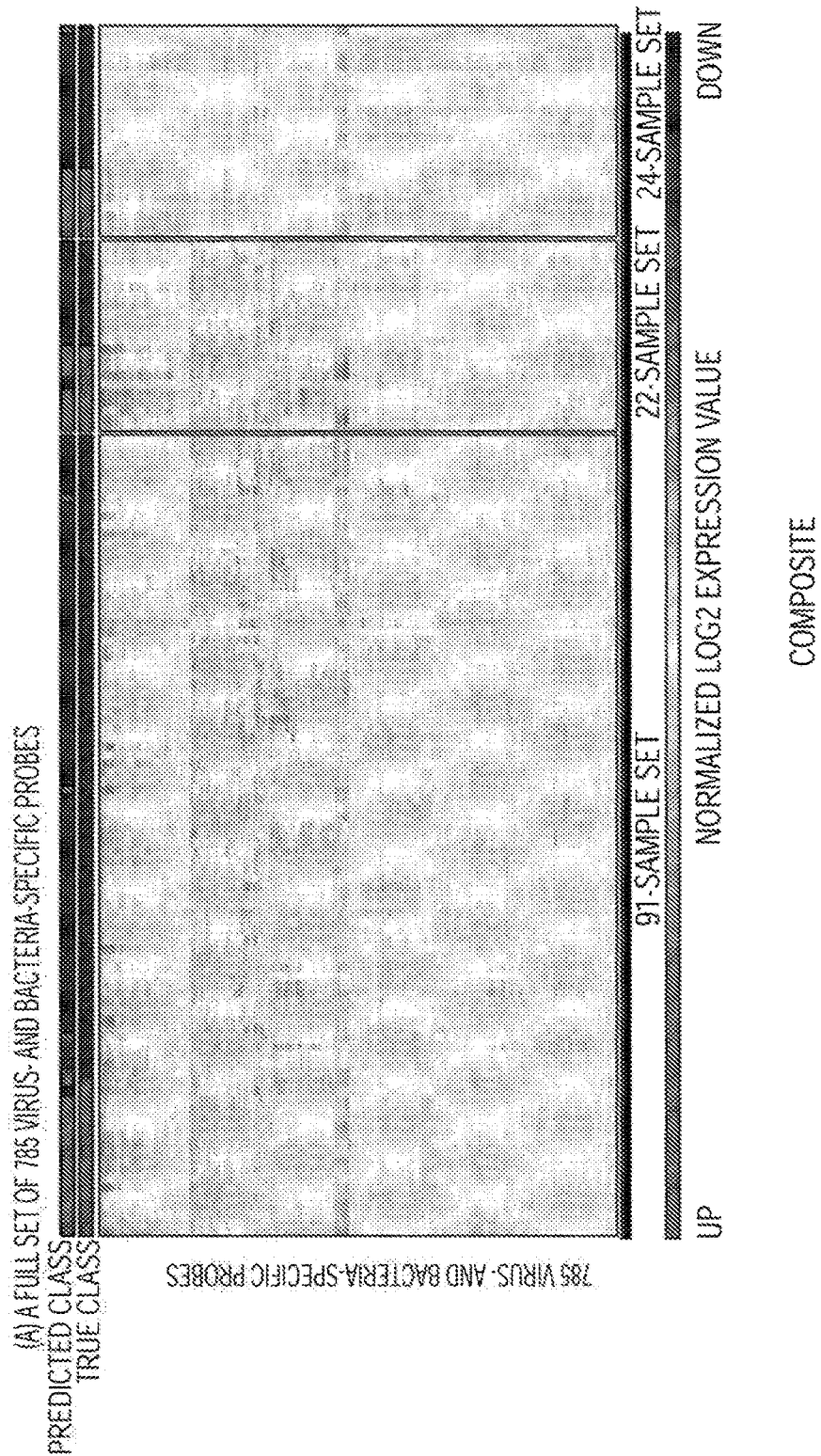
FIG. 10A Con.

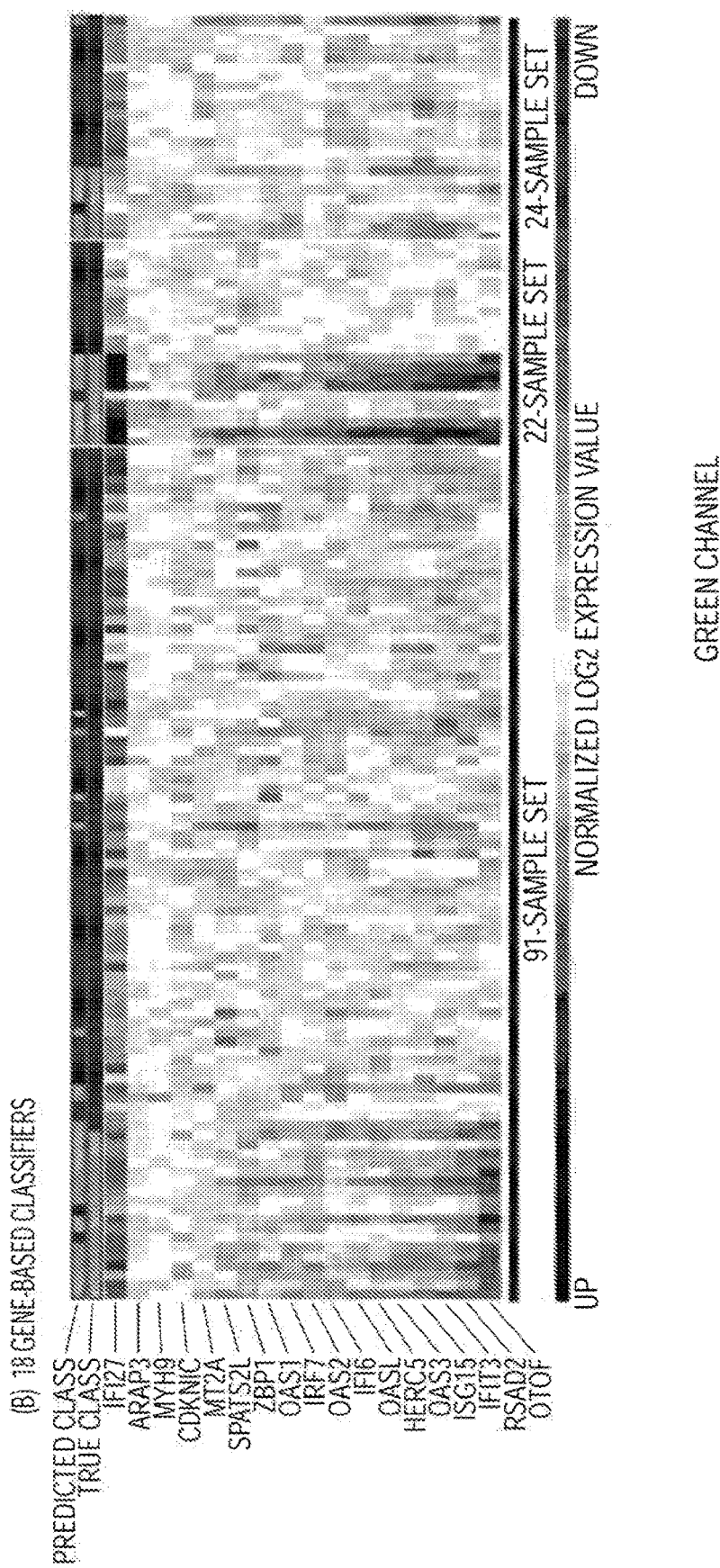
FIG. 10B Con.

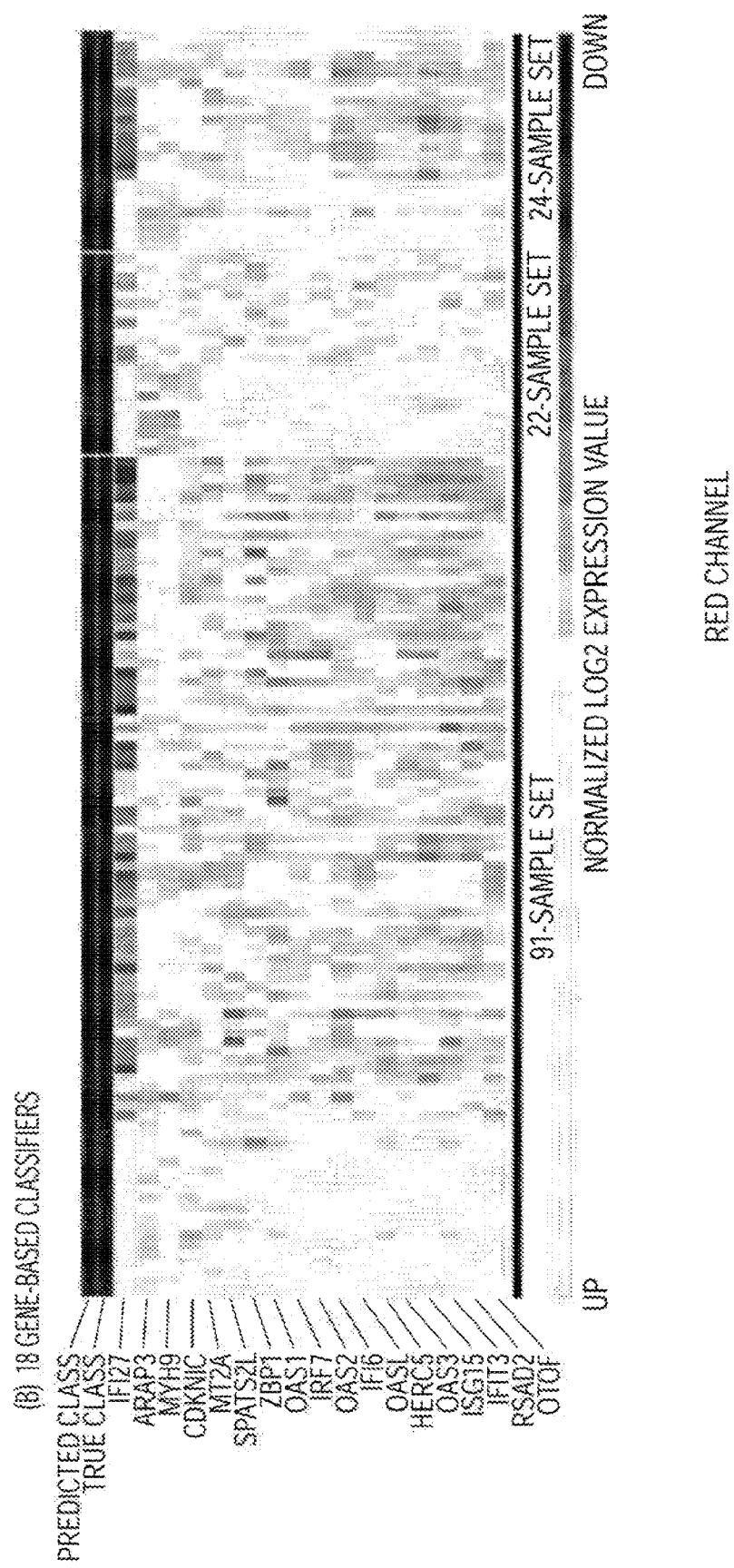
FIG. 10B Con.

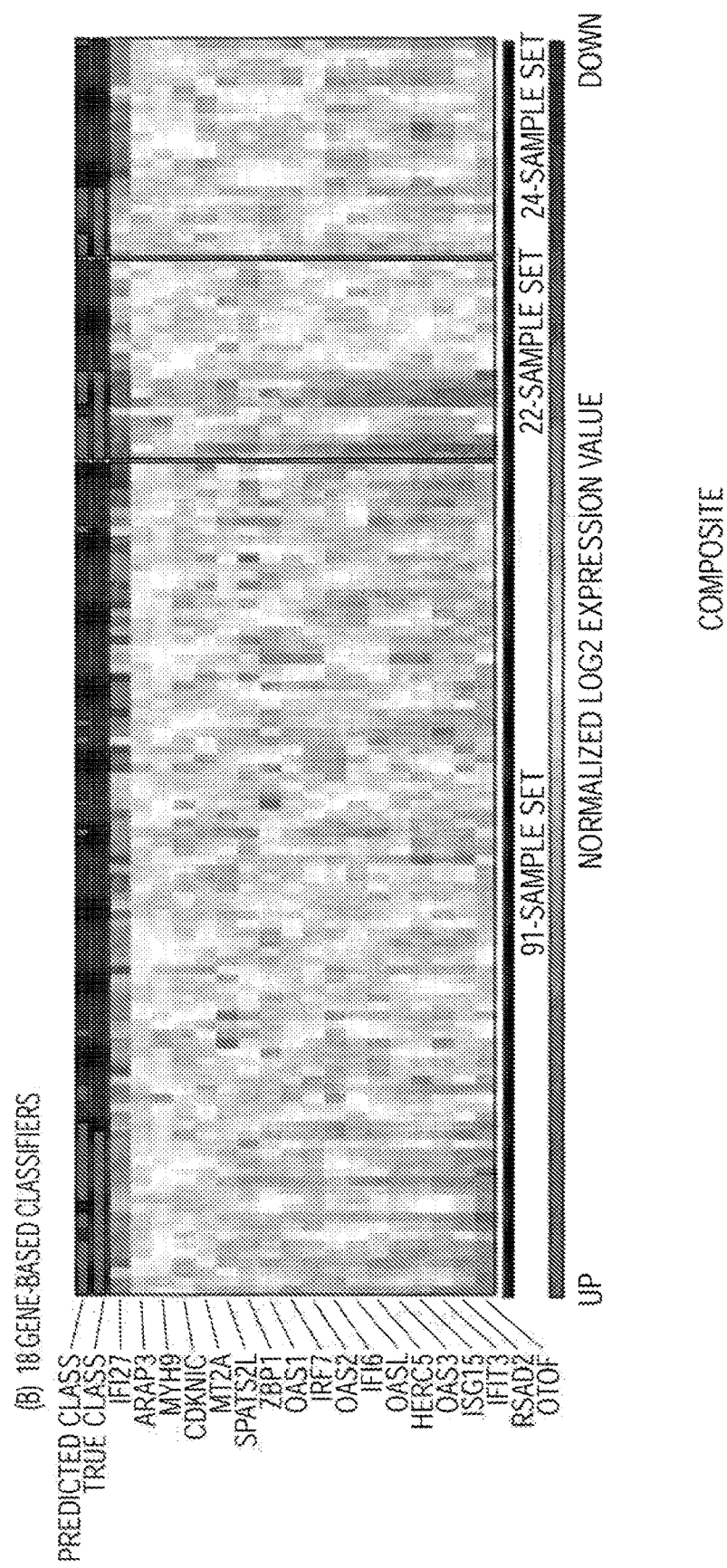
FIG. 10B Con.

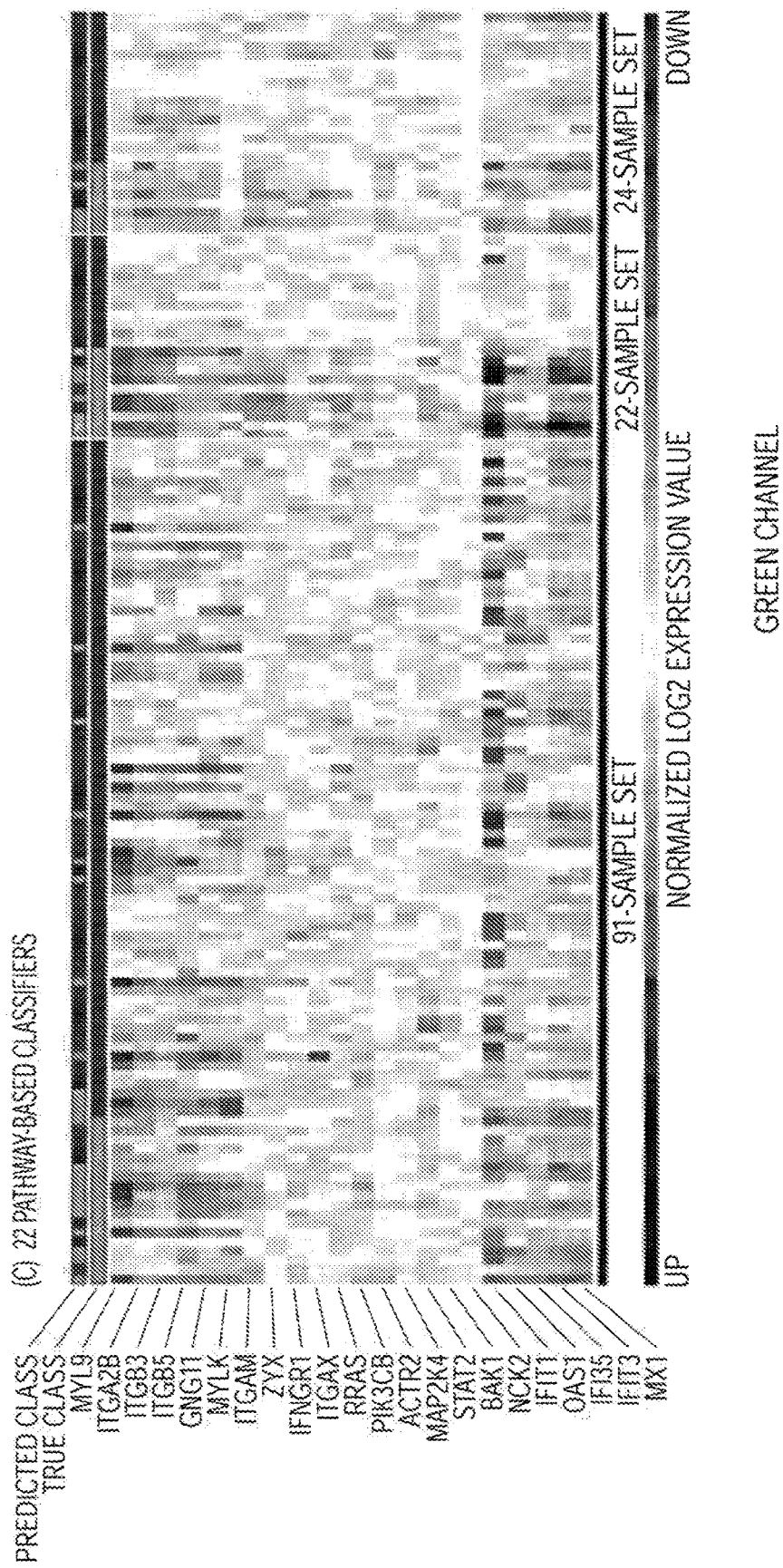
FIG. 10C Con.

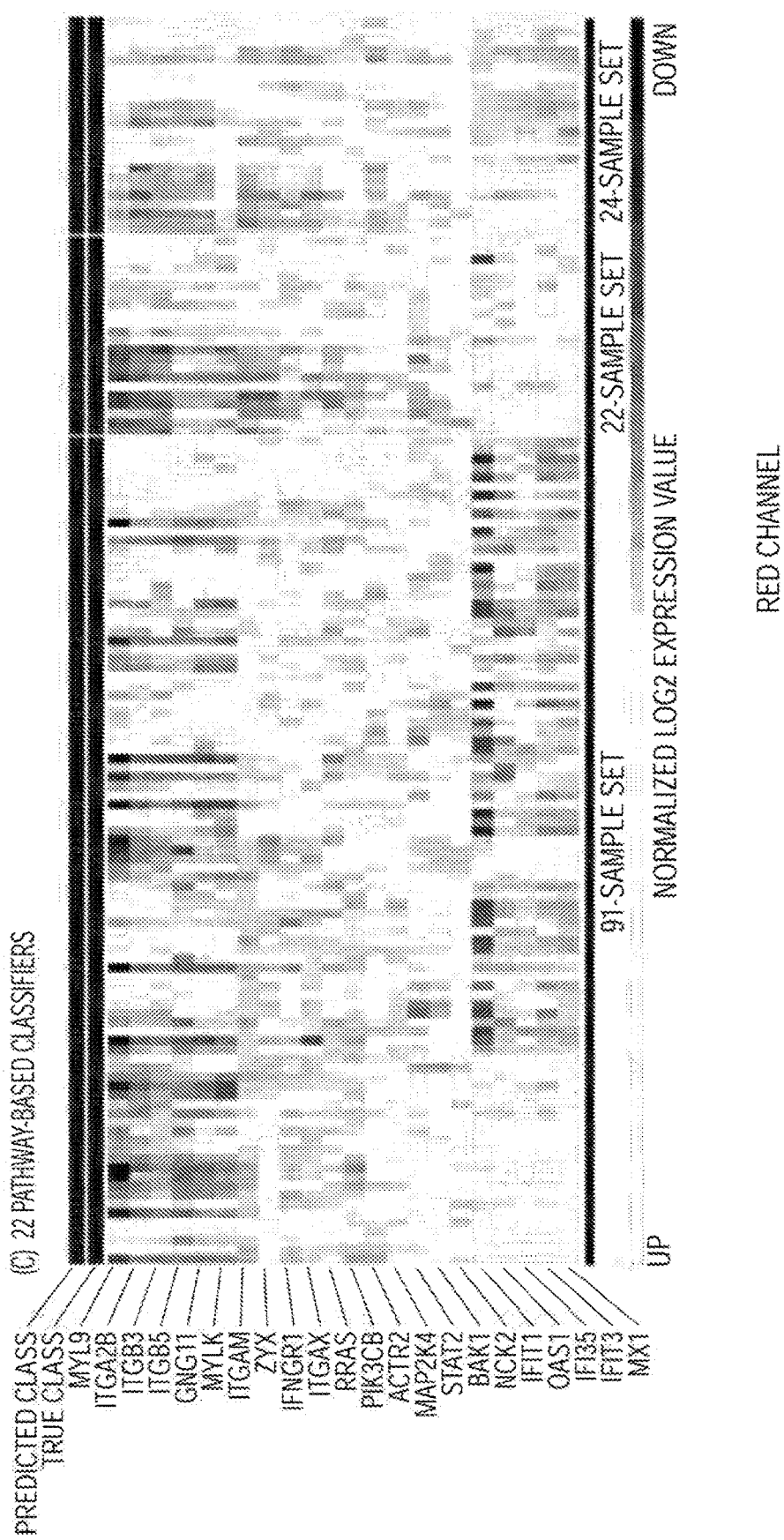
FIG. 10C Con.

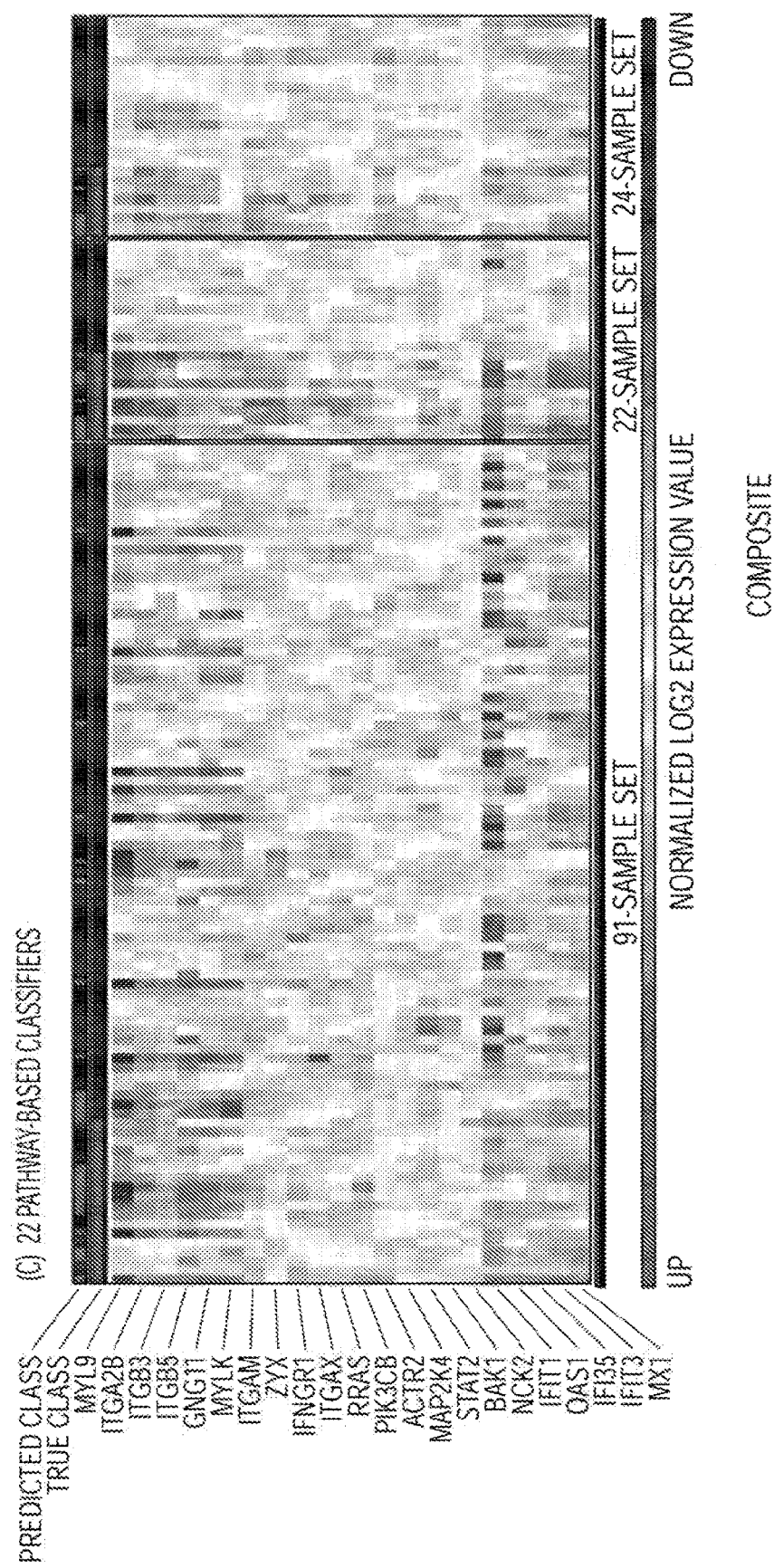
FIG. 10C Con.

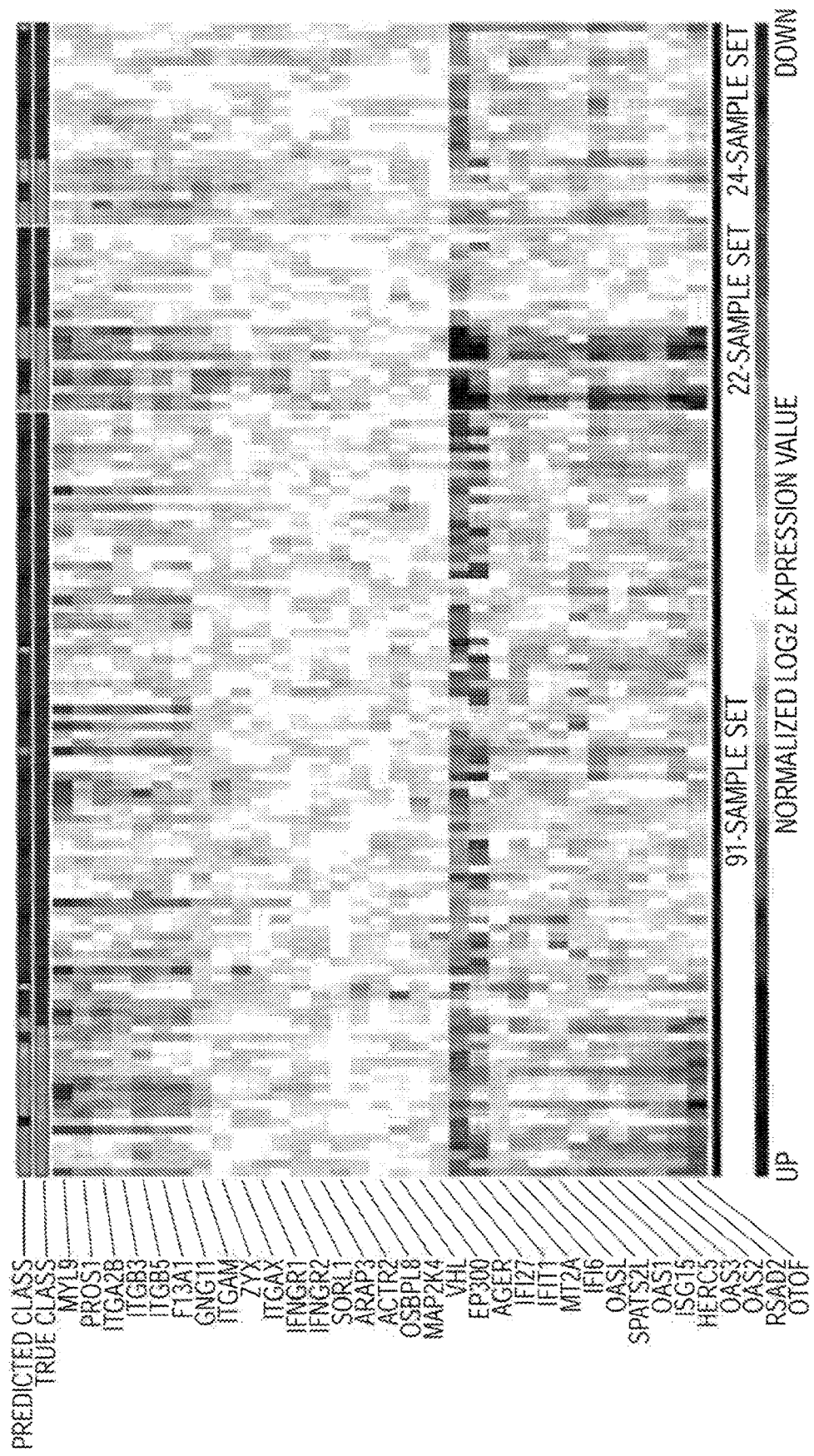
FIG. 10D Con.

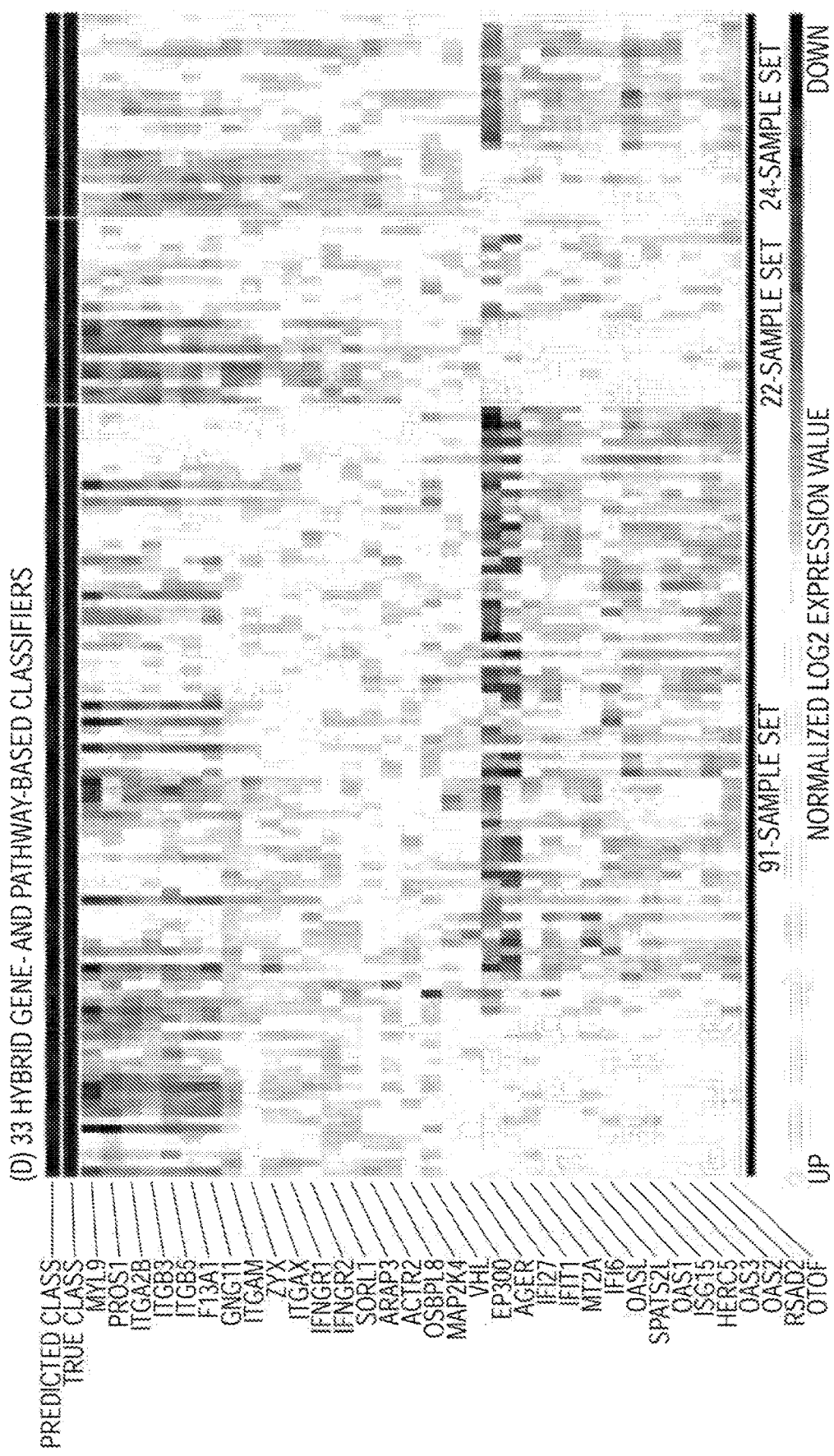
FIG. 10D Con.

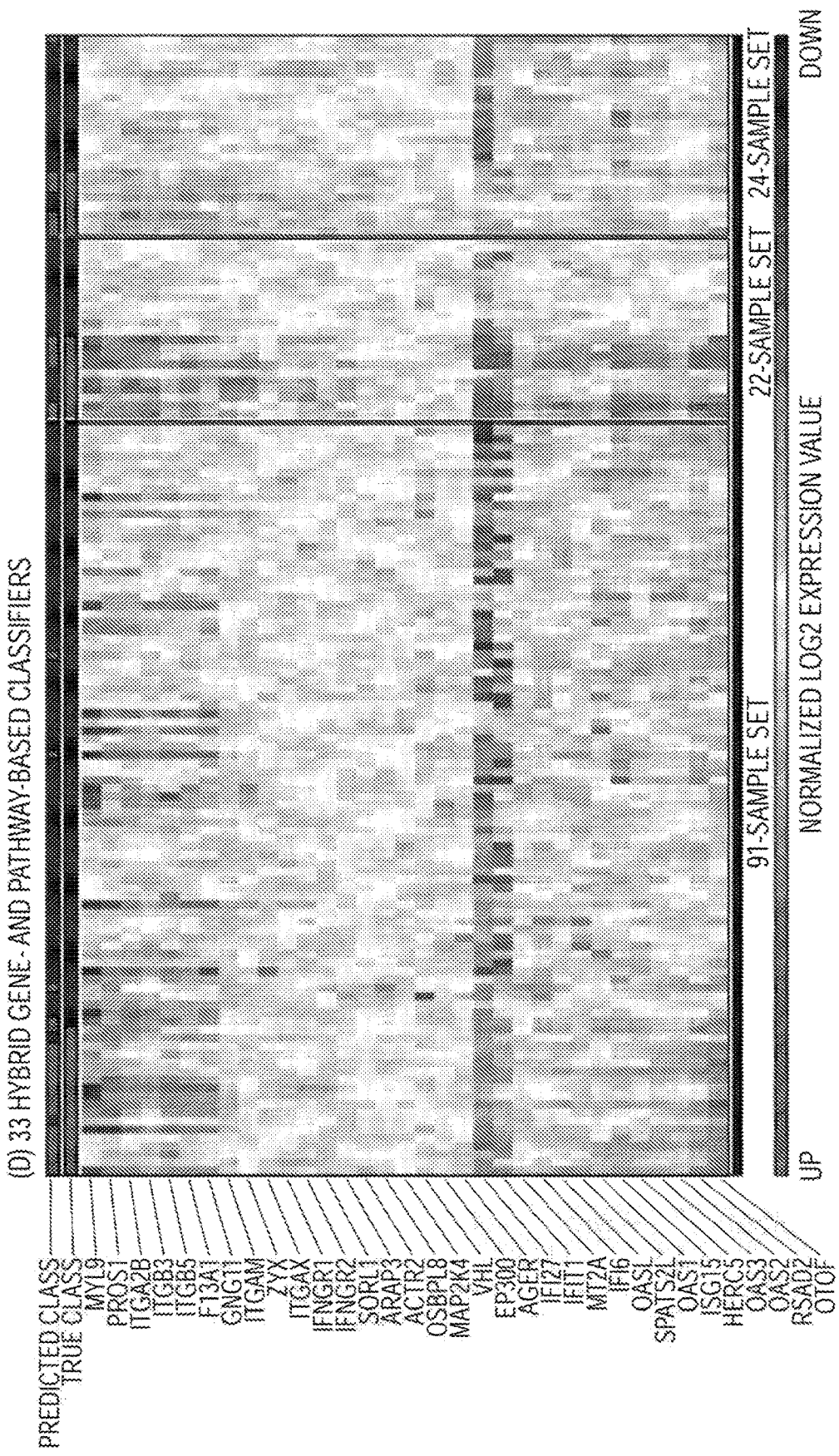
FIG. 10D Con.

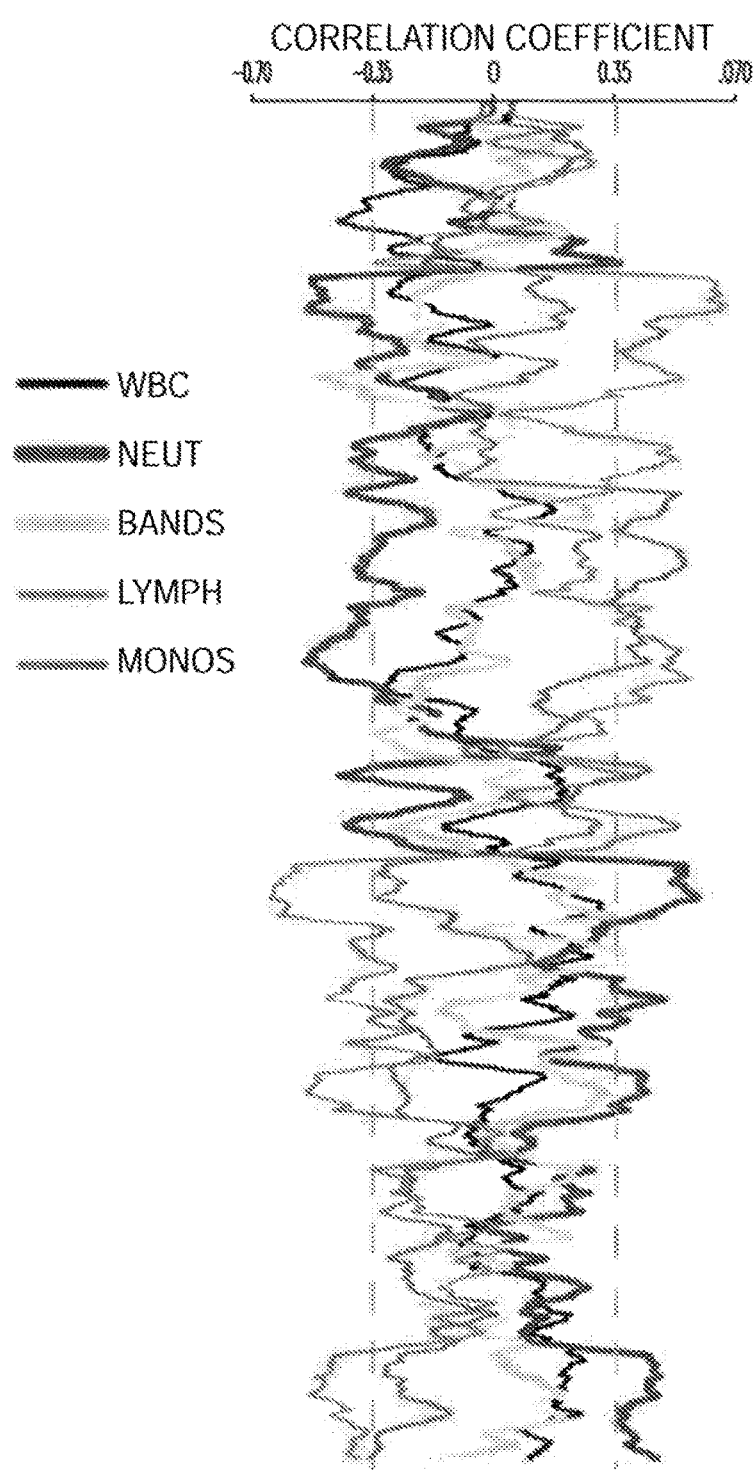

FIG. 11B Con.
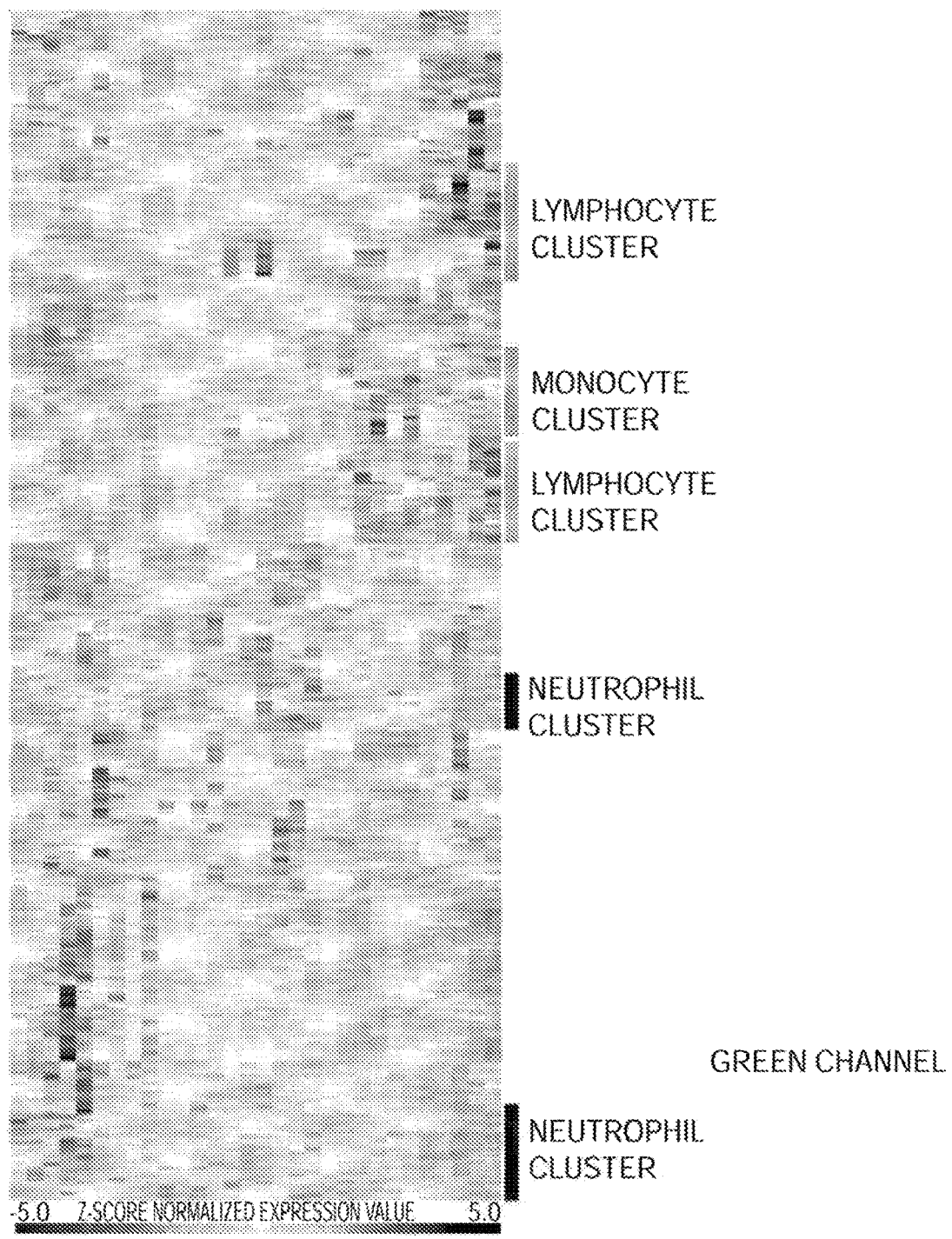

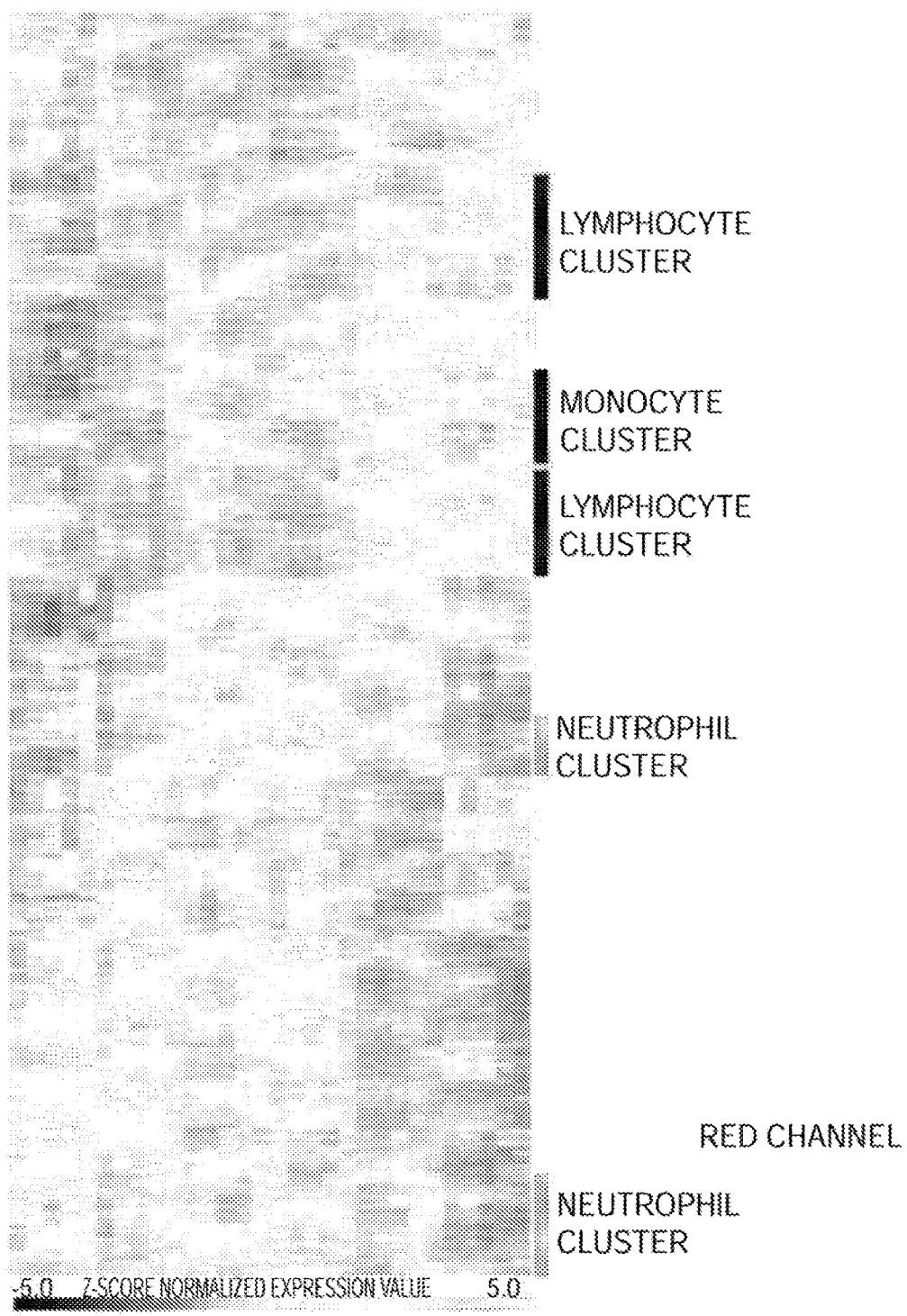
FIG. 11B Con

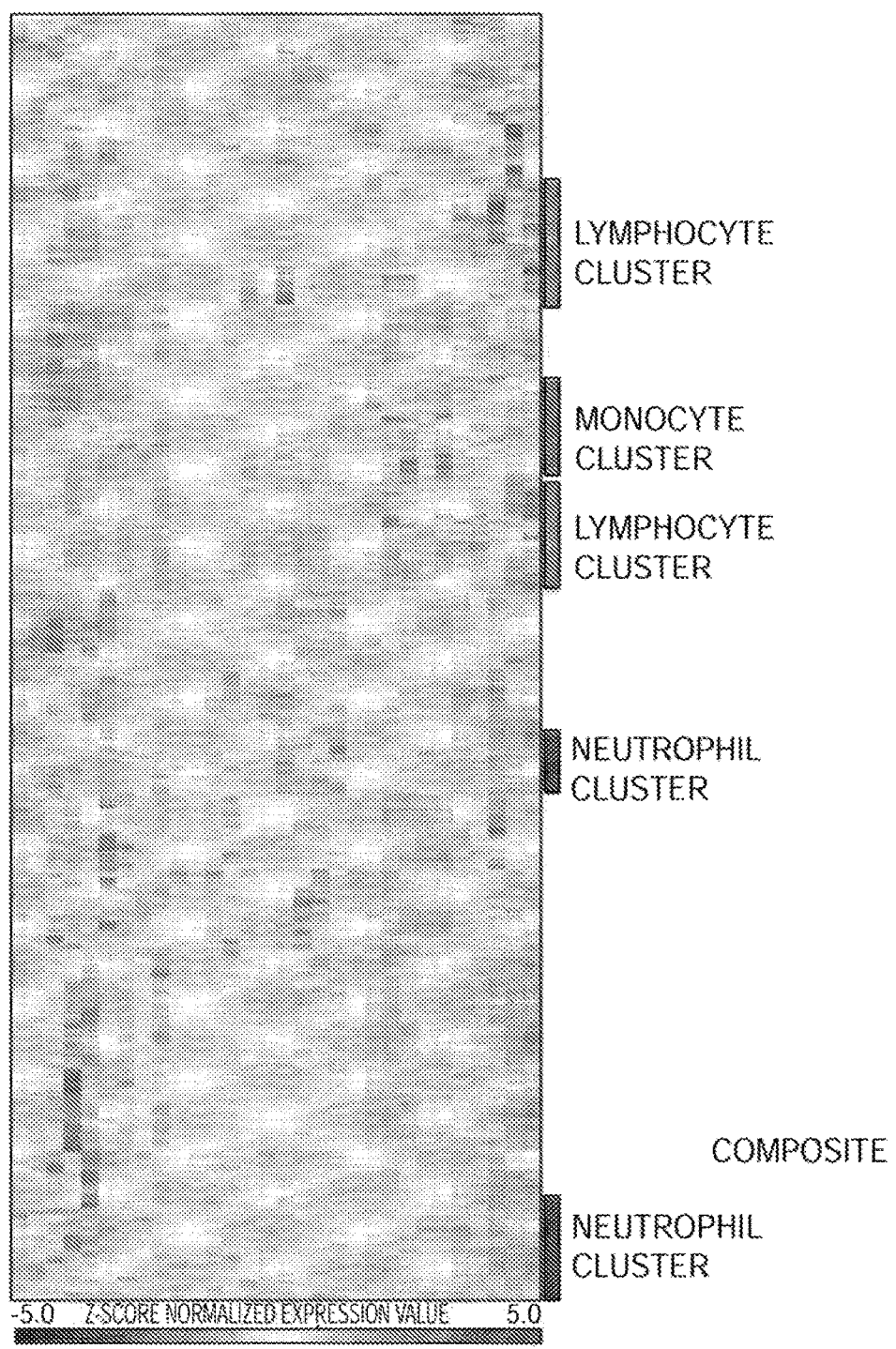
FIG. 11B Con.

DIAGNOSTIC METHODS FOR INFECTIOUS DISEASE USING ENDOGENOUS GENE EXPRESSION

CROSS REFERENCE TO RELATED APPLICATIONS

This application claims the benefit of U.S. application Ser. No. 15/080,236, which claims priority benefit of International Application PCT/US14/57164, Filed on Sep. 24, 2014, which claims priority to U.S. Provisional Application Ser. No. 61/881,508 filed Sep. 24, 2013. Each of these applications is incorporated herein by reference, each in its entirety.

STATEMENT REGARDING FEDERALLY SPONSORED RESEARCH

This invention was made with government support under NIH Grants 1UAH2A1083266-01 from the NIAID, UL1 RR024992 from the NIH-National Center for Research Resources, and the Training Grant T32HD049338 from the NICHD. The government has certain rights in the invention.

INTRODUCTION

Despite absence of bacterial infection, many febrile children are treated with antibiotics. Virus and bacteria interact with different pattern recognition receptors in circulating blood leukocytes, triggering specific host transcriptional programs mediating immune response. Unique transcriptional signatures can be defined that discriminate viral from bacterial causes of certain infectious disorders. Viral infections can be a cause of Fever Without an Apparent Source (FWS) in young children. Host transcriptional profiles can be useful if a pathogen is not detected or if the pathogenic role of a detected agent is in question.

Circulating blood leukocytes can react to pathogens by recognizing pathogen-specific molecular patterns through pattern recognition receptors leading to up or down-regulation of the expression of host genes associated with immune functions (Takeuchi, O., et al. 2010. *Cell* 140: 805-820 and Thompson, M. R., et al. 2011. *Viruses* 3: 920-940). Host transcriptional programs can be differentially activated with different pathogens (Paschos. K., et al. 2010. *Trends Microbial.* 18(10):439-447).

Other studies have attempted to use host transcriptional signatures to distinguish respiratory viral infections from respiratory bacterial infections using "acute viral respiratory signatures" (Ramilo, O., et al. 2007, *Blood* 109: 2066-2077; Ramilo, O., et al. 2009, *Cell Host Microbe* 6: 199-200; Zaas, A. K., et al. 2009, *Cell Host Microbe* 6: 207-217).

Host transcriptional analysis has additionally been applied in other previous studies. Popper, S. J., et al. 2009, *J. Infect. Dis.* 200: 657-666, used specific gene expression profiles to distinguish Kawasaki disease from adenovirus infections. Ardura, M. I., et al. 2009, *PLoS One* 4(5):e5446, characterized acute invasive *S. aureus* infections. Berry, M. P., et al. 2010, *Nature* 466: 973-977, distinguished active tuberculosis from other infectious and inflammatory diseases. Pankla, R., et al. 2009, *Genome Biol.* 10: R127 distinguished septicemic melioidosis from other causes. Stojanov, S., et al. 2011, *Proc. Nat'l. Acad. Sci. USA* 108: 7148-7153, identified potential biomarkers to aid in distinguishing PFAPA flares from asymptomatic intervals, HPF (hereditary periodic fevers) flares, and healthy controls. Loughman, J. A., et al. *J. Infect. Dis.* 2009, 199: 294-301, demonstrated staphylococcal gene expression and regulation directly in human tissue. Wang, Z. Q., et al. *J. Med. Virol.* 2012, 84: 1254-1266, identified a gene expression profile to evaluate the effects of HAdV-36 on gene transcription.

PCT/US2007/075713 (WO 2008/024642 A2) of Banchereau, J. F., et al., describes specific gene expression biomarkers for the differential diagnosis of *S. aureus, E. coli*, and influenza infections. PCT/US2010/046042 (WO 2011/066008 A2) of Banchereau, J. F., et al., describes blood transcriptional signatures of active versus latent *Mycobacterium tuberculosis* infections.

Bleeker, S. E., et al. "Predicting serious bacterial infection in young children with Fever Without Apparent Source." *Acta Paediatr.* 2001 90: 1226-32 used predictors from patient history, examination, and laboratory tests to determine bacterial causes of some subjects with FWS. The laboratory tests were white blood cell count, serum C-reactive protein and the presence of >70 white blood cells in urinalysis. Their diagnostic methods do not include an analysis of changes in host gene expression.

The current clinical standard for diagnosis of Fever Without an Apparent Source is a white blood cell count test using a cutoff of $15,000/mm^3$ as recommended by the American Academy of Pediatrics in their guideline for the management of febrile children 0-36 months of age (Baraff, L. J., et al. 1993, *Ann. Emerg. Med.* 22: 1198-1210). Previous studies indicate that white blood cell count is an inadequate tool for distinguishing between viral and bacterial infection, a distinction often used to determine whether or not to treat the patient with antibiotics (Rudinsky, S. L., et al. 2009, *Acad. Emerg. Med.* 16: 585-590 and Herz, A. M., et al. 2006, *Pediatr. Infect. Dis. J.* 25: 293-300), 30% of white blood cell count test results for diagnosis of Fever Without an Apparent Source are inaccurate. There is thus a need for a more accurate methods of diagnosis for Fever Without an Apparent Source.

U.S. application Ser. No. 11/268,373 (US20080020379 A1) of Agan, B. K., et al. provides a specific set of host gene expression markers for identification of pathogenic infections with 47 genes as the minimal number of genes to classify febrile versus non-febrile patients.

Analysis of host transcriptional profiles has been applied to the diagnosis of inflammatory and hematological diseases. For example in Allantaz, F., et al. 2007, *J. Exp. Med.* 204: 2131-2144; Aaroe, J., et al. 2010, *Breast Cancer Res* 12:R7; Alizadeh, A. A., et al. 2000, *Nature* 403: 503-511; and Chaussabel, D., et al. 2011, "Blood Transcriptional Fingerprints to Assess the Immune Status of Human Subjects," Immunologic Signatures of Rejection, ed. Marincola F M (Springer, New York), pp 105-125.

The application of molecular viral detection tests to clinical medicine can detect asymptomatic as well as symptomatic infection (Colvin, J. M., et al. 2012, *Pediatrics* 130: e1455-1462) and has thus created a need to determine the clinical significance of the detection of viral nucleic acid in an individual patient.

In recent studies, infection with specific viruses has been confirmed in children with FWS (Colvin, J. M., et al. 2012, *Pediatrics* 130(6): e1455-1462; Wylie, K. M., et al. *PLoS One.* 2012; 7(6):e27735; and Hu, X., et al. *Proc. Nat'l. Acad. Sci. USA.* 2013 110:12792-12797).

While some other previous studies provide clinical information in certain groups of subjects and for some particular diseases and/or infections, they can be limited in application and accuracy. Thus, there is a need for more accurate diagnostic methods for diseases such as Fever Without an Apparent Source (FWS). Additionally, there is a need for diagnostic methods for more accurately discriminating subjects with viral from bacterial infections.

SUMMARY

The present inventor has developed a prognostic model for diagnosis of a pathogen-associated or pathogen-based disease in a subject. The expression levels of endogenous prognostic genes can provide clinically beneficial assays as well as biological insights. In various embodiments, testing expression levels of endogenous prognostic genes can be supplemented with assays to determine presence, absence, and/or quantity of a pathogen.

The present inventor discloses methods of diagnosis of a pathogen-associated disease in a subject. Additionally disclosed are methods of distinguishing a viral-caused infection from a bacterial-caused infection or a combination thereof. Additionally disclosed are methods of diagnosis of a viral pathogen-associated disease and methods of diagnosis of Fever Without an Apparent Source (FWS).

In various embodiments, the present teachings include: host transcriptional profiles that can distinguish symptomatic from asymptomatic viral infection; virus-specific transcriptional profiles for DNA and RNA viruses that cause systemic infection; and viral and bacterial-specific transcriptional profiles that can distinguish between infections caused by different pathogens. In various embodiments, diagnostic methods of the present teachings include detecting transcriptional changes in multiple endogenous genes in multiple pathways in febrile children who are infected with DNA viruses, RNA viruses, or bacteria.

Host transcriptional analysis can be a clinically relevant testing method, and additionally, can supplement pathogen-based nucleic acid amplification assays. Host transcriptional analysis can provide results associated with etiology. In some embodiments, host transcriptional analysis can provide results associated with etiology even when no pathogens are confirmed from the direct detection testing for microbial pathogens.

In some embodiments, host blood transcriptional signatures associated with categories of infectious etiology, can be defined in a subject with FWS, such as a young child with FWS. In some embodiments, host blood transcriptional signatures can be of increased accuracy and predictive value than white blood cell count-based criteria alone in discriminating a febrile child with a viral infection from a febrile child with a bacterial infection. In some embodiments, host blood transcriptional signatures can be a supplement to tests that detect the presence of a possible pathogen but do not address its pathogenic role in the subject. In some embodiments, some genes of the Interferon Signaling Pathway can be uniquely activated in a febrile child with a viral infection. In some embodiments, some genes of the Integrin Signaling Pathway can be uniquely activated in a child with a bacterial infection. In some embodiments, host transcriptional profiles can be used to classify a febrile child with a viral or a bacterial infection with more accuracy than a blood white blood cell (WBC) count.

In some embodiments, the present teachings include methods of diagnosis of a pathogen-based disease in a subject, and methods of determining etiology of a pathogen-based disease in a subject. In various configurations, these methods comprise: a) providing at least one biological sample from a human subject; b) determining presence, absence and/or quantity of a bacterial pathogen, a viral pathogen, or a combination thereof, by a pathogen culture, a serum antibody detection test, a pathogen antigen detection test, a pathogen DNA detection test, a pathogen RNA detection test, or a combination thereof; and c) determining in the at least one sample, expression levels of at least one endogenous gene in which aberrant expression levels are associated with infection with a pathogen, by a microarray hybridization assay, an RNA-seq assay, a polymerase chain reaction assay, a LAMP assay, a ligase chain reaction assay, a Southern blot assay, a Northern blot assay, a Western blot assay, an enzyme-linked immunosorbent assay (ELISA) or a combination thereof, whereby the subject is diagnosed with the disease if the subject comprises the pathogen and the subject has an aberrant level of expression of at least one gene associated with aberrant expression levels associated with infection with the pathogen. In some configurations, the subject is diagnosed with the disease if the subject has an aberrant level of expression of at least 1.5 fold increase or decrease of the at least one gene, wherein an aberrant level of expression of the at least one gene is associated with infection with the pathogen. In some configurations, the at least one endogenous gene can consist of one gene. In some configurations, the at least one endogenous gene can consist of two genes. In some configurations, the at least one endogenous gene can consist of three genes. In some configurations, the at least one endogenous gene can consist of four genes. In some configurations, the at least one endogenous gene can consist of five genes. In some configurations, the at least one endogenous gene can consist of six genes. In some configurations, the at least one endogenous gene can consist of seven genes. In some configurations, the at least one endogenous gene can consist of eight genes. In some configurations, the at least one endogenous gene can consist of nine genes. In some configurations, the at least one endogenous gene can consist of ten genes. In some configurations, the at least one endogenous gene can consist of eleven genes. In some configurations, the at least one endogenous gene can consist of twelve genes. In some configurations, the at least one endogenous gene can consist of thirteen genes. In some configurations, the at least one endogenous gene can consist of fourteen genes. In some configurations, the at least one endogenous gene can consist of fifteen genes. In some configurations, the at least one endogenous gene can consist of sixteen genes. In some configurations, the at least one endogenous gene can consist of seventeen genes. In some configurations, the at least one endogenous gene can consist of eighteen genes. In some configurations, the at least one endogenous gene can consist of nineteen genes. In some configurations, the at least one endogenous gene can consist of twenty genes. In some configurations, the at least one endogenous gene can consist of 21 genes. In some configurations, the at least one endogenous gene can consist of 22 genes. In some configurations, the at least one endogenous gene can consist of 23 genes. In some configurations, the at least one endogenous gene can consist of 24 genes. In some configurations, the at least one endogenous gene can consist of 25 genes. In some configurations, the at least one endogenous gene can consist of 26 genes. In some configurations, the at least one endogenous gene can consist of 27 genes. In some configurations, the at least one endogenous gene can consist of 28 genes. In some configurations, the at least one endogenous gene can consist of 29 genes. In some configurations, the at least one endogenous gene can consist of 30 genes. In some configurations, the at least one endogenous gene can consist of 31 genes. In some configurations, the at least one endogenous gene can consist of 32 genes. In some configurations, the at least one endogenous gene can consist of 33 genes. In some configurations, the disease can be Fever Without an Apparent Source. In some configurations, the pathogen can be a virus. In some configurations, the virus can be selected from the group consisting of an adenovirus, an enterovirus, a human herpesvirus 6 (HHV-6) and a rhinovirus. In some configurations, the pathogen can be a bacterium. In some configurations, the bacterium can be selected from the group consisting of an *Escherichia coli*, a *Staphylococcus aureus*, a *Streptococcus pneumoniae* and a combination thereof. In some configurations, the at least one endogenous gene can be selected from the group consisting of IFI27, ISG15, OTOF, IFIT3, ITGAM and ITGAX. In some configurations, the at least one gene can comprise, consist essentially of, or consist of OTOF and ITGAX. In some configurations, the at least one gene can be selected from the group consisting of OTOF and ITGAX. In some configurations, the at least one gene can comprise, consist essentially of, or consist of IFI27 and ITGAM. In some configurations, the at least one gene can be selected from the group consisting of IFI27 and ITGAM. In some configurations, the determining expression levels can comprise, consist essentially of, or consist of a real time polymer se chain reaction assay, a reverse transcriptase polymerase chain reaction assay, or a combination thereof. In some configurations, the determining expression levels can comprise, consist essentially of, or consist of an oligonucleotide array assay, a probe hybridization assay, a gene expression array assay, a cDNA microarray hybridization assay or a combination thereof. In some configurations, the microarray hybridization assay can comprise, consist essentially of, or consist of from 1 to 47,300 probes, or about 47.300 probes. In some configurations, the microarray hybridization assay can comprise, consist essentially of, or consist of from 1 to 5700 probes, or about 5700 probes. In some configurations, the microarray hybridization assay can comprise, consist essentially of, or consist of from 1 to 50 probes, or about 50 probes. In some configurations, the microarray hybridization assay can comprise, consist essentially of, or consist of from 1 to 10 probes, or about 10 probes. In some configurations, the microarray hybridization assay can comprise, consist essentially of, or consist of between 18 and 33 probes, or about 33 probes. In some configurations, the microarray hybridization assay can comprise, consist essentially of, or consist of from 1 to 260 probes, or about 260 probes. In some configurations, the microarray hybridization assay can comprise, consist essentially of, or consist of from 1 to 1321 probes, or about 1321 probes. In some configurations, the microarray hybridization assay can comprise, consist essentially of, or consist of from 1 to 18 probes, or about 18 probes. In some configurations, the microarray hybridization assay can comprise, consist essentially of, or consist of from 1 to 22 probes, or about 22 probes. In some configurations, the microarray hybridization assay can comprise, consist essentially of, or consist of from 1 to 33 probes, or about 33 probes. In some configurations, the microarray hybridization assay can comprise, consist essentially of, or consist of from 1 to 260 viral response-specific probes or about 260 viral response-specific probes and from 1 to 1321 bacterial response-specific probes or about 1321 bacterial response-specific probes. In some configurations, the microarray hybridization assay can comprise, consist essentially of, or consist of from 1 to 3467 HHV-6 response-specific probes or about 3467 HHV-6 response-specific probes. In some configurations, the microarray hybridization assay can comprise, consist essentially of, or consist of from 1 to 464 HHV-6 response-specific probes or about 464 HHV-6 response-specific probes. In some configurations, the microarray hybridization assay can comprise, consist essentially of, or consist of from 1 to 798 HHV-6 response-specific probes or about 798 HHV-6 response-specific probes. In some configurations, the microarray hybridization assay can comprise, consist essentially of, or consist of from 1 to 5604 adenovirus response-specific probes or about 5604 adenovirus response-specific probes. In some configurations, the microarray hybridization assay can comprise, consist essentially of, or consist of from 1 to 2078 adenovirus response-specific probes or about 2078 adenovirus response-specific probes. In some configurations, the microarray hybridization assay can comprise, consist essentially of, or consist of from 1 to 847 adenovirus response-specific probes or about 847 adenovirus response-specific probes. In some configurations, the microarray hybridization assay can comprise, consist essentially of, or consist of from 1 to 4184 enterovirus response-specific probes or about 4184 enterovirus response-specific probes. In some configurations, the microarray hybridization assay can comprise, consist essentially of, or consist of from 1 to 594 enterovirus response-specific probes or about 594 enterovirus response-specific probes. In some configurations, the microarray hybridization assay can comprise, consist essentially of, or consist of from 1 to 678 enterovirus response-specific probes or about 678 enterovirus response-specific probes. In some configurations, the microarray hybridization assay can comprise, consist essentially of, or consist of from 1 to 1234 bacterial response-specific probes or about 1234 bacterial response-specific probes. In some configurations, the microarray hybridization assay can comprise, consist essentially of, or consist of from 1 to 1939 bacterial response-specific probes or about 1939 bacterial response-specific probes. In some configurations, the at least one biological sample can be selected from the group consisting of peripheral blood mononuclear cells, a nasopharyngeal sample, a urine sample, a blood sample, a lumbar puncture sample, a bodily fluid, a biopsy sample, a tissue sample and a combination thereof. In some configurations, the at least one biological sample can comprise, consist essentially of, or consist of a peripheral blood sample. In some configurations, the at least one biological sample can comprise, consist essentially of, or consist of peripheral blood mononuclear cells. In some configurations, the at least one endogenous gene can be selected from the group consisting of Role of Pattern Recognition Receptors in Recognition of Bacteria and Viruses Pathway genes, TREM1 Signaling Pathway genes, Toll-like Receptor Signaling Pathway genes, Natural Killer Cell Signaling Pathway genes, Interferon Signaling Pathway genes, Activation of Interferon Regulatory Factors by Cytosolic Pattern Recognition Receptors Pathway genes, Integrin Signaling Pathway genes and a combination thereof. In some configurations, the at least one endogenous gene can comprise, consist essentially of, or consist of an Interferon Signaling Pathway gene. In some configurations, the at least one endogenous gene can comprise, consist essentially of, or consist of an Integrin Signaling Pathway gene. In some configurations, the human subject can be a human child, such as, without limitation, a human subject between 0 to 36 months of age. In some configurations, the human subject can be a human child, such as, without limitation, a human subject between 2 to 36 months of age.

In some embodiments, the present teachings include methods of distinguishing a viral-caused infection from a bacterial-caused infection or a combination thereof in a subject. In various configurations, these methods can comprise: a) obtaining at least one biological sample from a human subject; b) determining presence, absence and/or quantity of a viral pathogen by a pathogen culture, a serum antibody detection test, a pathogen antigen detection test, a pathogen DNA detection test, a pathogen RNA detection test or a combination thereof; c) determining presence, absence and/or quantity of a bacterial pathogen by a pathogen culture, a serum antibody detection test, a pathogen antigen detection test, a pathogen DNA detection test, a pathogen RNA detection test or a combination thereof; and d) determining in the at least one sample, expression level of at least one endogenous gene in which aberrant expression is associated with infection with a viral pathogen, and expression level of at least one endogenous gene in which aberrant expression is associated infection with a bacterial pathogen, by an assay selected from the group consisting of a microarray hybridization assay, an RNA-seq assay, a polymerase chain reaction assay, a LAMP assay, a ligase chain reaction assay, a Southern blot assay, a Northern blot assay, a Western blot assay, an enzyme-linked immunosorbent assay and a combination thereof, whereby the subject is diagnosed with a viral infection if the sample comprises a) a virus pathogenic for the infection and b) aberrant expression level of at least one endogenous gene associated with a viral infection, and whereby the subject is diagnosed with a bacterial infection if the sample comprises a) a bacterium pathogenic for the infection and b) aberrant expression level of at least one endogenous gene associated with a bacterial infection.

In various configurations, the at least one gene associated with a bacterial infection can be selected from the group consisting of FYN, CD247, EITPR3, CD3, ZAP70, PLCG1, PRKCH, LCK, LAT, PRKCQ, ITK, RHOU, GNA13, PPP1R12A, RHOT1, FCER1G, LYN, RALB, GNAQ, MARCKS, TGM2, ARHGEF11, MYL12A, EP300, MYL9, CREB5. FCGR2A, GNG10, GNG11, C1QB, NOD2, TLR2, TLR1, RNASEL, C5AR1, TLR4, MYD88, PIK3CB, C3AR1, TLR6, CASP1, TLR5, NLRC4, TLR8, IL1B, ITGB7, TSPAN4, PPP1R1, ZYX, VASP, ITGA2B, ITGB5, VCL, ITGB3, MYLK, ASAP1, ITGAM, ITGAX, KLRD1, KIR2DL3, KIR2DL4, KIR3DL3, KIR3DL1, HCST, CD247, NCR3, FCGR3B, SIGLEC9, FCER1G, JAK2, CASP5 and a combination thereof. In some configurations, the at least one gene associated with a bacterial infection can be selected from the group consisting of RHOU, GNA13, PPP1R12A, RHOT1, FCER1G, LYN, RALB, GNAQ, MARCKS, TGM2, ARHGEF11, MYL12A, EP300, MYL9, CREB5, FCGR2A, GNG10, GNG11, C1QB, NOD2, TLR2, TLR1, RNASEL, C5AR1, TLR4, MYD88, PIK3CB, C3AR1, TLR6, CASP1, TLR5, NLRC4, TLR8, IL1B, PPP1R1, ZYX, MYL12A, VASP, ITGA2B, ITGB5, VCL, ITGB3, MYLK, ASAP1, ITGAM, ITGAX, FCGR3B, SIGLEC9, FCER1G, JAK2, CASP5 and a combination thereof, wherein the at least one gene has an aberrant level of expression of at least a 1.5 fold increase compared to a control level. In some configurations, the at least one gene associated with a bacterial infection can be selected from the group consisting of FYN, CD247, EITPR3, CD3, ZAP70, PLCG1, PRKCH, LCK, LAT, PRKCQ, ITK, ITGB7, TSPAN4, KLRD1, KIR2DL3, KIR2DL4, KIR3DL3, KIR3DL1, HCST, CD247, NCR3 and a combination thereof, wherein the at least one gene has an aberrant level of expression of at least a 1.5 fold decrease compared to a control level. In some configurations, the at least one gene associated with a bacterial infection is selected from the group consisting of FYN, CD247, EITPR3, CD3, ZAP70, PLCG1, PRKCH, LCK, LAT, PRKCQ, ITK, ITGB7, TSPAN4, KLRD1, KIR2DL3, KIR2DL4, KIR3DL3, KIR3DL1, HCST, CD247, NCR3 and a combination thereof, wherein the at least one gene has an aberrant level of expression of at least a 1.5 fold decrease compared to a control level. In some configurations, the at least one gene associated with a bacterial infection can be an Annexin A3 gene. In various configurations, if the disease is determined to be due to a bacterial infection, the patient can be treated by routine methods such as administration of an antibiotic, which can be any antibiotic known to skilled artisans. In various configurations, if the disease is determined to be due to a viral-caused infection, the patient can be treated by routine methods such as administration of an anti-viral drug, which can be any anti-viral drug known to skilled artisans.

In some embodiments, the present teachings include methods of diagnosing or determining etiology of Fever Without an Apparent Source in a subject. In various configurations, these methods can comprise: a) providing at least one biological sample from a human subject; b) determining presence, absence and/or quantity of a bacterial pathogen, viral pathogen, or a combination thereof, by a pathogen culture, a serum antibody detection test, a pathogen antigen detection test, a pathogen DNA detection test, a pathogen RNA detection test, or a combination thereof; c) determining in the sample, expression levels of at least one endogenous gene associated with aberrant expression levels resulting from infection with the pathogen, by a microarray hybridization assay, an RNA-seq assay, a polymerase chain reaction assay, a LAMP assay, a ligase chain reaction assay, a Southern blot assay, a Northern blot assay, a Western blot assay, an enzyme-linked immunosorbent assay or a combination thereof, whereby the subject is diagnosed with the disease if the sample comprises the pathogen and the sample exhibits an aberrant level of expression of at least one gene associated with aberrant expression levels resulting from infection with the pathogen. In various configurations, if the FWS is determined to be due to a bacterial infection, the patient can be treated by routine methods such as administration of an antibiotic. In various configurations, if the disease is determined to be due to a viral infection, the patient can be treated by routine methods such as administration of an anti-viral drug. In various configurations, the sample can be a peripheral blood sample, a nasopharyngeal sample, a urine sample, a blood sample, a lumbar puncture sample, a bodily fluid, a biopsy sample, a tissue sample or a combination thereof in some embodiments, the present teachings include methods of diagnosing or determining etiology of a pathogen-associated disease. In various configurations, these methods can comprise: a) providing at least one biological sample from a human subject; b) determining presence, absence and/or quantity of a bacterial pathogen, viral pathogen, or a combination thereof, by an assay selected from the group consisting of a pathogen culture, a serum antibody detection test, a pathogen antigen detection test, a pathogen DNA detection test, a pathogen RNA detection test and a combination thereof; c) determining in the sample, expression levels of at least one endogenous gene selected from the group consisting of IFI27, ISG15, OTOF, IFIT3, ITGAM, ITGAX and a combination thereof, by an assay selected from the group consisting of a microarray hybridization assay, an RNA-seq assay, a polymerase chain reaction assay, a LAMP assay, a ligase chain reaction assay, a Southern blot assay, a Northern blot assay, a Western blot assay, an enzyme-linked immunosorbent assay, or a combination thereof, whereby the subject is diagnosed with the disease if the sample comprises the pathogen and the sample exhibits an aberrant level of expression of at least one gene selected from the group consisting of IFI27, ISG15, OTOF, IFIT3, ITGAM, ITGAX and a combination thereof.

In some embodiments, the present teachings include methods of diagnosing a viral pathogen-associated disease. In various configurations, these methods can comprise: a) providing at least one biological sample from a human subject; b) determining presence, absence and/or quantity of a virus selected from the group consisting of an adenovirus, an enterovirus, HHV-6, or a combination thereof, by a pathogen culture, a serum antibody detection test, a pathogen antigen detection test, a pathogen DNA detection test, a pathogen RNA detection test, or a combination thereof; c) determining in the sample, expression level of at least one endogenous gene that exhibits aberrant expression during infection with the virus, by an assay selected from the group consisting of a microarray hybridization assay, an RNA-seq assay, a polymerase chain reaction assay, a LAMP assay, a ligase chain reaction assay, a Southern blot assay, a Northern blot assay, a Western blot assay, an enzyme-linked immunosorbent assay and a combination thereof, whereby the subject is diagnosed with the disease if the sample comprises a) the virus and b) an aberrant expression level of the at least one gene.

In some embodiments, the present teachings include methods of diagnosing a pathogen-associated disease. In various configurations, these methods can comprise: a) obtaining at least one biological sample from a human subject; and b) determining in the sample, expression levels of at least one endogenous gene selected from the group consisting of IFI27, ISG15, OTOF, IFIT3, ITGAM, ITGAX and a combination thereof, by a microarray hybridization assay, an RNA-seq assay, a polymerase chain reaction assay, a LAMP assay, a ligase chain reaction assay, a Southern blot assay, a Northern blot assay, a Western blot assay, an enzyme-linked immunosorbent assay or a combination thereof, whereby the subject is diagnosed with the disease if the sample exhibits an aberrant level of expression of at least one gene selected from the group consisting of IFI27, ISG15, OTOF, IFIT3, ITGAM, ITGAX, and a combination thereof. In some configurations, the disease can be Fever Without an Apparent Source. In some configurations, the biological sample can comprise peripheral blood mononuclear cells.

In various configurations of the embodiments, the at least one aberrant level of expression can be at least a 2 fold increase or decrease compared to a control level. In various configurations of the embodiments, the at least one aberrant level of expression can be the at least one aberrant level of expression is at least a 1.5 fold increase or decrease compared to a control level. In various configurations of the embodiments, the at least one aberrant level of expression can be is at least a 1.5 fold increase or decrease compared to a control level.

In various configurations of the embodiments, the at least one gene associated with an adenoviral infection can be selected from the group consisting of ATM, PRKCH, PRKCQ, C1QB, C1QC, IRF7, OAS3, OAS1, OAS2, AK2, EIF2, IFIH1, DDX58, NOD2, TLR5, NLRC4, TLR8, C3AR1, IL1B, TLR1, TLR4, TLR6, MYD88, CASP1, IFIT3, IFI35, BCL2, MED14, IFNGR2, IFNAR1, IRF1, BAX, IRF9, PSMB8, IFITM1, JAK2, STAT2, TAP1, IKBKB, IKBKAP, KIAA1271, TRAF6, TNF, TBK1, TANK, IRF9, NFKBIA, IRF7, ISG15, ADAR, ZBP1, IFIT2, FOS, LY96, TLR5, IRAK3, TLR8, EIF2AK2, CD14, MAPK14, STAT4, HS.572649, CCR7, CD40LG, LTB, HLA-DOA, CREB5, FCGR3B, FCGR2A, IL1RN, LTBR, TYROBP, FCER1G, FCGR1A, FCGR1B and a combination thereof.

In various configurations of the embodiments, the at least one gene associated with an adenoviral infection can be selected from the group consisting of C1QB, C1QC, IRF7, OAS3, OAS1, OAS2, AK2, EIF2, IFIH1, DDX58, NOD2, TLR5, NLRC4, TLR8, C3AR1, IL1B, TLR1, TLR4, TLR6, MYD88, CASP1, IFIT3, IFI35, BCL2, IFNAR1, IRF1, BAX, IRF9, PSMB8, IFITM1, JAK2, STAT2, TAP1, TRAF6, TNF, TBK1, TANK, IRF9, NFKBIA, IRF7, ISG15, ADAR, ZBP1, IFIT2, FOS, LY96, TLR5, IRAK3, TLR8, EIF2AK2, CD14, MAPK14, CREB5, FCGR3B, FCGR2A, IL1RN, LTBR, TYROCBP, FCER1G, FCGR1A, FCGR1B and a combination thereof wherein the at least one gene has an aberrant level of expression of at least a 1.5 fold increase compared to a control level.

In various configurations of the embodiments, the at least one gene associated with an adenoviral infection can be selected from the group consisting of ATM, PRKCH, PRKCQ, MED14, IFNGR2, IKBKB, IKBKAP, KIAA1271, STAT4, HS.572649, CCR7, CD40LG, LTB, HLA-DOA and a combination thereof, wherein the at least one gene has an aberrant level of expression of at least a 1.5 fold decrease compared to a control level.

In various configurations of the embodiments, the at least one gene associated with an enteroviral infection can be selected from the group consisting of NLRC4, TLR8, TLR5, NOD2, RNASEL, TLR2, TLR1, C5AR1, MYD88, TLR6, CASP1, IL1B, C1QB, IRF7, OAS1, OAS3, EIF2AK2, DDX58, IFIH1, OAS2, IFIT1, IFIT3, IFI35, MX1, TAP1, STAT2, IFITM1 STAT1, JAK2, IRF7, ISG15, IFIT2, DHX58, ZBP1, FOS, LY96, MAP2K3, MAPK14, CASP5 and a combination thereof.

In various configurations of the embodiments, the at least one gene associated with an enteroviral infection can be selected from the group consisting of NLRC4, TLR8, TLR5, NOD2, RNASEL, TLR2, TLR1, C5AR1, MYD88, TLR6, CASP1, IL1B, C1QB, IRF7, OAS1, OAS3, EIF2AK2, DDX58, IFIH1, OAS2, IFIT1, IFIT3, IFI35, MX1, TAP1, STAT2, IFITM1, STAT1, JAK2, IRF7, ISG15, IFIT2, DHX58, ZBP1, FOS, LY96, MAP2K3, MAPK14, CASP5 and a combination thereof, wherein the at least one gene has an aberrant level of expression of at least a 1.5 fold increase compared to a control level.

In various configurations of the embodiments, the at least one gene associated with an HHV-6 infection can be selected from the group consisting of CCL5, PRKCH, TLR5, TLR2, NOD2, TLR8, TLR4, TLR6, C1QA, MYD88, RIPK2, IL1B, C3AR1, CASP1, C1QB, C1QC, OAS1, IRF7, OAS3, EIF2AK2, TLR7, OAS2, DDX58, IFIH1, IFIT3, IFIT1, SOCS1, MX1, IFI35, IFITM1, TAP1, STAT2, JAK2, STAT1, TYROBP, CD86, IL1B, CASP5, CCL2, TLR9, TRAF6, IRAK4, CHUK, CD14, MYD88, TLR1, FOS, LY96 and a combination thereof.

In various configurations of the embodiments, the at least one gene associated with an HHV-6 infection can be selected from the group consisting of TLR5, TLR2, NOD2, TLR8, TLR4, TLR6, C1QA, MYD88, RIPK2, IL1B, C3AR1, CASP1, C1QB, C1QC, OAS1, IRF7, OAS3, EIF2AK2, TLR7, OAS2, DDX58, IFIH1, IFIT3, IFIT1, SOCS1, MX1, IFI35, IFITM1, TAP1, STAT2, JAK2, STAT1, TYROBP, CD86, IL1B, CASP5, CCL2, TRAF6, IRAK4, CHUK, CD14, MYD88, TLR1, FOS, LY96 and a combination thereof, wherein the at least one gene has an aberrant level of expression of at least a 1.5 fold increase compared to a control level.

In various configurations of the embodiments, the at least one gene associated with an HHV-6 infection can be selected from the group consisting of CCL5, PRKCH and TLR9, wherein the at least one gene has an aberrant level of expression of at least a 1.5 fold decrease compared to a control level. In some configurations, the at least one gene can be selected from the group consisting of MYH9, ARAP3, CDKN1C, MT2A, SPATS2L, IRF7, ZBP1, OAS2, OAS1, ISG15, IFI6, HERC5, OAS3, RSAD2, OASL, IFIT3, OTOF and IFI27.

In various configurations of the embodiments, the at least one gene associated with a viral infection can be selected from the group consisting of CDKN1C, MT2A, SPATS2L, IRF7, ZBP1, OAS2, OAS1, ISG15, IFI6, HERC5, OAS3, RSAD2, OASL, IFIT3, OTOF and IFI27, wherein the at least one gene has an aberrant level of expression of at least a 1.5 fold increase compared to a bacterium-infected control level. In some configurations, the at least one gene can be selected from the group consisting of MYH9 and ARAP3, wherein the at least one gene has an aberrant level of expression of at least a 1.5 fold decrease compared to a bacterium-infected control level. In some configurations, the at least one gene can be selected from the group consisting of BAK1, RRAS, ACTR2, NCK2, PIK3CB, MAP2K4, ITGA2B, ITGB3, MYLK, MYL9, ITGB5, GNG11, ZYX, ITGAX, IFNGR1, ITGAM, STAT2, IFI35, MX1, OAS1, IFIT1 and IFIT3.

In various configurations of the embodiments, the at least one gene associated with a viral infection can be selected from the group consisting of BAK1, IFNGR1, STAT2, IFI35, MX1, OAS1, IFIT1 and IFIT3, wherein the at least one gene has an aberrant level of expression of at least a 1.5 fold increase compared to a bacterium-infected control level. In some configurations, the at least one gene can be selected from the group consisting of RRAS, ACTR2, NCK2, PIK3CB, MAP2K4, ITGA2B, ITGB3, MYLK, MYL9, ITGB5, GNG11, ZYX, ITGAX and ITGAM, wherein the at least one gene has an aberrant level of expression of at least a 1.5 fold decrease compared to a bacterium-infected control level. In some configurations, the at least one gene can be selected from the group consisting of OSBPL8, VHL, ACTR2, MAP2K4, F13A1, PROS1, ITGB3, MYL9, ITGA2B, ITGB5, GNG11, EP300, ZYX, ARAP3, AGER, ITGAX, SORL1, IFNGR1, IFNGR2, ITGAM, MT2A, SPATS2L, OAS2, OAS1, ISG15, IFI6, IFIT1, HERC5, OAS3, RSAD2, OASL, OTOF and IFI27. In some configurations, the at least one gene can be selected from the group consisting of IFNGR1, IFNGR2, MT2A, SPATS2L, OAS2, OAS1, ISG15, IFI6, IFIT1, HERC5, OAS3, RSAD2, OASL, OTOF and IFI27, wherein the at least one gene has an aberrant level of expression of at least a 1.5 fold increase compared to a bacterium-infected control level. In some configurations, the at least one gene can be selected from the group consisting of OSBPL8, VHL, ACTR2, MAP2K4, F13A1, PROS1, ITGB3, MYL9, ITGA2B, ITGB5, GNG11, EP300, ZYX, ARAP3, AGER, ITGAX, SORL1 and IGTAM, wherein the at least one gene has an aberrant level of expression of at least a 1.5 fold decrease compared to a bacterium-infected control level. In some configurations, the at least one gene can be selected from the group consisting of IFI27, ISG15, OTOF and IFIT3, whereby the subject is diagnosed with a viral infection if the subject has an aberrant level of expression of at least a 1.5 fold increase of at least one gene selected from the group consisting of IFI27, ISG15, OTOF and IFIT3, compared to bacterial-infected control level. In some configurations, the at least one gene can be selected from the group consisting of IFI27, IFIT3, and a combination thereof, whereby the subject can be diagnosed with febrile HHV-6 if the subject has an aberrant level of expression of at least a 1.5 fold increase of the at least one gene selected from the group consisting of IFI27 and IFIT3, compared to an afebrile HHV-6 control level or a febrile control level. In some configurations, the at least one gene can be selected from the group consisting of IFI27, ISG15, and a combination thereof, whereby the subject can be diagnosed with febrile adenovirus if the subject has an aberrant level of expression of at least a 1.5 fold increase of the at least one gene selected from the group consisting of IFI27 and ISG15, compared to an afebrile adenovirus control level or a febrile control level. In some configurations, the at least one gene can be selected from the group consisting of IFI27, ISG15 and IFIT3, whereby the subject is diagnosed with febrile enterovirus if the subject has an aberrant level of expression of at least a 1.5 fold increase of the at least one gene selected from the group consisting of IFI27, ISG15 and IFIT3, compared to an afebrile enterovirus control level or a febrile control level. In some configurations, the at least one gene can be selected from the group consisting of ITGAM and ITGAX, whereby the subject can be diagnosed with a bacterial infection if the subject has an aberrant level of expression of at least a 1.5 fold increase of the at least one gene selected from the group consisting of ITGAM and ITGAX, compared to an afebrile control level or a viral-infected control level.

In various configurations of the embodiments, diagnostic accuracy can be at least 70%. In various configurations of the embodiments, diagnostic accuracy can be at least 75%. In various configurations of the embodiments, diagnostic accuracy can be at least 80%. In various configurations of the embodiments, diagnostic accuracy can be at least 85%. In various configurations of the embodiments, diagnostic accuracy can be at least 90%.

In some embodiments, the present teachings include methods of determining etiology of a disease, such as, without limitation. Fever Without an Apparent Source (FWS) in a subject such as, for example, a human child. In various configurations, these methods can include a) providing a peripheral blood sample from a human subject; b) determining presence, absence and/or quantity of a bacterial pathogen, a viral pathogen, or a combination thereof, by a pathogen culture, a serum antibody detection test, a pathogen antigen detection test, a pathogen DNA detection test, a pathogen RNA detection test, or a combination thereof; c) determining in the sample, expression levels of at least one endogenous gene in which aberrant expression levels are associated with infection with a pathogen, by a microarray hybridization assay, an RNA-seq assay, a polymerase chain reaction assay, a LAMP assay, a ligase chain reaction assay, a Southern blot assay, a Northern blot assay, a Western blot assay, an enzyme-linked immunosorbent assay (ELISA) or a combination thereof, wherein the etiology of the disease is determined if the subject comprises the pathogen and the subject has an aberrant level of expression of at least 1.5 fold increase or decrease of at least one gene, wherein an aberrant level of expression of the at least one gene is associated with infection with the pathogen.

In various aspects, the present teachings include therapies selected on the basis of a transcriptional profile determined by the disclosed methods. These can include, without limitation, selection and administration of an appropriate antibiotic in the case of a disease determined to be caused by a bacterial infection, or selection and administration of an appropriate anti-viral drug in the case of a disease determined to be caused by a viral infection.

In some embodiments, the present teachings include an antibiotic for use in a method of treatment of Fever Without an Apparent Source (FWS) in a subject, characterized in that the subject has in a biological sample such as a peripheral blood sample at least a 1.5 fold increase in expression level compared to a control level of at least one endogenous gene, such as, without limitation, at least one endogenous gene selected from the group consisting FYN, CD247, EITPR3, CD13, ZAP70, PLCG1, PRKCH, LCK, LAT, PRKCQ, ITK, RHOU, GNA13, PPP1R12A, RHOT1, FCER1G, LYN, RALB, GNAQ, MARCKS, TGM2, ARHGEF11, MYL12A, EP300, MYL9, CREB5, FCGR2A, GNG10, GNG11, C1QB, NOD2, TLR2, TLR1, RNASEL, C5AR1, TLR4, MYD88, PIK3CB, C3AR1, TLR6, CASP1, TLR5, NLRC4, TLR8, IL1B, TGB7, TSPAN4, PPP1R1, ZYX, VASP, ITGA2B, ITGB5, VCL, ITGB3, MYLK, ASAP1, ITGAM, ITGAX, KLRD1, KIR2DL3, KIR2DL4, KIR3DL3, KIR3DL1, HCST, CD247, NCR3, FCGR3B, SIGLEC9, FCER1G, JAK2, CASP5 and a combination thereof.

In some embodiments, the present teachings include an antibiotic for use in a method of treatment of a disease caused by bacteria, characterized in that the patient has at least a 1.5 fold increase in transcription levels of one or more genes that increase in expression level upon bacterial infection, and/or at least a 1.5 fold decrease in transcription levels of one or more genes that decrease in expression level upon bacterial infection.

In some embodiments, the present teachings include an anti-viral drug for use in a method of treatment of a disease caused by a virus, characterized in that the patient has at least a 1.5 fold increase in transcription levels of one or more genes that increase in expression level upon viral infection, and/or at least a 1.5 fold decrease in transcription levels of one or more genes that decrease in expression level upon viral infection.

In some embodiments, the present teachings include an antibiotic for use in a method of treatment of a disease caused by bacteria, characterized in that the patient has been selected to have at least a 1.5 fold increase in transcription levels of one or more genes that increase in expression level upon bacterial infection, and/or at least a 1.5 fold decrease in transcription levels of one or more genes that decrease in expression level upon bacterial infection.

In some embodiments, the present teachings include an anti-viral drug for use in a method of treatment of a disease caused by a virus, characterized in that the patient has been selected to have at least at least a 1.5 fold increase in transcription levels of one or more genes that increase in expression level upon viral infection, and/or at least a 1.5 fold decrease in transcription levels of one or more genes that decrease in expression level upon viral infection.

In some embodiments, the present teachings include an antibiotic for use in a method of treatment of a disease caused by bacteria, characterized in that the method comprises a determination of whether the patient has at least a 1.5 fold increase in transcription levels of one or more genes that increase in expression level upon bacterial infection, and/or at least a 1.5 fold decrease in transcription levels of one or more genes that decrease in expression level upon bacterial infection.

In some embodiments, the present teachings include an anti-viral drug for use in a method of treatment of a disease caused by a virus, characterized in that the method comprises a determination of whether the patient has at least a 1.5 fold increase in transcription levels of one or more genes that increase in expression level upon viral infection, and/or at least a 1.5 fold decrease in transcription levels of one or more genes that decrease in expression level upon viral infection.

In some embodiments, the present teachings include an antibiotic for use in a method of treatment of Fever without an Apparent Source (FWS) in a subject, characterized in that the subject has in a sample such as a blood sample at least a 1.5 fold increase in expression level compared to a control level of at least one endogenous gene selected from the group consisting of RHOU, GNA13, PPP1R12A, RHOT1, FCER1G, LYN, RALB, GNAQ, MARCKS, TGM2, ARHGEF11, MYL12A, EP300, MYL9, CREB5, FCGR2A, GNG10, GNG11, C1QB, NOD2, TLR2, TLR1, RNASEL, C5AR1, TLR4, MYD88, PIK3CB, C3AR1, TLR6, CASP1, TLR5, NLRC4, TLR8, IL1B, PPP1R1, ZYX, MYL12A, VASP, ITGA23B, ITGB5, VCL, ITGB3, MYLK, ASAP1, ITGAM, ITGAX, FCGR3B3, SIGLEC9, FCER1G, JAK2, CASP5 and a combination thereof.

In some embodiments, the present teachings include an antibiotic for use in a method of treatment of Fever without an Apparent Source (FWS) in a subject, characterized in that the subject has in a sample such as a blood sample at least a 1.5 fold increase in expression level compared to a control level of at least one endogenous gene selected from the group consisting of FYN, CD247, EITPR3, CD3, ZAP70, PLCG1, PRKCH, LCK, LAT, PRKCQ, ITK, ITGB7, TSPAN4, KLRD1, KIR2DL3, KIR2DL4, KIR3DL3, KIR3DL1, HCST, CD247, NCR3 and a combination thereof.

In some embodiments, the present teachings include an antibiotic for use in a method of treatment of Fever without an Apparent Source (FWS) in a subject, characterized in that the subject has in a blood sample at least a 1.5 fold decrease in expression level compared to a control level of Annexin A3 gene.

In some embodiments, the present teachings include an anti-viral drug for use in a method of treatment of Fever with an Apparent Source (FWS) in a subject. In various aspects, the FWS can be characterized in that the subject can have in a sample such as a blood sample at least a 1.5 fold increase in expression level compared to a control level of at least one endogenous gene selected from the group consisting of IFI27, ISG15, OTOF, IFIT3, ITGAM, ITGAX and a combination thereof.

In some embodiments, the present teachings include an anti-viral drug for use in a method of treatment of an adenoviral infection in a subject, characterized in that the subject can have in a sample such as a blood sample an aberrant level of expression at least a 1.5 fold greater or lesser compared to a control level of at least one endogenous gene selected from the group consisting of ATM, PRKCH, PRKCQ, C1QB, C1QC, IRF7, OAS3, OAS1, OAS2, AK2, EIF2, IFIH1, DDX58, NOD2, TLR5, NLRC4, TLR8, C3AR1, IL1B, TLR1, TLR4, TLR6, MYD88, CASP1, IFIT3, IFI35, BCL2, MED14, IFNGR2, IFNAR1, IRF1, BAX, IRF9, PSMB8, IFITM1, JAK2, STAT2, TAP1, IKBKB, IKBKAP, KIAA1271, TRAF6, TNF, TBK1, TANK, IRF9, NFKBIA, IRF7, ISG15, ADAR, ZBP1, IFIT2, FOS, LY96, TLR5, IRAK3, TLR8, EIF2AK2, CD14, MAPK14, STAT4, HS.572649, CCR7, CD40LG, LTB, HLA-DOA, CREB5, FCGR3B, FCGR2A, IL1RN, LTBR, TYROBP, FCER1G, FCGR1A, FCGR1B and a combination thereof.

In some embodiments, the present teachings include an anti-viral drug for use in a method of treatment of an adenoviral infection in a subject, characterized in that the subject can have in a sample such as a blood sample an aberrant level of expression at least a 1.5 fold greater or lesser compared to a control level of at least one endogenous gene selected from the group consisting of C1QB, C1QC, IRF7, OAS3, OAS1, OAS2, AK2, EIF2, IFIH1, DDX58, NOD2, TLR5, NLRC4, TLR8, C3AR1, IL1B, TLR1, TLR4, TLR6, MYD88, CASP1, IFIT3, IFI35, BCL2, IFNAR1, IRF1, BAX, IRF9, PSMB8, IFITM1, JAK2, STAT2, TAP1, TRAF6, TNF, TBK1, TANK, IRF9, NFKBIA, IRF7, ISG15, ADAR, ZBP1, IFIT2, FOS, LY96, TLR5, IRAK3, TLR8, EIF2AK2, CD14, MAPK14, CREB5, FCGR3B, FCGR2A, IL1RN, LTBR, TYROBP, FCER1G, FCGR1A, FCGR1B and a combination thereof.

In some embodiments, the present teachings include an anti-viral drug for use in a method of treatment of an adenoviral infection in a subject, characterized in that the subject can have in a sample such as a blood sample an aberrant level of expression at least a 1.5 fold greater or lesser compared to a control level of at least one endogenous gene selected from the group consisting of ATM, PRKCH, PRKCQ, MED14, IFNGR2, IKBKB, IKBKAP, KIAA1271, STAT4, HS.572649, CCR7, CD40LG, LTB, HLA-DOA and a combination thereof and a combination thereof.

In some embodiments, the present teachings include an anti-viral drug for use in a method of treatment of an enteroviral infection in a subject, characterized in that the subject can have in a sample such as a blood sample an aberrant level of expression at least a 1.5 fold greater compared to a control level of at least one endogenous gene selected from the group consisting of NLRC4, TLR8, TLR5, NOD2, RNASEL, TLR2, TLR1, C5AR1, MYD88, TLR6, CASP1, IL1B, C1QB, IRF7, OAS1, OAS3, EIF2AK2, DDX58, IFIH1, OAS2, IFIT1, IFIT3, IFI35, MX1, TAP1, STAT2, IFITM1, STAT1, JAK2, IRF7, ISG15, IFIT2, DHX58, ZBP1, FOS, LY96, MAP2K3, MAPK14, CASP5 and a combination thereof.

In some embodiments, the present teachings include an anti-viral drug for use in a method of treatment of an enteroviral infection in a subject, characterized in that the subject can have in a sample such as a blood sample an aberrant level of expression at least a 1.5 fold greater or lesser compared to a control level of at least one endogenous gene selected from the group consisting of CCL5, PRKCH, TLR5, TLR2, NOD2, TLR8, TLR4, TLR6, C1QA, MYD88, RIPK2, IL1B, C3AR1, CASP1, C1QB, C1QC, OAS1, IRF7, OAS3, EIF2AK2, TLR7, OAS2, DDX58, IFIH1, IFIT3, IFIT1, SOCS1, MX1, IFI35, IF1TM1, TAP1, STAT2, JAK2, STAT1, TYROBP, CD86, IL1B, CASP5, CCL2, TLR9, TRAF6, IRAK4, CHUK, CD14, MYD88, TLR1, FOS, LY96 and a combination thereof.

In some embodiments, the present teachings include an anti-viral drug for use in a method of treatment of an enteroviral infection in a subject, characterized in that the subject can have in a sample such as a blood sample an aberrant level of expression at least a 1.5 fold greater compared to a control level of at least one endogenous gene selected from the group consisting of NLRC4, TLR8, TLR5, NOD2, RNASEL, TLR2, TLR1, C5AR1, MYD88, TLR6, CASP1, IL1B, C1QB, IRF7, OAS1, OAS3, EIF2AK2, DDX58, IFIH1, OAS2, IFIT1, IFIT3, IFI35, MX1, TAP1, STAT2, IFITM1, STAT1, JAK2, IRF7, ISG15, IFIT2, DHX58, ZBP1, FOS, LY96, MAP2K3, MAPK14, CASP5 and a combination thereof.

In some embodiments, the present teachings include an anti-viral drug for use in a method of treatment of an enteroviral infection in a subject, characterized in that the subject has in a blood sample an aberrant level of expression at least a 1.5 fold greater or lesser compared to a control level of at least one endogenous gene selected from the group consisting of CCL5, PRKCH, TLR5, TLR2, NOD2, TLR8, TLR4, TLR6, C1QA, MYD88, RIPK2, IL1B, C3AR1, CASP1, C1QB, C1QC, OAS1, IRF7, OAS3, EIF2AK2, TLR7, OAS2, DDX58, IFIH1, IFIT3, IFIT1, SOCS1, MX1, IFI35, IFITM1, TAP1, STAT2, JAK2, STAT1, TYROBP, CD86, IL1B, CASP5, CCL2, TLR9, TRAF6, IRAK4, CHUK, CD14, MYD88, TLR1, FOS, LY96 and a combination thereof.

In some embodiments, the present teachings include an anti-viral drug for use in a method of treatment of an HHV-6 infection in a subject, characterized in that the subject can have in a sample such as a blood sample an aberrant level of expression at least a 1.5 fold greater or lesser compared to a control level of at least one endogenous gene selected from the group consisting of CCL5, PRKCH, TLR5, TLR2, NOD2, TLR8, TLR4, TLR6, C1QA, MYD88, RIPK2, IL1B, C3AR1, CASP1, C1QB, C1QC, OAS1, IRF7, OAS3, EIF2AK2, TLR7, OAS2, DDX58, IFIH1, IFIT3, IFIT1, SOCS1, MX1, IFI35, IFITM1, TAP1, STAT2, JAK2, STAT1, TYROBP, CD86, IL1B, CASP5, CCL2, TLR9, TRAF6, IRAK4, CHUK, CD14, MYD88, TLR1, FOS, LY96 and a combination thereof.

In some embodiments, the present teachings include an anti-viral drug for use in a method of treatment of an HHV-6 infection in a subject, characterized in that the subject can have in a sample such as a blood sample an aberrant level of expression at least a 1.5 fold greater compared to a control level of at least one endogenous gene selected from the group consisting of TLR5, TLR2, NOD2, TLR8, TLR4, TLR6, C1QA, MYD88, RIPK2, IL1B, C3AR1, CASP1, C1QB, C1QC, OAS1, IRF7, OAS3, EIF2AK2, TLR7, OAS2, DDX58, IFIH1, IFIT3, IFIT1, SOCS1, MX1, IFI35, IFITM1, TAP1, STAT2, JAK2, STAT1, TYROBP, CD86, IL1B, CASP5, CCL2, TRAF6, IRAK4, CHUK, CD14, MYD88, TLR1, FOS, LY96 and a combination thereof.

In some embodiments, the present teachings include an anti-viral drug for use in a method of treatment of an HHV-6 infection in a subject, characterized in that the subject can have in a sample such as a blood sample an aberrant level of expression at least a 1.5 fold greater or lesser compared to a control level of at least one endogenous gene selected from the group consisting of CCL5, PRKCH, TLR9 and a combination thereof.

In some embodiments, the present teachings include an anti-viral drug for use in a method of treatment of an HHV-6 infection in a subject, characterized in that the subject can have in a sample such as a blood sample an aberrant level of expression of at least 1.5 fold increase compared to a control level of at least one endogenous gene selected from the group consisting of CDKN1C, MT2A, SPATS2L, IRF7, ZBP1, OAS2, OAS1, ISG15, IFI6, HERC5, OAS3, RSAD2, OASL, IFIT3, OTOF and IFI27.

In some embodiments, the present teachings include an anti-viral drug for use in a method of treatment of an HHV-6 infection in a subject, characterized in that the subject can have in a sample such as a blood sample an aberrant level of expression of at least 1.5 fold decrease compared to a control level of at least one endogenous gene selected from the group consisting of MYH9 and ARAP3.

In some embodiments, the present teachings include an anti-viral drug for use in a method of treatment of an HHV-6 infection in a subject, characterized in that the subject can have in a sample such as a blood sample an aberrant level of expression of at least 1.5 fold increase compared to a control level of at least one endogenous gene selected from the group consisting of CDKN1C, MT2A, SPATS2L, IRF7, ZBP1, OAS2, OAS1, ISG15, IFI6, HERC5, OAS3, RSAD2, OASL, IFIT3, OTOF and IFI27 and at least 1.5 fold decrease compared to a control level of at least one endogenous gene selected from the group consisting of MYH9 and ARAP3.

In some embodiments, the present teachings include an antibiotic for use in a method of treatment of a bacterial infection in a subject, characterized in that a sample such as a blood sample of the subject can have at least a 1.5 fold decrease in expression of at least one endogenous gene selected from the group consisting of CDKN1C, MT2A, SPATS2L, IRF7, ZBP1, OAS2, OAS1, ISG15, IFI6, HERC5, OAS3, RSAD2, OASL, IFIT3, OTOF and IFI27. In some embodiments, the present teachings include an antibiotic for use in a method of treatment of a bacterial infection in a subject, characterized in that a sample such as a blood sample of the subject can have at least a 1.5 fold increase in expression of at least one endogenous gene selected from the group consisting of MYH9, ARAP3 or a combination thereof. In some embodiments, the present teachings include an antibiotic for use in a method of treatment of a bacterial infection in a subject, characterized in that a sample such as a blood sample of the subject can have at least a 1.5 fold increase in expression of at least one endogenous gene selected from the group consisting of MYH9 and ARAP3.

In some embodiments, the present teachings include an antibiotic for use in a method of treatment of a bacterial infection in a subject, characterized in that a sample such as a blood sample of the subject can have at least a 1.5 fold decrease in expression of at least one endogenous gene selected from the group consisting of CDKN1C, MT2A, SPATS2L, IRF7, ZBP1, OAS2, OAS1, ISG15, IFI6, HERC5, OAS3, RSAD2, OASL, IFIT3, OTOF and IF27, and at least 1.5 fold increase in expression of at least one endogenous gene selected from the group consisting of MYH9, ARAP3 and a combination thereof.

In some embodiments, the present teachings include an antibiotic for use in a method of treatment of a bacterial infection, characterized in that a sample such as a blood sample of the subject can have an aberrant level of expression at least 1.5 fold greater or lesser compared to a control level of at least one endogenous gene selected from the group consisting of FYN, CD247, EITPR3, CD3, ZAP70, PLCG1, PRKCH, LCK, LAT, PRKCQ, ITK, RHOU, GNA13, PPP1R12A, RHOT1, FCER1G, LYN, RALB, GNAQ, MARCKS, TGM2, ARHGEF11, MYL12A, EP300, MYL9, CREB5, FCGR2A, GNG10, GNG11, C1QB, NOD2, TLR2, TLR1, RNASEL, C5AR1, TLR4, MYD88, PIK3CB, C3AR1, TLR6, CASP1, TLR5, NLRC4, TLR8, IL1B, ITGB7, TSPAN4, PPP1R1, ZYX, VASP, ITGA2B, ITGB5, VCL, ITGB3, MYLK, ASAP1, ITGAM, ITGAX, KLRD1, KIR2DL3, KIR2DL4, KIR3DL3, KIR3DL1, HCST, CD247, NCR3, FCGR3B, SIGLEC9, FCER1G, JAK2, CASP5 and a combination thereof.

In some embodiments, the present teachings include an antibiotic for use in a method of treatment of a bacterial infection, characterized in that a sample such as a blood sample of the subject can have an aberrant level of expression of at least one endogenous gene selected from the group consisting of RHOU, GNA13, PPP1R12A, RHOT1, FCER1G, LYN, RALB, GNAQ, MARCKS, TGM2, ARHGEF11, MYL12A, EP300, MYL9, CREB5, FCGR2A, GNG10, GNG11, C1QB, NOD2, TLR2, TLR1, RNASEL, C5AR1, TLR4, MYD88, PIK3CB, C3AR1, TLR6, CASP1, TLR5, NLRC4, TLR8, IL1B, PPP1R1, ZYX, MYL12A, VASP, ITGA2B, ITGB5, VCL, ITGB3, MYLK, ASAP1, ITGAM, ITGAX, FCGR3B, SIGLEC9, FCER1G, JAK2, CASP5 and a combination thereof. In some configurations, the aberrant level of expression can be at least 1.5 fold greater or lesser compared to a control level of the at least one endogenous gene selected from the group consisting of RHOU, GNA13, PPP1R12A, RHOT1, FCER1G, LYN, RALB, GNAQ, MARCKS, TGM2, ARHGEF11, MYL12A, EP300, MYL9, CREB5, FCGR2A, GNG10, GNG11, C1QB, NOD2, TLR2, TLR1, RNASEL, C5AR1, TLR4, MYD88, PIK3CB, C3AR1, TLR6, CASP1, TLR5, NLRC4, TLR8, IL1B, PPP1R1, ZYX, MYL12A, VASP, ITGA2B, ITGB5, VCL, ITGB3, MYLK, ASAP1, ITGAM, ITGAX, FCGR3B, SIGLEC9, FCER1G, JAK2, CASP5 and a combination thereof.

In some embodiments, the present teachings include an anti-viral drug for use in a method of treatment of an enteroviral infection in a subject, characterized in that the subject can have in a sample such as a blood sample an aberrant level of expression that is at least 1.5 fold greater or lesser compared to a control level of at least one endogenous gene selected from the group consisting of adenoviral infection is selected from the group consisting of NLRC4, TLR8, TLR5, NOD2, RNASEL, TLR2, TLR1, C5AR1, MYD88, TLR6, CASP1, IL1B, C1QB, IRF7, OAS1, OAS3, EIF2AK2, DDX58, IFIH1, OAS2, IFIT1, IFIT3, IFI35, MX1, TAP1, STAT2, IFITM1, STAT1, JAK2, IRF7, ISG15, IFIT2, DHX58, ZBP1, FOS, LY96, MAP2K3, MAPK14, CASP5 and a combination thereof.

In some embodiments, the present teachings include an anti-viral drug for use in a method of treatment of an enteroviral infection in a subject, characterized in that the subject can have in a sample such as a blood sample an aberrant level of expression that is at least a 1.5 fold increase compared to a control level of at least one endogenous gene selected from the group consisting of NLRC4, TLR8, TLR5, NOD2, RNASEL, TLR2, TLR1, C5AR1, MYD88, TLR6, CASP1, IL1B, C1QB, IRF7, OAS1, OAS3, EIF2AK2, DDX58, IFIH1, OAS2, IFIT1, IFIT3, IFI35, MX1, TAP1, STAT2, IFITM1, STAT1, JAK2, IRF7, ISG15, IFIT2, DHX58, ZBP1, FOS, LY96, MAP2K3, MAPK14, CASP5 and a combination thereof.

In some embodiments, the present teachings include an anti-viral drug for use in a method of treatment of an HHV-6 infection in a subject, characterized in that the subject can have in a sample such as a blood sample an aberrant level of expression that is at least a 1.5 fold decrease compared to a control level of at least one endogenous gene selected from the group consisting of CCL5, PRKCH and TLR9.

In some embodiments, the present teachings include an anti-viral drug for use in a method of treatment of a viral infection in a subject, characterized in that the subject can have in a sample such as a blood sample an aberrant level of expression that is at least a 1.5 fold increase of at least one endogenous gene selected from the group consisting of CDKN1C, MT2A, SPATS2L, IRF7, ZBP1, OAS2, OAS1, ISG15, IFI6, HERC5, OAS3, RSAD2, OASL, IFIT3, OTOF and IFI27, compared to a bacterium-infected control level.

In some embodiments, the present teachings include an anti-viral drug for use in a method of treatment of a viral infection in a subject, characterized in that the subject has in a sample such as a blood sample an aberrant level of expression that is at least a 1.5 fold decrease of at least one endogenous gene selected from the group consisting of MYH9 and ARAP3, compared to a bacterium-infected control level.

In some embodiments, the present teachings include an anti-viral drug for use in a method of treatment of a viral infection in a subject, characterized in that the subject can have in a sample such as a blood sample an aberrant level of expression that is at least a 1.5 fold increase of at least one endogenous gene selected from the group consisting of BAK1, IFNGR1, STAT2, IFI35, MX1, OAS1, IFIT1 and IFIT3, compared to a bacterium-infected control level.

In some embodiments, the present teachings include an anti-viral drug for use in a method of treatment of a viral infection in a subject, characterized in that the subject can have in a sample such as a blood sample an aberrant level of expression that is at least a 1.5 fold decrease of at least one endogenous gene selected from the group consisting of RRAS, ACTR2, NCK2, PIK3CB, MAP2K4, ITGA2B, ITGB3, MYLK, MYL9, ITGB5, GNG11, ZYX, ITGAX and ITGAM, compared to a bacterium-infected control level.

In some embodiments, the present teachings include an anti-viral drug for use in a method of treatment of a viral infection in a subject, characterized in that the subject can have in a sample such as a blood sample an aberrant level of expression that is at least a 1.5 fold increase of at least one endogenous gene selected from the group consisting of IFNGR1, IFNGR2, MT2A, SPATS2L, OAS2, OAS1, ISG15, IFI6, IFIT1, HERC5, OAS3, RSAD2, OASL, OTOF and IFI27, compared to a bacterium-infected control level.

In some embodiments, the present teachings include an anti-viral drug for use in a method of treatment of a viral infection in a subject, characterized in that the subject can have in a blood sample an aberrant level of expression that is at least a 1.5 fold decrease of at least one endogenous gene selected from the group consisting of OSBPL8, VHL, ACTR2, MAP2K4, F13A1, PROS1, ITGB3, MYL9, ITGA2B, ITGB5, GNG11, EP300, ZYX, ARAP3, AGER, ITGAX, SORL1 and IGTAM, compared to a bacterium-infected control level.

In some embodiments, the present teachings include an anti-viral drug for use in a method of treatment of a viral infection in a subject, characterized in that the subject can have in a sample such as a blood sample an aberrant level of expression that is at least a 1.5 fold increase of at least one endogenous gene selected from the group consisting of IFI127, ISG15, OTOF and IFIT3, compared to a bacterium-infected control level.

In some embodiments, the present teachings include an anti-viral drug for use in a method of treatment of febrile HHV-6 in a subject, characterized in that the subject can be selected to have in a sample such as a blood sample expression that is at least a 1.5 fold increase of at least one endogenous gene selected from the group consisting of IFI27, IFIT3, and a combination thereof compared to an afebrile HHV-6 control level or a febrile control level.

In some embodiments, the present teachings include an anti-viral drug for use in a method of treatment of febrile HHV-6 in a subject, characterized in that the subject can be selected to have in a sample such as a blood sample expression that is at least a 1.5 fold increase of at least one endogenous gene selected from the group consisting of IFI27, ISG15, and a combination thereof compared to an afebrile adenovirus control level or a febrile control level.

In some embodiments, the present teachings include an anti-viral drug for use in a method of treatment of febrile enterovirus in a subject, characterized in that the subject can be selected to have in a sample such as a blood sample expression that is at least a 1.5 fold increase of at least one endogenous gene selected from the group consisting of IFI27, ISG15, and a combination thereof, compared to an afebrile enterovirus control level or a febrile control level.

In some embodiments, the present teachings include an antibiotic for use in a method of treatment of bacterial infection in a subject, characterized in that the subject can be selected to have in a blood sample expression that is at least a 1.5 fold increase of at least one endogenous gene selected from the group consisting of ITGAM and ITGAX, compared to an afebrile control level or a viral-infected control level.

BRIEF DESCRIPTION OF THE DRAWINGS

For some drawings that were originally in color, a composite of 3 color channels (red, green and blue), along with individual color channels, are shown.

FIG. 5A-G illustrate blood transcriptional profiles of febrile adenovirus-positive children and profiles of afebrile adenovirus-positive children and afebrile controls.

FIG. 6A-G illustrate blood transcriptional profiles of enterovirus-positive febrile children and virus-negative afebrile children.

FIG. 7A-G illustrate blood transcriptional profiles of febrile children with acute bacterial infections and profiles of virus negative afebrile children.

FIG. 9A-D illustrate quantile-normalized raw signal intensity of the classifier probes in febrile children.

DETAILED DESCRIPTION

Abbreviations

Figure 1:
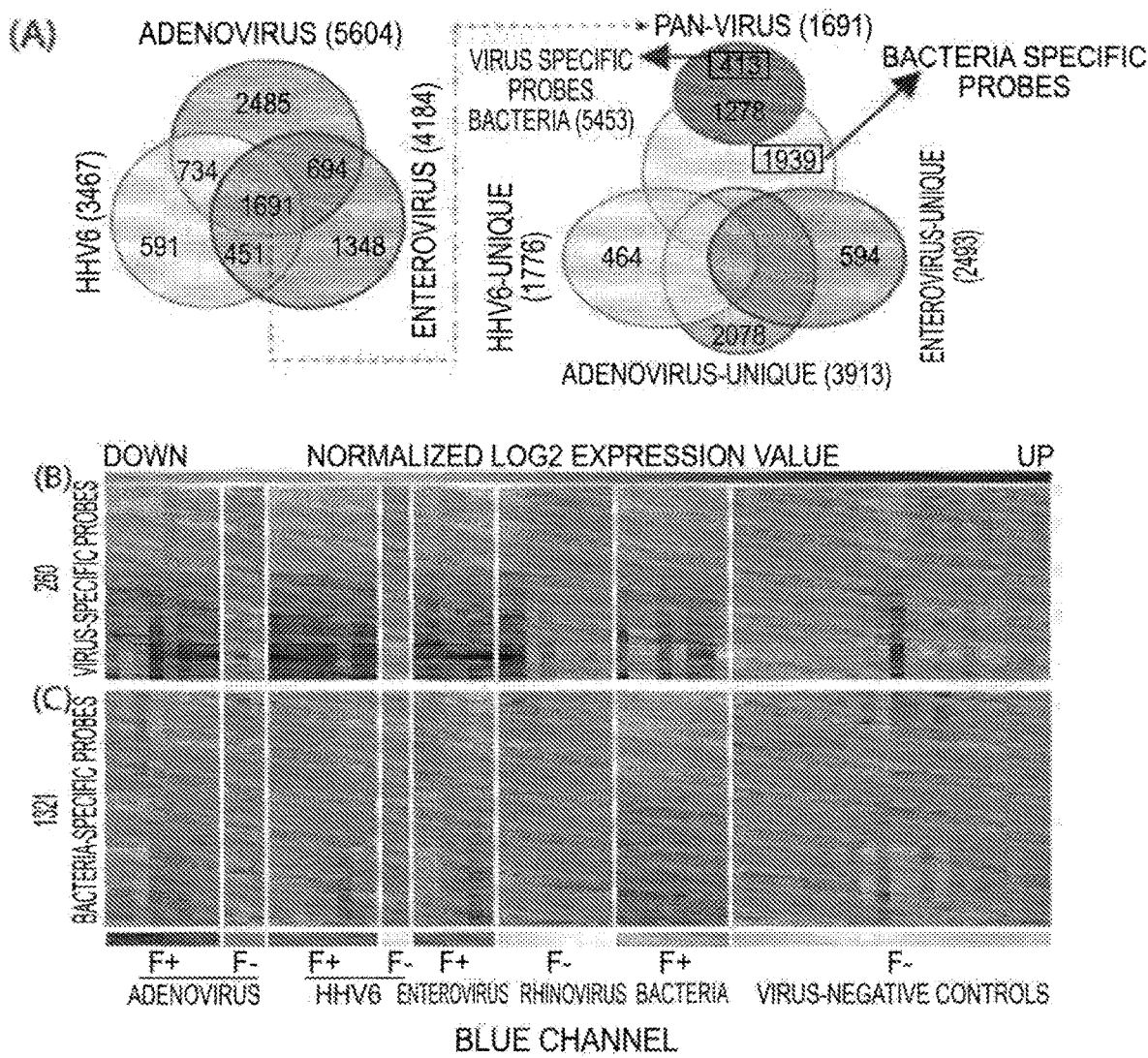
FIG. 1 illustrates identification of virus- and bacterial response-specific probes.

ANOVA Analysis of variance
BAX Bcl-2-associated X protein
FDR False discovery rate
FWS Fever Without an Apparent Source
GAPDH Glyceraldehyde 3-phosphate dehydrogenase
GEO Gene expression omnibus
HHV-6 Human herpesvirus 6
IFN Interferon
LAMP Loop-mediated isothermal amplification
Lymph Lymphocyte
Mono Monocyte
MRSA Methicillin-resistant *Staphylococcus aureus*
MSSA Methicillin-sensitive *Staphylococcus aureus*
Neut Neutrophil
PAM Prediction Analysis of Microarrays
PCR Polymerase chain reaction
RIN RNA integrity number
RNA-seq RNA Sequencing, Whole Transcriptome Shotgun Sequencing
Tm Melting temperature
QC Quality control WBC White blood cell
ΔΔCt Comparative CT Method Unless defined otherwise, technical and scientific terms used herein have the same meaning as commonly understood by one of ordinary skill in the art to which the present teachings belong. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide a person of skill in the art with general guides to many of the terms used in the present application.

One skilled in the art will recognize many methods and materials similar or equivalent to those described herein, which could be used in the practice of the present teachings. The present teachings are in no way limited to the methods and materials described. For purposes of the present teachings, the following terms are defined below.

As used herein, "microarray" refers to an ordered arrangement of hybridizable array elements including but not limited to polynucleotide probes, on a substrate.

As used herein, "biological sample" is any sampling of cells, tissues, or bodily fluids containing cells. Examples of biological samples include, but are not limited to, peripheral blood mononuclear cells, a nasopharyngeal sample, a urine sample, a blood sample, a lumbar puncture sample, a bodily fluid, a biopsy sample, a tissue sample and a combination thereof.

As used herein. "blood" includes whole blood, plasma, and serum.

As used herein, "aberrant expression levels" includes an increase or decrease of gene expression compared to baseline, or compared to an appropriate comparison group.

Methods and compositions described herein utilize laboratory techniques well known to skilled artisans. Such techniques can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Methods in Enzymology (Academic Press, Inc.); Handbook of Experimental Immunology, 4th edition D. M. Weir & C. C. Blackwell, eds., Blackwell Science Inc., 1987); Current Protocols in Molecular Biology (F. M. Ausubel et al., eds., 1987); and PCR: The Polymerase Chain Reaction, (Mullis et al., eds., 1994). Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients. Fourth Edition, Pharmaceutical Press. 2003. As used in the present description and any appended claims, the singular forms "a", "an" and "the" are intended to include the plural forms as well, unless the context indicates otherwise.

Methods of gene expression profiling can include methods based on hybridization analysis of polynucleotides, and methods based on sequencing of polynucleotides. Methods for quantification of mRNA expression in a sample include northern blotting and in situ hybridization (Parker & Barnes, Methods in Molecular Biology 106:247-283 (1999)); RNAse protection assays (Hod, Y., Biotechniques 1992, 13:852-854); and reverse transcription-polymerase chain reaction (RT-PCR) (Weis et al., Trends in Genetics 8:263-264 (1992)). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). For example, RT-PCR can be used to compare mRNA levels in different sample populations, in normal and infected tissues, with or without drug treatment, to characterize patterns of gene expression, to discriminate between closely related mRNAs, and/or to analyze RNA structure.

A first step for an RT-PCR analysis can be extraction and/or isolation of mRNA from a sample. In some embodiments, starting material can be total RNA isolated from a human PBMC. RNA can be isolated from a variety of PBMCs, such as, without limitation, a lymphocyte, a leukocyte, a monocyte or a macrophage.

Methods for mRNA extraction are well known in the art and are disclosed in standard textbooks of molecular biology, including Ausubel et al., Current Protocols of Molecular Biology, John Wiley and Sons (1997). RNA isolation can be performed using a purification kit, buffer set and protease from commercial manufacturers, such as Qiagen, according to manufacturer's instructions. For example, total RNA from cells in culture can be isolated using Qiagen RNeasy® mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). RNA from tissue samples can be isolated using RNA Stat-60 (Tel-Test). RNA prepared from a biological sample can be isolated, for example, by cesium chloride density gradient centrifugation.

A first step in gene expression profiling by RT-PCR can be reverse transcription of an RNA template into cDNA, followed by amplification in a PCR reaction. For example, extracted RNA can be reverse-transcribed using a GeneAmp RNA PCR kit (Perkin Elmer, Waltham, Mass. USA), following manufacturer's instructions. cDNA can then be used as template in a subsequent PCR amplification and quantitative analysis using, for example, a TaqMan® (Life Technologies, Inc., Grand Island, N.Y.) assay.

Taqman® RT-PCR (Life Technologies, Carlsbad, Calif., USA) can be performed using commercially available equipment, such as, for example, an ABI PRISM 7700TM Sequence Detection System™ (Perkin-Elmer-Applied Biosystems, Foster City, Calif., USA), or Lightcycler (Roche Molecular Biochemicals, Mannheim, Germany). RT-PCR can be performed using an internal standard such as mRNA for glyceraldehyde-3-phosphate-dehydrogenase (GAPDH) and/or β-actin as a control (see. e.g., Held et al., Genome Research 6: 986-994, 1996).

In some embodiments, PCR primers and probes can be designed based upon intron sequences present in the gene to be amplified. In such aspects, a first step in primer/probe design can be the delineation of intron sequences within the genes. This can be accomplished using publicly available software, such as the DNA BLAST software (Kent, W. J., Genome Res. 12(4): 656-664, 2002). Subsequent steps can include the following established methods of PCR primer and probe design.

In some configurations, in order to avoid non-specific signals, repetitive sequences within introns can be masked when designing primers and probes. This can be accomplished by using software such as the Repeat Masker program available on-line through the Baylor College of Medicine. This program can be used to screen DNA sequences against a library of repetitive elements and returns a query sequence in which the repetitive elements are masked. Masked intron sequences can then be used to design primer and probe sequences using a commercially or otherwise publicly available primer/probe design package, such as Primer Express (Applied Biosystems); MGB assay-by-design (Applied Biosystems); Primer3 (Rozen, S., and Skaletsky, H. J., (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386); Methods Mol. Biol. 132, 365-386, 2000).

Factors considered in PCR primer design can include primer length, melting temperature (Tm), G/C content, specificity, complementary primer sequences, and 3'-end sequence. PCR primers can be, but are not limited to, 17-30 bases in length, and contain about 20% from 10% to 80%, or about 80% G+C bases, such as, for example, about 50%, from 50 to 60%, or about 60% G+C bases. In various configurations, Tm's can be between 50 and 80° C., e.g. about 50 to 70° C.

Further guidelines for PCR primer and probe design can be found in various published sources, e.g. Dieffenbach, C. W. et al., "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. Methods Mol. Biol. 70:520-527 (1997), the entire disclosures of which are hereby expressly incorporated by reference.

In some embodiments, differential gene expression can be identified, or confirmed using a microarray technique. In these methods, polynucleotide sequences of interest (including cDNAs and oligonucleotides) can be plated, or arrayed, on a microchip substrate. The arrayed sequences can be hybridized with specific DNA probes from cells or tissues of interest. RNA can be isolated from a variety of biological sources. In an embodiment of the microarray technique, PCR-amplified inserts of cDNA clones can be applied to a substrate in a dense array. Microarrayed genes, immobilized on a microchip, can be suitable for hybridization under stringent conditions.

In some embodiments, fluorescently labeled cDNA probes can be generated through incorporation of fluorescent nucleotides by reverse transcription of RNA extracted from tissues of interest. Labeled cDNA probes applied to a chip can hybridize with specificity to loci of DNA on the array. After washing to remove non-specifically bound probes, a chip can be scanned by confocal laser microscopy or by another detection method, such as a CCD (charge coupled device) camera. Quantification of hybridization of each arrayed element can allow for assessment of corresponding mRNA.

In some configurations, dual color fluorescence can be used. With dual color fluorescence, separately labeled cDNA probes can be generated from two sources of RNA and can be hybridized pairwise to an array. The relative abundance of transcripts from the two sources corresponding to each specified gene can be determined simultaneously. In various configurations, the miniaturized scale of the hybridization can afford a convenient and rapid evaluation of an expression pattern for large numbers of genes. In various configurations, such methods can have sensitivity to detect rare transcripts, which are expressed at fewer than 1000, fewer than 100, or fewer than 10 copies per cell. In various configurations, such methods can detect at least approximately two-fold differences in expression levels (Schena et al., Proc. Natl. Acad. Sci. USA 93(2): 106-149 (1996)). In various configurations, microarray analysis can be performed by commercially available equipment, following manufacturer's protocols, such as by using Affymetrix GenChip technology, or Incyte's microarray technology.

Non-limiting representative protocols for profiling gene expression including mRNA isolation, purification, primer extension and amplification are given in various published journal articles (for example: Godfrey, T. E., et al. 2000, *J. Molec. Diagnostics* 2: 84-91; Specht, K, et al., 2001, *Am. J. Pathol.* 158: 419-29). RNA can be extracted, and protein and DNA can be removed. After analysis of the RNA concentration, RNA repair and/or amplification steps can be included, and RNA can be reverse transcribed using gene specific promoters followed by RT-PCR. Data can be analyzed to identify a treatment option(s) available to the patient on the basis of the characteristic gene expression pattern identified in the examined biological sample.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates detection of viruses in young children with Fever Without an Apparent Source (FWS).

Subjects were drawn from a study of children between 2 to 36 months of age with Fever Without an Apparent Source (Table 1) and afebrile children having ambulatory surgery who were recruited at St. Louis Children's Hospital as described previously (Colvin, J. M., et al. 2012, *Pediatrics* 130(6):e1455-1462). The febrile and afebrile groups were similar with respect to age, gender, and season of recruitment, but differed with respect to race, with more African-American children in the febrile group (57% vs. 13%). Patients were enrolled according to Institutional Review Board-approved protocol. The study was approved by the Washington University Human Research Protection Office. Each subject was tested for multiple viruses in blood and nasopharyngeal samples using panels of virus-specific PCR assays as described (Colvin, J. M., et al. 2012, *Pediatrics* 130(6):e1455-1462). Subjects were selected for the study of gene expression profiles if they were positive for a single virus in one or both samples. The viruses included were adenovirus, HHV-6, enterovirus, and rhinovirus. Also included were subjects who had a definite bacterial infection (bacteremia, urinary tract infection, skin and soft tissue infection, bone or joint infection) and whose samples were negative for viruses tested, as well as a group of subjects selected from the afebrile control group whose samples were also negative for viruses tested (Colvin, J. M., et al. 2012, *Pediatrics* 130(6):e1455-1462). Statistical analysis did not reveal race as a confounding variable.

TABLE 1

Demographics of 65 cases in the study

| Patient ID | Pathogen | Fever | Sex | Age (mo) | Ethnicity | Antibiotics used | WBC (×1,000) | Neut (%) | Bands (%) | Lymph (%) | Mono (%) | WBC status by age-specific normal values | WBC status by cutoff of 15,000 |
|---|---|---|---|---|---|---|---|---|---|---|---|---|---|
| 9006 | Adenovirus | Yes | Female | 4 | White | Yes | 26.7 | 78 | 5 | 14 | 3 | Increased | >15,000 |
| 9010 | Adenovirus | Yes | Male | 24 | Black | Yes | 25.6 | 66 | 9 | 18 | 10 | Increased | >15,000 |
| 9021 | Adenovirus | Yes | Female | 2 | Black | Yes | 25.2 | 33 | 7 | 31 | 27 | Increased | >15,000 |
| 9170 | Adenovirus | Yes | Female | 13 | Black | Yes | 16.2 | 78 | 10 | 3 | 6 | Increased | >15,000 |
| 9203 | Adenovirus | Yes | Female | 9 | White | Yes | 30.9 | 54 | 12 | 23 | 10 | Increased | >15,000 |
| 9282 | Adenovirus | Yes | Female | 17 | White | Yes | 17.1 | 72 | 10 | 10 | 7 | Normal | >15,000 |
| 9289 | Adenovirus | Yes | Female | 15 | Other | No | 24.6 | 84 | 0 | 12 | 4 | Increased | >15,000 |
| 9340 | Adenovirus | Yes | Male | 2 | White | Yes | 15.2 | 37 | 1 | 44 | 16 | Normal | >15,000 |
| 9081 | Adenovirus | No | Male | 7 | White | | | | | | | | |
| 9097 | Adenovirus | No | Female | 14 | White | | | | | | | | |
| 9134 | Adenovirus | No | Female | 26 | White | | | | | | | | |
| 9022 | HHV-6 | Yes | Female | 10 | Other | Yes | 15.1 | 85 | 0 | 13 | 2 | Normal | >15,000 |
| 9023 | HHV-6 | Yes | Female | 12 | Black | No | 10.1 | 70 | 2 | 23 | 5 | Normal | Not >15,000 |
| 9032 | HHV-6 | Yes | Male | 3 | Black | Yes | 8.9 | 41 | 2 | 42 | 12 | Normal | Not >15,000 |
| 9064 | HHV-6 | Yes | Female | 7 | Black | No | 6.1 | 66 | 0 | 25 | 8 | Normal | Not >15,000 |
| 9156 | HHV-6 | Yes | Male | 3 | Black | No | 7 | 15 | 9 | 48 | 22 | Normal | Not >15,000 |
| 9300 | HHV-6 | Yes | Male | 2 | Black | No | 6.1 | 52 | 3 | 26 | 11 | Normal | Not >15,000 |
| 9415 | HHV-6 | Yes | Male | 12 | White | No | 5.7 | 47 | 0 | 41 | 11 | Decreased | Not >15,000 |
| 9575 | HHV-6 | Yes | Male | 25 | White | Yes | 5.6 | 42 | 1 | 48 | 6 | Normal | Not >15,000 |
| 9437 | HHV-6 | No | Male | 17 | White | | | | | | | | |
| 9515 | HHV-6 | No | Male | 18 | Black | | | | | | | | |
| 9008 | Enterovirus | Yes | Male | 8 | White | No | 12.1 | 58 | 0 | 29 | 13 | Normal | Not >15,000 |
| 9016 | Enterovirus | Yes | Male | 29 | White | No | 12.2 | 70 | 0 | 24 | 6 | Normal | Not >15,000 |
| 9267 | Enterovirus | Yes | Male | 2 | White | Yes | 7.9 | 42 | 1 | 52 | 4 | Normal | Not >15,000 |
| 9450 | Enterovirus | Yes | Female | 16 | Black | Yes | 15 | 49 | 1 | 44 | 5 | Normal | >15,000 |
| 9467 | Enterovirus | Yes | Male | 32 | Black | Yes | 11.7 | 80 | 7 | 9 | 4 | Normal | Not >15,000 |
| 9587 | Enterovirus | Yes | Female | 10 | Black | | | | | | | | |
| 9087 | Rhinovirus | No | Male | 3 | White | | | | | | | | |
| 9113 | Rhinovirus | No | Male | 7 | White | | | | | | | | |
| 9118 | Rhinovirus | No | Male | 26 | White | | | | | | | | |
| 9133 | Rhinovirus | No | Male | 5 | White | | | | | | | | |
| 9149 | Rhinovirus | No | Male | 6 | White | | | | | | | | |
| 9150 | Rhinovirus | No | Female | 12 | White | | | | | | | | |
| 9151 | Rhinovirus | No | Female | 30 | White | | | | | | | | |
| 9163 | Rhinovirus | No | Female | 32 | White | | | | | | | | |
| 9298 | *E. coli* | Yes | Female | 10 | White | Yes | 30.6 | 84 | 0 | 11 | 5 | Increased | >15,000 |
| 9359 | Bacteria | Yes | Male | 16 | Black | Yes | 20.3 | 73 | 1 | 22 | 2 | Increased | >15,000 |
| 9397 | MRSA | Yes | Male | 3 | Black | Yes | 16 | 66 | 1 | 25 | 8 | Normal | >15,000 |
| 9468 | *Salmonella* | yes | Male | 25 | White | No | 17.8 | 55 | 0 | 26 | 5 | Increased | >15,000 |
| 9501 | *E. coli* | Yes | Male | 4 | White | Yes | 12.2 | 67 | 2 | 20 | 8 | Normal | Not >15,000 |
| 9519 | MRSA | Yes | Male | 32 | White | Yes | 16 | 65 | 0 | 25 | 6 | Increased | >15,000 |
| 9523 | MRSA | Yes | Female | 30 | Black | Yes | 19.8 | 53 | 0 | 38 | 6 | Increased | >15,000 |
| 9602 | MRSA | Yes | Male | 20 | Black | Yes | 17.1 | 72 | 0 | 20 | 8 | Normal | >15,000 |
| 9050 | Control | No | Male | 10 | White | | | | | | | | |
| 9051 | Control | No | Male | 17 | Black | | | | | | | | |
| 9057 | Control | No | Male | 10 | White | | | | | | | | |
| 9059 | Control | No | Male | 9 | White | | | | | | | | |
| 9061 | Control | No | Male | 4 | Black | | | | | | | | |
| 9062 | Control | No | Male | 17 | White | | | | | | | | |
| 9066 | Control | No | Female | 6 | White | | | | | | | | |
| 9067 | Control | No | Female | 4 | White | | | | | | | | |
| 9075 | Control | No | Male | 3 | White | | | | | | | | |
| 9091 | Control | No | Male | 11 | White | | | | | | | | |
| 9093 | Control | No | Male | 10 | White | | | | | | | | |
| 9110 | Control | No | Female | 12 | Black | | | | | | | | |
| 9114 | Control | No | Male | 25 | White | | | | | | | | |
| 9115 | Control | No | Male | 2 | White | | | | | | | | |
| 9116 | Control | No | Male | 17 | White | | | | | | | | |
| 9117 | Control | No | Male | 28 | White | | | | | | | | |
| 9125 | Control | No | Female | 33 | White | | | | | | | | |
| 9137 | Control | No | Female | 20 | White | | | | | | | | |
| 9146 | Control | No | Male | 22 | White | | | | | | | | |

TABLE 1-continued

Demographics of 65 cases in the study

| Patient ID | Pathogen | Fever | Sex | Age (mo) | Ethnicity | Antibiotics used | WBC (×1,000) | Neut (%) | Bands (%) | Lymph (%) | WBC status Mono by age-specific (%) normal values | WBC status by cutoff of 15,000 |
|---|---|---|---|---|---|---|---|---|---|---|---|---|
| 9147 | Control | No | Female | 9 | White | | | | | | | |
| 9187 | Control | No | Female | 5 | White | | | | | | | |
| 9294 | Control | No | Male | 11 | White | | | | | | | |

Example 2

This example illustrates preparation of biological samples, including RNA from blood samples.

In these investigations, whole blood and nasopharyngeal samples were collected for virus-specific PCR and high-throughput sequencing. Additionally, a blood sample was collected in a Tempus™ Blood RNA Tube (Applied Biosystems, Carlsbad, Calif.) and stored at −80° C. for subsequent gene expression analysis.

Total RNA was isolated from whole blood collected in Tempus™ Blood RNA tubes (Applied Biosystems, Carlsbad, Calif.) according to the manufacturer's instructions. RNA quality was determined by gel-chip image (showing 28S, 18S and 5S bands) and RNA integrity number (RIN, generally a >7 RIN indicates good quality RNA) using an Agilent 2100 Bioanalyzer (Agilent, Palo Alto, Calif.). All but 3 of the RNA preparations had RIN scores ≥7.0. Total RNA concentration was obtained from an absorbance ratio at 260 nm and 280 nm using a NanoDrop ND-100 spectrometry instrument (NanoDrop Inc., Wilmington, Del.).

Example 3

This example illustrates gene expression microarray assays.

In these investigations, gene expression microarray analyses were conducted on blood samples from 35 febrile children positive for adenovirus, human herpesvirus 6 (HHV-6), or enterovirus infection or with acute bacterial infection, and 22 afebrile controls. Gene expression microarray assays were carried out at the Genome Technology Access Center in Washington University in St Louis. RNA transcripts were amplified by T7 linear amplification with the Illumina 3TVT Direct Hybridization Assay Kit (Illumina Inc., San Diego, Calif.), and biotin-labeled cRNA targets were hybridized to the Illumina Human-HT12 v4 Expression BeadChips (>47,000 probes), which were scanned on an Illumina BeadArray Reader. Scanned images were quantitated by Illumina Beadscan software (v3). Quantified data were imported into Illumina GenomeStudio software (version 2011.1) to generate expression profiles and to make data quality assessments. These data have been deposited into GEO database at the National Center for Biotechnology Information (GEO ID: GSE40396).

Example 4

This example illustrates microarray data analysis including differential expression analysis, pathway analysis, and identification of classifier genes, class prediction and unsupervised hierarchical clustering.

In these investigations, host transcriptional response was analyzed at the level of up- and down-regulation of individual genes and of functional gene pathways. Differences were detected of up- and down-regulation of individual genes in transcriptional profiles in febrile children positive for any of the three viruses and with acute bacterial infection. Several approaches to developing panels of probes were used. A panel of individual gene probes was developed based on the strength of statistical association with a type of infection. A panel was developed of genes from two pathways that differentially activated: the Interferon Signaling Pathway, activated in febrile virus-positive children, and the Integrin Signaling Pathway, activated in children with acute bacterial infection. A hybrid approach was additionally used, in which genes were selected from each of the gene-based and pathway-based approaches. The large set of gene-based probes (1581) and each of the three "shrunken" approaches that used between 18 and 33 probes functioned for classification purposes.

For microarray data analysis, expression profiles were generated in the GenomeStudio and imported into Partek Genome Suite (version 6.6, Partek Inc., Saint Louis, Mo.). Data quality was assessed across individual samples using principal component analysis and hierarchical clustering analysis that could identify specific sample clusters that were associated with nonexperimental factors (such as chip effect, age, gender, and array QC metrics). Five of 70 samples that had the lowest number of detectable probes were identified as outliers and eliminated without further analysis. A total of ~26,300 probes that had been detected (detection p-value <0.01) in at least one of the 70 samples were kept in downstream statistical analysis and quantile-normalized for differential expression analysis.

For differential expression analysis, analysis of variance (ANOVA) was performed in Partek Genome Suite for genes with differential expression in viral and bacterial infection and afebrile controls, with adjustment for batch effect (hybridization date and individual chips). P-values from the ANOVA were corrected for false discovery rate (FDR, or q-value). With the exception of symptomatic enterovirus infection, analyses were conducted with p-value <0.05 and FDR at 5%.

For pathway analysis, pathways that were most activated for each virus and for bacterial infection were identified from the Ingenuity® Pathway Analysis (Ingenuity® Systems, Redwood City, Calif.) library of canonical pathways. The significance of the association between the data set and the canonical pathway was assessed in two ways: 1) The ratio of the number of up- and down-regulated probes from the data set included in the pathway divided by the total number of probes that were included in the canonical pathway; 2) statistical evaluation using Fisher's exact test of the probability that the association between the genes in the dataset and the canonical pathway is explained by chance alone.

Identification of classifier genes, class prediction and unsupervised hierarchical clustering: The K-nearest neighbor classification algorithm embedded in the Prediction Analysis of Microarrays (PAM) tool was used to identify classifier genes presenting the highest capability to discriminate the two classes of bacterial and viral infection (Tibshirani, R., et al. 2002, "Diagnosis of multiple cancer types by shrunken centroids of gene expression," *Proc. Nat'l. Acad. Sci. USA*, 99(10):6567-6572). With 10-nearest neighbors and 10-fold cross-validation, PAM calculates misclassification error rate in the training set of data for each of the two classes according to varying threshold (a unique statistical parameter). A threshold is chosen when the misclassification error is minimized for both classes to define a subset of probes from the entire training data set, designated as classifier probes. These classifier probes were used for class prediction on testing data sets. Hierarchical clustering was used with the complete linkage algorithm to evaluate the accuracy of classification.

Transcriptional profiles of virus-positive febrile children and febrile children with acute bacterial infection differed from those of afebrile virus-positive and afebrile virus-negative children.

Microarray data was analyzed from Illumina Human HT12 Bead-Chips comprising 47,300 probes hybridized with RNA samples extracted from whole blood specimens from 22 febrile children (8 positive for human herpesvirus 6 [HHV-6], 8 positive for adenovirus and 6 positive for enterovirus, and 8 with acute bacterial infection). The same microarray assay was performed on blood samples from 35 afebrile children (2 positive for HHV-6, 3 positive for adenovirus, 8 positive for rhinovirus, and 22 virus-negative control children).

By using a strategy based on intersecting various probe sets as described previously (Chaussabel D. et al. 2005, *Annals NY Acad. Sci.* 1062:146-154), probes sets were intersected that were significantly up- or down-regulated for each of the virus-positive groups and the febrile acute bacterial infection group compared to afebrile virus-negative control children (FIG. 1A).

FIG. 1 illustrates identification of virus- and bacterial response-specific probes for distinguishing virus-positive febrile children and febrile children with acute bacterial infection from virus-negative afebrile children. FIG. 1A illustrates a Venn diagram showing identification of virus- and bacterial response-specific probes. Sets of probes differentially expressed in febrile children positive for 1 or more of the 3 viruses compared to virus-negative afebrile control children were intersected and 1691 "panvirus" probes were identified and intersected with the set of probes that were differentially expressed in children with febrile acute bacterial infection compared to virus-negative afebrile control children. From this analysis, 413 virus-specific and 1939 bacterial response-specific probes were identified, including probes specific for individual viruses. FIG. 1B illustrates heat maps of gene expression of viral response-specific probes. FIG. 1C illustrates heat maps of gene expression of bacterial response-specific probes. FIG. 1B and FIG. 1C illustrate heat-maps showing gene expression based on 260 viral response-specific probes (FIG. 1B) and 1321 bacterial response-specific probes (FIG. 1C) in children with febrile and afebrile viral and bacterial infections and afebrile virus-negative control children. These probes were selected in the same manner as the 413 virus-specific and 1939 bacterial response-specific probes described above except that for this selection, with the exclusion of 2 of 22 virus-negative controls. Probes that were not annotated in GenBank Build36 (National Center for Biotechnology Information) were also excluded. F+, febrile, F−, afebrile. Each row represents a gene with expression value normalized to the mean of the afebrile virus-negative control group and each column represents one individual. In original color, red represents up-regulation and blue represents down-regulation.

Using this method 260 probes with significant up- or down-regulation specifically in virus-positive febrile children and 1321 probes with significant up- or down-regulation specifically in children with febrile acute bacterial infection were identified. Analysis of the 260 viral probes revealed overlap in gene expression profiles for febrile children who were positive for adenovirus, HHV-6, or enterovirus infection, which were very different from the profiles of most afebrile children (FIG. 1B). Profiles of virus-positive and virus-negative afebrile children were indistinguishable. Analysis using the 1321 bacterial probes displayed similar patterns of gene expression for most of the children with fever and acute bacterial infection that differed from those of the other groups, with a few exceptions (FIG. 1C).

The extensive differences in gene expression profiles between febrile and afebrile children were further analyzed for each virus and for acute bacterial infection by principal component analysis and by analysis of genes grouped into Ingenuity® canonical pathways (www.ingenuity.com). Results for HHV-6 are shown in FIG. 2, and results for adenovirus, enterovirus, and acute bacterial infection are available as FIGS. 5, 6, and 7.

FIG. 2 illustrates blood leukocyte transcriptional profiles of febrile and afebrile HHV-6-positive children compared to those of afebrile virus-negative children.

Figure 2A:
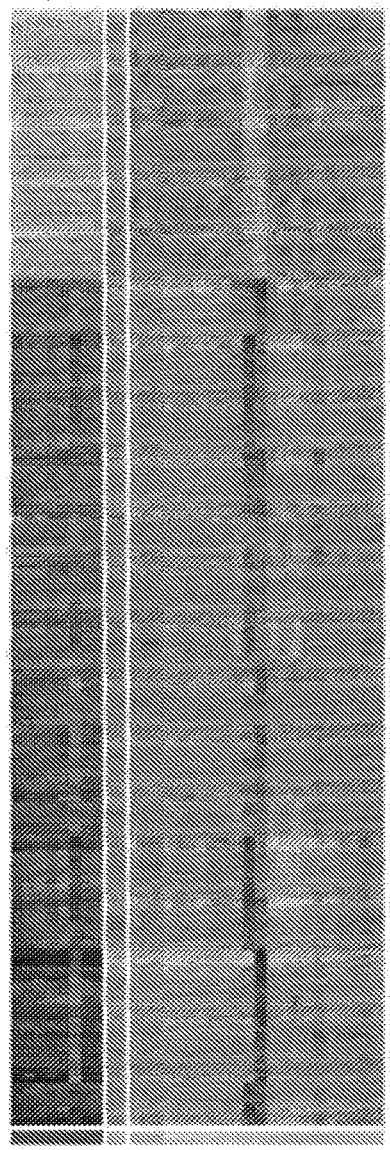
FIG. 2A-F illustrate blood leukocyte transcriptional profiles of febrile and afebrile HHV-6-positive children compared to those of afebrile virus-negative children.
Figure 2A:
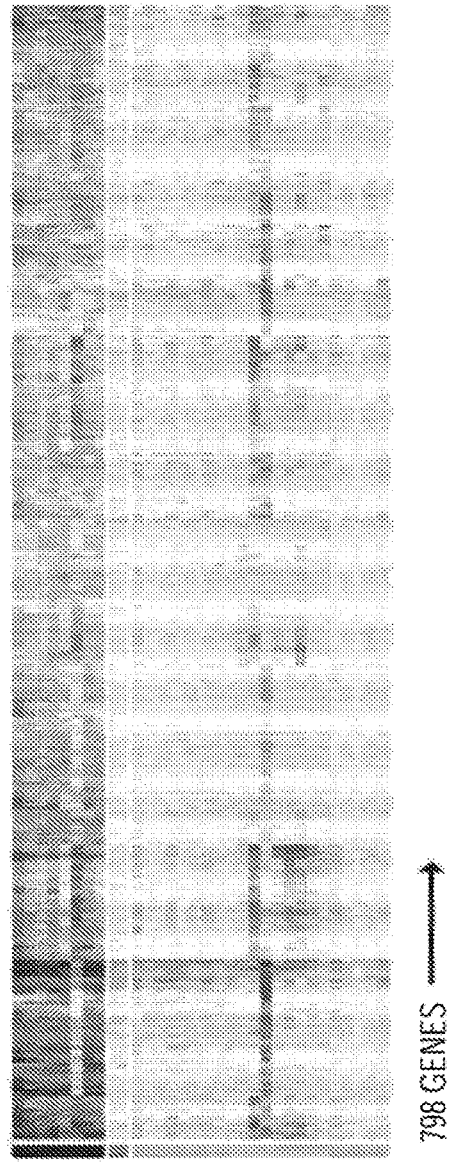
Figure 2B:
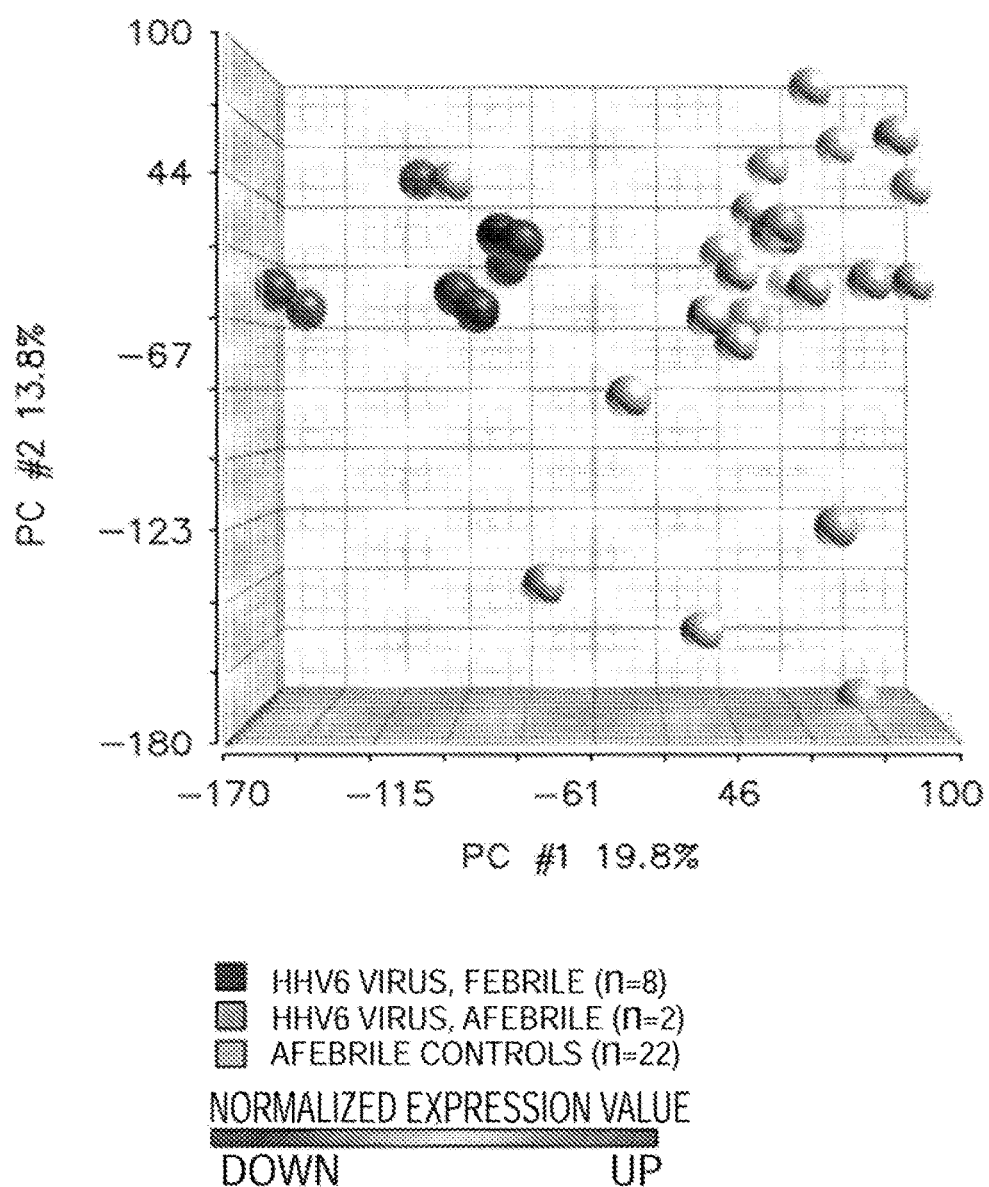
Figure 2C:
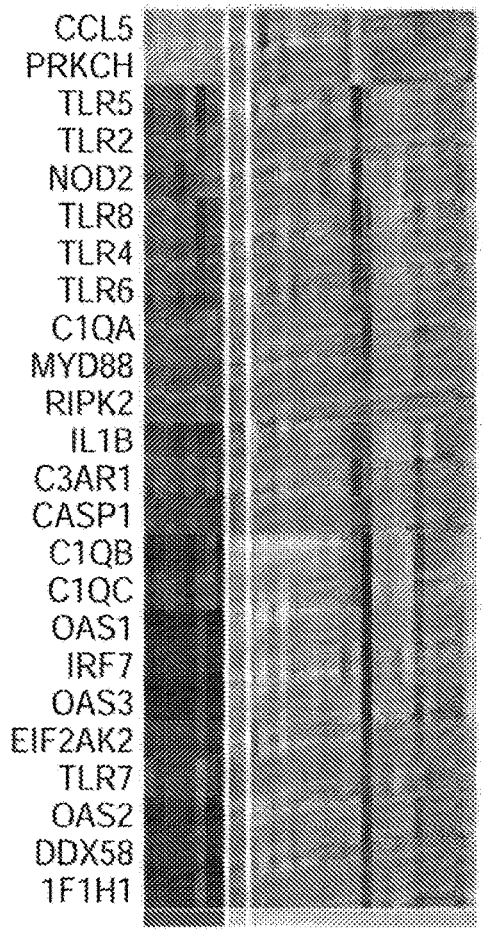
Figure 2C:
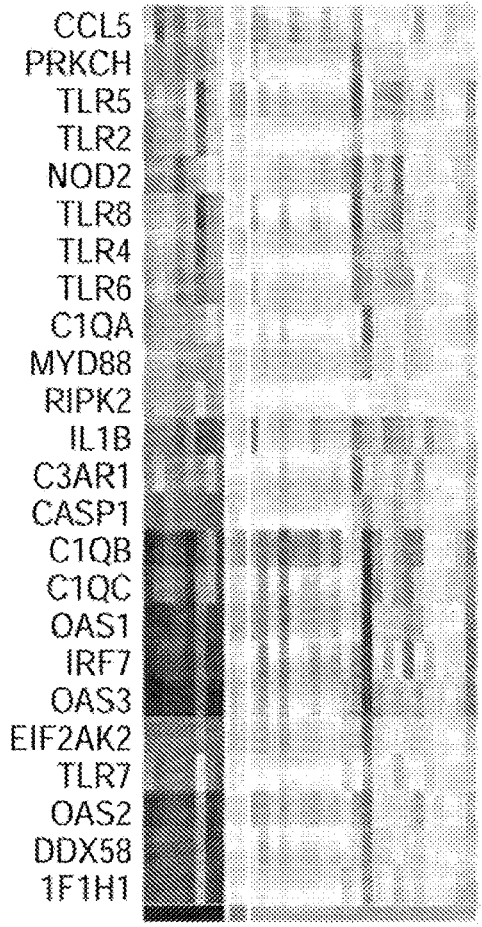
Figure 2D:
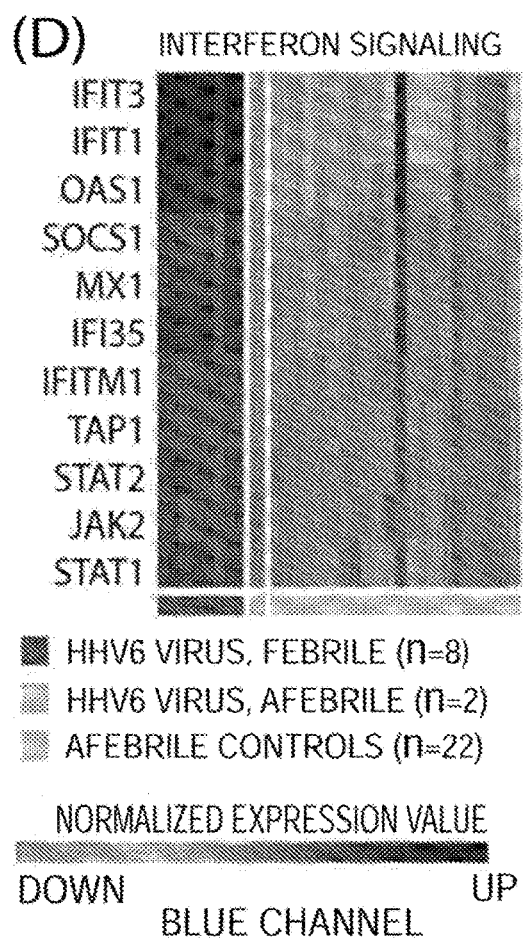
Figure 2D:
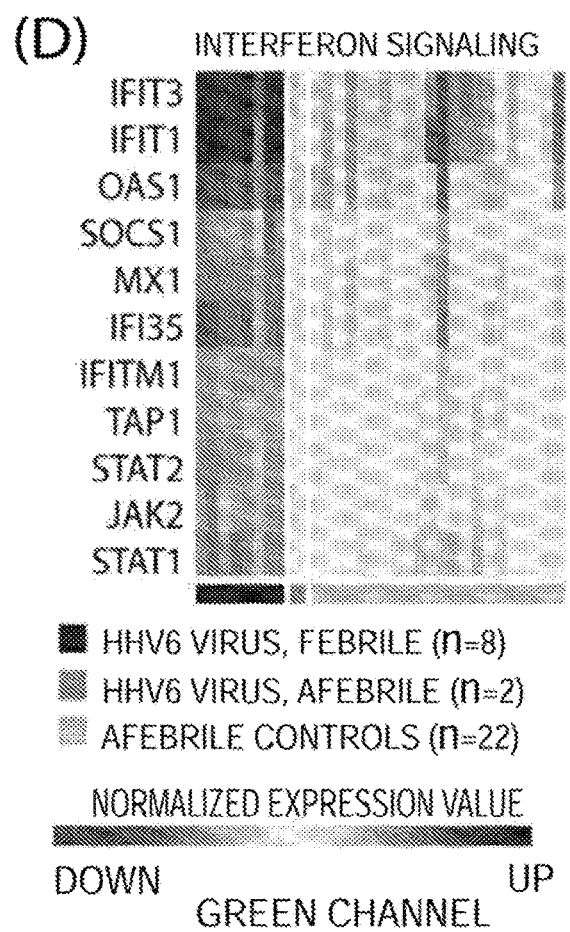
Figure 2E:
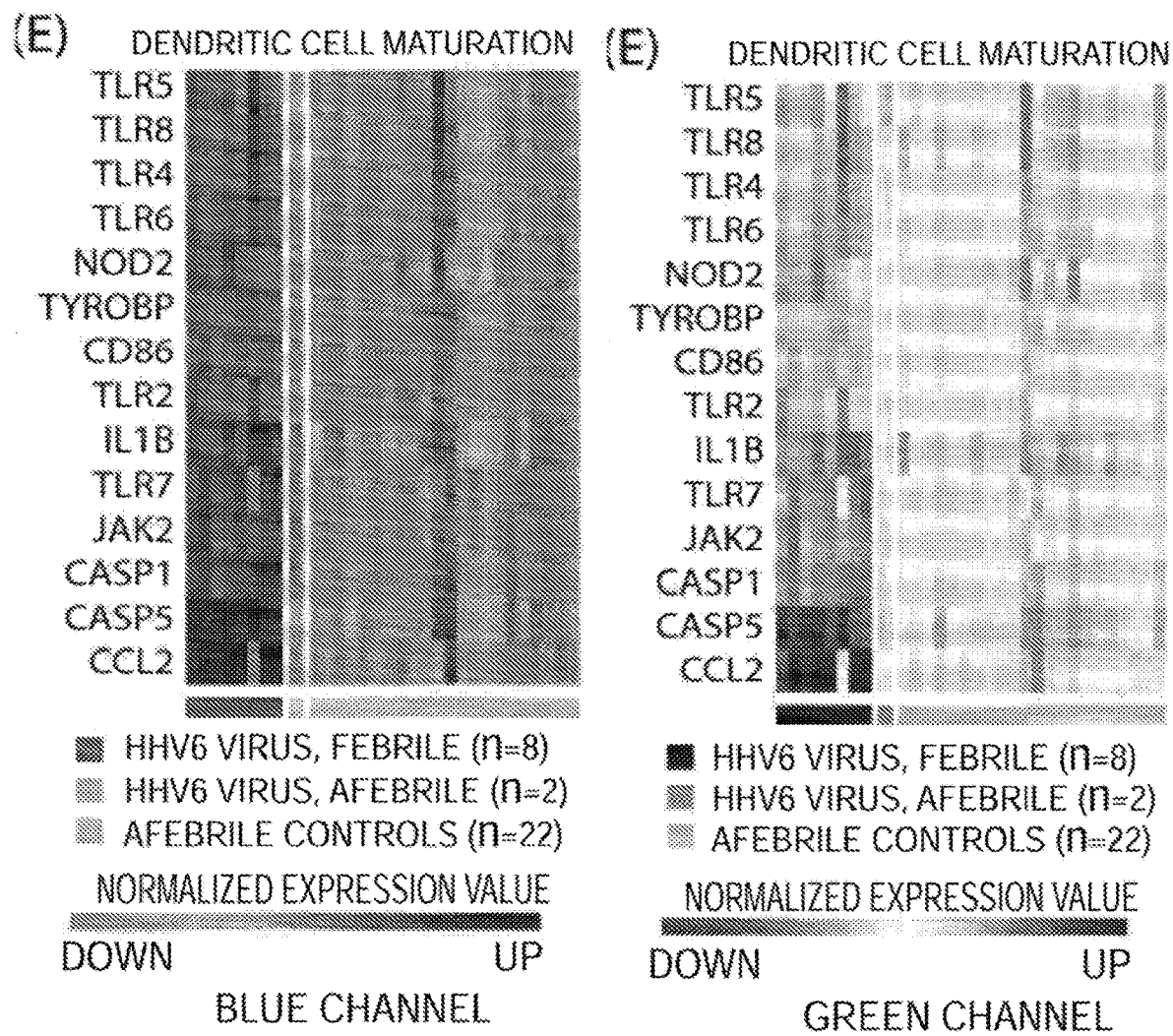
Figure 2F:
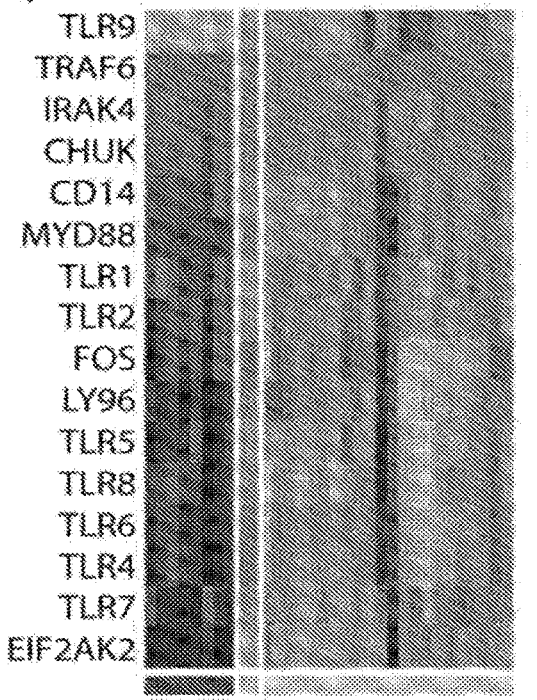
Figure 2F:
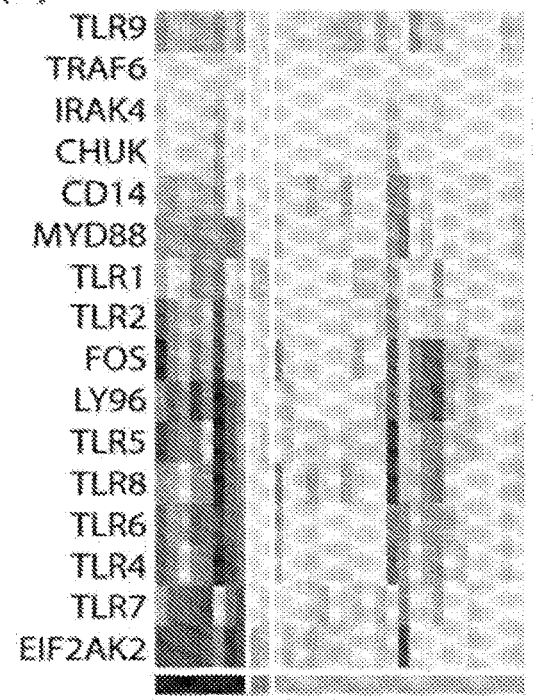

In these investigations, microarray analysis was conducted on RNA extracted from blood samples of 10 children positive for HHV6 (8 febrile, 2 afebrile), and 22 afebrile virus-negative children. FIG. 2A illustrates clustering of probe sets with a statistically significant >2-fold difference between HHV-6-positive febrile children and afebrile virus-negative control children (FDR 5%). FIG. 2B illustrates a principal component analysis of differentially expressed genes, with each oval representing one child. FIGS. 2C-2F illustrate clustering of differentially expressed genes in FIG. 2A according to expression intensity in 4 Ingenuity® canonical pathways. Each row represents a gene whose expression value is normalized to the mean of the afebrile virus-negative control group. Gene names are listed to the left. Each column represents one individual. In original color, red represents up-regulation and blue represents down-regulation.

FIG. 5 illustrates blood transcriptional profiles of febrile adenovirus-positive children as different from the profiles of healthy children and afibrile children with adenovirus infections.

Figure 5A:
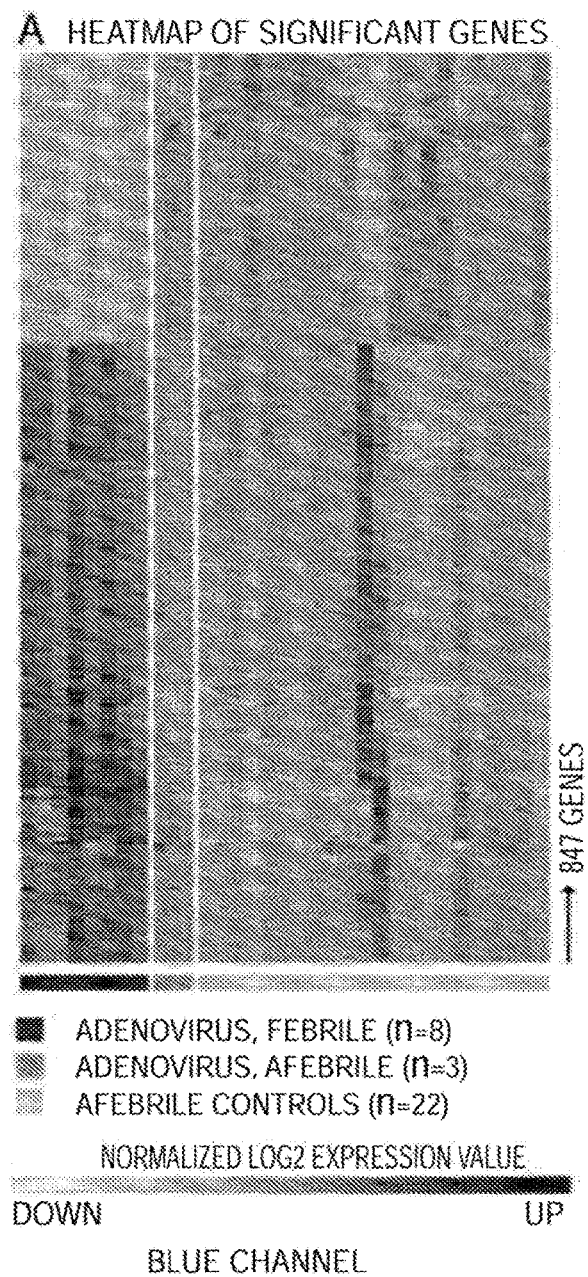
Figure 5A:
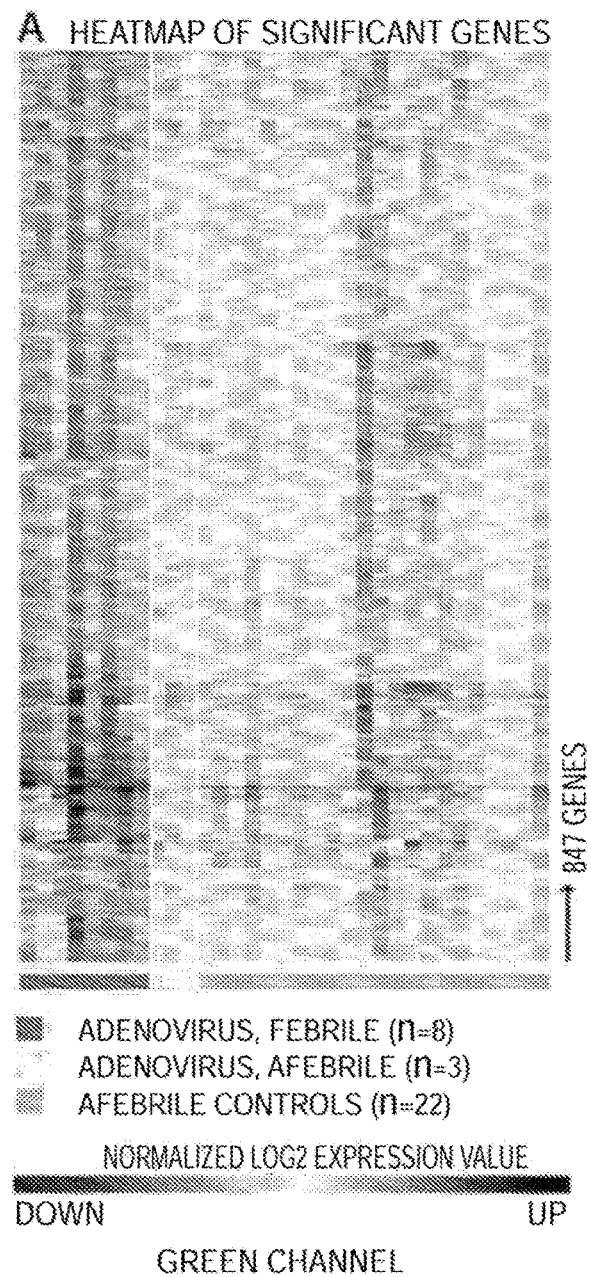
Figure 5B:
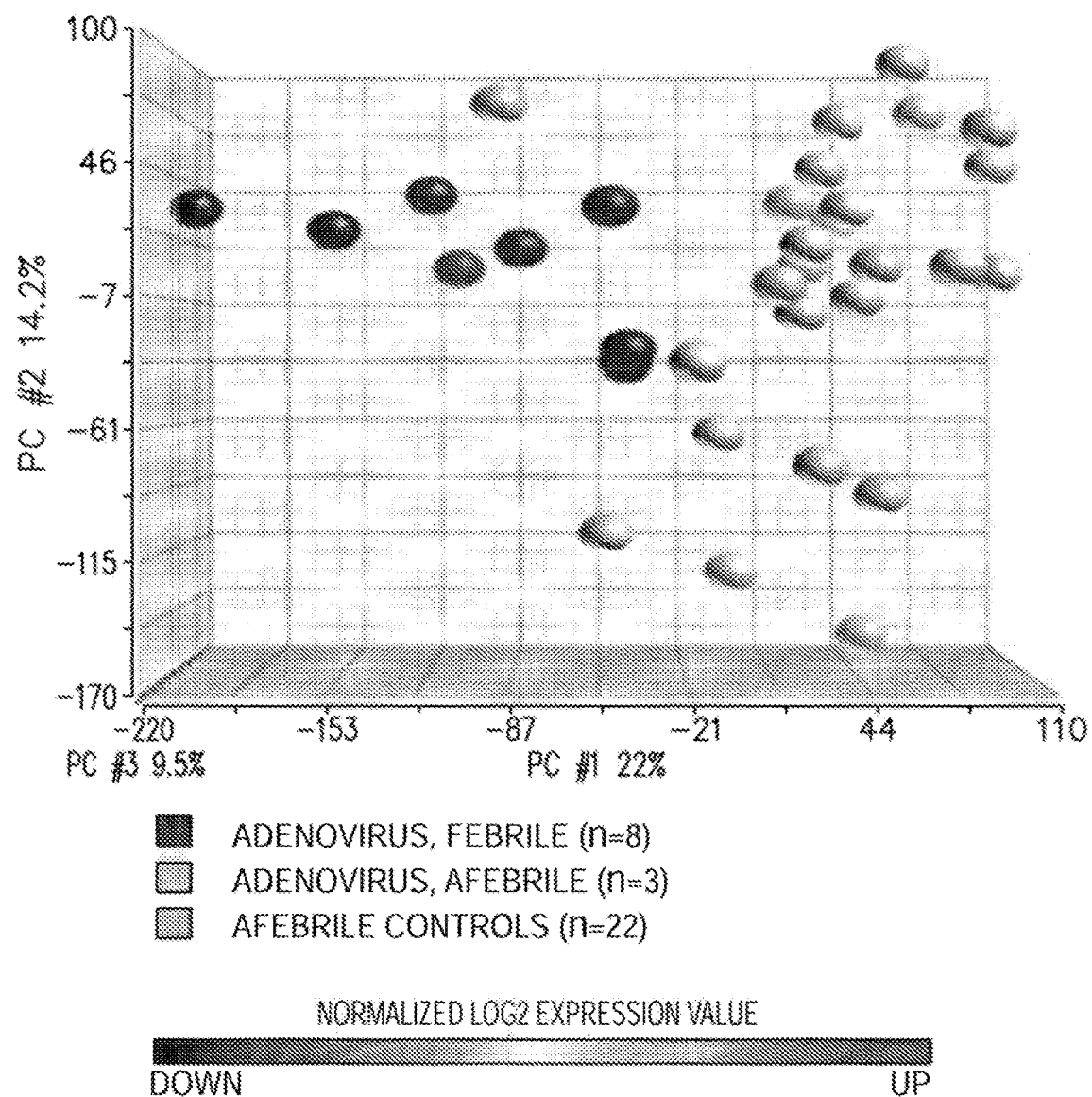
Figure 5C:
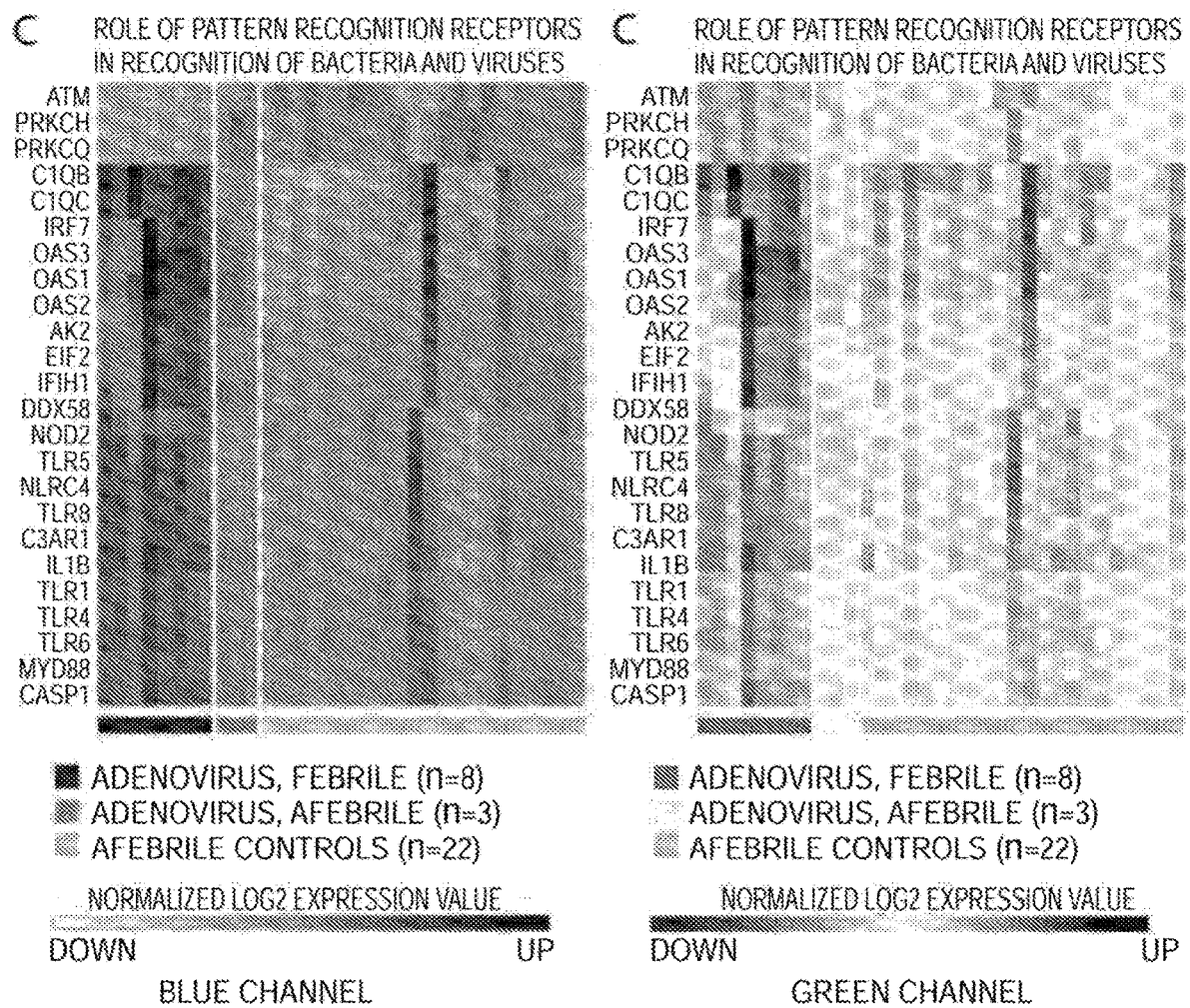
Figure 5D:
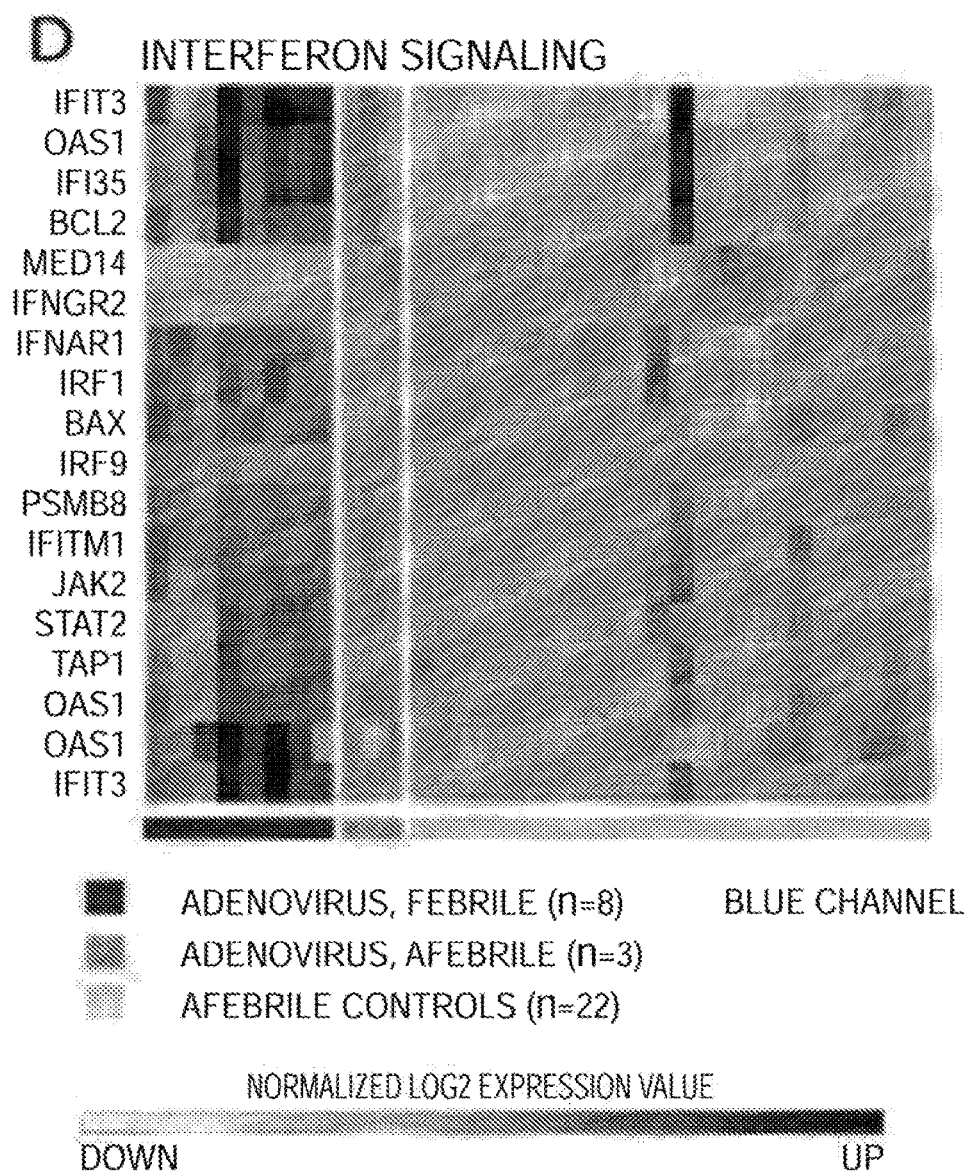
Figure 5G:
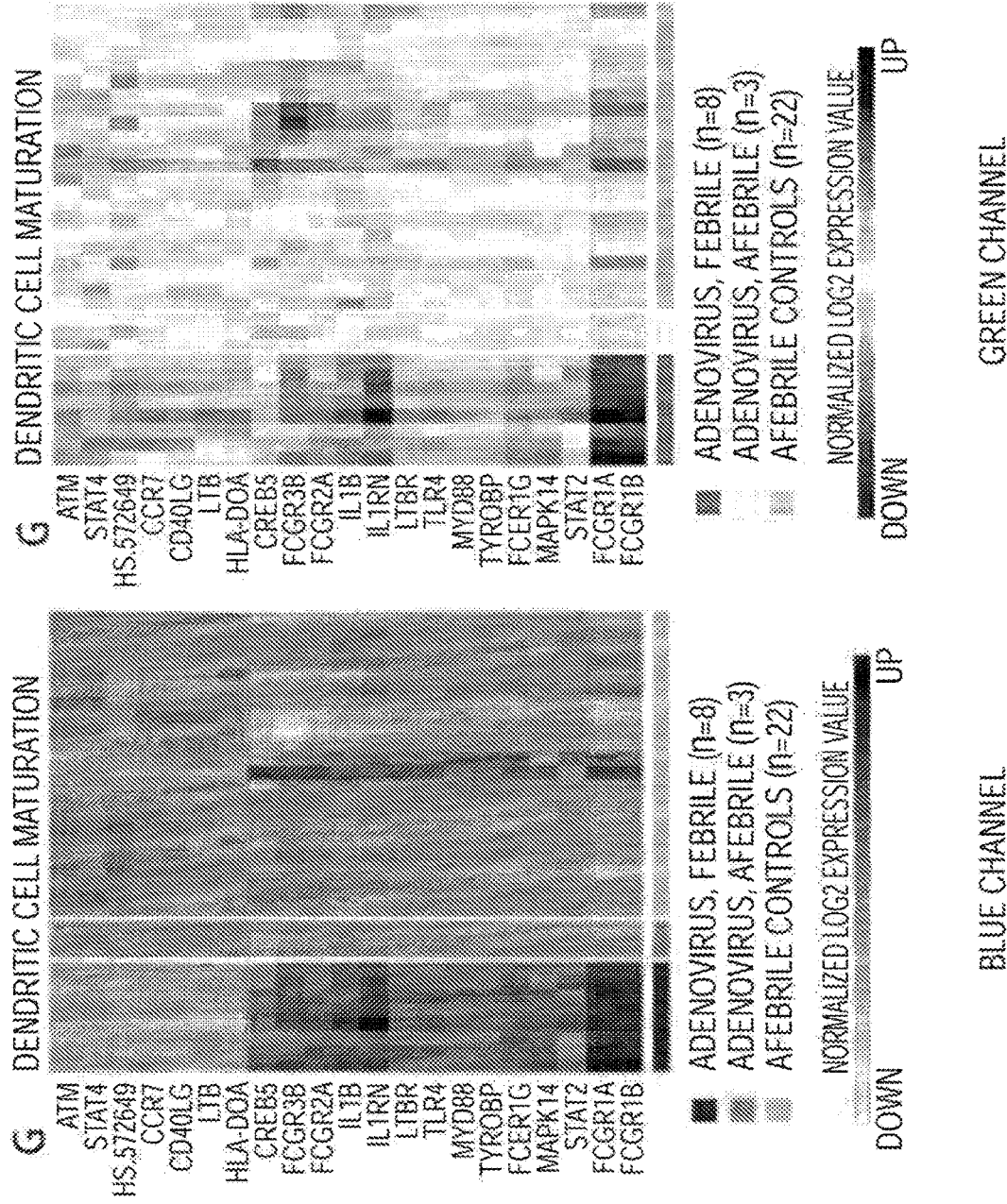

In these investigations, microarray analysis was conducted on RNA extracted from blood samples of 11 children with confirmed adenovirus infection (8 febrile and 3 afebrile children) and 22 afebrile virus-negative children. FIG. 5A illustrates clustering of probe sets with a statistically significant and greater than two-fold difference between adenovirus-positive febrile children and virus-negative afebrile controls (false discovery rate (FDR) at 5%). FIG. 5B illustrates a principal component analysis of differentially expressed genes, with each oval representing one child. FIG. 5C-5G illustrate clustering of differentially expressed genes from FIG. 5A according to expression intensity in five Ingenuity, canonical pathways. Each row represents a gene with expression value that is normalized to the mean of the afebrile virus-negative control group. Gene names are listed to the left. Each column represents one individual. In original color, red represents up-regulation, and blue represents down-regulation.

FIG. 6 illustrates blood transcriptional profiles of enterovirus-positive febrile children as different from the profiles of virus-negative afebrile children.

Figure 6A:
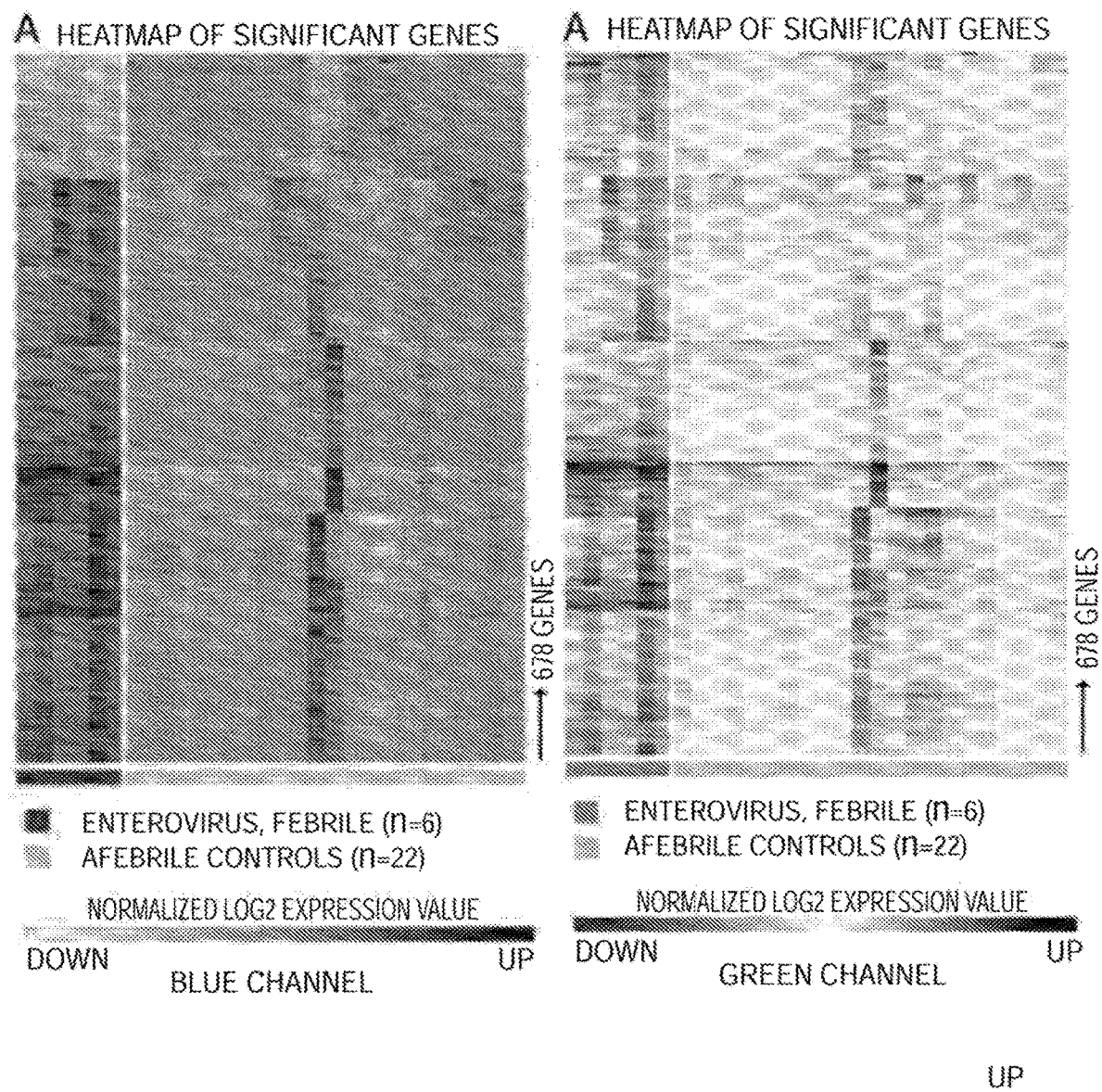
Figure 6B:
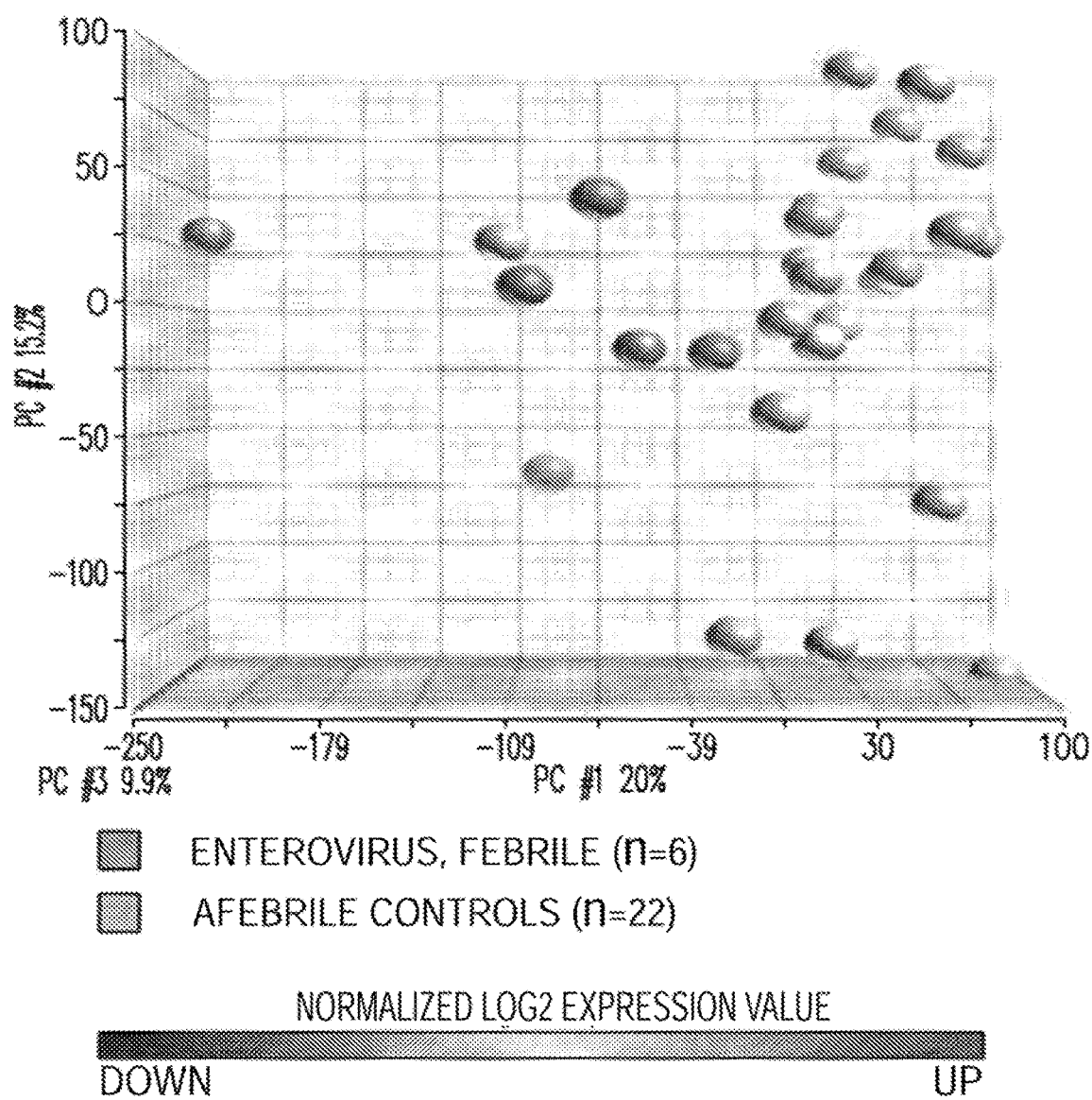
Figure 6C:
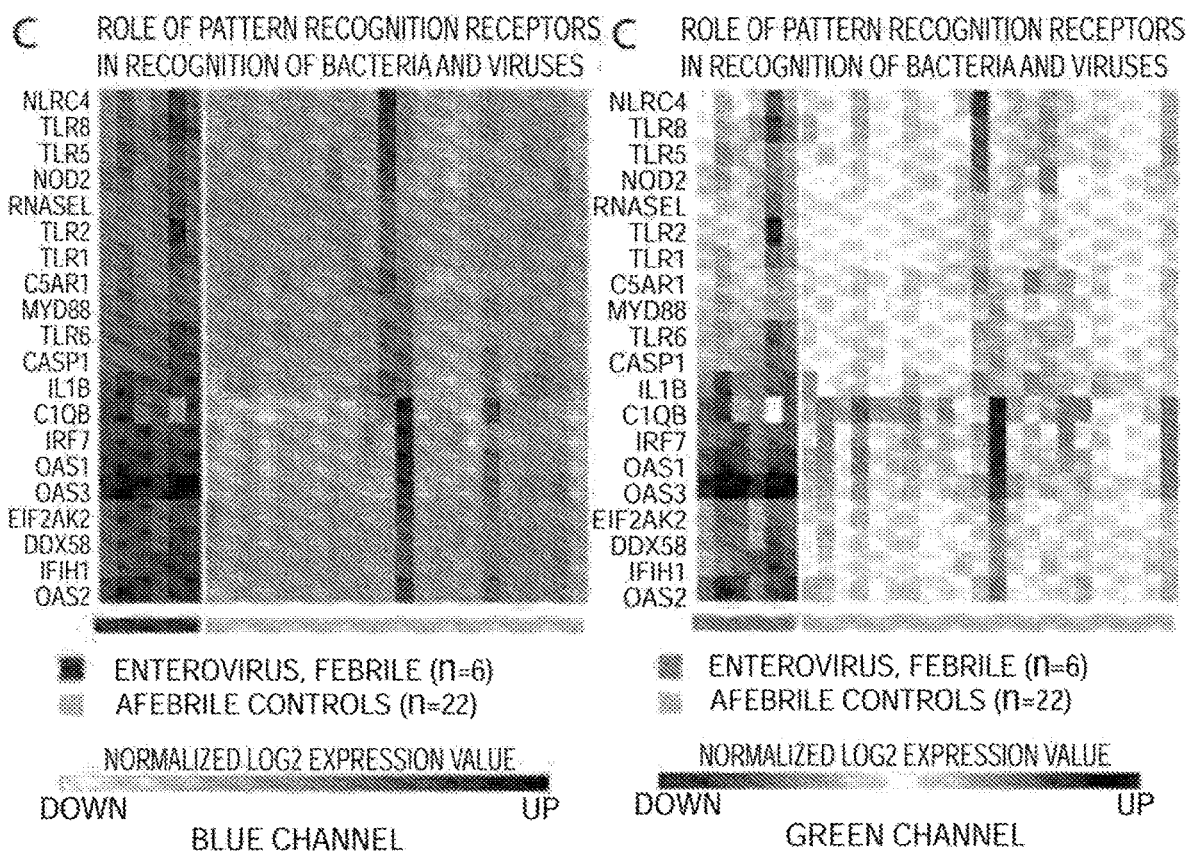
Figure 6D:
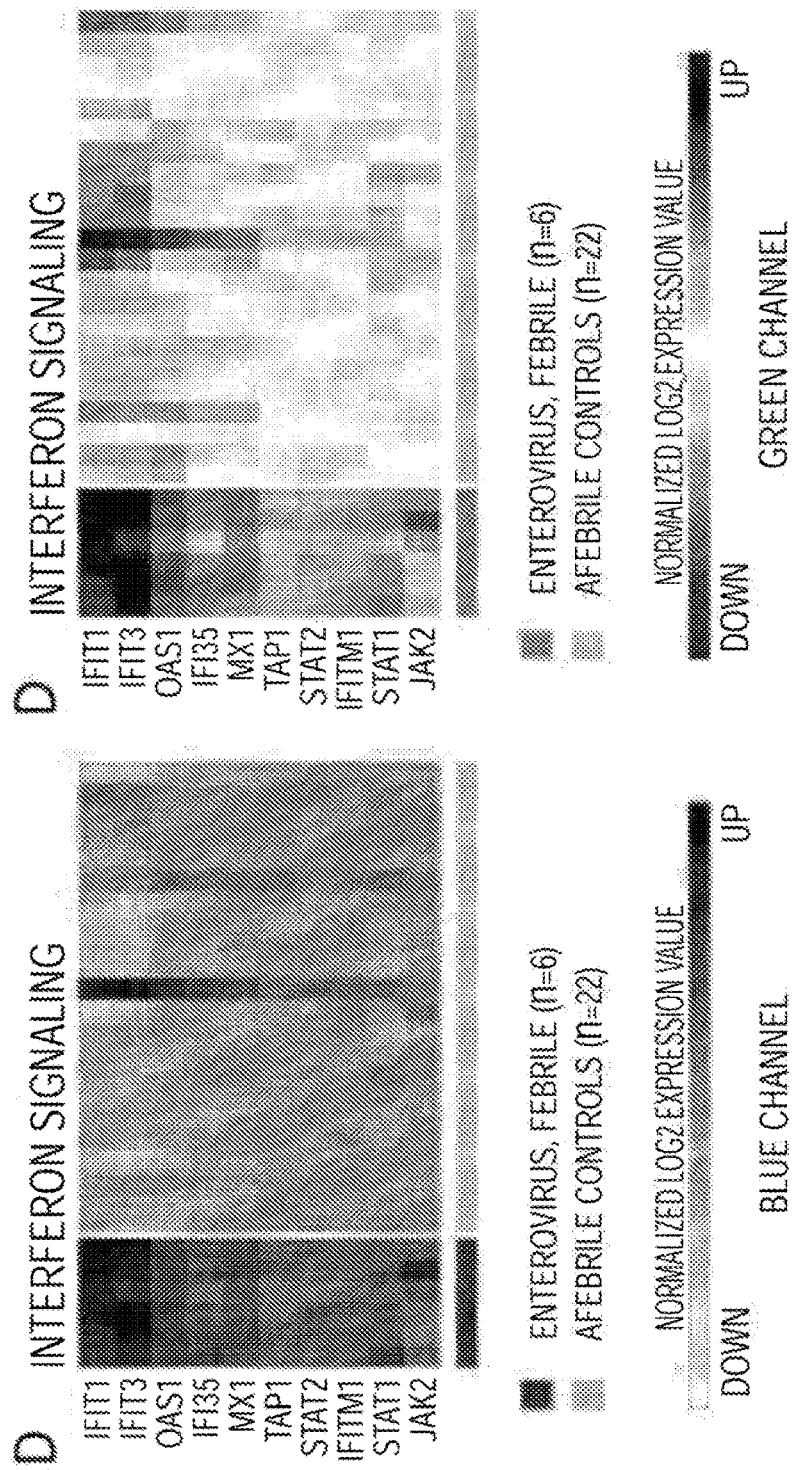
Figure 6E:
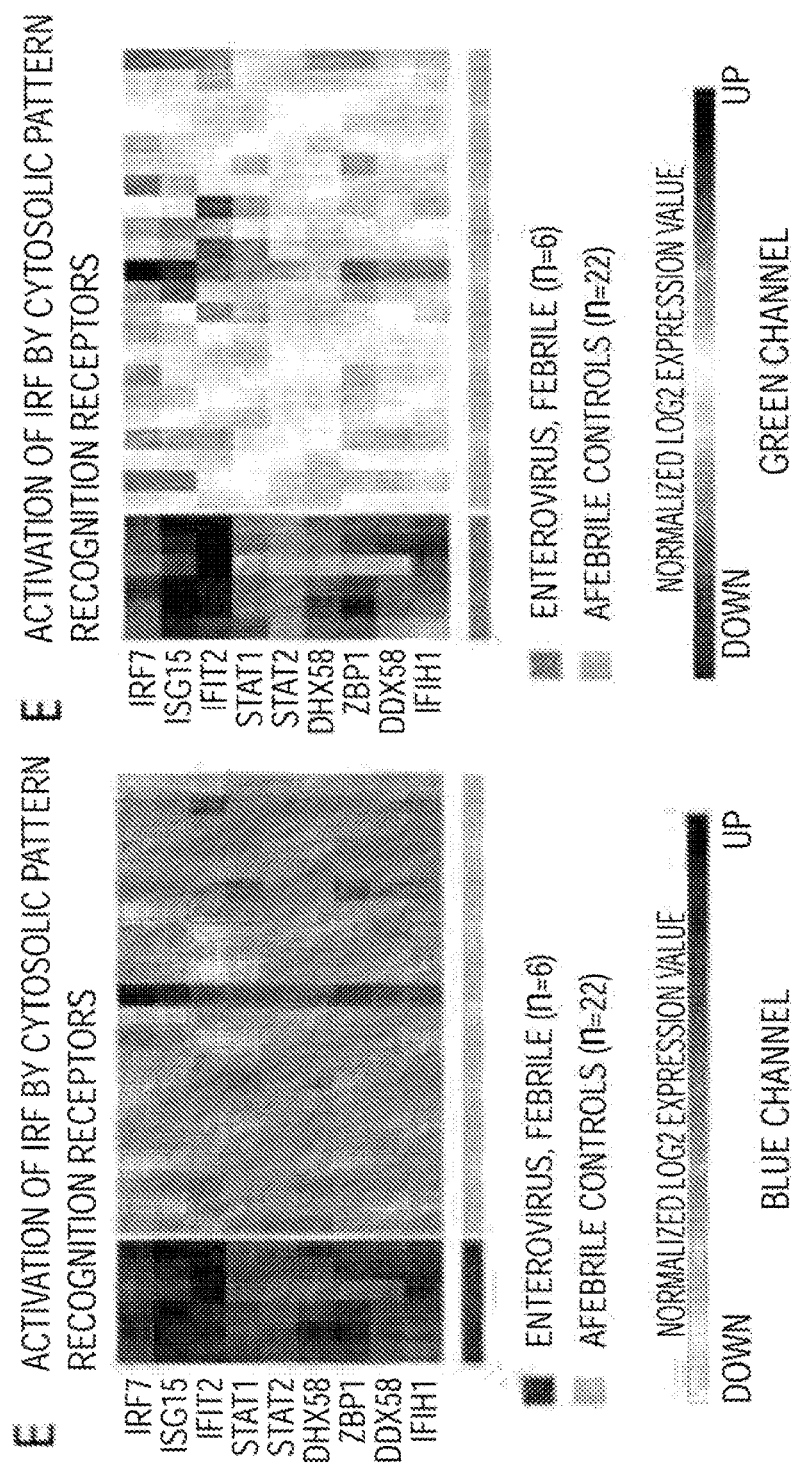
Figure 6F:
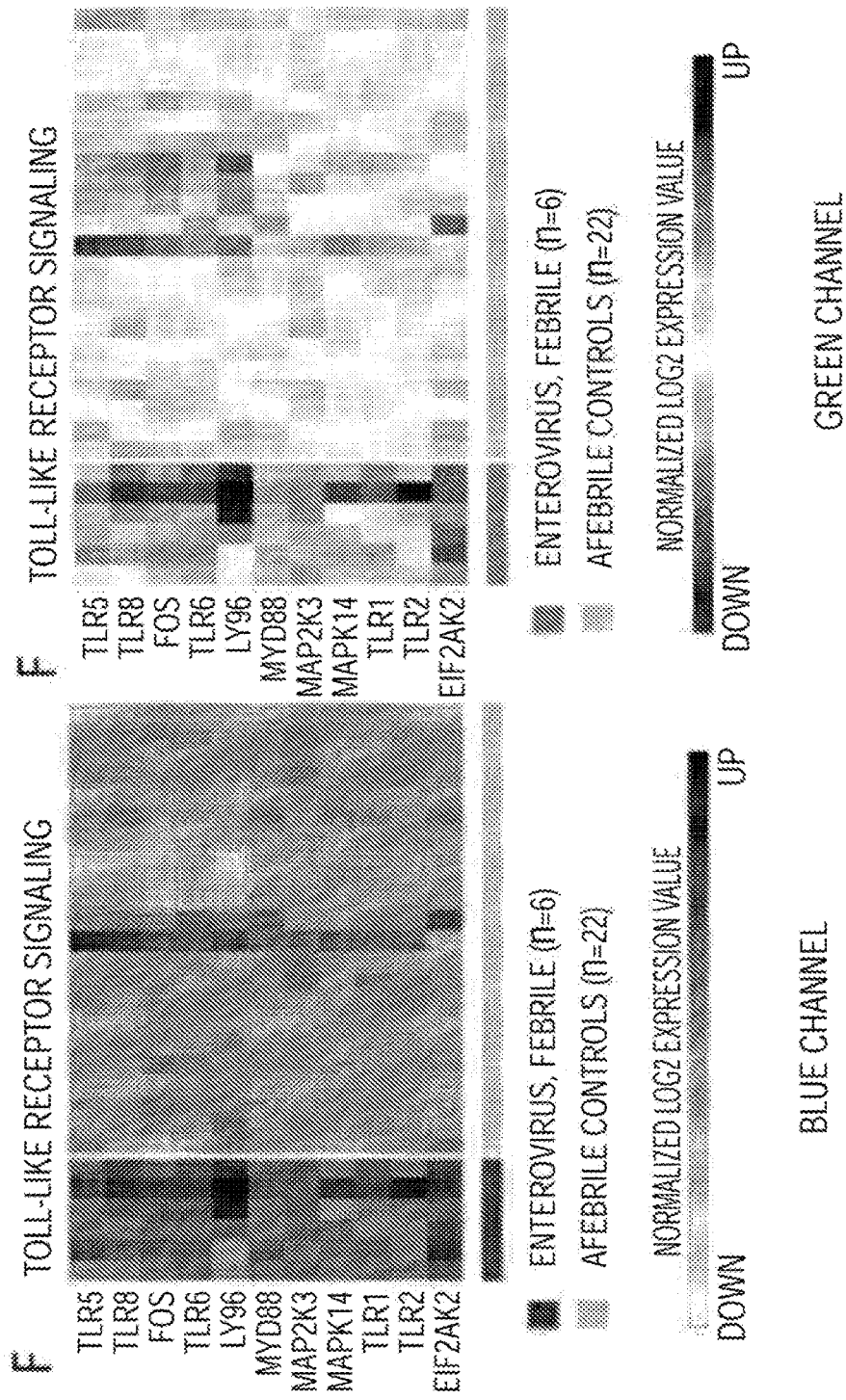

In these investigations, microarray analysis was conducted on RNA extracted from whole-blood samples of 6 enterovirus-positive febrile and 22 virus-negative afebrile children. FIG. 6A illustrates clustering of probe sets with a statistically significant greater than two-fold difference between enterovirus-positive febrile children and virus-negative afebrile controls (P<0.05, FDR at 20%). FIG. 6B illustrates a principal component analysis of differentially expressed genes, with each oval representing one child. FIG. 6C-6G illustrates clustering of differentially expressed genes in FIG. 6A according to expression intensity in five Ingenuity® canonical pathways. Each row represents a gene with expression value that is normalized to the mean of the afebrile virus-negative control group. Gene names are listed to the left. Each column represents one individual. In original color, red represents up-regulation, and blue represents down-regulation.

FIG. 7 illustrates blood transcriptional profiles of febrile children with acute bacterial infections as different from the profiles of virus-negative afebrile children.

Figure 7A:
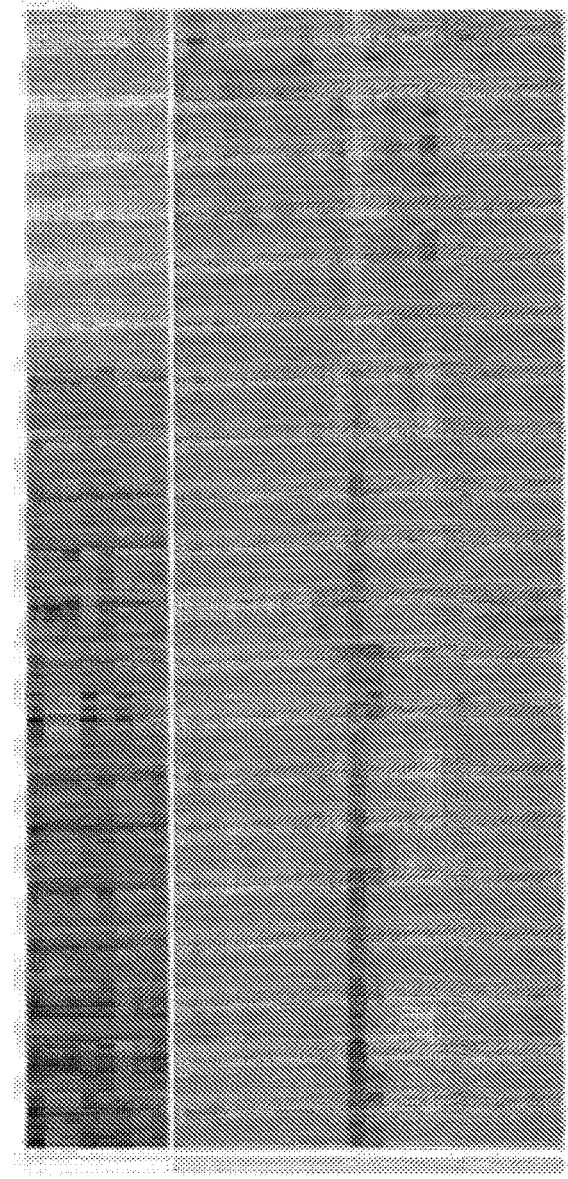
Figure 7A:
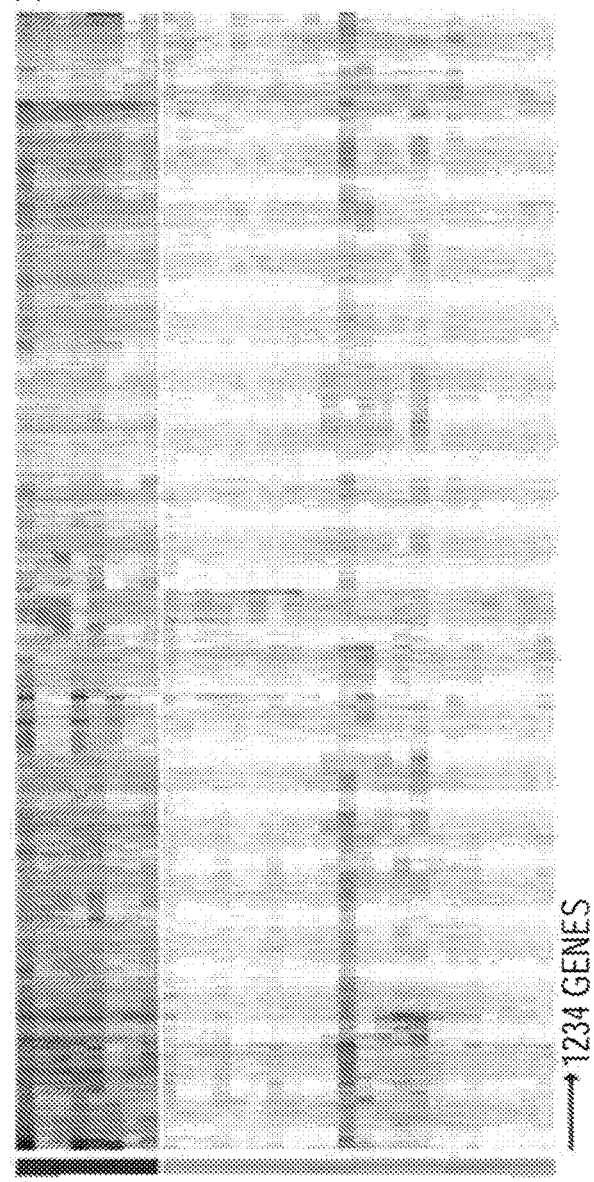
Figure 7B:
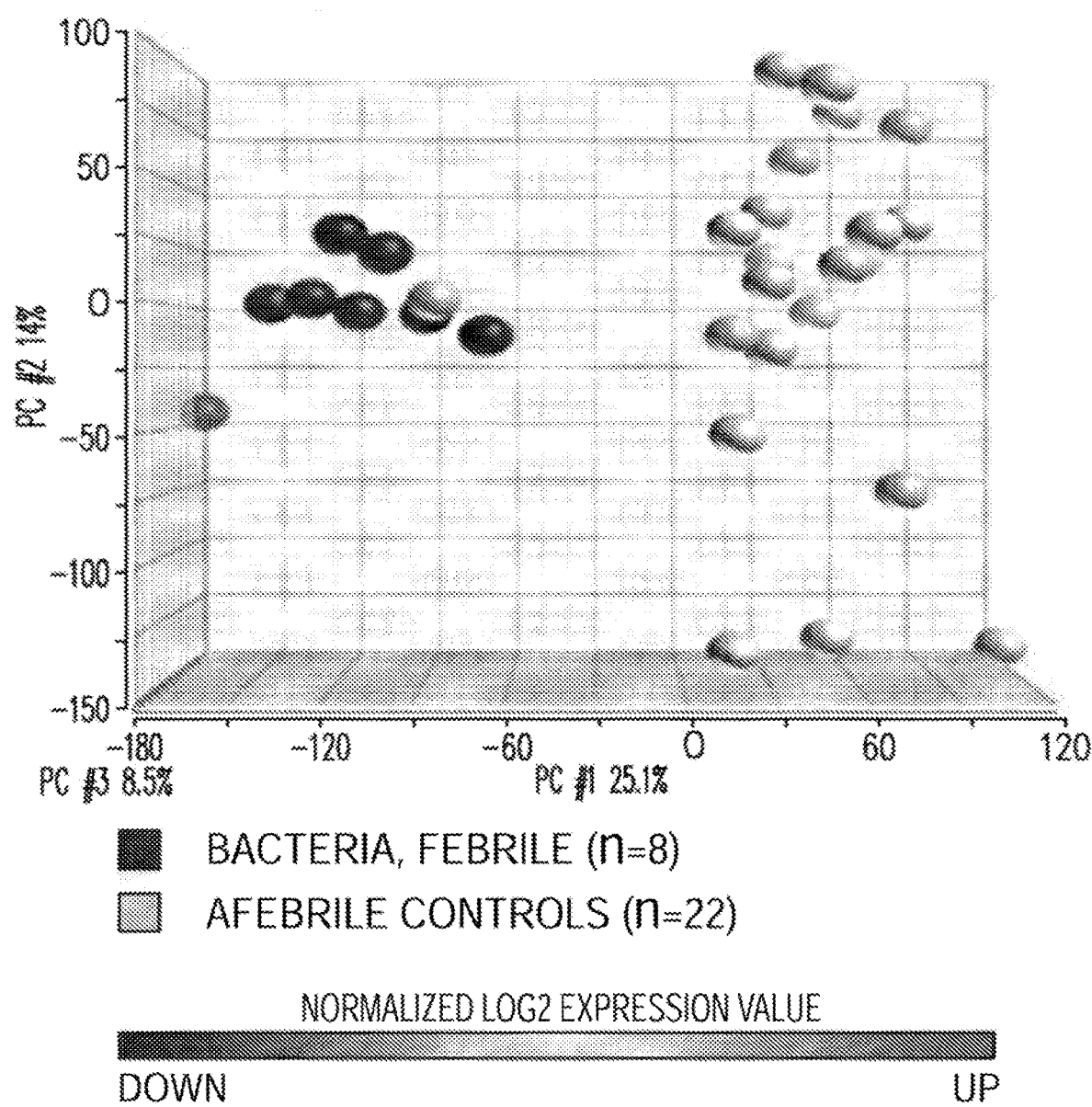
Figure 7C:
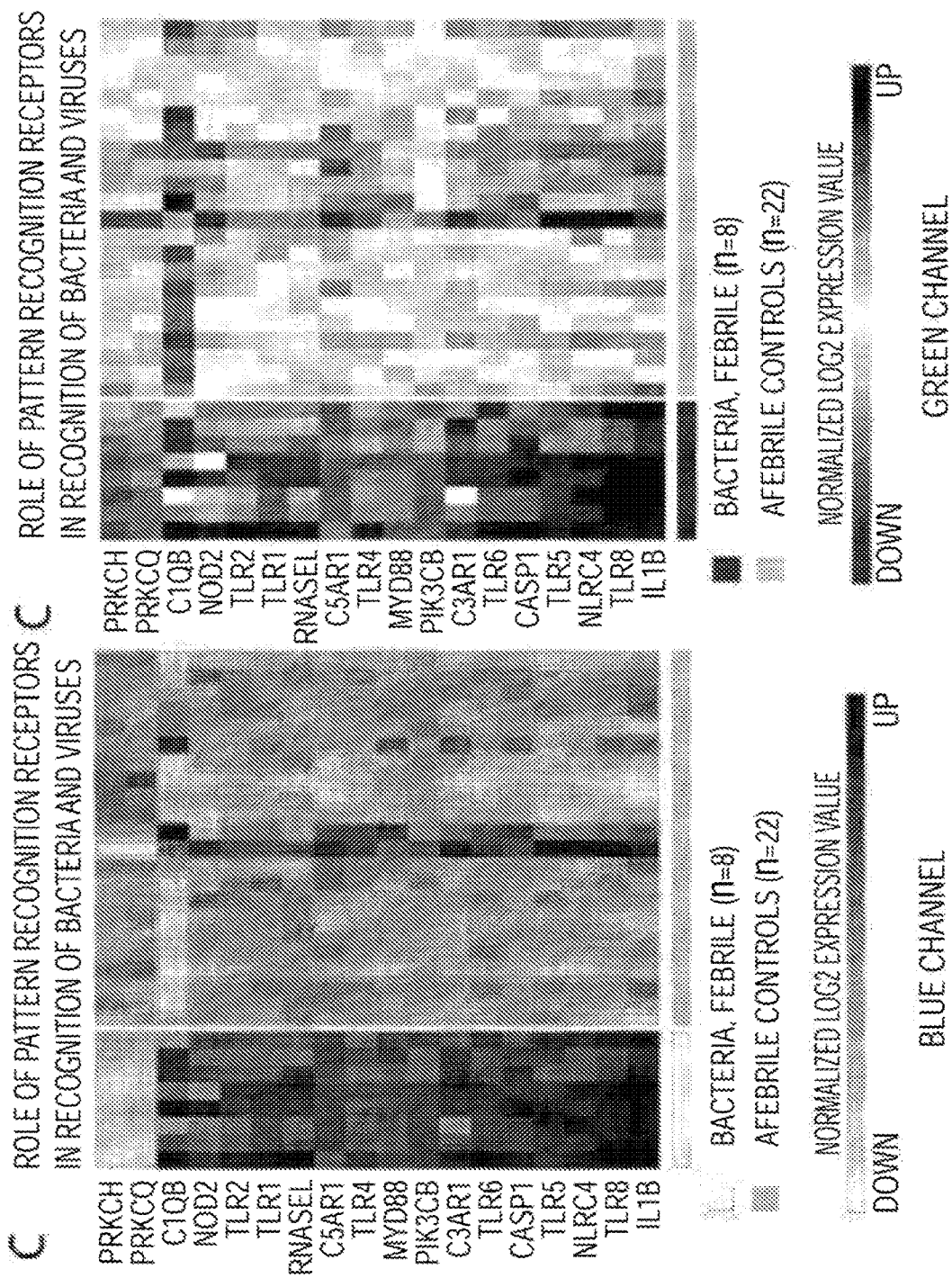
Figure 7D:
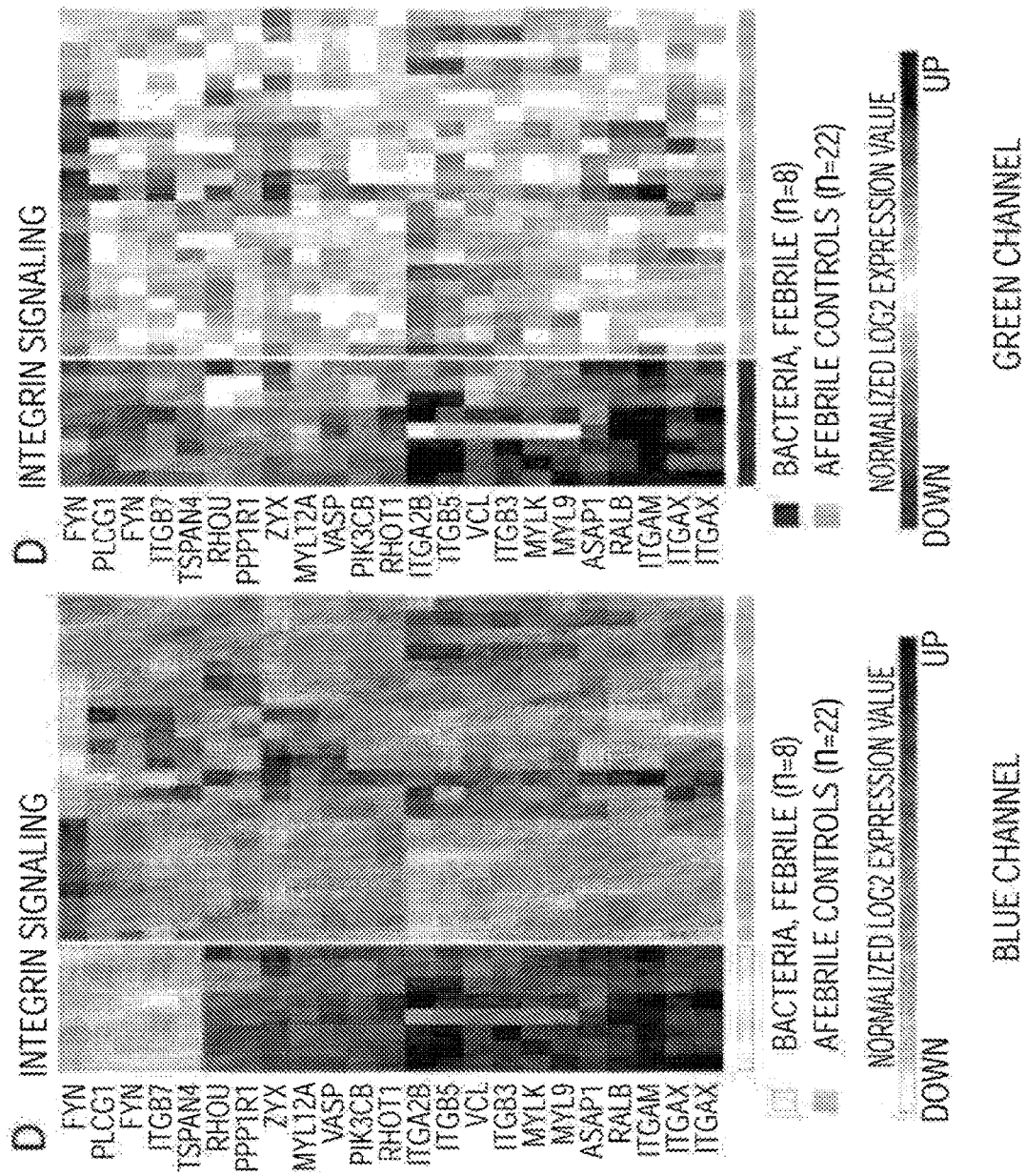
Figure 7E:
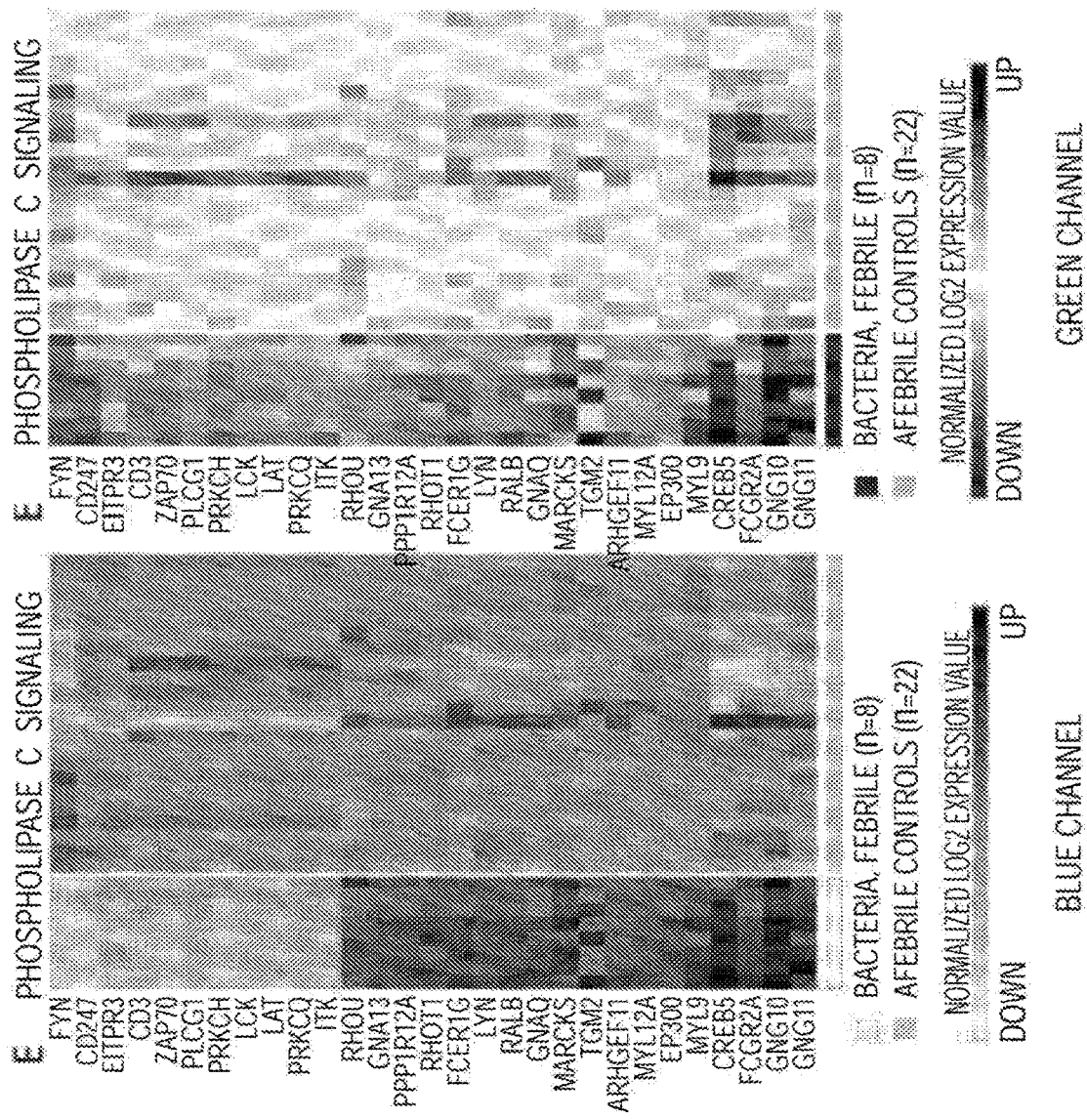
Figure 7F:
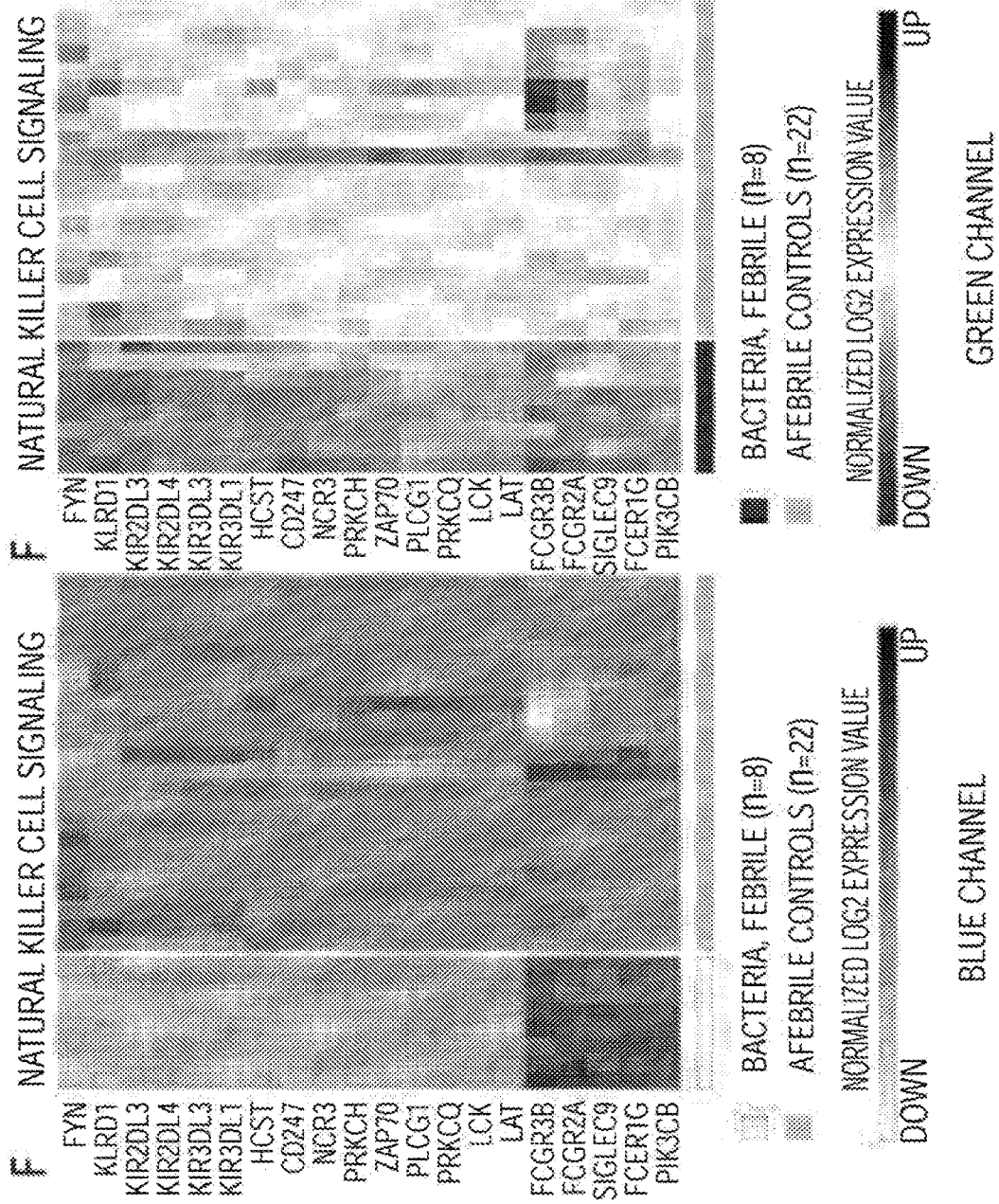

In these investigations, microarray analysis was conducted on RNA extracted from whole-blood samples of 8 febrile children with confirmed bacterial infection and 22 virus-negative afebrile children. FIG. 7A illustrates clustering of probe sets with a statistically significant greater than two-fold difference between febrile children with acute bacterial infection and virus-negative afebrile controls (FDR at 5%). FIG. 7B illustrates a principal component analysis of differentially expressed genes, with each oval representing one child. FIG. 7C-7G illustrate clustering of differentially expressed genes from FIG. 7A according to expression intensity in five Ingenuity® canonical pathways. Each row represents a gene with an expression value that is normalized to the mean of the afebrile virus-negative control group. Gene names are listed to the left. Each column represents one individual. In original color, red represents up-regulation, and blue represents down-regulation.

Figure 8A:
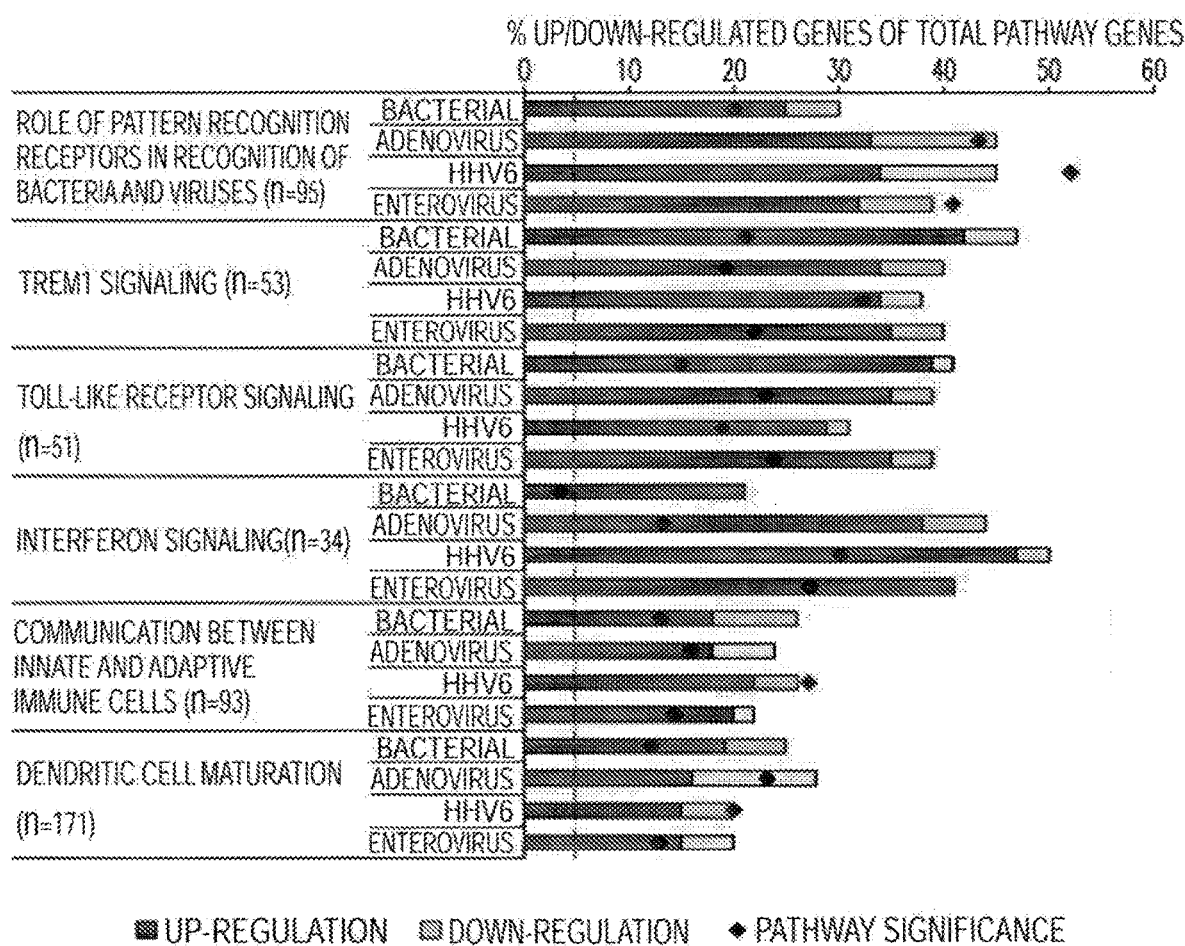
FIG. 8A-B illustrate selected up- and down-regulated Ingenuity® canonical pathways identified for febrile children positive for adenovirus, HHV-6, or enterovirus and febrile children with acute bacterial infections.
Figure 8B:
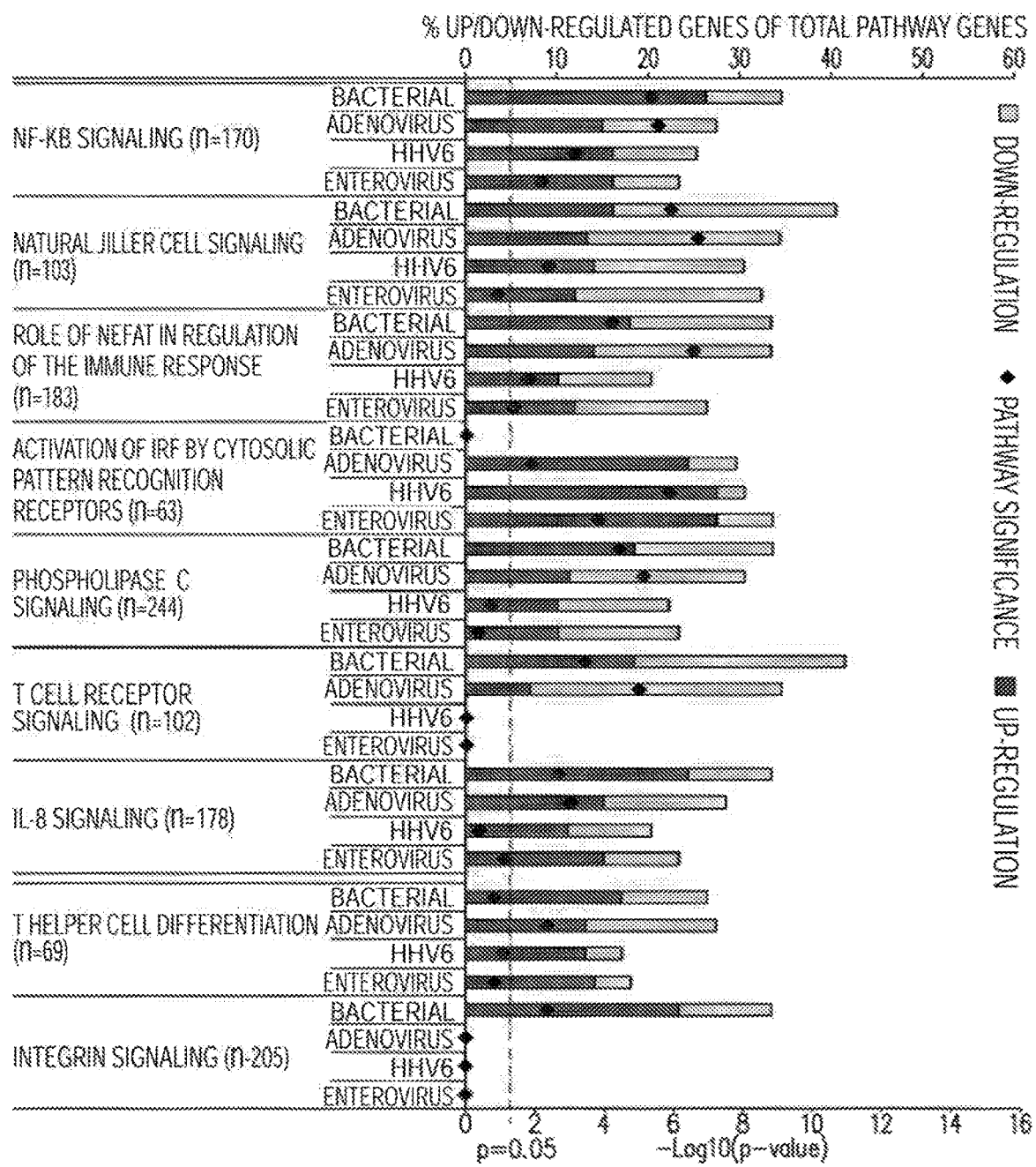

Pathways with the most significant transcriptional changes for children with each of the three viral infections and with acute bacterial infection are shown in FIG. 8A and FIG. 8B.

FIG. 8A and FIG. 8R illustrate selected significantly up- and down-regulated Ingenuity canonical pathways identified for febrile children positive for adenovirus, human herpesvirus 6 (HHV-6), or enterovirus and febrile children with acute bacterial infections. The pathways were arranged in ascending order by average P value of four infections for a pathway (i.e., the most significantly up- or down-regulated pathway is at the top).

Comparison of individual probes between HHV-6-positive febrile children with virus-negative afebrile children yielded 3467 probes with significant transcriptional changes, including 798 probes with 2-fold or greater changes (606 up- and 192 down-regulated, FIG. 2A). A principal component analysis of the transcriptional profiles confirmed clear differences between the febrile and afebrile HHV-6-positive children (FIG. 28).

A sample from the one child in the virus-negative afebrile control group with a transcriptional pattern in the heat-maps shown in FIG. 1B and FIG. 1C similar to those with febrile infection was classified with the febrile infections in the principal component analysis. An up-regulated gene was IFI27/ISG12A. Analysis of transcriptional pathways showed some pathways with up-regulation of many component genes as illustrated in FIG. 2C-FIG. 2F.

The gene expression profile of adenovirus-positive febrile children is illustrated in FIG. 5. Statistical comparison of transcriptional profiles between adenovirus-positive febrile children and virus-negative afebrile children showed 5604 probes with significant transcriptional changes including 847 with a 2-fold or greater increase (576) or decrease (271) in expression level. Principal component analysis confirmed the differences between the febrile and afebrile adenovirus-positive children. IFI27/ISG12A was up-regulated. FIG. 8 displays the pathways with the significant transcriptional changes.

Comparison of transcriptional profiles of enterovirus-positive febrile children and virus-negative afebrile control children yielded 4184 probes with significant changes as shown in FIG. 6. The magnitude of these transcriptional changes was generally less than those for adenovirus and HIV-6, and therefore FDR was set at 20% to maximize the possibility of detecting either up- or down-regulated genes. This yielded 678 probes with 2-fold or greater transcriptional change (559 up- and 119 down-regulated). IFI27/ISG12A was an up-regulated gene. The pathways with significant transcriptional changes in febrile enterovirus-positive children are shown in FIG. 8.

Statistical comparison of microarray data between febrile children with acute bacterial infection and virus-negative afebrile control children yielded 1234 probes with 2-fold or greater change with either up-regulation (850) or down-regulation (384) (FIG. 7). An up-regulated gene was Annexin A3 (14.6-fold).

Transcriptional pathways were differentially activated in febrile children with viral and bacterial infections. Some Ingenuity® canonical pathways had significant transcriptional changes in febrile children positive for one of the three viruses (HHV-6, adenovirus, enterovirus) or with acute bacterial infection. Pathways that were activated in each of the four infection groups were Role of Pattern Recognition Receptors in Recognition of Bacteria and Viruses, TREM1 Signaling, and Toll-like Receptor Signaling. Some genes from the Natural Killer Cell Signaling pathway were down-regulated in each of the four infection groups. The Interferon Signaling Pathway and the Activation of Interferon Regulatory Factors by Cytosolic Pattern Recognition Receptors Pathway were more activated in febrile virus-positive children compared to febrile children with acute bacterial infection. In contrast, genes in the Integrin Signaling Pathway were activated in bacterial infection. Transcriptional changes in each of these pathways are displayed in FIG. 8.

Figure 3:
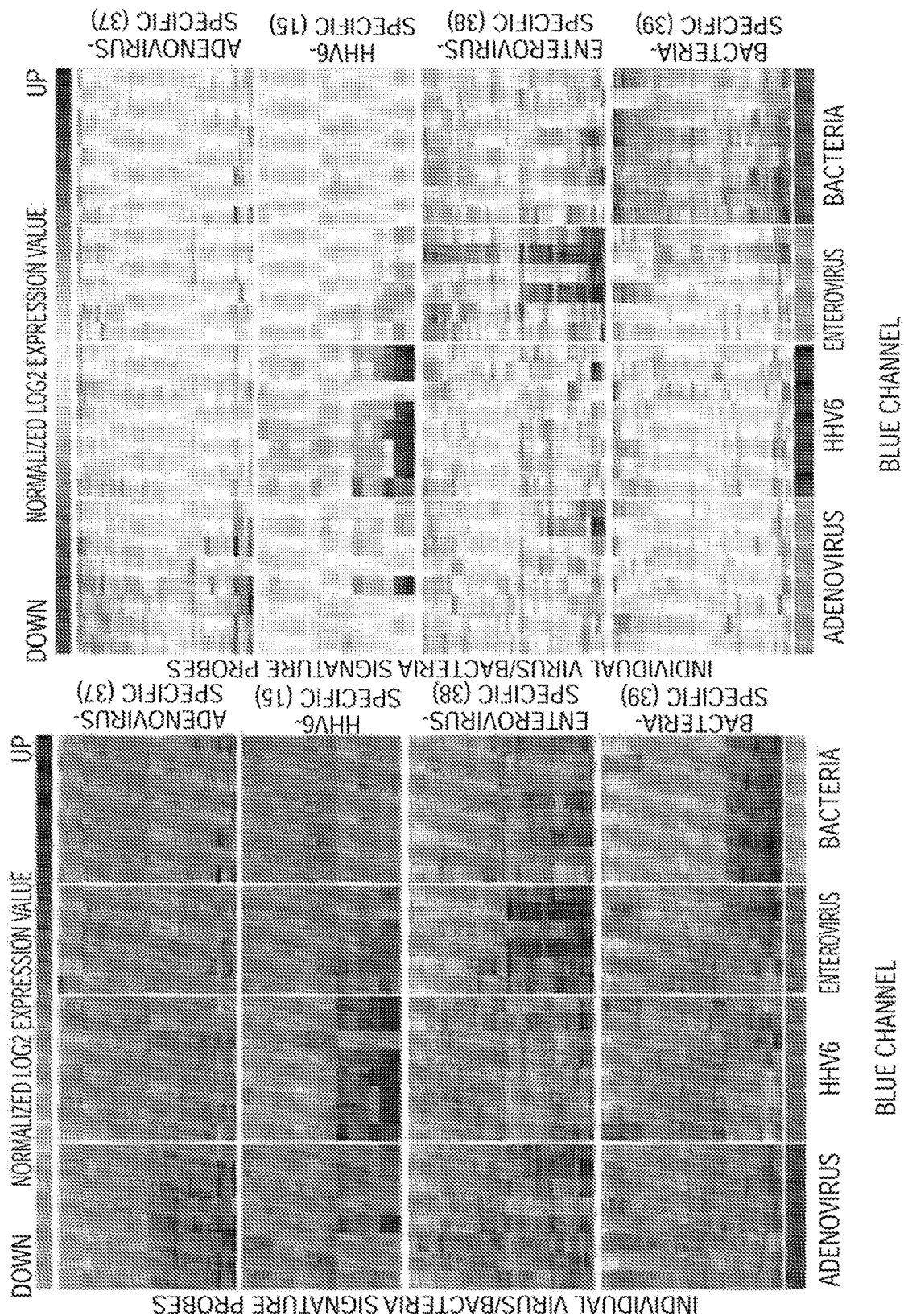
FIG. 3 illustrate probes specific for individual viruses and for bacteria.
Figure 4A:
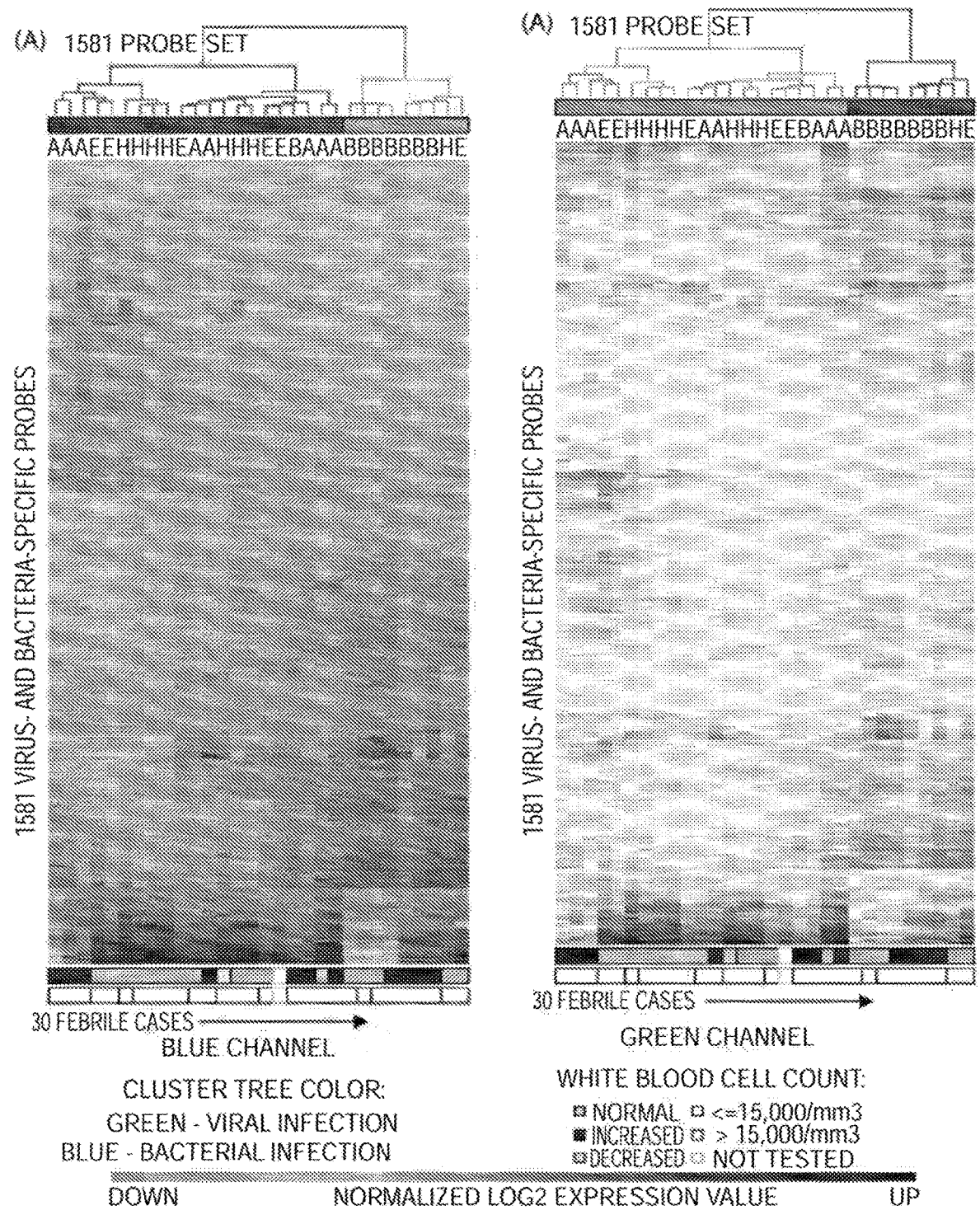
FIG. 4A-D illustrate classifier probes discriminating febrile children positive for viruses from febrile children with acute bacterial infections.
Figure 4B:
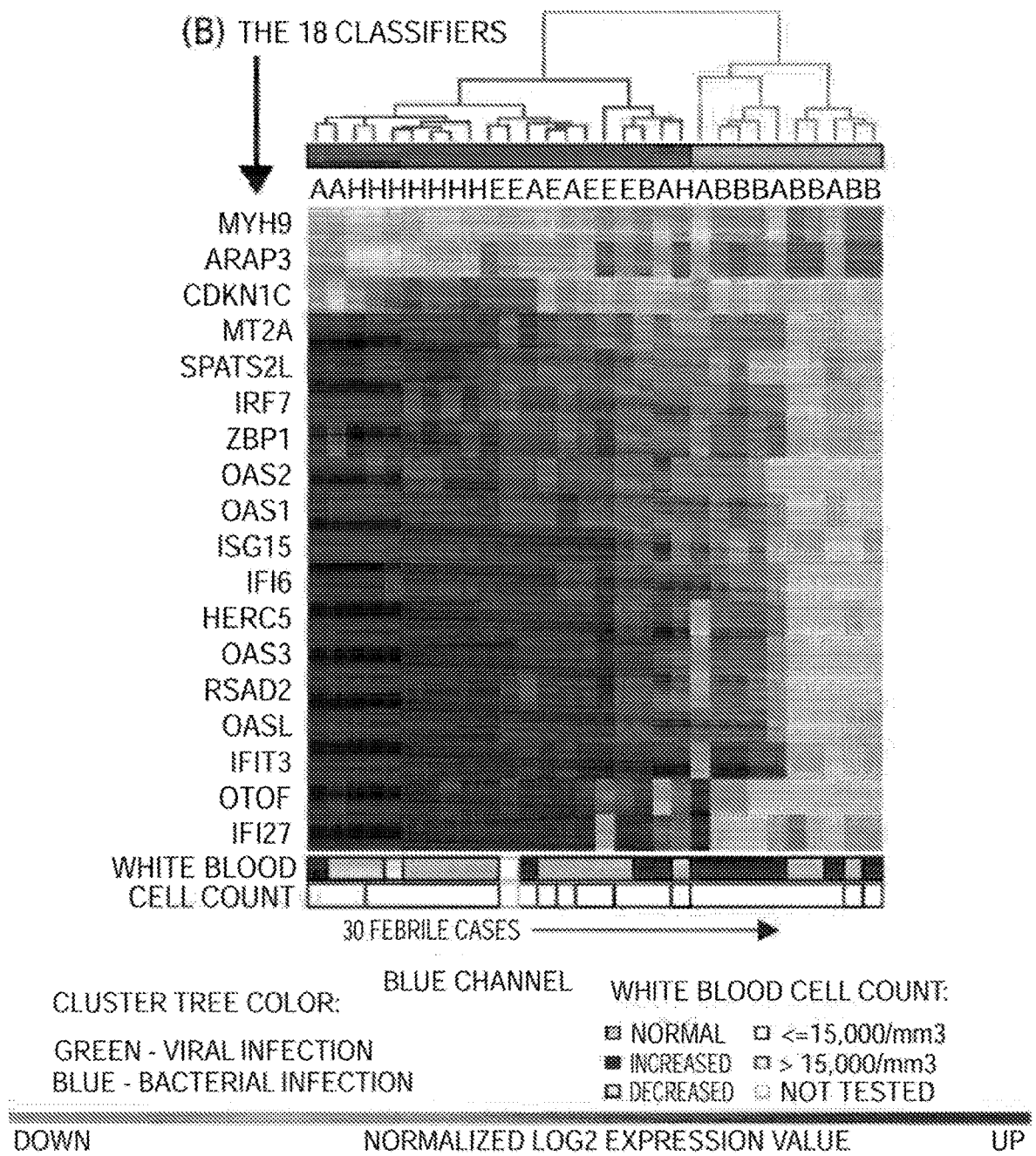
Figure 4C:
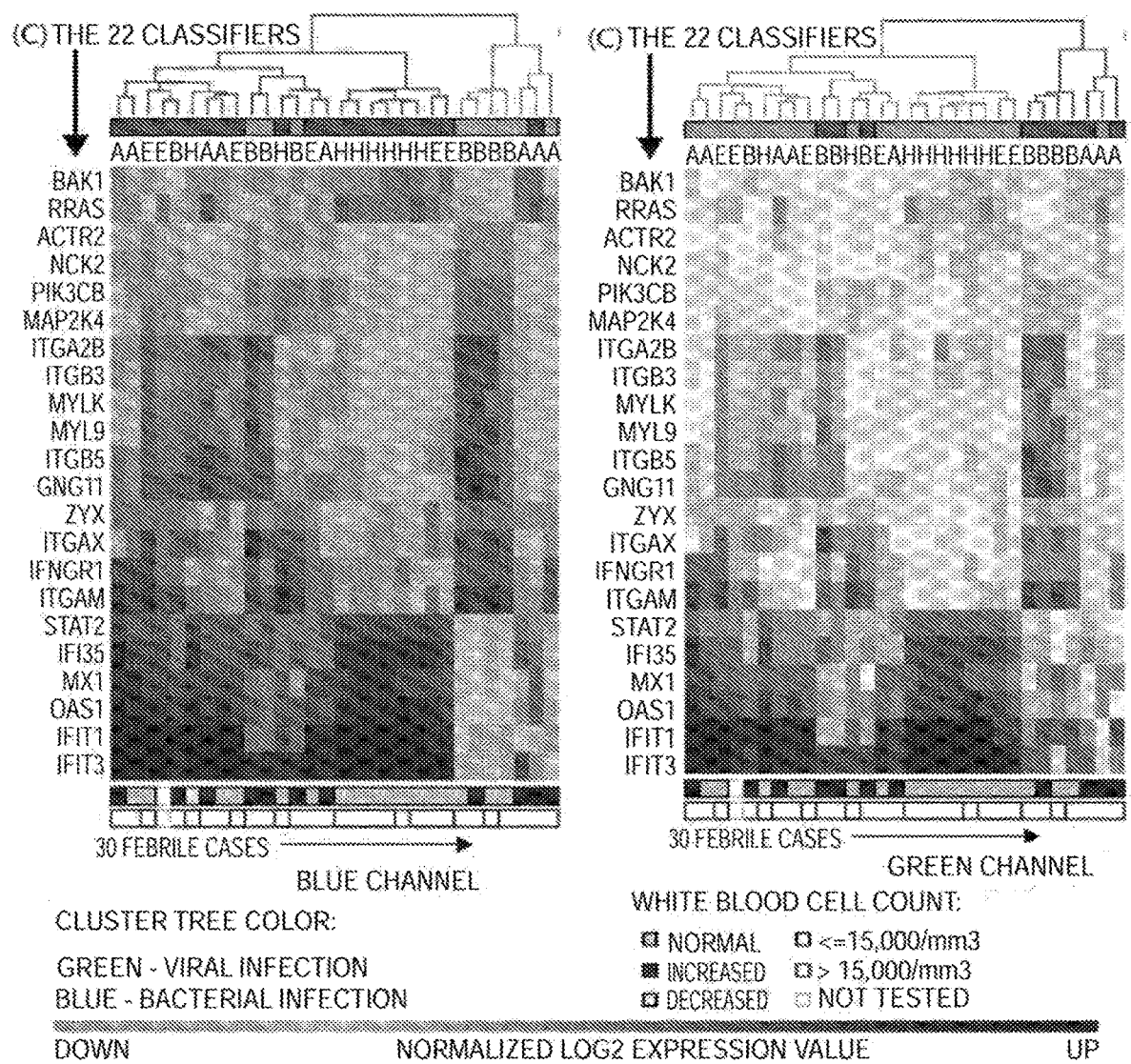
Figure 4D:
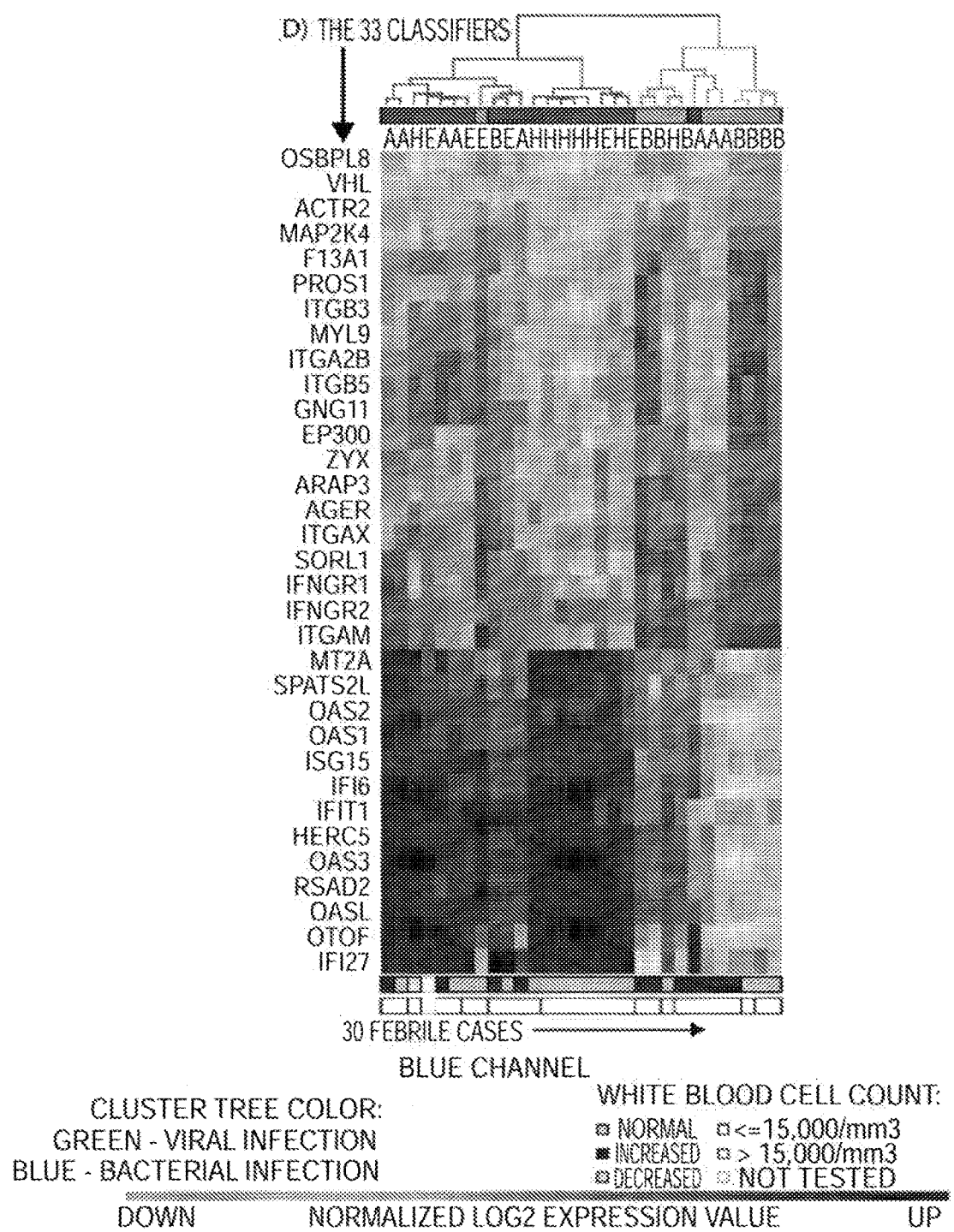

Unique sets of genes were associated with specific viral and bacterial infections in febrile children. In some examples, signaling pathways were similarly activated among the different viruses tested in this study, but with significant variations in the expression level of many individual genes. 2078 probes were identified with significant transcriptional changes uniquely present in adenovirus-positive febrile children, 464 uniquely present in HHV-6-positive febrile children, 594 uniquely present in enterovirus-positive febrile children and 1939 uniquely present in febrile children with acute bacterial infection (FIG. 1A). Using the shrunken centroid algorithm (Tibshirani, R., et al. 2002, Proc. Nat'l. Acad. Sci. USA 99(10):6567-6572), subsets of specific gene probes for each of the individual viruses and for acute bacterial infection were identified (Table 2). These virus-specific transcriptional profiles and the profile specific for acute bacterial infection are shown in FIG. 3.

TABLE 2

Individual virus- and bacteria-specific profile gene probes with strongest effects
Table 2 These probes were had significant up- or down-regulation in children positive for only one virus or with acute bacterial infection using an adjusted P value of 0.05.

| Gene symbol | Accession | Adenovirus vs. control | | HHV-6 vs. control | | Enterovirus vs. control | | Bacteria vs. control | |
|---|---|---|---|---|---|---|---|---|---|
| | | Fold change | Adjusted P value | Fold change | Adjusted P value | Fold change | Adjusted P value | Fold change | Adjusted P value |
| RETN | NM_020415.2 | 6.626 | 0.001 | 1.746 | 0.273 | 1.554 | 0.475 | 1.997 | 0.172 |
| OLFM4 | NM_006418.3 | 5.776 | 0.011 | 1.029 | 0.655 | 1.570 | 0.539 | 3.150 | 0.117 |
| LY2 | NM_000239.1 | 2.130 | 0.011 | −1.050 | 0.622 | −1.225 | 0.530 | 1.045 | 0.493 |
| RPS6KA5 | NM_004755.2 | −1.701 | 0.037 | −1.179 | 0.467 | 1.027 | 0.672 | 1.223 | 0.331 |
| TSPYL2 | NM_022117.1 | −1.692 | 0.002 | −1.113 | 0.437 | −1.197 | 0.390 | −1.250 | 0.160 |
| ITPR1 | NM_002222.4 | −1.625 | 0.008 | −1.143 | 0.415 | 1.092 | 0.580 | 1.345 | 0.120 |
| CCL8 | NM_005623.2 | 2.353 | 0.104 | 12.885 | 0.000 | 2.003 | 0.379 | 1.059 | 0.505 |
| CCL2 | NM_002982.3 | 2.179 | 0.113 | 9.752 | 0.000 | 2.271 | 0.294 | −1.197 | 0.448 |
| LRRC50 | NM_178452.3 | 1.212 | 0.334 | 3.426 | 0.000 | 1.347 | 0.439 | −1.074 | 0.470 |
| VPS28 | NM_016208.2 | −1.069 | 0.434 | −1.625 | 0.015 | −1.048 | 0.640 | 1.084 | 0.423 |
| NMEA | NM_005009.2 | 1.108 | 0.363 | −1.562 | 0.020 | 1.163 | 0.491 | −1.116 | 0.376 |
| MBNL3 | NM_133486.1 | 1.305 | 0.346 | 1.349 | 0.440 | 3.190 | 0.096 | 1.649 | 0.228 |
| HAGH | NM_005326.4 | 1.342 | 0.212 | −1.103 | 0.567 | 2.162 | 0.096 | 1.100 | 0.449 |
| TMPRSS9 | NM_182973.1 | 1.236 | 0.238 | 1.048 | 0.610 | 2.057 | 0.059 | 1.301 | 0.226 |
| KLC3 | NM_177417.1 | 1.076 | 0.453 | −1.142 | 0.498 | 1.999 | 0.083 | 1.307 | 0.246 |
| STGGALNAC4 | NM_175039.3 | 1.288 | 0.195 | −1.056 | 0.601 | 1.945 | 0.079 | −1.045 | 0.482 |
| PROS1 | NM_000313.1 | 1.162 | 0.294 | −1.029 | 0.628 | 1.265 | 0.382 | 2.473 | 0.001 |
| SCGB1C1 | NM_145651.2 | −1.017 | 0.522 | 1.152 | 0.492 | 1.230 | 0.495 | 2.463 | 0.004 |
| ARAP3 | NM_022481.5 | 1.005 | 0.535 | −1.104 | 0.545 | 1.269 | 0.446 | 2.201 | 0.007 |
| STXBP5 | NM_138244.2 | −1.284 | 0.160 | −1.281 | 0.244 | 1.094 | 0.595 | 2.050 | 0.004 |
| GZMH | NM_033423.3 | −1.929 | 0.106 | −1.733 | 0.234 | −2.088 | 0.260 | −5.258 | 0.003 |
| KIR2DL3 | NM_014511.3 | −1.016 | 0.629 | −1.092 | 0.601 | −1.642 | 0.346 | −3.389 | 0.007 |
| KIR2DL4 | NM_002255.3 | 1.165 | 0.384 | 1.062 | 0.613 | −1.408 | 0.405 | −2.646 | 0.008 |
| KIR3DL1 | NM_013289.1 | −1.018 | 0.524 | −1.101 | 0.572 | −1.354 | 0.433 | −2.572 | 0.008 |
| MTIX | NM_005952.2 | 1.107 | 0.414 | 1.291 | 0.309 | 1.170 | 0.545 | −1.787 | 0.041 |
| OS8PL5 | NM_145638.1 | −1.014 | 0.519 | 1.187 | 0.325 | −1.101 | 0.566 | −1.767 | 0.007 |

Gene transcription in children positive for only one virus and children with acute bacterial infection were each compared with gene transcription in afebrile virus-negative control children. Candidate genes were derived using the shrunken centroid algorithm procedure in the Prediction of Microarray Analysis tool from Stanford University (http://www-stat.stanford.edu/~tibs/SAM/). Probes were sorted within each virus/bacteria group by descending fold change (when up-regulated) or ascending fold change (when down-regulated). Bold and italic fonts indicate genes that at adjusted P value <0.05. FIG. 3 illustrates probes specific for individual viruses and for bacteria. In these investigations, viral-specific and bacterial response-specific probes were subjected to the shrunken centroid algorithm individually for each of the 4 pathogen groups to find a non-limiting reduced number of probes with ability to differentiate among pathogen groups. Each row represents a probe and each column displays probes for one febrile child positive for the indicated virus or with acute bacterial infection.

Classifier probes were identified to distinguish viral and bacterial infections in febrile children with validation on independent datasets. Host transcriptional profiles unique to either viral or bacterial infection were characterized to assist in making this clinical discrimination. Individual-gene-based and pathway-based approaches for selecting probes were compared. For the gene-based approach, a "master set" was used, including the 1581 (260 viral- and 1321 bacterial-specific) probes described above and a limited subset of 18 of the 1581 selected using the shrunken centroid algorithm. For the pathway-based approach, the shrunken centroid algorithm was used to select 22 probes from the Interferon Signaling Pathway (selectively activated in virus-positive febrile children) and the Integrin Signaling Pathway (selectively activated in febrile children with acute bacterial infection). The hybrid approach used 33 probes selected using the shrunken centroid algorithm from the master set and from the Interferon Signaling and Integrin Signaling Pathways. 9 classifiers were selected from the 3 sets of classifiers described above and validated by RT-qPCR. High correlation in expression level was found for 9 classifier genes between RT-qPCR and microarray results (FIG. 9, Table 3).

TABLE 3

Correlation in expression level between RT-qPCR and microarray results

| Classifier | Pearson correlation of coefficient | P value |
|---|---|---|
| IFI27 | 0.722 | 2.17E−07 |
| IFIT1 | 0.903 | 3.55E−15 |
| ISG15 | 0.775 | 6.79E−09 |
| ITGAM | 0.925 | 4.29E−17 |
| ITGAX | 0.813 | 3.11E−10 |
| ITGB5 | 0.886 | 6.86E−14 |
| OASL | 0.937 | 1.66E−18 |
| OTOF | 0.927 | 2.55E−17 |
| PROS1 | 0.705 | 5.47E−07 |

Classification of cases was carried out using unsupervised hierarchical clustering and the K-nearest neighbor algorithm. The "true class" of each case was based on virus-specific PCRs and bacterial cultures as previously described (Colvin J M, et al. 2012, *Pediatrics* 130(6):e1455-1462). The classifications derived from the use of probes selected by each approach are shown in FIG. 4.

FIG. 4 illustrate classifier probes that discriminate febrile children positive for viruses from febrile children with acute bacterial infections. FIG. 4A illustrates 1581 gene-based classifiers. FIG. 4B illustrates 18 gene-based classifiers. FIG. 4C illustrates 22 pathway-based classifiers. FIG. 4D illustrates 33 classifiers selected from gene-based and pathway-based classifier sets. In each panel, patients are displayed as columns and probes as rows. Gene symbols are shown in blue for bacterial infection-specific genes and in green for viral infection-specific genes. Expression values presented in the heat map were normalized to the mean of the afebrile virus-negative control cases. Hierarchical clustering was used to classify patients into two groups with the majority of cases classified as either viral (green tree branch) or bacterial (blue tree branch). Classification as predicted using the K-nearest neighbor algorithm is shown as a bar above each heat map, with green showing classification as viral and blue showing classification as bacterial. True class was determined by virus-specific PCR and bacterial cultures, and is designated by green (viral) or blue (bacterial) letters: A, adenovirus; B, Bacteria; E, enterovirus; 1, HHV-6. Classification based on patients' white blood cell (WBC) count is shown beneath each heat map. The upper strip shows classification based on age-specific normal values and the lower strip shows classification based on a cutoff of 15,000 cells per cu mm.

The signal intensity of the probes is shown in FIG. 9, and classification performance of each set is summarized in Table 4. Correct classification based on hierarchical clustering ranged from 77-90% and 83-90% based on the K-nearest neighbor method.

robustness of classifier probes for distinguishing viral and bacterial infection. The validation data included three different cohorts analyzed using three different microarray platforms, each of which differed from ours. 95% accuracy was achieved in distinguishing viral and bacterial infection using the 1581 probes and 88-91% accuracy in using the other three sets of probes (Table 4, FIG. 10).

Example 5

This example illustrates RT-qPCR validation assays.

For RT-qPCR validation assays, primers and probes of assay-on-demand were purchased from Life Technologies (Applied Biosystems, Forster City, Calif.), and master mix was from Quanta Biosciences (Gaithersburg, Md.) for reverse transcription and quantitative PCR (RT-qPCR) assays. The assays were carried out in triplicate on an ABI 7500 real-time PCR instrument following manufacturer's protocols. Assays had >80% PCR efficiency and <15% coefficient of variance in triplicate reactions.

Performance of probe sets was validated using three previously published microarray data sets (Ramilo O, et al. 2007, *Blood* 109(5):2066-2077). Comparisons were made across different microarray platforms. Selected probes achieved classifications that were 88-95% concordant with the classifications of the validation sets.

FIG. 10 illustrates validation of three sets of classifier probes discriminating virus-positive febrile children from febrile children with acute bacterial infection using three

TABLE 4

Prediction Accuracy of Four Sets of Classifier Probes

| Data set | Microarray | N* | All 1581 virus-specific and bacteria-specific probes without selection | 18 classifiers from 1581 virus-specific and bacteria-specific probes† | 22 classifiers from Ingenuity* Interferon and Integrin pathway genus‡ | 33 classifiers selected using a combined gene- and pathway-based approach†‡ |
|---|---|---|---|---|---|---|
| Present study | Human-HT12 | 30 | 27 (90%)§ | 26 (87%) | 27 (90%) | 25 (83%) |
| Ramilo study¶ | U133Plus2 | 22 | 21 (95%) | 21 (95%) | 19 (86%) | 18 (82%) |
| Ramilo study | Human-WG6 | 24 | 23 (96%) | 22 (92%) | 18 (75%) | 21 (88%) |
| Ramilo study | U133A | 91 | 86 (95%) | 82 (90%) | 81 (89%) | 85 (93%) |
| Ramilo combined | all 3 sets | 137 | 130 (95%) | 123 (90%) | 121 (88%) | 124 (91%) |

*Number of cases in data set
†785 of 1581 gene-based probes were identified in the Ramilo data sets
‡182 of 239 pathway-based genes were identified in the Ramilo data sets
§Number (percent) of classified cases
¶Ramilo O, et al. (2007) Blood 109(5): 2066-2077

Figure 9A:
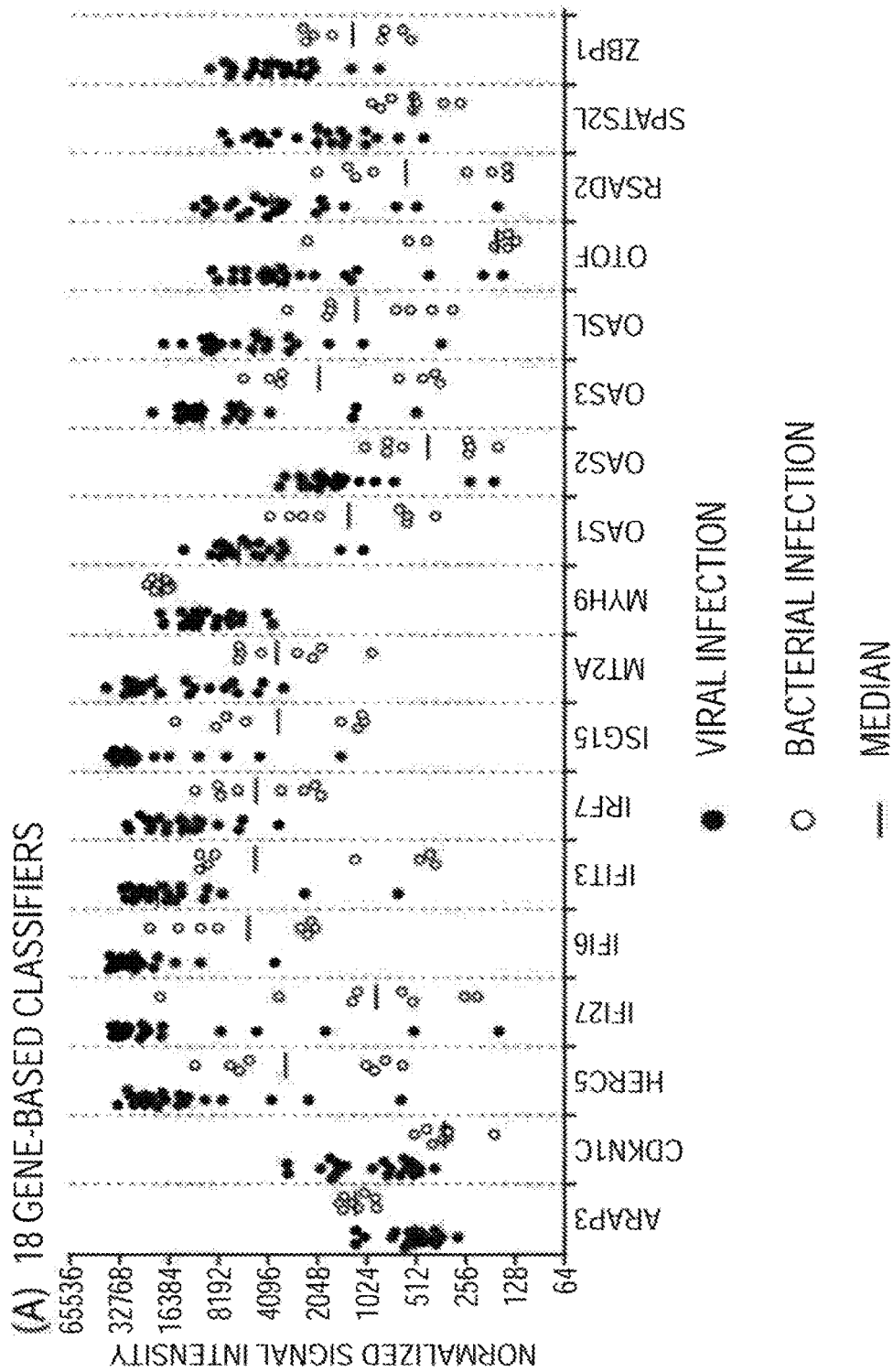
Figure 9B:
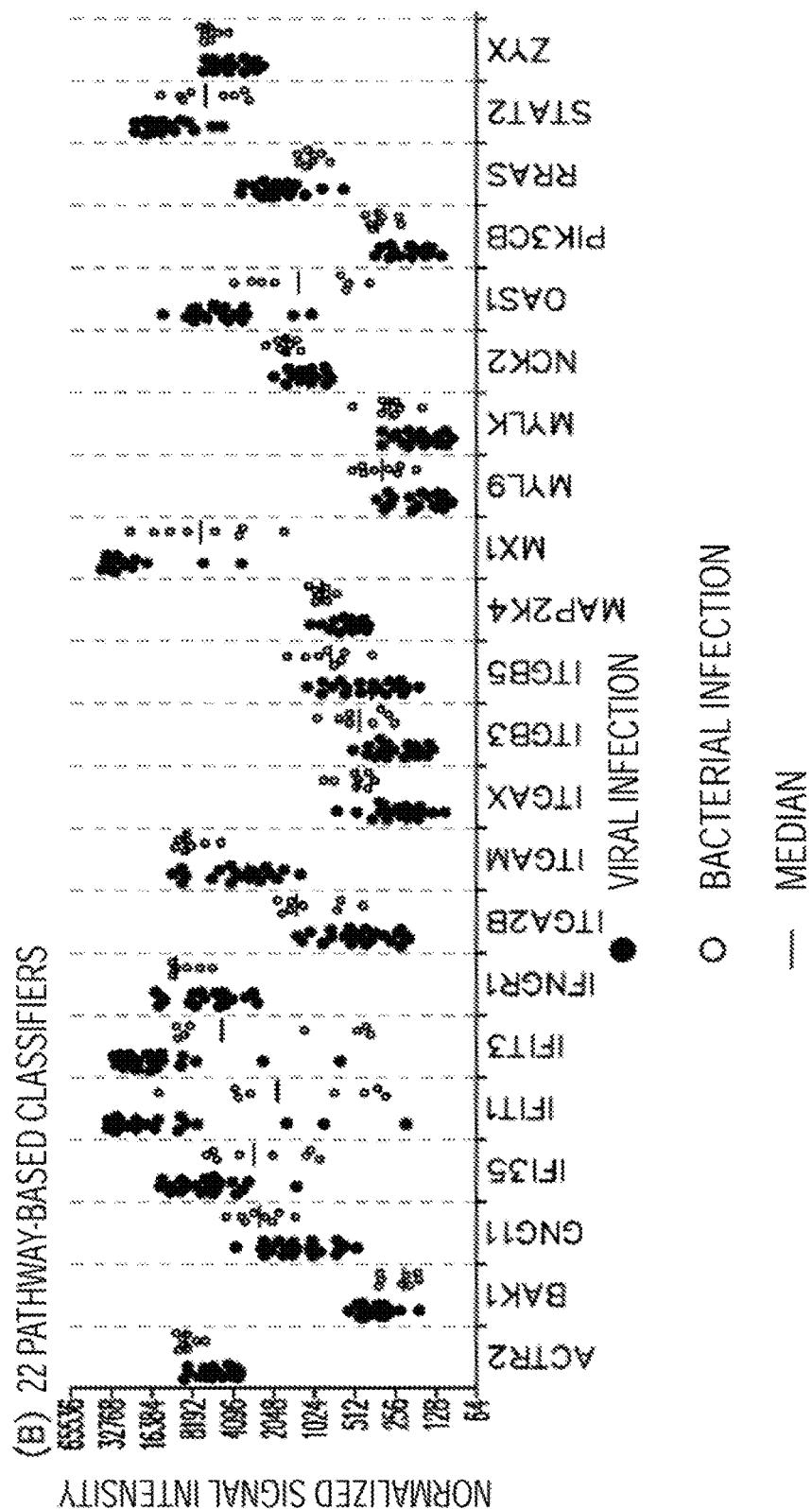
Figure 9D:
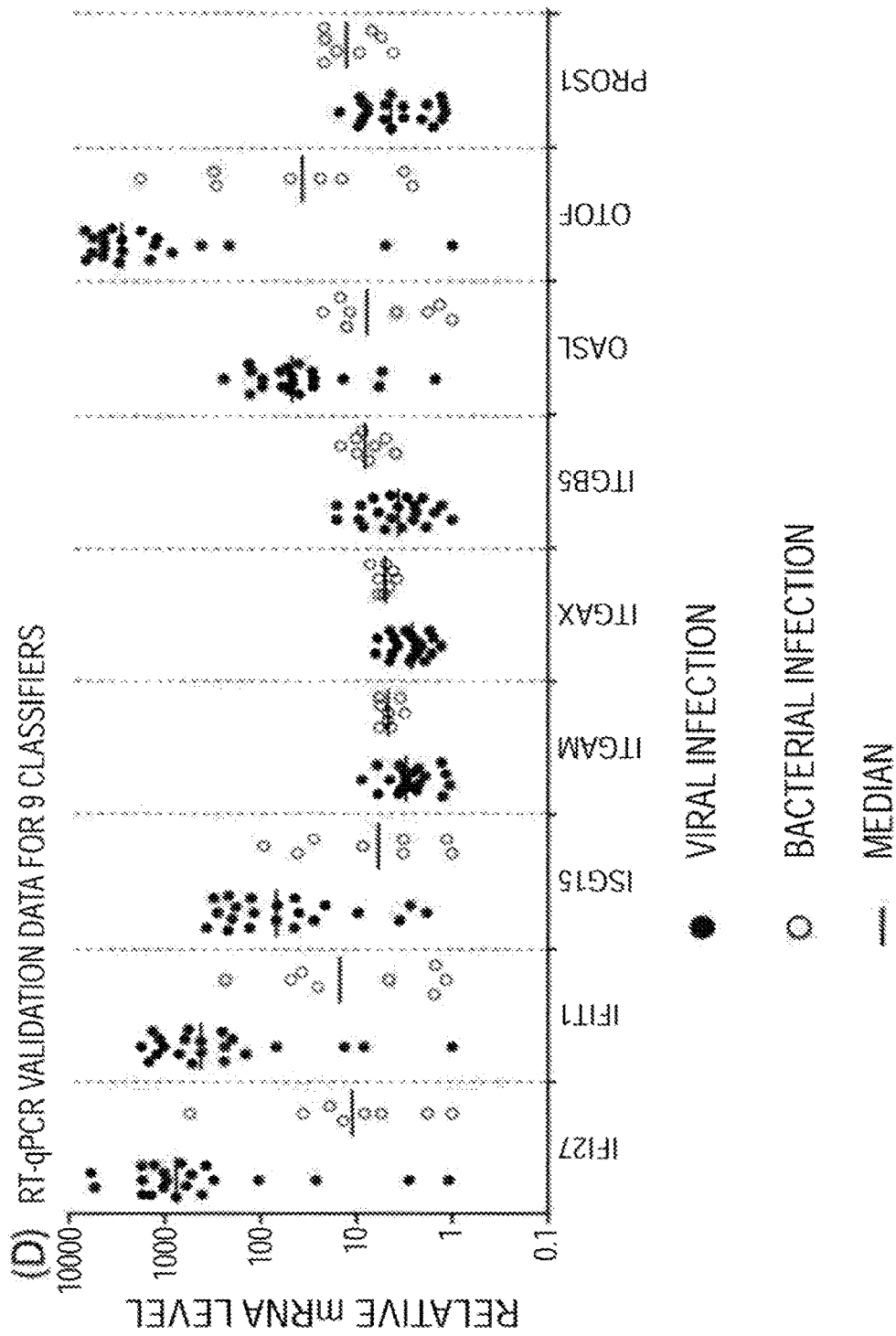

FIG. 9 illustrates quantile-normalized raw signal intensity of classifier probes in 30 febrile children (22 virus-positive children and 8 children with acute bacterial infection) in our study. FIG. 9A illustrates 18 classifiers identified from 260 viral- and 1,321 bacterial response-specific probes. FIG. 9B illustrates 22 classifiers identified from 34 genes in the Ingenuity® IFN signaling pathway and 205 genes in the Ingenuity® (Ingenuity Systems, Inc., Redwood City, Calif.) integrin signaling pathway. FIG. 9C illustrates 33 classifiers identified from using both gene-level and pathway-based approaches. FIG. 9D illustrates relative expression data of nine classifier genes, generated in quantitative RT-PCR (RT-qPCR) validation assays for 29 of 30 febrile children (one RNA sample with HHV-6 infection was not available for the assays). The expression level was calculated using ΔΔCt method and normalized to endogenous reference GAPDH. In FIG. 9A-9D, each dot represents one sample.

Figure 10A:
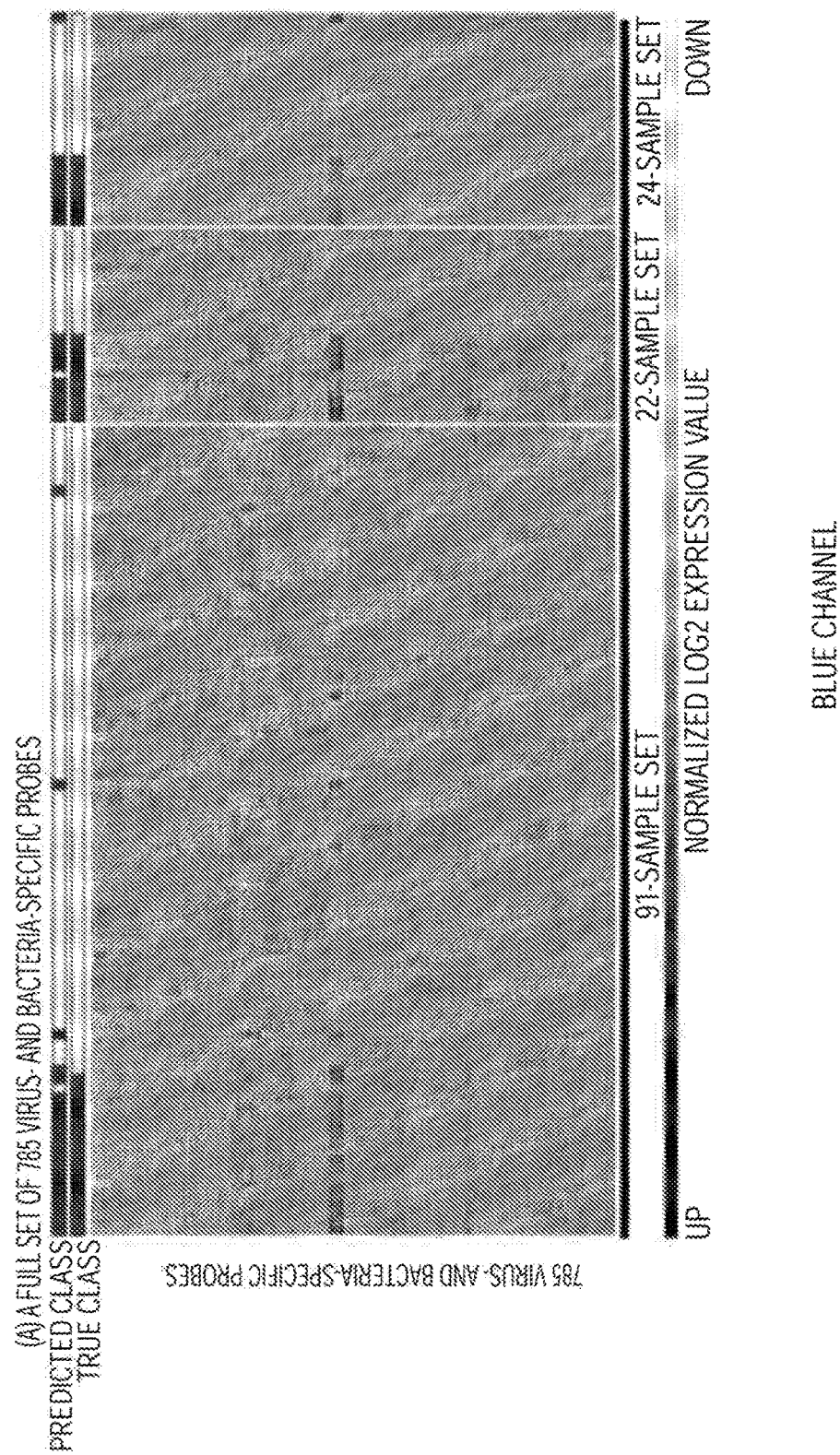
FIG. 10A-D illustrate validation of three sets of classifier probes discriminating virus-positive febrile children from febrile children with acute bacterial infection using three independent cohorts of subjects.
Figure 10B:
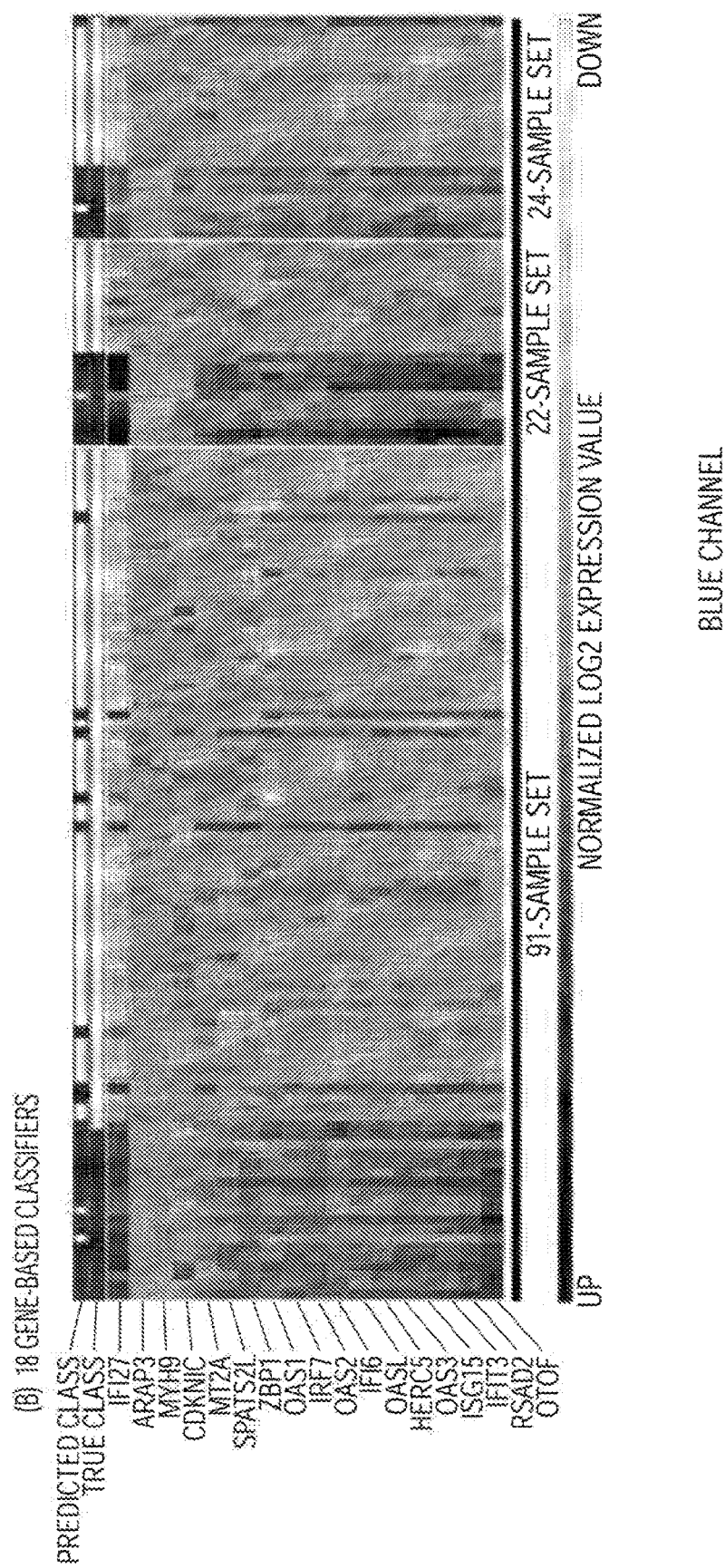
Figure 10C:
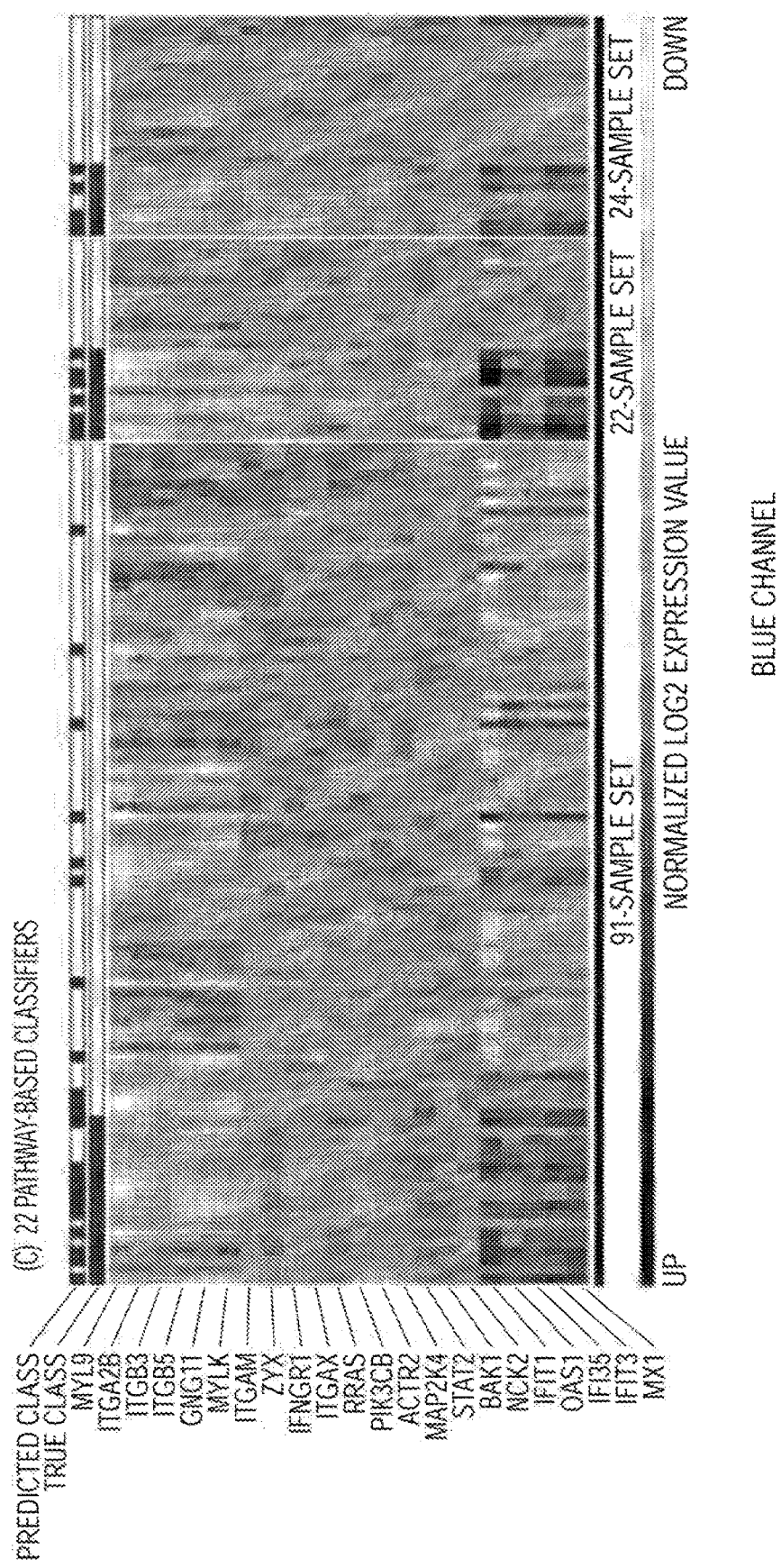
Figure 10D:
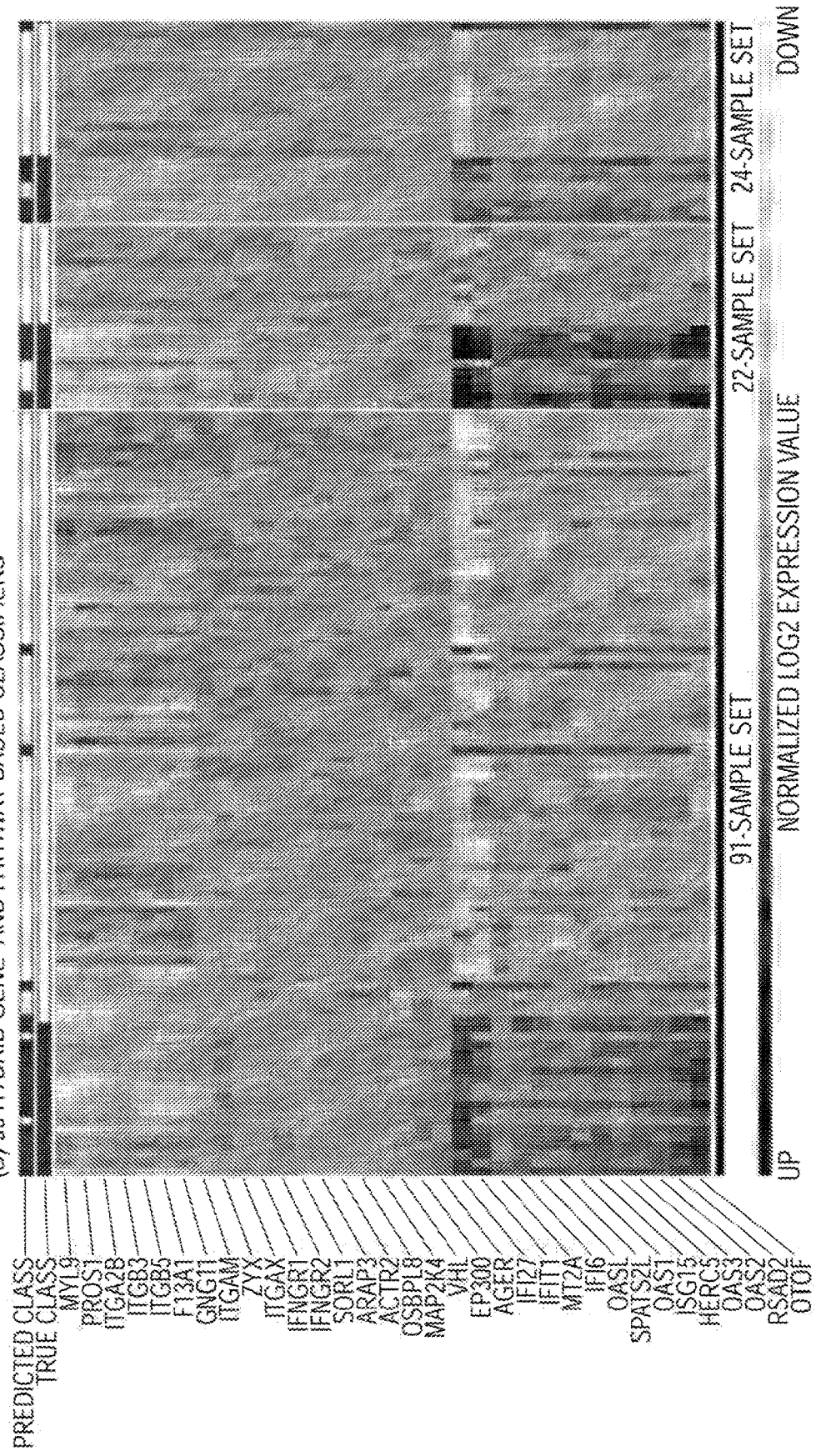

Independent datasets from Ramilo O, et al. 2007, Blood 109(5): 2066-2077 were used to test the clinical validity and independent cohorts of patients. The 91-sample validation set included 18 subjects with influenza A, 29 subjects with *Escherichia coli*, 31 subjects with *Staphylococcus aureus*, and 13 subjects with *Streptococcus pneumoniae*. This set was profiled with the Affymetrix (Santa Clara, Calif. USA) Human Genome U133A Array platform. The 22-sample validation set included seven children with influenza A, three children with influenza B, six children with *S. aureus*, and six children with *S. pneumonia*. This validation set was profiled with the Affymetrix Human Genome U1133 Plus 2.0 Array platform. The 24-sample validation set included 5 subjects with influenza A, 3 subjects with influenza B, 13 subjects with *S. aureus*, and 3 subjects with *S. pneumoniae*, and it was profiled with the Illumina Sentrix Human-6 Expression BeadChip platform. FIG. 10A illustrates validation with a set of 785 probes overlapped across three datasets with 1,581 virus- and bacterial response-specific probes. FIG. 10B illustrates validation with gene-based classifiers. FIG. 10C illustrates validation with pathway-based classifiers. FIG. 10D illustrates validation with hybrid gene- and pathway-based classifiers. For FIG. 10A-FIG. 10D: Patient groups are indicated by stripes at the top of the heat map. In original color, predicted class is labeled with green for viral or blue for bacterial infection. Gene names in green in original signify genes selected from the viral-specific gene set (or the IFN signaling pathway genes), and gene names in blue in original represent genes selected from the bacterial-specific gene set (or the integrin signaling pathway genes). Heat map rows are gene probes, whereas columns are individual subjects. Overall prediction accuracy was 95% (130/137), 88%(120/137), 88% (121/137), and 91% (124/137) with FIG. 10A a full set of 785 probes overlapped across all three datasets with 1.581 viral- and bacterial response-specific probes, FIG. 10B gene-based classifiers (n=18), FIG. 10C pathway-based classifiers (n=22), and FIG. 10D hybrid gene- and pathway-based classifiers (n=33), respectively. Patient groups are indicated by colored stripes at the top of the heat map. True class indicates status determined by virus-specific PCR assays and bacterial cultures, and it was assigned to these cases in Ramilo, O., et al. (2007). *Blood* 109(5):2066-2077). Predicted class was determined by prediction made with the classifier probes, and in the original color, it is labeled with green for viral or blue for bacterial infection. In original color, gene names in green signify genes selected from the viral-specific gene set (or the IFN signaling pathway genes), and gene names in blue represent genes selected from the bacterial-specific gene set (or the integrin signaling pathway genes). Expression values presented in the heat-maps were normalized to the mean of cases with bacterial infection within each dataset. Heat-map rows are gene probes, whereas columns are individual subjects.

Example 6

This example illustrates utilizing the Pearson test to determine correlation between gene expression profiles and white blood cell counts/differentials.

In these investigations, the Pearson test was used to find significant correlations of differentially expressed genes with white blood cell and differential counts in the 30 febrile cases. The differential expression was defined with $p<0.05$ and fold-change >1.5 in comparisons between febrile groups and healthy controls. The original p-value of the correlation coefficient was adjusted by multiple test correction and the adjusted p-value was set at 0.05 for significance. Age-specific normal values for white blood cell count used by the clinical laboratory at St. Louis Children's Hospital: <1 week: 5.0-30.0 K/cu mm; 1 week-1 month: 5.0-20.0 K/cu mm; 1 month-2 years: 6.0-17.5 K/cu mm; 2-6 years: 5.0-15.5 K/cu mm: 6-12 years: 4.5-13.5 K/cu mm; >12 years: 3.8-9.8 K/cu mm.

A Pearson correlation test was performed for 4716 probes that were different from virus-negative controls in febrile children. The total white blood cell count was not associated with gene expression level, but expression of several clusters of genes was significantly associated with neutrophil, lymphocyte, or monocyte counts, suggesting that those clusters of genes might be activated in specific types of cells (FIG. 11).

Figure 11:
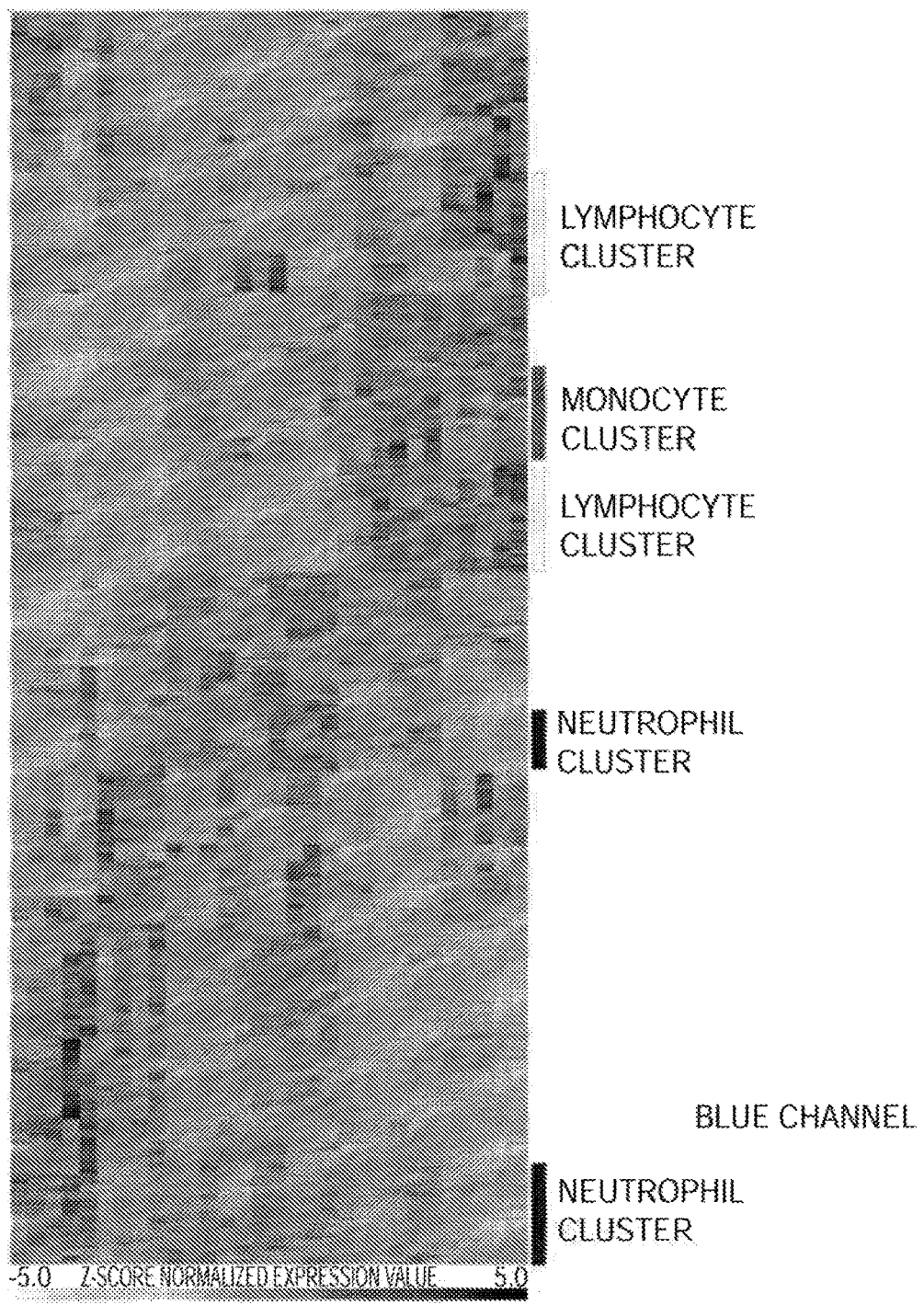
FIG. 11A-B illustrate samples from febrile subjects with confirmed viral/bacterial infection.

FIG. 11 illustrates correlation of transcriptional changes and leukocyte subpopulations in febrile young children. In these investigations, whole-blood samples were collected from 30 febrile children with confirmed viral/bacterial infection. Probe sets with at least a 1.5-fold change in level of expression over virus-negative afebrile controls are shown. The expression pattern of the corresponding 4,716 probe sets is displayed in hierarchical cluster format, where rows represent genes and columns represent individual samples. Correlation coefficients were calculated between the expression level of each probe set and white blood cell counts (total, neutrophil, lymphocyte, bands, and monocyte counts) across 30 patients. The correlation values are plotted as moving averages of 50 probe sets (along the vertical axis). FIG. 11A illustrates correlation of transcriptional changes and leukocyte subpopulations in the subjects. FIG. 11B illustrates an expression pattern of corresponding 4,716 probe sets in cluster format. Rows represent genes and columns represent individual samples. Dashed lines indicate the lowest values of correlation coefficients significant (adjusted $P<0.05$) for each parameter.

Host transcriptional profile results were more accurate compared to traditional white blood cell count for discriminating bacterial from viral infection. Previous studies indicate that white blood cell count is an inadequate tool for distinguishing between viral and bacterial infection, a distinction often used to determine whether or not to treat the patient with antibiotics (Rudinsky, S. L., el al. 2009, *Acad Emerg Med* 16(7):585-590 and Herz, A. M., et al. 2006, *Pediatr Infect Dis J* 25(4):293-300). Classification based on transcriptional profiles was compared with classification based on white blood cell count, using a cutoff of 15,000/$mm^3$ as recommended by the American Academy of Pediatrics in their guideline for the management of febrile children 0-36 months of age (Baraff, L. J., et al. 1993, *Ann. Emerg. Med.* 22(7): 1198-1210). A different set of cutoffs was also analyzed based on age-specific normal values for white blood cell count used by the clinical laboratory at St. Louis Children's Hospital. The classifier gene probes were more accurate for distinguishing bacterial and viral infection than either of the white blood cell criteria as illustrated in FIG. 4.

Example 7

This example illustrates diagnosis of a symptomatic adenovirus infection in a subject.

In this example, a patient exhibits symptoms that initially appear attributable to a viral or bacterial infection. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture and a serum antibody detection test. The health practitioner additionally orders a test to determine expression levels of 260 viral response-specific endogenous genes and 1321 bacterial response-specific endogenous genes by a microarray hybridization assay. The pathogen culture is negative and the serum antibody test is positive for an adenovirus. The microarray hybridization assay reveals an increase in expression of 165 of the 260 viral response-specific endogenous genes and a decrease of 1200 of the 1321 bacterial response-specific endogenous genes. The patient is diagnosed with a symptomatic adenovirus infection.

Example 8

This example illustrates diagnosis of a symptomatic bacterial infection in a subject.

In this example, a patient exhibits symptoms that initially appear attributable to a viral or bacterial infection. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture and a serum antigen detection test. The health practitioner additionally orders a test to determine expression levels of 260 viral response-specific endogenous genes and 1321 bacterial response-specific endogenous genes by a microarray hybridization assay. The pathogen culture is positive for S. aureus and the serum antibody test is negative. The microarray hybridization assay reveals a decrease in expression of 206 of the 260 viral response-specific endogenous genes and an increase in 1145 of the 1321 bacterial response-specific endogenous genes. The patient is diagnosed with a symptomatic bacterial infection, specifically S. aureus infection.

Example 9

This example illustrates a method of diagnosis of Fever Without an Apparent Source in a subject.

A patient exhibits symptoms of Fever Without an Apparent Source. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture and a serum antibody detection test. The health practitioner additionally orders a test to determine expression levels of the following endogenous genes: OSBPL8, VHL, ACTR2, MAP2K4, F13A1, PROS1, ITGB3, MYL9, ITGA2B, ITGB5, GNG11, EP300, ZYX, ARAP3, AGER, ITGAX, SORL1, IFNGR1, IFNGR2, ITGAM, MT2A, SPATS2L, OAS2, OAS1, ISG15, IFI6, IFIT1, HERC5, OAS3. RSAD2, OASL, OTOF and IFI27 by microarray hybridization assay. The pathogen culture is negative and the serum antibody test is positive for an enterovirus. The microarray hybridization assay reveals an increase in expression of IFNGR1, IFNGR2, MT2A, SPATS2L, OAS2, OAS1, ISG15, IFI6, IFIT1, HERC5, OAS3, RSAD2, OASL, OTOF and IFI27 and a decrease in expression of OSBPL8, VHL. ACTR2, MAP2K4, F13A1, PROS1, ITGB3, MYL9, ITGA2B, ITGB5, GNG11, EP300, ZYX, ARAP3, AGER, ITGAX, SORL1 and IGTAM. The patient is diagnosed with a symptomatic enterovirus infection.

Example 10

This example illustrates a method of diagnosis of Fever Without an Apparent Source in a subject.

A patient exhibits symptoms of Fever Without an Apparent Source. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture and a serum antibody detection test. The health practitioner additionally orders a test to determine expression levels of the following endogenous genes: BAK1, RRAS, ACTR2, NCK2, PIK3CB, MAP2K4, ITGA2B3, ITGB3, MYLK, MYL9, ITGB5, GNG11, ZYX, ITGAX, IFNGR1, ITGAM, STAT2, IFI35, MX1, OAS1, IFIT1 and IFIT3 by microarray hybridization assay. The pathogen culture is indefinite and the serum antibody test is negative. The microarray hybridization assay reveals an increase in expression of BAK1, IFNGR1, STAT2, IFI35, MX1, OAS1, IFIT1 and IFIT3 and a decrease in expression of RRAS, ACTR2, NCK2, PIK3CB, MAP2K4, ITGA2B, ITGB3, MYLK, MYL9, ITGB5, GNG11, ZYX, ITGAX and ITGAM. The patient is preliminarily diagnosed with an unknown and symptomatic viral infection.

Example 11

This example illustrates a method of distinguishing a viral-caused infection from a bacterial-cause infection or a combination thereof.

A patient exhibits symptoms that initially appear attributable to a viral or bacterial infection. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture and a serum pathogen antigen detection test. The health practitioner additionally orders a test to determine expression levels of the following endogenous genes: MYH9, ARAP3, CDKN1C, MT2A, SPATS2L, IRF7, ZBP1, OAS2, OAS1, ISG15. IFI6, HERC5, OAS3, RSAD2, OASL, IFIT3, OTOF and IFI27 by microarray hybridization assay. The pathogen culture is negative and the serum antigen test is positive for adenovirus. The microarray hybridization assay reveals an increase in expression of CDKN1C, MT2A, SPATS2L, IRF7, ZBP1, OAS2, OAS1, ISG15, IFI6, HERC5, OAS3, RSAD2, OASL, IFIT3, OTOF and IFI27 and a decrease in expression of MYH9 and ARAP3. The patient is diagnosed with a symptomatic viral infection.

Example 12

This example illustrates a method of distinguishing a viral-caused infection from a bacterial-cause infection or a combination thereof.

A patient exhibits symptoms that initially appear attributable to a viral or bacterial infection. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture and a serum pathogen antigen detection test. The health practitioner additionally orders a test to determine expression levels of the following endogenous genes: MYH9, ARAP3, CDKN1C, MT2A, SPATS2L, IRF7, ZBP1, OAS2, OAS1, ISG15, IFI6, HERC5, OAS3, RSAD2, OASL, IFIT3, OTOF and IFI27 by microarray hybridization assay. The pathogen culture is positive for E. coli and the serum antigen test is negative. The microarray hybridization assay reveals a decrease in expression of CDKN1C, MT2A, SPATS2L, IRF7, ZBP1, OAS2, OAS1, ISG15, IFI6, HERC5, OAS3, RSAD2, OASL, IFIT3, OTOF and IF27 and an increase in expression of MYH9 and ARAP3. The patient is diagnosed with a symptomatic bacterial infection.

Example 13

This example illustrates a method of diagnosis of a pathogen-associated disease.

A patient exhibits symptoms that initially appear attributable to a viral or bacterial infection. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture and a serum pathogen antigen detection test. A health practitioner orders at least one test to determine expression levels of the following endogenous genes: IFI27, ISG15, OTOF, IFIT3, ITGAM, and ITGAX by microarray hybridization assay. The pathogen culture is negative and the serum antigen test is positive for adenovirus. The microarray hybridization assay reveals a decrease in expression of ITGAM, and ITGAX and an increase in expression of IFI27, ISG15, OTOF, and IFIT3. The patient is diagnosed with a symptomatic adenovirus infection.

Example 14

This example illustrates a method of diagnosis of a pathogen-associated disease.

A patient exhibits symptoms that initially appear attributable to a viral or bacterial infection. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture and a serum pathogen antigen detection test. A health practitioner orders at least one test to determine expression levels of the following endogenous genes: IFI27, ISG15, OTOF, IFIT3, ITGAM, and ITGAX by microarray hybridization assay. The pathogen culture is positive for *E. coli* and the serum antigen test is negative. The microarray hybridization assay reveals an increase in expression of ITGAM, and ITGAX and a decrease in expression of IFI27, ISG15, OTOF, and IFIT3. The patient is diagnosed with a symptomatic bacterial infection.

Example 15

This example illustrates a method of diagnosis of a viral pathogen-associated disease.

A patient exhibits symptoms that initially appear attributable to a viral or bacterial infection. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture and a serum pathogen antigen detection test. A health practitioner orders at least one test to determine expression levels of the following endogenous genes: IFI27, ISG15, OTOF, IFIT3, ITGAM, and ITGAX by microarray hybridization assay. The pathogen culture is negative and the serum antigen test is positive for HHV-6. The microarray hybridization assay reveals a decrease in expression of ITGAM, and ITGAX and an increase in expression of IFI27, ISG15, OTOF, and IFIT3. The patient is diagnosed with a symptomatic HHV-6 infection.

Example 16

This example illustrates a method of diagnosis of a viral pathogen-associated disease.

A patient exhibits symptoms that initially appear attributable to a viral or bacterial infection. A health practitioner obtains a whole blood sample, a nasopharyngeal sample, and a blood sample in a Tempus™ Blood RNA Tube (Applied Biosystems, Carlsbad, Calif.) from the subject. A health practitioner orders a pathogen culture, a serum pathogen antigen test, and a serum antibody detection test. The health practitioner additionally orders a test to determine expression levels of the following endogenous genes: MYH9, ARAP3, CDKN1C, MT2A, SPATS2L, IRF7, ZBP1, OAS2, OAS1, ISG15, IFI6, HERC5, OAS3, RSAD2, OASL, IFIT3, OTOF and IFI27 by microarray hybridization assay. The pathogen culture is negative, the serum antibody test is negative, and the serum antigen test is positive for enterovirus. The microarray hybridization assay reveals an increase in expression of CDKN1C, MT2A, SPATS2L, IRF7, ZBP1, OAS2, OAS1, ISG15, IFI6, HERC5, OAS3, RSAD2, OASL, IFIT3, OTOF and IFI27 and a decrease in expression of MYH9 and ARAP3. The patient is diagnosed with a symptomatic enterovirus infection.

Example 17

This example illustrates a method of diagnosis of a pathogen-associated disease.

A patient exhibits symptoms that initially appear attributable to a viral or bacterial infection. A health practitioner obtains a blood sample in a Tempus™ Blood RNA Tube (Applied Biosystems, Carlsbad, Calif.) from the subject. The health practitioner orders a test to determine expression levels of the following endogenous genes: MYH9, ARAP3, CDKN1C, MT2A, SPATS2L, IRF7, ZBP1, OAS2, OAS1, ISG15, IFI6, HERC5, OAS3, RSAD2, OASL, IFIT3, OTOF and IFI27 by microarray hybridization assay. The microarray hybridization assay reveals an increase in expression of CDKN1C, MT2A, SPATS2L, IRF7, ZBP1, OAS2, OAS1, ISG5, IFI6, HERC5, OAS3, RSAD2, OASL, IFIT3, OTOF and IFI27 and a decrease in expression of MYH9 and ARAP3. The patient is diagnosed with a symptomatic viral infection.

Example 18

This example illustrates a method of diagnosis of a pathogen-associated disease.

A patient exhibits symptoms that initially appear attributable to a viral or bacterial infection. A health practitioner obtains a blood sample in a Tempus™ Blood RNA Tube (Applied Biosystems, Carlsbad, Calif.) from the subject. The health practitioner orders a test to determine expression levels of the following endogenous genes: MYH9, ARAP3, CDKN1C, MT2A, SPATS2L, IRF7, ZBP1, OAS2, OAS1, ISG15, IFI6, HERC5, OAS3, RSAD2, OASL, IFIT3, OTOF and IFI27 by microarray hybridization assay. The microarray hybridization assay reveals a decrease in expression of CDKN1C, MT2A, SPATS2L, IRF7, ZBP1, OAS2, OAS1, ISG15, IFI6, HERC5, OAS3, RSAD2, OASL, IFIT3, OTOF and IFI27 and an increase in expression of MYH9 and ARAP3. The patient is diagnosed with a symptomatic bacterial infection.

Gene and transcript sequences are all known in the art. Sequences are available from databases such as those of the National Center for Biotechnology Information. All references cited are hereby incorporated by reference, each in its entirety.

What is claimed is:
1. A method of determining etiology of a Fever without an Apparent Source (FWS) in a subject comprising:
   a) obtaining at least one blood sample from the subject with FWS;
   b) detecting expression levels of SPATS2L and OTOF in the blood sample;
   c) determining that the subject with FWS has FWS caused by a viral etiology when the levels of SPATS2L and OTOF as detected in step b) exhibit an increased level of expression relative to a control sample obtained from a febrile subject infected with a bacteria or a control sample obtained from a healthy control subject; and
   d) administering an anti-viral drug to the subject determined to have FWS caused by viral etiology.

2. The method of claim 1, wherein step b) further comprises detecting expressions levels of ISG15, OAS3, and IFI6.

3. The method of claim 2, wherein the subject with FWS has FWS caused by a viral etiology when the levels of SPATS2L and OTOF and the levels of one or more of ISG15, OAS3 and IFI6 as detected in step b) exhibit an increased level of expression relative to a control sample obtained from a febrile subject infected with a bacteria or a control sample obtained from a healthy control subject.

4. The method of claim 1, wherein step b) further comprises detecting expressions levels of EP300, ZYX, ITGAX, PROS1, and MAP2K4.

5. The method of claim 1, further comprising obtaining a second biological sample from the subject and detecting in the second sample the presence, absence or quantity of a viral pathogen.

6. A method of determining etiology of a Fever without an Apparent Source (FWS) in a subject comprising:
   a) obtaining at least one blood sample from the subject with FWS;
   b) detecting expression levels of SPATS2L and OTOF in the blood sample;
   c) determining that the subject with FWS has FWS caused by a bacterial etiology when the levels of SPATS2L and OTOF as detected in step b) exhibit a decreased level of expression relative to a control sample obtained from a febrile subject infected with a virus or a control sample obtained from a healthy control subject; and
   d) administering an anti-bacterial drug to a subject determined to have FWS caused by bacterial etiology.

7. The method of claim 6, wherein step b) further comprises detecting expressions levels of ISG15, OAS3, and IFI6.

8. The method of claim 7, wherein the subject with FWS has FWS caused by a bacterial etiology when the levels of SPATS2L and OTOF and the levels of one or more of ISG15, OAS3 and IFI6 as detected in step b) exhibit a decreased level of expression relative to a control sample obtained from a febrile subject infected with a bacteria or a control sample obtained from a healthy control subject.

9. The method of claim 6, wherein step b) further comprises detecting expressions levels of EP300, ZYX, ITGAX, PROS1, and MAP2K4.

10. The method of claim 6, further comprising obtaining a second biological sample from the subject and detecting in the second sample the presence, absence or quantity of a bacterial pathogen.

* * * * *